United States Patent
Pouillot et al.

(10) Patent No.: US 11,779,617 B2
(45) Date of Patent: *Oct. 10, 2023

(54) PHAGE THERAPY

(71) Applicant: PHERECYDES PHARMA, Romainville (FR)

(72) Inventors: Flavie Pouillot, Paris (FR); Helene Blois, Paris (FR)

(73) Assignee: PHERECYDES PHARMA, Romainville (FR)

( * ) Notice: Subject to any disclaimer, the term of this patent is extended or adjusted under 35 U.S.C. 154(b) by 239 days.

This patent is subject to a terminal disclaimer.

(21) Appl. No.: 17/153,911

(22) Filed: Jan. 21, 2021

(65) Prior Publication Data

US 2021/0228659 A1 Jul. 29, 2021

Related U.S. Application Data

(63) Continuation of application No. 15/524,271, filed as application No. PCT/EP2015/075949 on Nov. 6, 2015, now Pat. No. 10,898,530.

(30) Foreign Application Priority Data

Nov. 7, 2014 (EP) .................................... 14306788

(51) Int. Cl.
*A61K 35/76* (2015.01)
*C12N 7/00* (2006.01)

(52) U.S. Cl.
CPC ............... *A61K 35/76* (2013.01); *C12N 7/00* (2013.01); *C12N 2795/00021* (2013.01); *C12N 2795/00032* (2013.01); *C12N 2795/10121* (2013.01); *C12N 2795/10132* (2013.01); *C12N 2795/10221* (2013.01); *C12N 2795/10232* (2013.01)

(58) Field of Classification Search
None
See application file for complete search history.

(56) References Cited

U.S. PATENT DOCUMENTS

| 10,077,431 | B2* | 9/2018 | Pouillot | ................... C12N 7/00 |
| 10,260,051 | B2* | 4/2019 | Pouillot | ................ A61P 31/04 |
| 10,898,530 | B2* | 1/2021 | Pouillot | ................ A61K 35/76 |
| 2017/0000831 | A1 | 1/2017 | Pouillot et al. | |
| 2019/0002840 | A1 | 1/2019 | Pouillot et al. | |

FOREIGN PATENT DOCUMENTS

| EP | 2465926 | 6/2012 |
| WO | WO 02/07742 | 1/2002 |
| WO | WO 2009/075884 | 6/2009 |

OTHER PUBLICATIONS

GenBank: GU815091.1 (2010) (Year: 2010).*

(Continued)

*Primary Examiner* — Michelle S Horning
(74) *Attorney, Agent, or Firm* — SALIWANCHIK, LLOYD & EISENSCHENK

(57) ABSTRACT

The present invention relates to bacteriophage therapy. More particularly, the present invention relates to novel bacteriophages having a high specificity against *Pseudomonas aeruginosa* strains, their manufacture, components thereof, compositions comprising the same and the uses thereof in phage therapy.

14 Claims, 5 Drawing Sheets

Specification includes a Sequence Listing.

(56) References Cited

OTHER PUBLICATIONS

Alemayehu, D. et al. "Bacteriophages ΦMR299-2 and ΦNH-4 Can Eliminate *Pseudomonas aeruginosa* in the Murine Lung and on Cystic Fibrosis Lung Airway Cells" *MBio*, Mar./Apr. 2012, pp. 1-9, vol. 3, No. 2.
Fu, W. et al. "Bacteriophage Cocktail for the Prevention of Biofilm Formation by *Pseudomonas aeruginosa* on Catheters in an In Vitro Model System" *Antimicrobial Agents and Chemotherapy*, Jan. 2010, pp. 397-404, vol. 54, No. 1.
Reardon, S. "Phage therapy gets revitalized" *Nature*, Jun. 5, 2014, pp. 15-16, vol. 510.
Wright, A. et al. "A controlled clinical trial of a therapeutic bacteriophage preparation in chronic otitis due to antibiotic-resistant *Pseudomonas aeruginosa*; a preliminary report of efficacy" *Clinical Otolaryngology*, 2009, pp. 349-357, vol. 34.
Database EMBL [Online] Accession No. JN254800, "Pseudomonas phage NH-4, complete genome" Jul. 14, 2011, pp. 1-41, XP-002718982.
Database EMBL [Online] Accession No. AM910650, "Pseudomonas phage LUZ24, complete genome" Nov. 16, 2007, pp. 1-26, XP-002718980.
Database EMBL [Online] Accession No. FM887021, "Pseudomonas phage SN, complete genome" Dec. 9, 2008, pp. 1-36, XP-002718979.
Database EBI [Online] Accession No. FM897211, "Pseudomonas phage 14-1, complete genome" Dec. 14, 2008, pp. 1-2, XP-002738707.
NCBI [online], "Pseudomonas phage JG024, complete genome" retrieved from the internet on Jan. 14, 2015, URL: http://www.ncbi.nlm.nih.gov/nuccore/GU815091, Dec. 16, 2010, pp. 1-64.
Database EBI [Online] Accession No. KF856712, "Pseudomonas phage philBB-PAA2, complete genome" Dec. 4, 2013, p. 1, XP-002738709.
Database EMBL [Online] Accession No. AB560486, "Pseudomonas phage KPP12 DNA, complete genome" Aug. 23, 2012, pp. 1-35, XP-002718984.
Database EBI [Online] Accession No. FM201281, "Pseudomonas phage LBL3 complete genome" Aug. 22, 2008, pp. 1-2, XP-002738708.
Database EMBL [Online] Accession No. FM201282, "Pseudomonas phage LMA2 complete genome" Jul. 22, 2008, pp. 1-37, XP-002718985.
Written Opinion in International Application No. PCT/EP2015/075949, dated Jan. 14, 2016, pp. 1-8.
Ceyssens, P.-J. et al. "Comparative analysis of the widespread and conserved PB1-like viruses infecting *Pseudomonas aeruginosa*" *Environmental Microbiology*, 2009, pp. 2874-2883, vol. 11, No. 11.
Fukuda, K. et al. "*Pseudomonas aeruginosa* Keratitis in Mice: Effects of Topical Bacteriophage KPP12 Administration" *PLOS One*, Oct. 2012, pp. 1-8, vol. 7, No. 10, Article No. e47742.
Garbe, J. et al. "Characterization of JG024, a pseudomonas aeruginosa PB1-like broad host range phage under simulated infection conditions" *BMC Microbiology*, Nov. 26, 2010, pp. 1-10, vol. 10, No. 1.
Krylov, V. et al. "A Genetic Approach to the Development of New Therapeutic Phages to Fight *Pseudomonas aeruginosa* in Wound Infections" *Viruses*, Dec. 21, 2012, pp. 15-53, vol. 5.
Mcvay, C.S. et al. "Phage Therapy of *Pseudomonas aeruginosa* Infection in a Mouse Burn Wound Model" *Antimicrobial Agents and Chemotherapy*, Jun. 2007, pp. 1934-1938, vol. 51, No. 6.
Oikonomou, O. et al. "Investigation of carbapenem heteroresistance among different sequence types of *Pseudomonas aeruginosa* clinical isolates reveals further diversity" *J. Med. Microbiology*, May 19, 2011, pp. 1556-1558, vol. 60, No. 10.
Database EMBL [Online] Accession No. FM887021, "Comparative analysis of the widespread and conserved PB1-like viruses infecting Pseudomonas aeruginosa" Dec. 16, 2008, pp. 1-36, XP-002718979.
Database EMBL [Online] Accession No. JN254801, "Bacteriophages PhiMR299-2 and PhiNH-4 Can Eliminate Pseudomonas aeruginosa in the Murine Lung and on Cystic Fibrosis Lung Airway Cells" Apr. 27, 2012, pp. 1-32, XP-055161973.
Database EMBL [Online] Accession No. EU716414, "Comparative analysis of the widespread and conserved PB1-like viruses infecting Pseudomonas aeruginosa" Jan. 6, 2009, pp. 1-39, XP-002718981.
Database EMBL [Online] Accession No. KC294142, "Pseudomonas aeruginosa phage PaP4" Jan. 16, 2013, pp. 1-29, XP-002718983.
Written Opinion in International Application No. PCT/EP2014/072905, dated Jan. 27, 2015, pp. 1-11.
Wang, I.-N., et al. "HOLINS: The Protein Clocks of Bacteriophage Infections" *Annu. Rev. Microbiol.* 2000, pp. 1-34, vol. 54.
Carter, C.D. et al. "Bacteriophage cocktail significantly reduces *Escherichia coli* O157:H7 contamination of lettuce and beef, but does not protect against recontamination" *Bacteriophage*, Jul. 2012, pp. 178-185, vol. 2, No. 3.
Pouillot, F. et al. "Genetically Engineered Virulent Phage Banks in the Detection and Control of Emergent Pathogenic Bacteria" *Biosecurity and Bioterrorism: Biodefense Strategy, Practice, and Science*, Jun. 1, 2010, pp. 155-169, vol. 8, No. 2.
Stone, R. "Bacteriophage Therapy: Stalin's Forgotten Cure" *Science*, Oct. 25, 2002, pp. 728-731, vol. 298, No. 5594.
Database EMBL [Online] Accession No. M38308, "Bacteriophage T7 RNA polymerase gene, complete cds" Nov. 7, 1990, p. 1, XP-002725532.
Database EMBL [Online] Accession No. AY303349, "Enterobacteria phage RB69, complete genome" Jul. 1, 2003, pp. 1-58, XP-002725574.
Database EMBL [Online] Accession No. AY370674, "Enterobacteria phage K1-5, complete genome" Feb. 3, 2004, pp. 1-12, XP-002725533.
Database EMBL [Online] Accession No. AM084414, "Enterobacteria phage K1F, complete genome" Dec. 5, 2005, pp. 1-13, XP-002725538.
Database EMBL [Online] Accession No. EF056009, "Enterobacteria phage N4, complete genome" Nov. 15, 2006, pp. 1-18, XP-002725539.
Database EMBL [Online] Accession No. EU330206, "Enterobacteria phage phiEco32, complete genome" Jan. 5, 2008, pp. 1-25, XP-002725530.
Database EMBL [Online] Accession No. DQ832317, "*Escherichia coli* bacteriophage rv5, complete sequence" Jun. 30, 2008, pp. 1-42, XP-002725541.
Database EMBL [Online] Accession No. EU734171, "Enterobacteria phage BA14, complete genome" Jul. 2, 2008, pp. 1-13, XP-002725534.
Database EMBL [Online] Accession No. EU734174, "Enterobacteria phage 13a, complete genome" Jul. 2, 2008, pp. 1-14, XP-002725540.
Database EMBL [Online] Accession No. AZU35935, "Bacteriophage F488/08 genomic DNA, SEQ ID 3" May 10, 2012, pp. 1-30, XP-002725537.
Database EMBL [Online] Accession No. JX128259, "*Escherichia* phage ECML-134, complete genome" Jul. 29, 2012, pp. 1-53, XP-002725536.
Database EMBL [Online] Accession No. JN986844, "Enterobacteria phage vB_EcoP_ACG-C91, complete genome" Nov. 1, 2012, pp. 1-13, XP-002725531.
Written Opinion in International Application No. PCT/EP2015/050355, dated May 6, 2015, pp. 1-12.
Baker et al. "Protein Structure Prediction and Structural Genomics" *Science*, Oct. 5, 2001, pp. 93-96, vol. 294, No. 5540.
Attwood, T. K. "The Babel of Bioinformatics" *Science*, 2000, pp. 471-473, vol. 290, No. 5491.
Cuevas, J. M. et al. "Point Mutation Rate of Bacteriophage ΦX174" *Genetics*, Oct. 2009, pp. 747-749, vol. 183.
Ofir, G. et al. "Contemporary Phage Biology: From Classic Models to New Insights" *Cell*, Mar. 8, 2018, pp. 1260-1270, vol. 172.
Database GenBank [Online] Accession No. JQ067092.2, "Pseudomonas phage PaMx42, complete genome" 2012, pp. 1-25.
Drulis-Kawa, Z. et al. "Learning from Bacteriophages—Advantages and Limitations of Phage and Phage-Encoded Protein Applications" *Current Protein and Peptide Science*, 2012, pp. 699-722, vol. 13.
Wang, W. "Study on Biological Characteristics and Coverage on Clinical Strains of Wide Tropism Pseudomonas Aeruginosa Phages" *J Clin Res*, Jul. 2014, pp. 1259-1262, vol. 31, No. 7.
Lavigne, R. et al. "Group I introns in *Staphylococcus bacteriophages*" *Future Virol.*, 2013, pp. 997-1005, vol. 8, No. 10.
Ceyssens, P.-J. et al. "The intron-containing genome of the lytic *Pseudomonas* phage LUZ24 resembles the temperature phage PaP3" *Virology*, 2008, pp. 233-238, vol. 377.

* cited by examiner

PHAGE THERAPY

CROSS-REFERENCE TO RELATED APPLICATIONS

This application is a continuation of U.S. application Ser. No. 15/524,271, filed May 4, 2017, now U.S. Pat. No. 10,898,530, which is the U.S. national stage application of International Patent Application No. PCT/EP2015/075949, filed Nov. 6, 2015.

The Sequence Listing for this application is labeled "Seq-List.txt" which was created on Apr. 26, 2017 and is 465 KB. The entire content of the sequence listing is incorporated herein by reference in its entirety.

The present invention relates to novel bacteriophage compositions, their manufacture and the uses thereof. The invention is particularly suited for the treatment of an infection in a mammal particularly in the respiratory system.

BACKGROUND OF THE INVENTION

Bacteriophages (or phages) are small viruses displaying the ability to infect and kill bacteria while they do not affect cells from other organisms. Initially described almost a century ago by William Twort, and independently discovered shortly thereafter by Félix d'Herelle, more than 6000 different bacteriophages have been discovered so far and described morphologically, including bacterial and archeal viruses. The vast majority of these viruses are tailed while a small proportion are polyhedral, filamentous or pleomorphic. They may be classified according to their morphology, their genetic content (DNA vs. RNA), their specific host, the place where they live (marine virus vs. other habitats), and their life cycle. As intra-cellular parasites of bacterial cells, phages display different life cycles within the bacterial host: lytic, lysogenic, pseudo-lysogenic, and chronic infection (Weinbauer, 2004; Drulis-Kawa, 2012). Lytic phages cause lysis of the host bacterial cell as a normal part of their life cycles. Lysogenic phages (also termed temperate phages) can either replicate by means of the lytic life cycle and cause lysis of the host bacterium, or they can incorporate their DNA into the host bacterial DNA and become noninfectious prophages. Whatever the type of cycle of a phage, the first step is the attachment to receptors of the bacterial cell wall before phage material may enter the bacteria. This specific process influences the spectrum of the possible phage-bacteria interactions.

Bacteriophages are commonly used as research tools to modify bacteria in laboratory experiments.

Because of their target host cell specificity, the use of phages as a therapy to treat acute and chronic infections has been considered, particularly in dermatology, ophthalmology, urology, stomatology, pediatrics, otolaryngology or surgery. This concept of therapeutic use of phages to treat bacterial infection was, however, highly controversial from the very beginning and not widely accepted by the public or medical community. Early studies were widely criticized for lack of appropriate controls and inconsistent results. The lack of reproducibility and many conflicting results obtained in the various published studies led the Council on Pharmacy and Chemistry of the American Medical Association to conclude that the evidence for the therapeutic value of lytic filtrates was for the most part contradictory, unconvincing, and recommended additional research to confirm its purported benefits.

Since the introduction of antibiotics in the 1940s, little attention was paid to this field of therapeutics, especially in the Western world. But the extensive use of antibiotics has led to the widespread emergence and spread of antibiotic-resistant bacteria around the world, causing increasingly serious problems. It has therefore become a major therapeutic challenge to overcome the limited therapeutic options remaining to treat major multi-drug resistant microbes.

Since its initial discovery in the late 19th century (Fordos 1859), the Gram-negative bacterium *Pseudomonas aeruginosa* has gained a notorious place in the list of infamous human pathogens (Williams and al, 1894, Freeman and al, 1916). The arrival of the antibiotic era largely palliated the previously fatal outcome of acute infections in healthy patients. Only a relative improvement has been achieved in the eradication of chronic infections, which develop mainly in individuals suffering from cystic fibrosis or severe burns or who are immunocompromised (Gang et al, 1999, Jones and al, 2010). Two intrinsically related factors in the fatal outcome of infection in these patients are the rapid prescription of inappropriate antibiotic treatments and the development or acquisition of multidrug-resistant strains. While the use of (an) appropriate antibiotic(s) has been reported as an essential factor in the eradication of *P. aeruginosa* infections (Kang and al, 2005, Micek and al, 2005), conversely, antibiotic abuse significantly contributes to increasing resistance by exerting a continuous selective pressure for the acquisition of such capabilities. Antibiotics alone do not account for the high prevalence of multidrug-resistant variants: *P. aeruginosa* has multiple, chromosomally encoded intrinsic mechanisms of resistance, including low permeability of the cell envelope and numerous multidrug efflux pumps. Another major factor accounting for the successful invasive behavior and persistence of this bacterium is its high adaptability, allowing rapid colonization of different environments.

Furthermore, pathogenic bacteria such as *P. aeruginosa* are able to form biofilms, which contribute to their increased resistance to antibiotics. Such biofilms may comprise more than one type of bacteria supported and surrounded by an excreted extracellular matrix, and assist bacteria to colonize various surfaces. Biofilms allow bacteria to attach to surfaces and to reach population densities which would otherwise be unsupportable, imparting increased resistance to not only antibiotics but many environmental stresses including toxins such as heavy metals, bleaches and other cleaning agents. It is known that bacteria within biofilms can be 100 to 1000 times more resistant to antibiotics than the same strain of bacteria growing in planktonic forms. Such an increased resistance means that bacteria that are apparently sensitive to antibiotics in a laboratory test may be resistant to therapy in a clinical setting. Even if some are cleared, biofilms may provide resistant reservoirs permitting rapid colonization once antibiotics are no longer present. It is therefore obvious that biofilms are major factors in many human diseases. Chemical treatments are unsuited to use against biofilms since this is precisely what they have evolved to counter. Physical abrasion does provide a mean to disrupt biofilms. Unfortunately, many surfaces where biofilms supports bacterial pathogenesis are poorly suited to rigorous abrasion, i.e. bones, joints, implanted medical devices, etc. For example, the surfaces of wounds or burns are extremely sensitive and delicate. Even where abrasion is both suitable and in routine use, clearing of biofilms is limited. Oral plaque on the surface of teeth is a biofilm and is partially cleared by regular brushing. However, bacteria are maintained on unbrushed surfaces (for example in the gaps between teeth) and can recolonize cleared surfaces both rapidly and effectively. From this, it is clear that existing approaches to clearing biofilms are of limited efficacy.

The capability for quick adaptation and their ability to form biofilms are the main reasons that identify *P. aeruginosa* as opportunistic pathogens. They have acquired the status of hospital pathogens, and may be isolated from clinical samples taken from the wounds, sputum, bladder, urethra, vagina, ears, eyes and respiratory tract. The emergence of resistance to the most powerful new antibiotics in such clinical *P. aeruginosa* strains, occurring even during treatment, makes the fight with *P. aeruginosa* hospital pathogens a great problem.

Therefore, there is a great need for new antibacterial agents or compositions that can be used to destroy *P. aeruginosa* strains, even when organized in bacterial biofilms, suitable for use in human or animal therapy, as well, as for decontaminating materials.

SUMMARY OF THE INVENTION

The inventors have isolated and characterized new bacteriophages presenting strong and specific lytic activity to *Pseudomonas aeruginosa* (*P. aeruginosa*) strains. These bacteriophages, especially is combinations, provide very potent antibacterial effect and can be used as active agents in pharmaceutical or veterinary preparations, particularly to treat *P. aeruginosa* bacterial infections.

An object of the invention is to provide antibacterial compositions comprising at least two bacteriophages having lytic activity against a *Pseudomonas aeruginosa* (*P. aeruginosa*) strain, said at least two bacteriophages being selected from the bacteriophages having a genome comprising a nucleotide sequence of anyone of SEQ ID NOs: 1 to 7 or a sequence having at least 90% identity thereto.

A further object of the invention relates to a bacteriophage having lytic activity to a *Pseudomonas aeruginosa* (*P. aeruginosa*) strain and having a genome comprising a nucleotide sequence selected from anyone of SEQ ID NOs: 2 to 7 or a sequence having at least 95% identity thereto.

The bacteriophages of the invention exhibit strong lytic activity to multi drug resistant strains of *P. aeruginosa*, in particular to antibiotic-resistant pathogenic strains such as cephalosporinase-, carbenicillinases-, carbapenemase- and/or extended-spectrum β-lactamases-resistant strains, and are therefore particularly suitable and advantageous to treat bacterial infections.

The invention further concerns an isolated nucleic acid molecule contained in a bacteriophage of the invention, preferably an isolated nucleic acid molecule comprising a nucleotide sequence selected from anyone of SEQ ID NOs: 2 to 7 or a sequence having at least 95% identity thereto, as well as an isolated polypeptide encoded by said nucleic acid.

Another object of the invention is a composition comprising a nucleic acid or polypeptide as defined above.

The compositions of the invention typically further comprise a pharmaceutically or veterinary acceptable excipient or carrier. They may be liquid, semi-liquid, solid or lyophilized.

Another object of the invention relates to a bacteriophage, nucleic acid, polypeptide or composition as defined above, for use in the treatment of an infection in a mammal, for modifying the microbial flora in a mammal, for decontaminating a material and/or for killing a *P. aeruginosa* bacterium or for compromising the integrity of a bacterial biofilm.

The invention also relates to a bacteriophage, nucleic acid, polypeptide or composition as defined above, for use to improve a subject condition by modifying the microbial flora in said subject. The microbial flora may be modified by correcting, adapting or restoring a proper balance of microorganisms in said flora.

The invention also relates to a method for treating an infection in a mammal, comprising the administration to said mammal of at least one bacteriophage, nucleic acid, polypeptide or composition as defined above.

The invention also relates to a method for treating a surface or material suspected of being contaminated with a *P. aeruginosa* bacterium, comprising applying to said surface or material at least one bacteriophage, nucleic acid, polypeptide or composition as defined above. The surface or material may be a surface of any device, vessel or laboratory material, cloth, etc.

A further object of the invention relates to a kit comprising a composition as defined above and a means for applying the same to a subject or surface.

The invention may be used in any mammal, preferably in human beings, or to treat any material, including laboratory materials or medical devices.

DETAILED DESCRIPTION OF THE INVENTION

Figure 1:
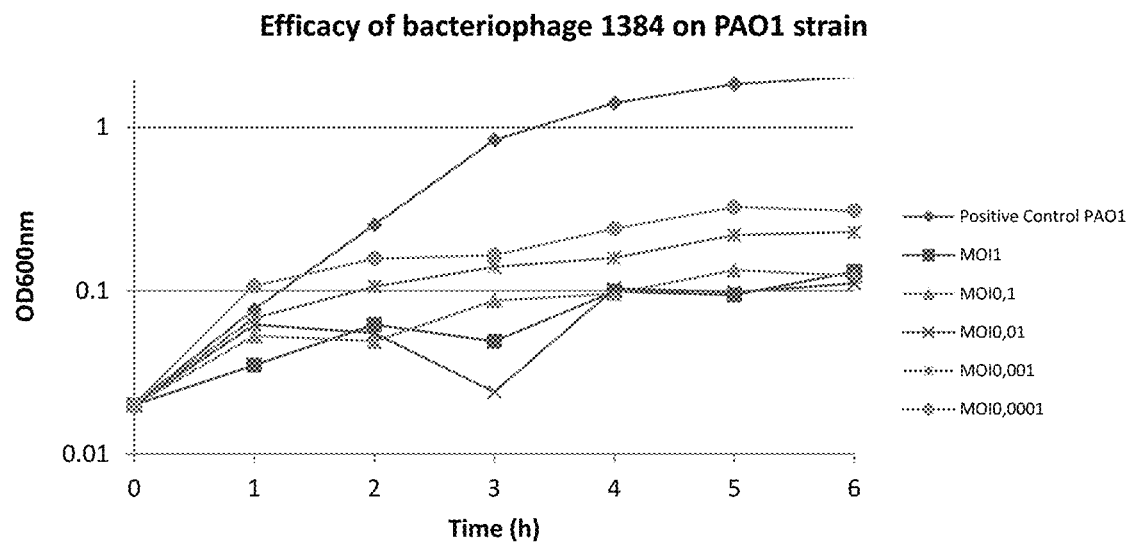
FIG. 1: Efficacy of bacteriophage 1384 on PAO1 strain.

The present invention relates to novel bacteriophages, components thereof, compositions comprising the same, their manufacture, and the uses thereof as antibacterial agents, particularly for the treatment of an infection in a mammal or for improving a subject condition by modifying the microbial flora in said subject.

Definitions

To facilitate understanding of the invention, a number of terms are defined below.

As used herein, the term "bacteriophage" or "phage" refers to a functional phage particle comprising a nucleic acid genome packaged in a proteinaceous envelope or capsid. The term also refers to portions of the bacteriophage, including, e.g., a head portion, or an assembly of phage components, which provide substantially the same functional activity.

The term "phenotypic characteristic" designates more preferably the morphology and/or host-range of a bacteriophage. Methods for phenotyping bacteriophages are well known per se in the part and include, for example, determining bacterial host range and/or activity against the biofilm produced by certain bacterial strains.

The term "lytic activity" as used in the invention designates the property of a bacteriophage to cause lysis of a bacterial cell. The lytic activity of a bacteriophage can be tested on *P. aeruginosa* strains according to techniques known per se in the art (see also experimental section).

The term "variant" of a reference bacteriophage designates a bacteriophage having variation(s) in the genomic sequence and/or polypeptide(s) encoded thereby as compared to said reference bacteriophage, while retaining the same phenotypic characteristic as the reference bacteriophage. Variants typically comprise e.g., silent mutations, conservative mutations, minor deletions, and/or minor replications of genetic material, and retain phenotypic characteristics of the reference bacteriophage. In a preferred embodiment, variants according to the invention retain any observable characteristic or property that is dependent upon the genome of the bacteriophage of the invention, i.e. phenotypic characteristics of said bacteriophage and/or lytic activity against the *P. aeruginosa* strains. Preferred variants have less than 5% nucleic acid variation as compared to the genome of the reference bacteriophage, even more preferably less than 4%, more preferably less than 2%. Alternatively, or in combination, variants have preferably less than 5% amino acid variation in a coded polypeptide sequence as compared to a polypeptide of the reference bacteriophage.

The terms "ESBL *P. aeruginosa* strain" refers to cephalosporinase and/or extended-spectrum β-lactamases producing *P. aeruginosa* strains, including various forms of antibiotic resistance such as AmpC β-lactamase or Class A carbenicillin hydrolyzing β-lactamases, etc.

The term "specific" or "specificity" in relation to a bacteriophage refers to the type of host that said bacteriophage is able to infect. A bacteriophage "specific" for *P. aeruginosa* more preferably designates a bacteriophage which can infect one or several *P. aeruginosa* strains and which cannot infect non-*P. aeruginosa* bacteria under physiological conditions.

As used herein, the term "polypeptide" refers to polypeptides of any size, including small peptides of e.g., from 5 to 20 amino acids, longer polypeptides, proteins or fragments thereof.

The term "PLE" or "Productive Lytic Effect" designates the ratio between burst size and productive lytic time of a given bacteriophage. Burst size and productive lytic time are parameters defining phage-host interaction and correspond, respectively, to the mean yield of bacteriophage particles produced by infection of one bacterium by one phage, and to the time taken by a free bacteriophage to lyse a bacterial cell.

In the context of the present specification, the term "isolated bacteriophage" should be considered to mean a bacteriophage removed from its natural environment and/or separated from a component of its natural environment. The term designates, particularly, a phage that is e.g., cultivated in vitro, purified, and/or formulated with any suitable diluent or excipient. In relation to a nucleic acid or polypeptide, the term "isolated" designates e.g., a nucleic acid molecule or polypeptide which is separated from at least one component of its natural environment such as, e.g., a protein, lipid, and/or nucleic acid.

The terms "pharmaceutically or veterinary acceptable" as used herein refers to any material (e.g., carrier, excipient or diluent) that is compatible for use in a mammalian subject. Such includes physiologically acceptable solutions or vehicles that are harmless or do not cause any significant specific or non-specific immune reaction to an organism or do not abrogate the biological activity of the active compound. For formulation of the composition into a liquid preparation, saline, sterile water, Ringer's solution, buffered physiological saline, albumin infusion solution, dextrose solution, maltodextrin solution, glycerol, ethanol, and mixtures thereof may be used as a pharmaceutically or veterinary acceptable excipient or carrier. If necessary, other conventional additives such as thickeners, diluents, buffers, preservatives, surface active agents, antioxidants and bacteriostatic agents may be added. Further, diluents, dispersants, surfactants, binders and lubricants may be additionally added to the composition to prepare injectable formulations such as aqueous solutions, suspensions, and emulsions, oral formulations such as pills, capsules, granules, or tablets, or powdered formulations.

As used herein, "PFU" means plaque forming unit, as it is well defined in the art. Lytic bacteriophages lyse the host cell, causing a zone of clearing (or plaque) on a culture plate. Theoretically, each plaque is formed by one phage and the number of plaques multiplied by the dilution factor is equal to the total number of phages in a test preparation.

The term "treatment" or "therapy" designates a curative or a prophylactic treatment of a disease. A curative treatment is defined as a treatment that results in a cure of a disease, or a treatment that alleviates, reduces, stabilizes, or eliminates the symptoms of a disease or the suffering that it causes, directly or indirectly, or that improves a subject condition or reduces progression of a disease. A prophylactic treatment comprises a treatment resulting in the prevention of a disease, and/or a treatment reducing and/or delaying the incidence of a disease or the risk of its occurrence.

The term "biofilm" as used herein designates a heterogeneous bacterial formation growing on various surfaces; preferably a bacterial community growing embedded in an exopolysaccharide matrix adhered onto solid biological or non-biological surfaces.

The term "compromise" as used herein refers to any alteration of the integrity. By compromising a bacterial biofilm, it is understood a penetration of the biofilm by bacteriophage, an infection of biofilm-associated bacteria and/or a lysis thereof and/or a partial or an entire clearing of the biofilm (i.e., by stopping colonization and/or disrupting biofilms).

The term "sample", as used herein, means any sample containing cells. Examples of such samples include body fluids such as blood, plasma, saliva, or urine, as well as biopsies, organs, tissues or cell samples. The sample may be treated prior to its use.

As used herein, the term "subject" or "patient" refers to an animal, preferably a mammal, even more preferably a human, including adult and child. The term "subject" also encompasses non-human animals, in particular non-human mammals such as pets (e.g., dogs, cats), horses, cows, goats, pigs, sheep and non-human primates, among others.

The term "efficacy" of treatment or "response" to a bacteriophage therapy as used herein refers to a treatment which results in a decrease in the number of *P. aeruginosa* strains in a subject after bacteriophage treatment when compared to the number of *P. aeruginosa* strains before treatment. A "good responder" subject refers to a subject who shows or will show a clinically significant recovery when treated with a bacteriophage therapy.

The term "Cocktail" of bacteriophages designates a combination of different types of bacteriophages. The bacteriophages in a cocktail are preferably formulates together in a same vessel or packaging, although they may be used as kits of parts wherein some of the bacteriophages are formulated or packaged separately and combined when used or administered.

Description of Embodiments

The present invention is related to novel bacteriophage therapies. More particularly, the present invention relates to novel bacteriophages having a high specificity against *Pseudomonas aeruginosa* strains, their manufacture, components thereof, compositions comprising the same and the uses thereof in phage therapy.

Bacteriophages:

In a first aspect, the invention discloses the isolation and characterization of novel bacteriophages that are specific for *P. aeruginosa* strains and present, either alone or in combination(s), remarkable host range spectrum of lytic activity. These bacteriophages have been selected from environmental samples, isolated, sequenced, and characterized. They are, individually and in combination(s), active against *P. aeruginosa* strains. They are remarkably effective against pathogenic *P. aeruginosa* strains, including antibiotic-resistant *P. aeruginosa* strains such as an ESBL *P. aeruginosa* strain. Furthermore, bacteriophages of the invention have a remarkable productive lytic effect ("PLE") comprised between 1 and 7. In addition, the bacteriophages of the invention are specific for *P. aeruginosa* strains, i.e., they do not cause lysis of non-*P. aeruginosa* bacteria. As will be illustrated further, the invention shows that these bacteriophages can be combined and formulated in conditions suitable for use as pharmaceutical or veterinary agents to exhibit targeted and very potent antibacterial effect against a controlled spectrum of *P. aeruginosa* strains.

More specifically, the following bacteriophages have been isolated. Their corresponding nucleic acid sequence is also indicated.

TABLE 1

| SEQ ID | Bacteriophage |
| --- | --- |
| SEQ ID NO: 1 | BP1384 |
| SEQ ID NO: 2 | BP1777 |
| SEQ ID NO: 3 | BP1792 |
| SEQ ID NO: 4 | BP1797 |
| SEQ ID NO: 5 | BP1800 |
| SEQ ID NO: 6 | BP1902 |
| SEQ ID NO: 7 | BP1940 |

The lytic profile of these bacteriophages has been determined on a broad number of *P. aeruginosa* strains. These bacteriophages have been selected for their potency and combination potential, as disclosed in the following table. In this table, the lytic effect of the bacteriophages on reference and pathogen-resistant strains are presented, confirming their high lytic potential.

TABLE 2

| | Phage | | | | | | |
| --- | --- | --- | --- | --- | --- | --- | --- |
| Strain | 1384 | 1777 | 1792 | 1797 | 1800 | 1902 | 1940 |
| LMG 24882 | + | + | pm | + | + | + | − |
| LMG 24886 | + | + | − | − | − | + | + |
| LMG 24887 | + | pm | + | + | + | pm | + |
| LMG 24891 | + | + | + | + | + | + | − |
| LMG 24892 | + | + | + | + | + | pm | + |
| LMG 24893 | + | pm | + | + | + | + | + |
| LMG 24896 | + | + | + | + | + | + | pm |
| LMG 24901 | pm | − | + | + | + | − | pm |
| LMG 24903 | − | pm | + | + | + | − | + |
| LMG 24904 | pm | − | + | + | + | + | − |
| LMG 24905 | − | − | pm | + | + | pm | − |
| LMG 24907 | − | − | + | + | + | − | − |
| LMG 24909 | + | + | + | + | + | + | pm |

TABLE 2-continued

| | Phage | | | | | | |
| --- | --- | --- | --- | --- | --- | --- | --- |
| Strain | 1384 | 1777 | 1792 | 1797 | 1800 | 1902 | 1940 |
| LMG 24913 | − | − | + | + | − | + | pm |
| LMG 24914 | − | − | + | + | + | − | + |
| LMG 24916 | − | − | + | + | + | − | + | pm: partial lysis

As can be seen from table 2, combinations (or cocktails) of these bacteriophages may be produced that are able to kill all of the tested *P. aeruginosa* strains, thereby producing broad spectrum antibacterial compositions. As an illustrative example, a cocktail of all of the 7 bacteriophages can kill all tested bacteria.

Moreover, the specificity of the bacteriophages has been tested on many non-*P. aeruginosa* strains. More particularly, the experimental section demonstrates that the bacteriophages of the invention have no lytic effect on any bacteria selected from *Escherichia coli, Acinetobacter baumanii, Enterobacter aerogenes, Enterobacter asburiae, Enterobacter cloacae, Klebsiella pneumoniae, Proteus mirabilis, Staphylococcus aureus, Stenotrophomonas maltophila* and *Serratia marcescens*. These bacteriophages, alone or in combination(s), thus represent potent agents for treating *P. aeruginosa* infections.

A particular object of the invention thus resides in a bacteriophage having lytic activity to a *P. aeruginosa* strain and having a genome comprising a nucleotide sequence selected from anyone of SEQ ID NOs: 2 to 7 or a sequence having at least 95% identity thereto, preferably at least 96%, 97%, 98% or 99% identity thereto.

The bacteriophages of the invention may be cultured, expanded, isolated, purified, and used in e.g., phage therapy of *P. aeruginosa*-mediated disorders, as will be disclosed in more details below. Furthermore, variants of these bacteriophages retaining a phenotypic (e.g., specificity and lytic activity) of the bacteriophages can be produced and/or isolated by techniques known per se in the art.

The bacteriophages of the invention can be prepared by standard culture, isolation and purification methods. For example, *P. aeruginosa* producing bacteria are cultured, infected by a sample of a bacteriophage, and then treated to remove bacterial cells and debris. The enriched bacteriophage solution can be plated in a medium, for example agar medium, with embedded susceptible host strains of *P. aeruginosa* to obtain plaques. Then, single plaque can be picked out for subsequent bacteriophage purification and amplification. One or more cycles of selective amplification of bacteriophages of the invention may be performed, for example by mixing bacteriophages with the competent *P. aeruginosa*, followed by addition of a growth medium and incubation at selected test growing conditions. Following centrifugation, the cleared amplified supernatant is filtered through filter and subjected to another cycle of selective amplification or tested for presence of lytic activity.

The titer of phage in a suspension and the visualization of plaque morphology of bacteriophages of the invention may then be assessed by known methods, for example by plaque counting. Additionally, processing bacteriophages of the invention in various forms (liquid, lyophilized, etc.) for short-, long-, freeze- or any other kind of storage can be carried out by any suitable method as it is well-known in the art (see e.g., Clark, 1962).

The activity of the bacteriophages of the invention can be assessed by methods well-known in the art, such as plaque assay also known as double agar method, based on the growing of bacteriophage with potential host bacteria and followed by assessing their ability to kill the host bacterial cell. In the plaque assay method, the bacteriophage induces lysis of target *P. aeruginosa* strains after a period of incubation in soft agar medium, resulting in zones of clearing on the plate known as plaques.

Nucleic Acids and Polypeptides

The invention relates to a nucleic acid contained in a bacteriophage of the invention, or any fragment of such a nucleic acid. The term fragment designates, more preferably, a fragment containing (or consisting of) an open reading frame. The nucleic acid may be DNA or RNA, single- or double-stranded.

The nucleic acid can be isolated from the deposited bacteriophages, or produced using recombinant DNA technology (e.g., polymerase chain reaction (PCR) amplification, cloning), enzymatic or chemical synthesis, or combinations thereof, according to general techniques known per se in the art. Also included are homologous sequences and fragments thereof including, but not limited to, natural allelic variants and modified nucleic acid sequences in which nucleotides have been inserted, deleted, substituted, and/or inverted.

In a particular embodiment, the invention relates to a nucleic acid comprising a sequence selected from anyone of SEQ ID NOs: 2-7, or a sequence having at least 95%, 96%, 97%, 98%, 99% or more sequence identity to anyone of SEQ ID NOs: 2-7.

The nucleic acid of the invention can be in free form, or cloned in a vector, such as a plasmid, viral vector, expression cassette, cosmid, etc.

In a further aspect, the invention also relates to an isolated polypeptide encoded by a nucleic acid sequence as defined above, preferably a nucleic acid sequence selected from SEQ ID NO: 2, SEQ ID NO: 3, SEQ ID NO: 4, SEQ ID NO: 5, SEQ ID NO: 6, or SEQ ID NO: 7. The polypeptide(s) may be produced by techniques known per se in the art such as synthesis, recombinant technology, or combinations thereof. The polypeptides may be isolated or purified, and used as antibacterial agents or as reagents for in vitro analyses.

Compositions of the Invention

One aspect of the invention relates to compositions comprising at least one bacteriophage as described above, more preferably at least 2 or more and, optionally, a pharmaceutically or veterinary acceptable excipient. As described, the bacteriophages of the invention have very potent lytic activity against *P. aeruginosa* strains. Combinations of these bacteriophages may be produced to expand the host spectrum and produce highly effective antibacterial compositions.

More particularly, the invention relates to an antibacterial composition comprising at least two bacteriophages having lytic activity against a *Pseudomonas aeruginosa* (*P. aeruginosa*) strain, said at least two bacteriophages being selected from the bacteriophages having a genome comprising a nucleotide sequence of anyone of SEQ ID NOs: 1 to 7 or a sequence having at least 90% identity thereto.

In a preferred embodiment, the compositions of the invention comprise at least three, even more preferably at least four distinct bacteriophages selected from the bacteriophages having a genome comprising a nucleotide sequence of anyone of SEQ ID NOs: 1 to 7 or a sequence having at least 90% identity thereto.

Particular compositions of the invention comprise at least a bacteriophage having a genome comprising a nucleotide sequence of SEQ ID NO: 3 or 4, or a sequence having at least 90% identity thereto.

Specific examples of compositions of the invention comprise:
a bacteriophage having a genome comprising a nucleotide sequence of SEQ ID NO: 1 or a sequence having at least 90% identity thereto, and a bacteriophage having a genome comprising a nucleotide sequence of SEQ ID NO: 3 or a sequence having at least 90% identity thereto;
a bacteriophage having a genome comprising a nucleotide sequence of SEQ ID NO: 1 or a sequence having at least 90% identity thereto, and a bacteriophage having a genome comprising a nucleotide sequence of SEQ ID NO: 4 or a sequence having at least 90% identity thereto;
a bacteriophage having a genome comprising a nucleotide sequence of SEQ ID NO: 1 or a sequence having at least 90% identity thereto, and a bacteriophage having a genome comprising a nucleotide sequence of SEQ ID NO: 5 or a sequence having at least 90% identity thereto;
a bacteriophage having a genome comprising a nucleotide sequence of SEQ ID NO: 3 or a sequence having at least 90% identity thereto, and a bacteriophage having a genome comprising a nucleotide sequence of SEQ ID NO: 4 or a sequence having at least 90% identity thereto;
a bacteriophage having a genome comprising a nucleotide sequence of SEQ ID NO: 3 or a sequence having at least 90% identity thereto, and a bacteriophage having a genome comprising a nucleotide sequence of SEQ ID NO: 5 or a sequence having at least 90% identity thereto;
a bacteriophage having a genome comprising a nucleotide sequence of SEQ ID NO: 1 or a sequence having at least 90% identity thereto, and a bacteriophage having a genome comprising a nucleotide sequence of SEQ ID NO: 3 or a sequence having at least 90% identity thereto, and a bacteriophage having a genome comprising a nucleotide sequence of SEQ ID NO: 4 or a sequence having at least 90% identity thereto;
a bacteriophage having a genome comprising a nucleotide sequence of SEQ ID NO: 1 or a sequence having at least 90% identity thereto, and a bacteriophage having a genome comprising a nucleotide sequence of SEQ ID NO: 3 or a sequence having at least 90% identity thereto, and a bacteriophage having a genome comprising a nucleotide sequence of SEQ ID NO: 4 or a sequence having at least 90% identity thereto, and a bacteriophage having a genome comprising a nucleotide sequence of SEQ ID NO: 5 or a sequence having at least 90% identity thereto.

In a preferred embodiment, the compositions of the invention comprise at least:
a bacteriophage having a genome comprising a nucleotide sequence of SEQ ID NO: 1 or a sequence having at least 90% identity thereto;
a bacteriophage having a genome comprising a nucleotide sequence of SEQ ID NO: 2 or a sequence having at least 90% identity thereto;
a bacteriophage having a genome comprising a nucleotide sequence of SEQ ID NO: 3 or a sequence having at least 90% identity thereto;

a bacteriophage having a genome comprising a nucleotide sequence of SEQ ID NO: 4 or a sequence having at least 90% identity thereto;

a bacteriophage having a genome comprising a nucleotide sequence of SEQ ID NO: 5 or a sequence having at least 90% identity thereto;

a bacteriophage having a genome comprising a nucleotide sequence of SEQ ID NO: 6 or a sequence having at least 90% identity thereto; and a bacteriophage having a genome comprising a nucleotide sequence of SEQ ID NO: 7 or a sequence having at least 90% identity thereto.

The compositions of the invention may further comprise additional antibacterial agents, particularly other bacteriophages having distinct host specificity.

Most preferred compositions of the invention are lytic against more that 85% of all bacterial strains of the LMG collection obtained from the BCCM/LMG Bacteria Collection. This collection contains a vast number of strains with a high genetic diversity among the bacterial species.

The compositions of the invention may comprise any effective amount of the selected bacteriophage(s). Preferably, they comprise between $10^{e4}$ and $10^{e12}$ PFU of each of said bacteriophages, preferably between $10^{e5}$ and $10^{e10}$. PFU. The relative amounts of each type of bacteriophage in a composition of the invention may be adjusted by a skilled artisan. Typically, When the antibacterial composition comprises several (n) distinct bacteriophages as defined above, the total relative amount % A of each bacteriophage in the composition is more preferably % $A=(100/n_i) \times V$, wherein $n_i$ represents the number of distinct types of bacteriophages and V is a variability factor comprised between 0.2 and 5. Most preferably, V is comprised between 0.3 and 3, even more preferably between 0.5 and 2, generally between 0.8 and 1.5. In a preferred typical embodiment, each type of bacteriophage is present in a composition of the invention in approximately equal relative amounts.

The antibacterial compositions of the invention may be in various forms, such as liquid, semi-liquid, solid or lyophilized formulations. The compositions of the invention preferably comprise a suitable diluent or carrier, such as a pharmaceutically or veterinary acceptable excipient or carrier. Compositions according to the present invention may include any excipient or carrier, such as thickeners, diluents, buffers, preservatives, surface active agents and the like, in addition to the bacteriophage(s) of choice. Such includes physiologically acceptable solutions or vehicles that are harmless or do not cause any significant specific or non-specific immune reaction to an organism or do not abrogate the biological activity of the bacteriophage. For liquid formulation, saline, sterile water, Ringer's solution, buffered physiological saline, albumin infusion solution, dextrose solution, maltodextrin solution, glycerol, ethanol, and mixtures thereof may be used as a pharmaceutically or veterinary acceptable excipient or carrier. If appropriate, other conventional additives such as thickeners, diluents, buffers, preservatives, surface active agents, antioxidants and bacteriostatic agents may be added. Further, diluents, dispersants, surfactants, binders and lubricants may be additionally added to the composition to prepare injectable formulations such as aqueous solutions, suspensions, and emulsions, oral formulations such as pills, capsules, granules, or tablets, or powdered formulations. Formulations for topical administration may include, band aids, dressings, patches, films, ointments, lotions, creams, gels, drops, suppositories, sprays, tampons, sanitary towels, liquids and powders. Formulations for decontamination or for medical use may also include aerosols or sprays.

The compositions of the invention may be used in the medical field, including the human or veterinary medical areas, for e.g. the treatment of an infection in a mammal or for improving a subject's condition. The compositions may be used to kill *P. aeruginosa* bacteria in an organism, for treating an infection. The composition may also be used for improving the condition of a mammal by modifying the microbial flora in said mammal. In particular, the compositions of the invention can specifically remove *P. aeruginosa* strains on the skin or mucous membranes of a mammal, thus modifying its microbial flora and restoring a proper balance.

In a particular embodiment, the invention also relates to a method for treating an infection in a mammal comprising the administration to said mammal of a composition or bacteriophage or nucleic acid or polypeptide as defined above.

The invention also relates to the use of a composition, bacteriophage, nucleic acid or polypeptide as described for the manufacture of a medicament for treating an infection in a mammal, or for restoring microbial flora in said mammal.

The compositions of the invention may be used to treat various *P. aeruginosa*-mediated infections, particularly of the respiratory system. The number of patients with pneumonia reached 2 to 3 million in USA and 3 to 4 million in Europe, in 2013. *Pseudomonas aeruginosa* is one of the major microbiological agents responsible for the pathology, especially in the young children and elderly populations, as well as, in immunocompromised, cystic fibrosis, high burn and poly-traumatized patients. Although epidemiological sources fluctuate and albeit a recent increase of gram-negative infections (including *P. aeruginosa*), estimations for 2014 indicate that at least 15% of pneumonia are caused by *P. aeruginosa* (e.g., 15.9% according to the *ECDC Annual Surveillance Report*—2013). From a conservative stand point, about 20% of these germs are resistant to several or all the antibiotics from our therapeutic arsenal (remarkably, the highest number or resistant cases is being observed in intensive care unit: See Worldwide Website: infectio-lille.com/diaporamas/DUAC/pyo-DUAC09-Cattoen.pdf).

As a consequence, estimated figures indicate that at least 90 000 pneumonia cases in USA and 120 000 in Europe are induced by antibiotic multi-resistant *P. aeruginosa* bacterial strains. The invention is thus particularly suited for treating pneumonia associated with, or caused by, *P. aeruginosa* infection. An object of the invention thus resides in a method of treating pneumonia in a subject in need thereof, comprising administering a composition of the invention to said subject. The method is particularly suited for treating pneumonia induced by antibiotic-resistant *P. aeruginosa* bacteria. The subject may be any human subject, such as children, adults or elderly people.

The compositions of the invention may be administered by any convenient route, including intravenous, oral, transdermal, subcutaneous, mucosal, intramuscular, intrapulmonary, intranasal, parenteral, rectal, vaginal and topical. In a preferred embodiment, the bacteriophages or compositions are administered by intrapulmonary or intranasal instillation. The compositions may be administered directly or indirectly, e.g., via a support. In this regard, the compositions may, for example, be applied or sprayed to the afflicted area. Compositions of the invention can also be administered by oral or parenteral routes. The dosage suitable for applying, spraying, or administering the compositions of the present invention can be adjusted by the skilled person depending on a variety of factors including formulation, mode of administration, age, weight, sex, condition, diet of the mammal being treated at the time of administration, route of administration, and reaction sensitivity. A physician having ordinary skills in the art can readily determine and prescribe the effective amount of the composition required.

The dosing can also be adjusted by the skilled person so that a lytic activity against antibiotic-resistant P. aeruginosa strains is obtained. An efficient dose to obtain a lytic activity in vivo typically includes a concentration of at least $10^{e4}$ PFU/ml, preferably from about $10^{e2}$ to $10^{e12}$ PFU/ml, depending on the administration route.

As shown in the experimental section, the bacteriophages and compositions of the invention are able to selectively kill P. aeruginosa bacteria in vitro or in vivo. The compositions can destroy mixtures of different P. aeruginosa bacteria, even in vivo, even at low dosage. Furthermore, the compositions of the invention are effective is killing bacteria embedded in biofilms, which is particularly important for pathogenic bacteria. Also, the compositions and bacteriophages of the invention are strictly unable to affect mammalian cells, and are therefore specific and devoid of side effects in vivo.

The invention also relates to the use of a composition, bacteriophage, nucleic acid or polypeptide of the invention for decontaminating a material. Due to their potent antibacterial effect, and to their ability to even compromise the integrity of a bacterial biofilm, the compositions of the invention can be used as decontaminating agent, to eliminate or at least cause a reduction in bacterial numbers on a material. Such methods may be applied for the treatment of a variety of biological or non-biological surfaces in both medical and non-medical contexts, including solid materials or devices such as, for example, contact lenses, surfaces of devices to be implanted into the body, pipes, ducts, laboratory vessels, textiles, etc.

Diagnostic/Predictive Tests of the Invention:

The invention also concerns a method for predicting or determining the efficacy of a bacteriophage therapy in a subject, wherein the method comprises a step of determining a lytic activity of one or more bacteriophages of the invention to a P. aeruginosa strain from a sample from said subject, such a lytic activity being indicative of an efficient treatment. In a preferred aspect, the method further optionally comprises a step of treating said subject by one or more bacteriophages having a lytic activity to a P. aeruginosa strain from a sample of said subject.

In another aspect, the invention provides a method for selecting a subject or determining whether a subject is susceptible to benefit from a bacteriophage therapy, wherein the method comprises the step of determining a lytic activity of one or more bacteriophages of the invention to a P. aeruginosa strain from a sample of said subject, a lytic activity of one or more bacteriophages of the invention to at least one P. aeruginosa strain indicating a responder subject.

Another object of the invention relates to a method for predicting the response of a subject to a bacteriophage therapy, wherein the method comprises the step of determining a lytic activity of one or more bacteriophage of the invention to a P. aeruginosa strain from a sample of said subject, a lytic activity of one or more bacteriophage of the invention to at least one P. aeruginosa strain being indicative of a good response to said therapy.

Further aspects and advantages of the invention will be disclosed in the following experimental section, which is illustrative only.

EXAMPLES

Materials and Methods
Host Range Determination.

The host ranges of bacteriophages were determined among a collection of 20 P. aeruginosa from the LMG collection. $10^9$ bacterial cells were mixed with melted agar and this mixture was poured on solid agar to make double layer agar plates. After solidification, isolated bacteriophage stock solutions were spotted on each plate with different bacterium strain. After allowing 20 min for the spots to be absorbed, the plates were inverted and incubated for 24 h at 37° C. before the degree of lysis was recorded (Postic, 1961; Yang, 2010).

Sequencing, Analysis and Annotation of Phage Genomes.

To isolate phage DNA, phages were propagated as described above. Phage DNA was isolated by extraction with phenol:chloroform:isoamyl alcohol (25:24:1, V/V), ethanol precipitation and resolution in water. Whole genome sequencing was done and the BLAST algorithm was used to determine the similarity to described genes in the National Center for Biotechnology Information [NCBI] database. The genomes were scanned for potential open reading frames (ORFs).

Example 1: Bacteriophage Isolation

Bacteriophages were isolated from environmental samples. Multi Drug Resistant (MDR) P. aeruginosa bacteria were used for isolating and enriching each virulent bacteriophage from environmental water. More particularly, environmental samples and overnight culture of bacteria in Luria Bertani (LB) were mixed and incubated at 37° C. for 24 h with shaking to enrich specific bacteriophages. At the end of incubation, drops of chloroform were added to the culture. The culture was spun down at 11,000 g for 5 minutes to remove bacterial cells and debris. The supernatant was subjected to 0.2 μm filter to remove the residual bacterial cells. The enriched phage solution was plated on LB agar medium with P. aeruginosa embedded. Plaques formed on the plates after 24 h incubation at 37° C. Single plaque was picked out for subsequent phage purification and amplification. The phage was then stored at 4° C. in a suspension in LB broth or physiological saline.

The titer of phage in a suspension was estimated by plaque counting (Postic, 1961). Ten-fold dilutions of a suspension were delivered on a dried lawn of the propagating strain. The plates were read after overnight incubation. The plaque-counting method also permitted visualization of plaque morphology.

7 highly active bacteriophages were selected. Their sequences were determined and are provided in the present application, in accordance with the following table:

TABLE 1

| SEQ ID | Bacteriophage |
| --- | --- |
| SEQ ID NO: 1 | BP1384 |
| SEQ ID NO: 2 | BP1777 |
| SEQ ID NO: 3 | BP1792 |
| SEQ ID NO: 4 | BP1797 |
| SEQ ID NO: 5 | BP1800 |
| SEQ ID NO: 6 | BP1902 |
| SEQ ID NO: 7 | BP1940 |

The activity of the bacteriophages, alone or in combination, was further tested in different models and conditions as described in the following examples.

Example 2: Bacteriophage Host Characteristics and Kinetics

One-step growth experiments were carried out according to the previous descriptions to determine first the productive lytic time, adsorption rate, and then the phage burst size. To determine the adsorption rate samples were taken at different time intervals to analyze the free phage particles in the solutions. For productive time and phage burst size determination, *P. aeruginosa* bacteria were mixed with phages solutions and phages were allowed to adsorb for 15 min. The mixture was subjected to centrifugation immediately at 5000 rpm for 10 min to remove free phage particles. The pellet was resuspended in 5 fresh LB medium and the culture was continuously incubated at 37° C. Samples were taken at 5 min intervals and phage titer was determined. These results permitted to calculate the number of phages produced per bacteria (burst size), the productive time and the productive lytic effect (PLE), as shown in table 3 below.

TABLE 3

| Phage | Productive lytic time (min) | Adsorption rate (ml − 1 min − 1) | BURST SIZE (PFU per bacterium) | PLE (PFU per bacterium per min) |
|---|---|---|---|---|
| 1384 | 80 | 8.64E−09 | 499 | 6.24 |
| 1777 | 13 | 9.27E−08 | 55 | 4.4 |
| 1792 | 16 | 1.46E−08 | 52 | 3.3 |
| 1797 | 28 | 1.81E−08 | 31 | 1.1 |
| 1800 | 13 | 1.61E−08 | 46 | 3.5 |
| 1902 | 18 | 2.75E−08 | 54 | 2.9 |
| 1940 | 10 | 6.08E−08 | 43 | 4.3 |

These results show that all phages have potent viral production capacity and absorption rates. Most phages have a PLE below 7, which demonstrates a remarkable profile. Phage 1777 is particularly effective in this regard. In addition, the different PLE and adsorption times permit to create cocktails with selected variability.

Example 3: Composition of Bacteriophages

The following cocktail compositions are constituted, each comprising between $10^9$ and $10^{11}$ pfu of each bacteriophage:

TABLE 4

| Cocktail | Phages |
|---|---|
| I | P1797 + P1902 |
| II | P1797 + P1800 + P1384 |
| III | P1777 + P1797 + P1940 + P1384 |
| IV | P1777 + P1792 + P1797 + P1800 + P1384 |
| V | P1777 + P1792 + P1797 + P1800 + P1902 + P1384 |
| VI | P1777 + P1792 + P1797 + P1800 + P1902 + P1940 + P1384 |
| VII | P1792 + P1384 |
| VIII | P1797 + P1384 |

Example 4: Antibacterial Activity

Various strains of bacteria are incubated with a bacteriophage cocktail of the invention at $2.10^9$ bacteriophages/ml for 24 h at 37° C. Cocktails are tested on the 16 distinct *P. aeruginosa* bacteria listed in table 2. The % of bacteria species sensitive to the cocktails are listed in table 5 below:

TABLE 5

| Cocktail | % Killed *P. aeruginosa* species |
|---|---|
| I | 100% |
| II | 100% |
| III | 100% |
| IV | 100% |
| V | 100% |
| VI | 100% |
| VII | 100% |
| VIII | 100% |

Bacteria were enumerated and used to the calculation of resistance rate (number of bacteria after incubation/number of bacteria plated) with cocktail VI. Resistance rates were obtained, as shown in the following table 6:

TABLE 6

| Bacteria | Rate (bacteria/ml) |
|---|---|
| LMG 24891 | 4.90E−06 |
| LMG 24945 | 2.40E−07 |
| LMG 24970 | 2.00E−08 |
| LMG 25082 | 1.30E−07 |
| LMG 25131 | <1.00E−08 |
| LMG 25194 | 7.75E−06 |

All tested bacteria are sensitive to compositions of the invention.

Example 5: Cocktail Specificity

The cocktail specificity was confirmed by testing on ten different gram-negative and gram-positive bacteria species, including *Escherichia coli* (several strains), *Acinetobacter baumanii*, *Enterobacter aerogenes* C, *Enterobacter asburiae*, *Enterobacter cloacae*, *Klebsiella pneumoniae*, *Proteus mirabilis*, *Staphylococcus aureus*, *Stenotrophomonas maltophila*, *Serratia marcescens*.

Table 7 shows the lack of lytic activity of the cocktail containing the 7 bacteriophages.

TABLE 7

| Bacterium Species/stains | Cocktail |
|---|---|
| *Acinetobacter baumanii* | — |
| *Escherichia coli* K12 | — |
| *Escherichia coli* S176 | — |
| *Escherichia coli* ECOR5 | — |
| *Escherichia coli* ECOR54 | — |
| *Escherichia coli* ECOR60 | — |
| *Escherichia coli* SH146 | — |
| *Enterobacter aerogens* | — |
| Enterobacter amnigeus | — |
| *Enterobacter asburiae* | — |
| *Enterobacter cloacae* | — |
| *Klebsiella pneumoniae* | — |
| *Proteus mirabilis* | — |
| *Serratia marcescens* | — |
| *Strenophomonas maltophila* | — |
| *Staphylococcus aureus* | — |

The above table clearly shows that no lytic activity on bacteria other than *P. aeruginosa* strains occurred. The bacteriophages and cocktail of the invention are therefore highly specific to *P. aeruginosa* strains.

Example 6: Efficiency of Each Bacteriophage on *P. aeruginosa* PAO1 Strain

PAO1 strain was selected because it is a commonly used laboratory strain. Bacteria were grown individually and each bacteriophage was added individually (FIG. 1-6) or in cocktail (FIG. 7) at a MOI of 1 to $10^{e-4}$, i.e. at a dilution ratio (bacteria/phage) of 1 to 10 000.

FIG. 1 shows that bacteriophage 1384 is efficient at MOIs of 1, 0.1 or 0.01.

Figure 2:
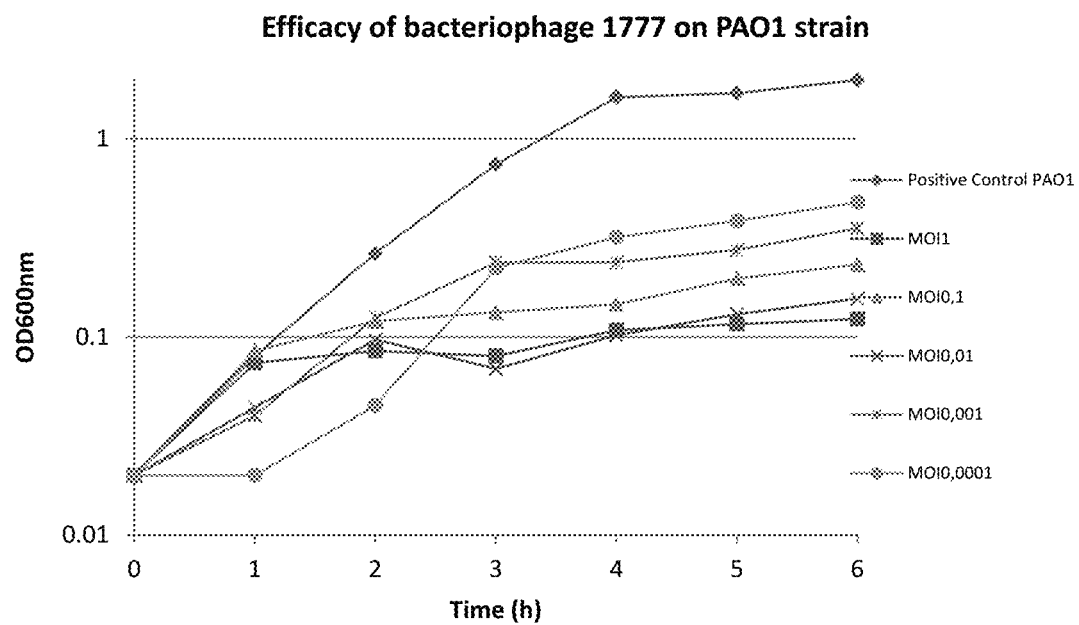
FIG. 2: Efficacy of bacteriophage 1777 on PAO1 strain.

FIG. 2 shows that bacteriophage 1777 is efficient at a MOI of 1.

Figure 3:
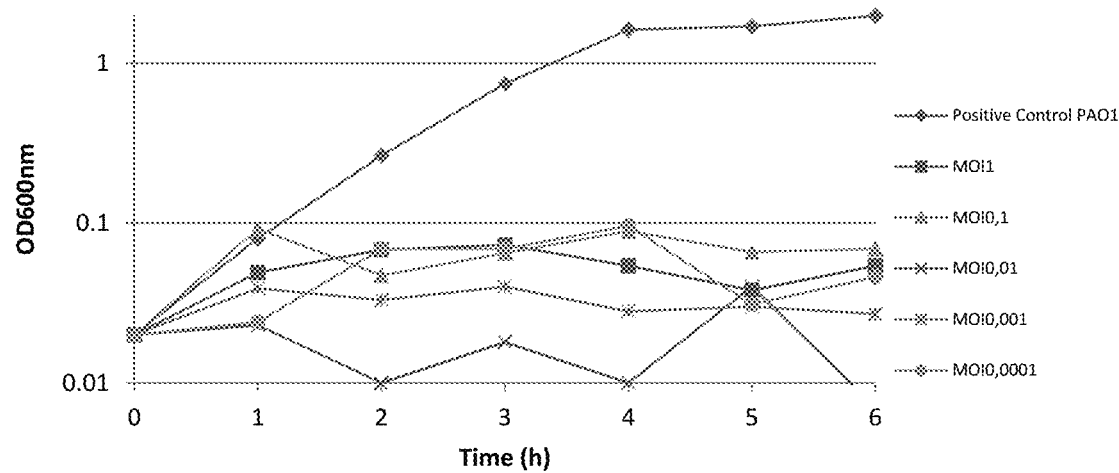
FIG. 3: Efficacy of bacteriophage 1792 on PAO1 strain.

FIG. 3 shows that Bacteriophage 1792 is active against PAO1 strain during at least 6 h even at a MOI $10^{e-4}$.

Figure 4:
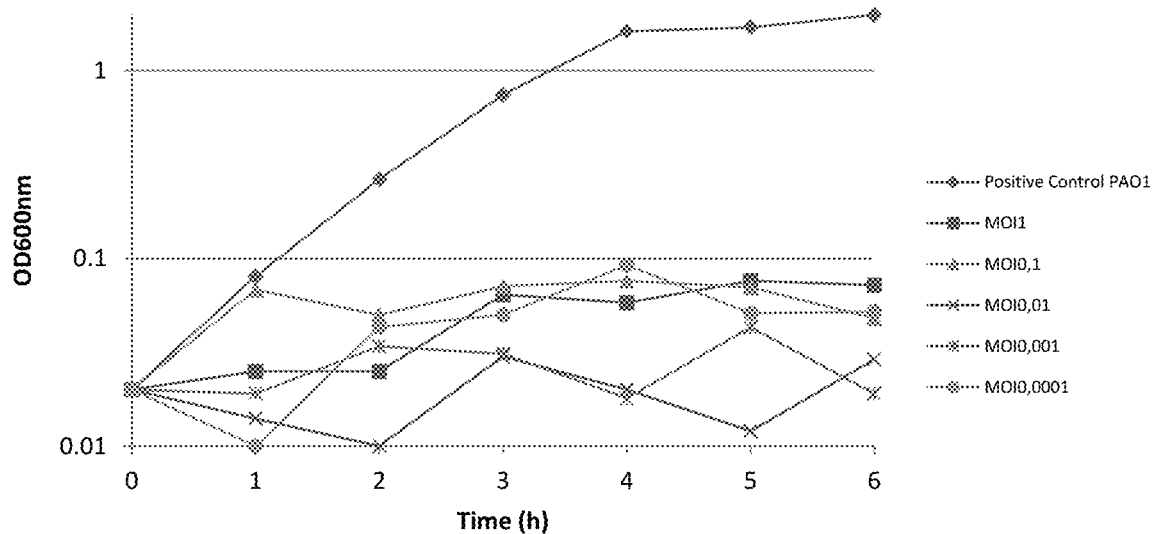
FIG. 4: Efficacy of bacteriophage 1797 on PAO1 strain.

FIG. 4 shows that bacteriophage 1797 is active against PAO1 strain during at least 6 h even at a MOI $10^{e-4}$.

Figure 5:
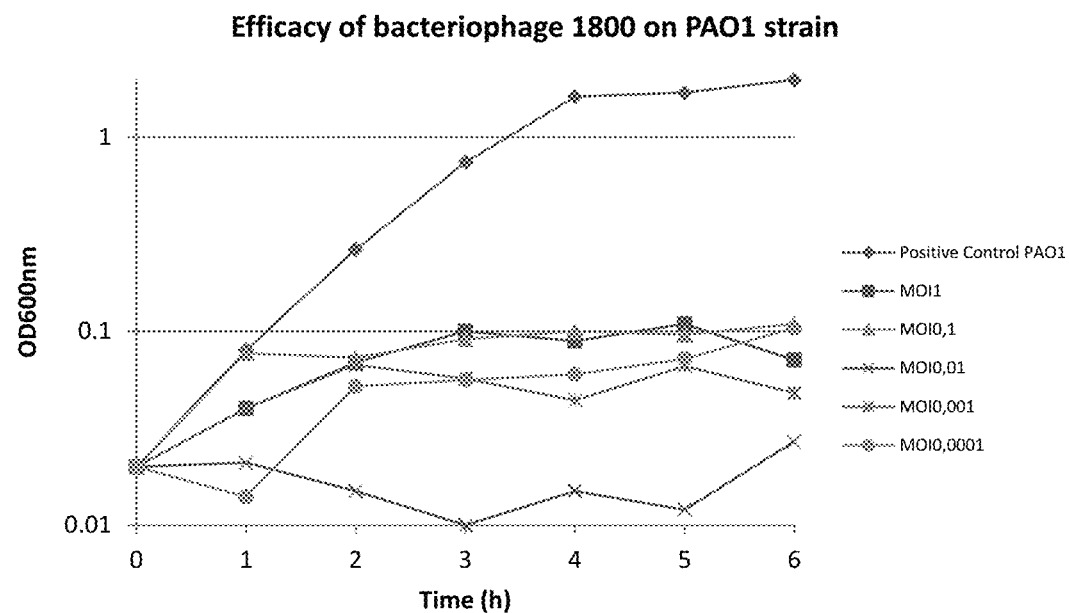
FIG. 5: Efficacy of bacteriophage 1800 on PAO1 strain.

FIG. 5 shows that bacteriophage 1800 is active against PAO1 strain during at least 6 h even at a MOI $10^{e-4}$.

Figure 6:
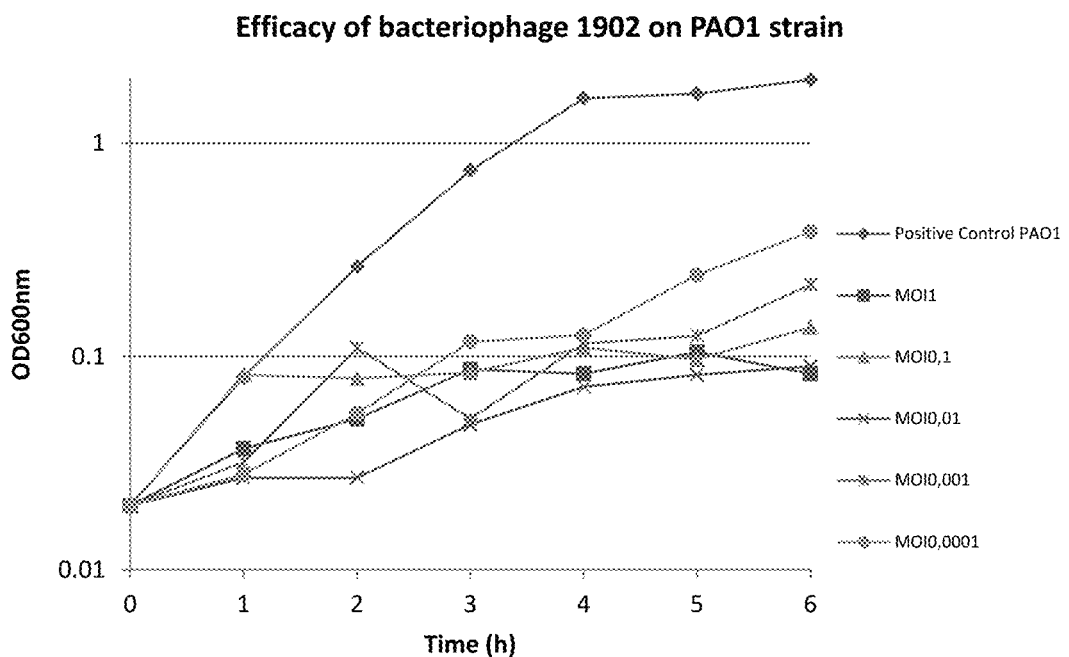
FIG. 6: Efficacy of bacteriophage 1902 on PAO1 strain.

FIG. 6 shows that, depending on the MOI, bacteriophage 1800 is active against PAO1 strain during at least 6 h.

Figure 7:
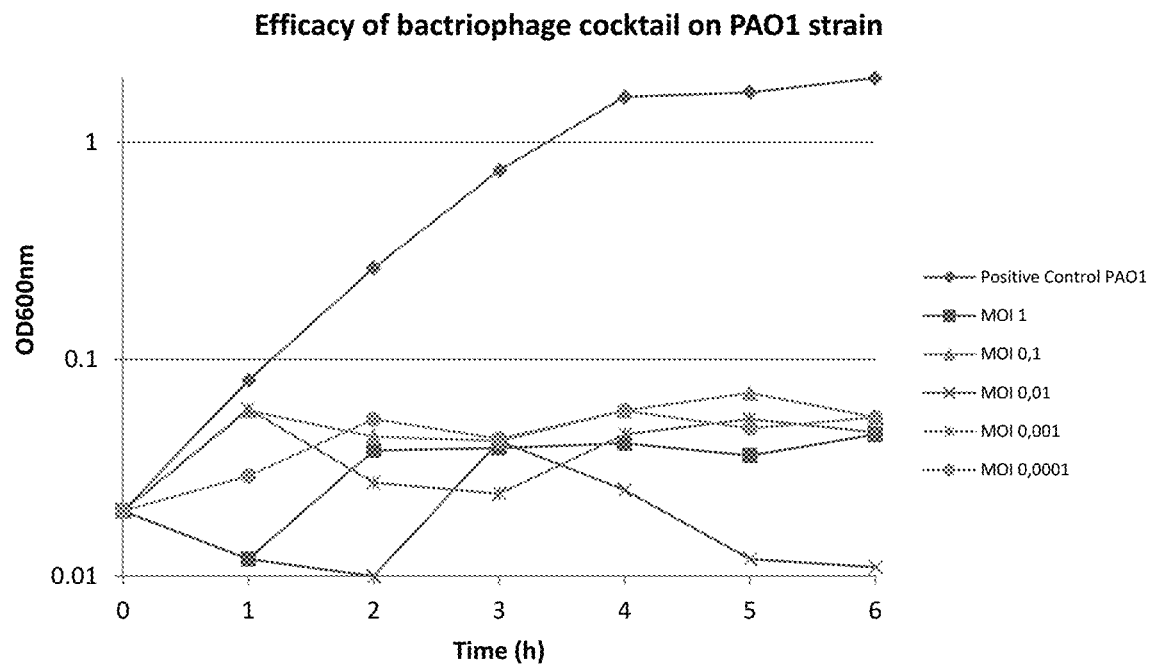
FIG. 7: Efficacy of bacteriophage cocktail on PAO1 strain.

FIG. 7 shows the efficacy of bacteriophage cocktail VI on PAO1 strain. The cocktail is highly active against PAO1 strain during at least 6 h even at a MOI $10^{e-4}$ and is more efficient than the phages individually.

Example 7: Efficiency of a Bacteriophage Cocktail of the Invention on Cystic Fibrosis Antibiotic Resistant *P. aeruginosa* Strains Several strains were chosen to represent *P. aeruginosa* that causes respiratory problems. They were grown individually and the bacteriophage cocktail VI was added at a MOI of 1 to $10^{e-4}$, i.e. at a dilution ratio (bacteria/phage) of 1 to 10 000.

TABLE 8 information about the bacterial strains

| Bacterium | Country | Year | Source | Resistance to antibiotics |
|---|---|---|---|---|
| CF1 | Canada | 2010 | Hospital | Aztreonam 16 Tobramycin 8 |
| CF2 | United State | 2010 | Analysis laboratory | Aztreonam 0.5 Tobramycin 8 |
| CF3 | France | 2014 | Patient expectoration | Multiresistant |

Figure 8:
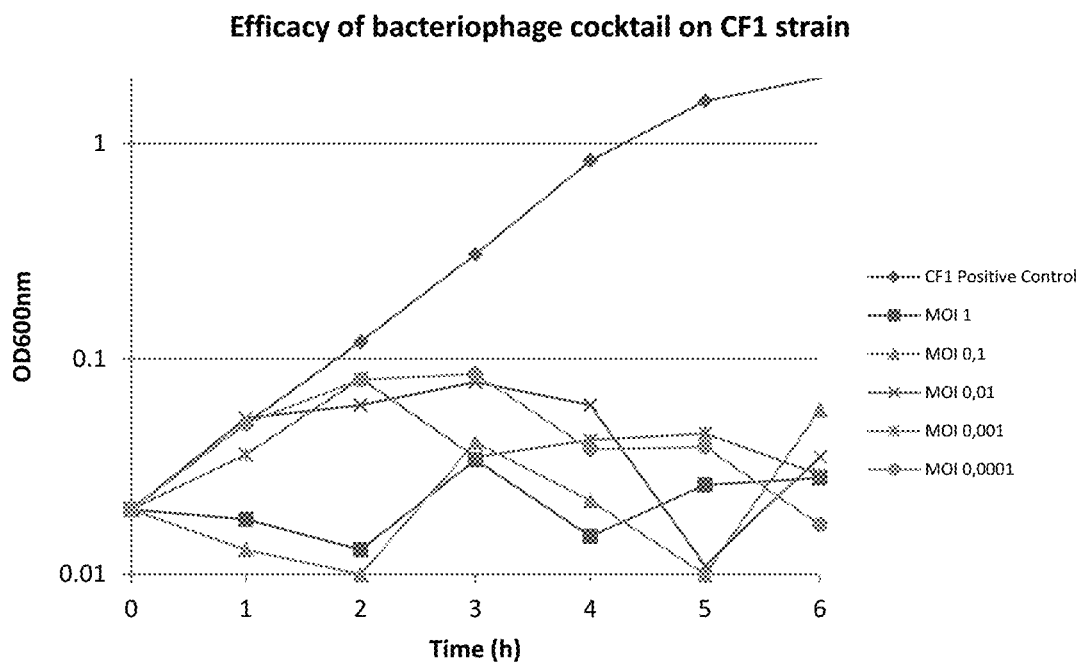
FIG. 8: Efficacy of bacteriophage cocktail on CF1 strain.
Figure 9:
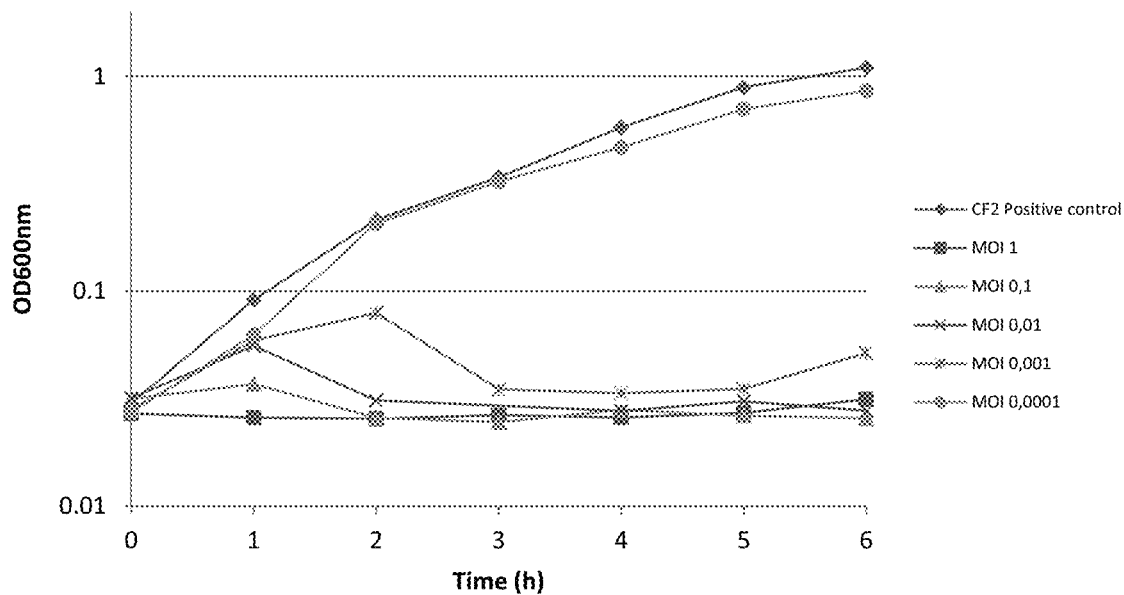
FIG. 9: Efficacy of bacteriophage cocktail on CF2 strain.
Figure 10:
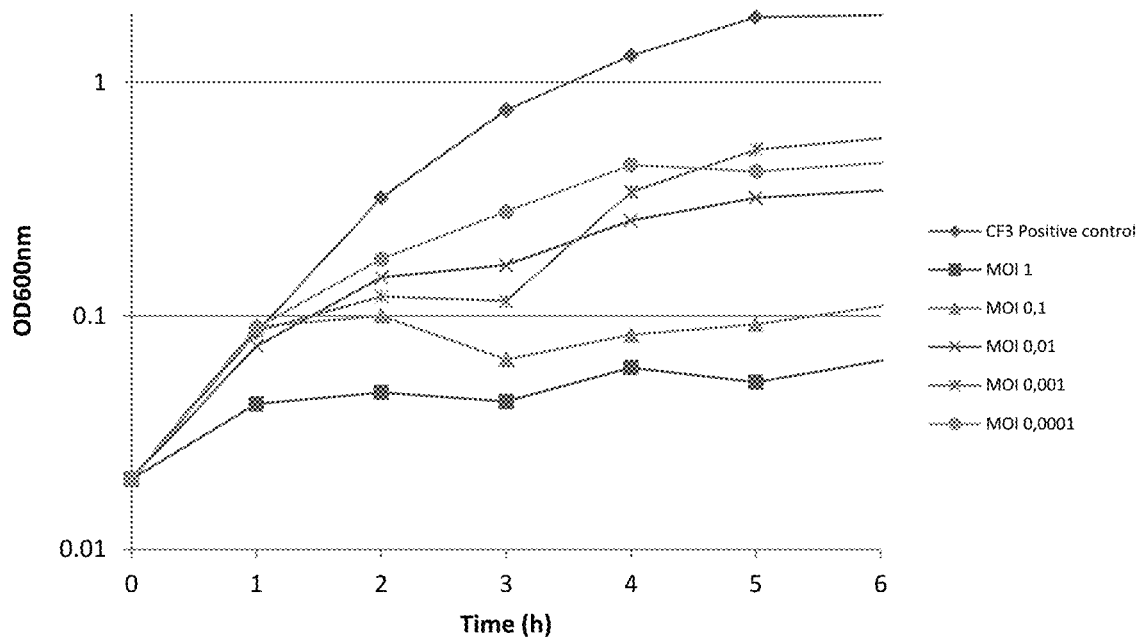
FIG. 10: Efficacy of bacteriophage cocktail on CF3 strain.

The results are presented in FIGS. 8, 9 and 10.

FIG. 8 shows that the cocktail is fully efficient on CF1 strain even after 6 h and with a very low MOI.

FIG. 9 shows that the cocktail is highly efficient on CF2 strain even after 6 h.

FIG. 10 shows that the cocktail is efficient on CF3 strain.

The results show that bacteriophage cocktail VI was very efficient on three nosocomial bacterial *P. aeruginosa* strains isolated from hospitalized patients, even after being diluted up to a ten thousand fold. These results thus demonstrate that compositions of the invention can be used to treat *P. aeruginosa* infection in vivo, and are active against multi-resistant bacterial strains.

REFERENCES

Clark W A, 1962, Appl Microbiol. Comparison of several methods for preserving bacteriophages. 1962 September; 10:466-71.

Drulis-Kawa Z, Majkowska-Skrobek G, Maciejewska B, Delattre A S, Lavigne R, 2012, Learning from bacteriophages—advantages and limitations of phage and phage-encoded protein applications; 13(8): 699-722.

Fordos J. 1859. Receuil des travaux de la Societé d'Emulation pour les Sciences Pharmaceutiques, vol 3 Societé d'Emulation pour les Sciences Pharmaceutiques, Paris, France.

Freeman L. 1916. Chronic general infection with the *Bacillus* pyocyaneus. Ann. Surg. 64:195-202.

Gang R K, Bang R L, Sanyal S C, Mokaddas E, Lari A R. 1999. *Pseudomonas aeruginosa* septicaemia in burns. Burns 25:611-616.

Jones A M, et al. 2010. Clinical outcome for cystic fibrosis patients infected with transmissible *Pseudomonas aeruginosa*: an 8-year prospective study. Chest 137:1405-1409.

Kang C I, et al. 2005. Bloodstream infections caused by antibiotic-resistant gram-negative bacilli: risk factors for mortality and impact of inappropriate initial antimicrobial therapy on outcome. Antimicrob. Agents Chemother. 49:760-766.

Micek S T, et al. 2005. *Pseudomonas aeruginosa* bloodstream infection: importance of appropriate initial antimicrobial treatment. Antimicrob. Agents Chemother. 49:1306-1311.

Strateva T. and Yordanov D. 2009. *Pseudomonas aeruginosa*—a phenomenon of bacterial resistance. Journal of Medical Microbiology 58, 1133-1148.

Weinbauer M G. Ecology of prokaryotic viruses. FEMS Microbiol Rev 2004; 28:127-81.

Williams E P, Cameron K. 1894. Infection by the *Bacillus* pyocyaneus a cause of infantile mortality. Public Health Pap. Rep. 20:355-360.

We claim:

1. An antibacterial composition comprising at least one bacteriophage having lytic activity against a *Pseudomonas aeruginosa* (*P. aeruginosa*) strain and a pharmaceutically acceptable excipient or carrier, said at least one bacteriophage being selected from the bacteriophages having a genome comprising a nucleotide sequence of any one of SEQ ID NOs: 2 to 7 or a sequence having at least 99% identity thereto, and said pharmaceutically acceptable excipient or carrier comprising a preservative in an amount effective to preserve the activity of the bacteriophage.

2. The composition of claim 1, comprising at least one bacteriophage selected from the group consisting of BP1777, BP1792, BP1797, BP1800, BP1902, and BP1940, said bacteriophage having a genome comprising the nucleotide sequence of SEQ ID NOs: 2 to 7, respectively.

3. The composition of claim 1, which is lytic against antibiotic-resistant *P. aeruginosa* strains.

4. The composition of claim 1, which is lytic against more that 90% of all bacterial strains of the LMG collection.

5. The composition of claim 1, wherein the pharmaceutically acceptable excipient or carrier comprises buffered physiological saline.

6. The composition of claim 1, in the form of a liquid, semi-liquid, solid or lyophilized formulation.

7. The composition of claim 6, which comprises between $10^{e4}$ and $10^{e12}$ PFU of each bacteriophage.

8. A method of treatment of an infection in a mammal in need thereof comprising contacting the mammal with an effective amount of an antibacterial composition, wherein said composition comprises at least one bacteriophage having lytic activity against a *Pseudomonas aeruginosa* (*P. aeruginosa*) strain, said at least one bacteriophage being selected from the bacteriophages having a genome comprising any one of SEQ ID NOs: 2 to 7 or a sequence having at least 99% identity thereto.

9. The method of claim 8, wherein the infection is an infection of the respiratory tract.

10. A method for improving the condition of a mammal by modifying the microbial flora in said mammal comprising contacting the mammal with an effective amount of an antibacterial composition, wherein said composition comprises at least one bacteriophage having lytic activity against a *Pseudomonas aeruginosa* (*P. aeruginosa*) strain, said at least one bacteriophage being selected from the bacteriophages having a genome comprising any one of SEQ ID NOs: 2 to 7 or a sequence having at least 99% identity thereto.

11. A method for decontaminating a material, comprising exposing the material to an effective amount of an antibacterial composition, wherein said composition comprises at least one bacteriophage having lytic activity against a *Pseudomonas aeruginosa* (*P. aeruginosa*) strain, said at least one bacteriophage being selected from the bacteriophages having a genome comprising any one of SEQ ID NOs: 2 to 7 or a sequence having at least 99% identity thereto.

12. The method of claim 8, wherein the composition comprises at least one of the bacteriophages selected from the group consisting of BP1777, BP1792, BP1797, BP1800, BP1902, and BP1940, said bacteriophage having a genome comprising the nucleotide sequence of SEQ ID NOs: 2 to 7, respectively.

13. The method of claim 10, wherein the composition comprises at least one of the bacteriophages selected from the group consisting of BP1777, BP1792, BP1797, BP1800, BP1902, and BP1940, said bacteriophage having a genome comprising the nucleotide sequence of SEQ ID NOs: 2 to 7, respectively.

14. The method of claim 11, wherein the composition comprises at least one of the bacteriophages selected from the group consisting of BP1777, BP1792, BP1797, BP1800, BP1902, and BP1940, said bacteriophage having a genome comprising the nucleotide sequence of SEQ ID NOs: 2 to 7, respectively.

* * * * *

SEQUENCE LISTING

```
<160> NUMBER OF SEQ ID NOS: 7

<210> SEQ ID NO 1
<211> LENGTH: 63902
<212> TYPE: DNA
<213> ORGANISM: Bacteriophage P1384
<220> FEATURE:
<221> NAME/KEY: misc_feature
<222> LOCATION: (63895)..(63902)
<223> OTHER INFORMATION: n is a, c, g, or t

<400> SEQUENCE: 1
tcgcgtttcg atgaggagat tatgccgata gtcagaatgg aagtaaagtg tctgagtgag      60
```

-continued

```
aaaaattctg cacaccgacg aacggttgtg ctcgaccgtc tgttgcggcg tcgatatact    120
cggcctattg ctaacaccgg actgattgga atgtacaaac tcaatcctgc gctgcgagcg    180
gtctggcgaa ctcgtgcccg ttacaaagtc atctatggcg gccggcgtc ttcgaagtcg    240 cacgacgctg gcggtatagc cgttttcctc gcggccaact acaagctaaa gttcctctgt    300
gctcgccagt ttcagaaccg catcagcgaa tcggtctaca cgttgatcaa ggacaagatc    360
gaaaactcag agtataatgg cgaattcatc ttcaccaaga actctatcaa gcacaagagt    420
accgggtcag agttcctatt ctatgggatc gcccgtaacc tgtcggaaat caagtccacc    480
gaaggcatcg acattctctg gcttgaggaa gctcactatc tgacccagga gcaatgggaa    540
gtcatcgagc cgaccatccg gaaagagaac tcagaaatct ggatcatctt caacccgaac    600
gaagtgaccg acttcgtgta tcagaacttc gtggtcaagc ccccgaaaga ttcctgcgtc    660
aagatgatca actggaatga aaatccgttc ctcagtgaga cgatgcttaa agtcattcac    720
gaagcatatg agcgcgaccg ggagcaggcc gagcacattt atggcgggat tccgaagact    780
ggaggcgaca aatccgtcat caacctcaag ttcatcctcg cggccatcga cgcccacaag    840
aaactcggct gggagccagc cggatcgaag cgcatcggct tcgacgttgc ggacgacggc    900
gatgatgcga acgccaccac gctcatgcac ggaaacgtca atgtgaagt ggacgaatgg    960 gacggcctgg aagatgaact gctcaagtcg tccagccgcg tttacaatct ggcgaagctg   1020
aaaggcgcct cggtcactta tgactccatc ggcgtcggcg ctcatgtcgg ttcgaagttc   1080
gccgagttga acgatgccag ccccgacttc aaacttatct atgatccatt caacgcgggc   1140
ggcgctgtcg ataagcctga tgatgtctac atgaagctgc cgcacacgac gatcaagaac   1200
aaagaccact tcagcaacat caaggcgcag aagtgggaag aagtcgcgac ccgattcagg   1260
aagacttatg aagcggttga gcatggaaag gtttatccat cgacgaatt gatttcgatc   1320 aactctgaaa cgattcaccc ggacaaacta aatcaattgt gtattgaact ttcgtcgccg   1380
cgcaaagacc tggacatgaa cggccggttc aaagtcgagt ccaagaagga tatgcgcgag   1440
aaacgcaaga tcaagtcacc gaacatcgct gactcggtga ttatgtcggc cattctgccg   1500
atccggaagc ccaaaggctt cttcgacttc taaacataga aaagcccgga tcgctccggg   1560
cttcgggtct tactcggtgt ggttcctggc gctgagtgtc gacgcaacgg cctcgccgac   1620
tcccagggct tcctggccgg ccgcgagcgc ttcggcttcc gactcgacga tgaaatcatc   1680
accttggcca tcgcctggcg gaacctcgac cagcacggct tcttcgcctt cgaaccgcag   1740
gtcataggtc ttttcgacgg acagaccgta acgagcgttg agcgcgtccc agagctgggc   1800
ctcataggtc cgcaggtctt gcagagcttt ctggtggctg agcatggcca tgtcaacagc   1860
ccgttgcagg gtttcgtcca ggacgttgaa tcgcatgcga agagaacgaa tccgctcgac   1920
cacttccgca tccactacat gcctttcgat catcgctttt cacctttgct gaatgttacg   1980
ttgtagccgt tgtcggccag ataggtcaag gcgccttcga agaagttcc gacaaggtgc   2040 ttgagctgca tttcgcgttg cgcggcgatc cagaatgccg ttccggagaa ctctgcgcgg   2100
ccttccgaca aaacctttcc atcaggcccg tcgatccgta catggacgga agatagcttc   2160
agcgccatca gtgaaccgtc cctgtgaagg cgcgcgccgc cgcgcattga tcgcaagggc   2220
actccctctg gatgcgcgcc aggtcgtttg catccagggc gtagagtttt ccatctacgg   2280
tatcgtgagc cattgcgatg tccggatatt cgttttcgtc caggccggat gccgcacgga   2340
tgttgttcca gatgccggca tgttccgcgc gatggcgcgc ggtcaactca tcttgctctt   2400
tgttcgccct ttcaacgaat ttctccagga gttcggtgaa tttctcatcg atgactcgtg   2460
```

```
cagacttgac agagctgagt cgaatcgggt cttctcttcat ggtgattctc ttttgctggt    2520
ggttgttcgc tgcccagacc tattcaaagt ctgggcagca tgatgaaaat gaacacgaag    2580
gctgcaaacg ccaatagcgt tcctgtaagc atttttggctt gactctgcac ctcagcgtac    2640
tgcttagtgg acattccgtg ctgcgccgcc tcggccgcga agcgagcttt cgcctcgata    2700
acttccgggc gcagcgacag gacatattct aaggcctctt cccgcgcttt tcggcctcga    2760
ccaacctagg gtcgcgggcc gagacttcgc tgtgccctgg cctcgcggga tgggcctgca    2820
gcgatggcgg aagttcggcg gccacgactc catagtcggc gcaggcccaa gcgatcccga    2880
tgaggatcgc gaggatggat tgaacgattc gtagcatcac tttgtcgcta gggaagctca    2940
tgatcaatcc tccacagacc gaacgatttc catgttgcgg ccggcattgg tcccggcatt    3000
gaaggcgcgc cgaccgtcgc tatcgtccag acgcatgagc ttagcaacat tgtacttctt    3060
gtagccagga tcgccgaaat gttcgtgaac cgcagcttcc ttcaccacaa ccagagacgt    3120
tccggcagaa gataccagct ccatgcgctt cctggttatg gcctgaaggc gatagctgat    3180
ttcctgggtc gcggccagct tgaattgcgc ggcaaccttg acgttgaatc gtccgtatcc    3240
ttgagccttc tgatactccc ggcacagacg atcaaccgct tcgacaaggg agttgaacat    3300
gttcaccgcc agctcaacgt ccgatttgta gcctttaaag cggacggcat gaccccagcg    3360
cttcgtagtc ccgccgtttg cggcgtgcca agaagccttg gcggtcgctc ggtgatcgtt    3420
gatgccaccg gcgaaatcca tgatgaagtc gttgtacgtc gccacggcca ccgagaagaa    3480
cttcatccag ttcgggattg cggaatagta acgagtcgcg atctgctcat cgaactcttc    3540
gcaaatctcg ccggtcactt cgaagtcgtg aaggtcatat ttgtccttca gcttcttcac    3600
acgctcggct gcaatggcag cttcgtgcgg gctggaggag tcggccgcca tggcagtcag    3660
tttgcggatg cggtctttcg ccttctcgat ggcttccggg gtgaattcgt tctggtaggt    3720
catggtcggt tccttttgtc tgaagggttt cgcgtttcaa tggagctatt ttgccttcat    3780
tcagaatgga agtaaagcat tttcttccac tatttcggca ttgactggaa gaaattccag    3840
atccaatcgc ctgctaccag caggaggatg agagcggcga agaacaagac ggcggccgcg    3900
agctgtgcgc ccggcttcag cttgggatgg ctgagcttgg gctctacggg aacgccgga    3960 gcgctggcgc tgcaaacggc atctcctgga ccgtagccga tgccgcgttc acgcgcctgg    4020
agcgacacca gggatttcag atgctcggtc tgcttttgcg actcttcgta gatgccggcg    4080
acggcgaacc agagggcgaa cacgacggac gtacacacaa cccaggcgcc ggtcagcagg    4140
agggccagcg ggccgatgac gaagacggta gcagccagga cgattgcgcc gccccagatg    4200
atgaagccgg ccagaccatt ggcgatgtcg atacagaact ttttcatttg cggattcctt    4260
cggctacagg atggagggga tttggaactc tgccgccgcg agcacatcgg tgacgacttc    4320
ccagagcgtc ggcaccgacc actggtagcg gtcgaagtcg gtttcgggat cgaagcccaa    4380
cgtcacatag gaagtggcag gccatttatg aacgctacct ttccgcatga gagtcgccac    4440
gcgtccgtca acgagcgggt tcgtcttgtg cggaacgtac gcagacatcg aatattgctg    4500
cccggcgtca acaacaaatc tttgcctctg gcgcagacat acagagccca caggattcca    4560
gccgcgaccc ccgcaagcct ggcgagccga agagtgttca taaccttcgt gagtcatttc    4620
gccgaggcaa gccgagcgat cctcgtaata gttgatgttc tccatcgatc caaccagtac    4680
cagagactcg aaatcgaatc tatgatcgtg gatggccgag tgattgaagc aaagccggcg    4740
cggcaactcc gggtgccaaa catggaggcg ccctgccggg agctggactt gaatgaaccc    4800
```

```
caggccgtgc agcgtgatct tgtccttcat cgggtcatgg acggtgctca tggataatcc    4860
tcagtagcag aaatgtatgg tgagagttac gatggccaag ccggtcgccc ataggagggc    4920
gaaccaggcc atggctttga tggttatgta gatcatccga agaactttcc ggcacagatc    4980
ggtccaatgc ccatttcgat ggatgcgtgg ttggtcaact cgcgaccgca gcaggagcat    5040
tgaccagtct tccggccgta ggcgactgcc gattccatcg gcttttcaaa catcttcaga    5100
acgtcgtcat gctcagtgtc ggtgcagtcg cgactcttga tgaatttgcc attggtgatc    5160
cggccgaggt agatgtcgcc caagacgtac aagctaccgg cgttccggct gtgagcgcta    5220
gcctctttca caataacgat gagcggctcc tcgccttcgc cagccaggcg gattttcggg    5280
cgcttgatgc cagattcttt cgccttctca aacgccttct cgattccgga aatgtccaga    5340
gtcggcgcag cagcttcctg cgcggccact ttctcgcgat atttggcgag ttttcgatg     5400
gcgcgcttcg cagcagcgat ctgattttct gtcaaggagc cgtatttata caacgactcc    5460
tgaaggctct gagcgaagct gaaggaattt ccagtccacc actcgacgat gtccgggtgc    5520
gcatcttcga aggctttaat tttgaggtcg cgctcttgcg ccgcgctaca gattttctcg    5580
atgcgctttt ctgccgcctt agcacggctc ttggcgcgct gctccgggct ggttttgtac    5640
tctttgtatc caacaccgcc gcaggcgaag caggcgcgac cataagacga agggccacgg    5700
tacaggccgg tgcctgcgca tttggtgcac ttgtcgcgat acagcttcac ttccttccgg    5760
gaattcgggc gagcgcccat ggacgcgtct tccagggtct tcggcgcttc gttgttgatc    5820
gctacggtag cgaagtcgtc acccaggtct tcgaagcctg tgaacagatt ctctgctgcg    5880
ttcatatcga ttctcctgtt tggaaagttc gtttcgatga gttgactata cgccagaaat    5940
gggaaaacgg tagcactttc gcactaccgt tcgtcgggtc gcagagggtc aggctacacg    6000
gatcaactgc gacatgactg ccaggttacg ctcggcgacg cctatgatga ggttggttcc    6060
gatgtcgaac ttccaagggt cttccctgtt cttgtcgtag aacggatttc tgaacagggt    6120
ccgccatgtc tcttcagtga agaacgtttt atggtccagg tcttggtggg cgatgttgga    6180
gttgtagaat ggaacaacga cattgagcgt cgcgccgact gccatggccc gctgcaggtc    6240
tttcaccaaa tcgatgacct gggctccggt gagatgttcg aagaagtgaa atgcgtagac    6300
cgccgtcaat tcgccgtctt catacggcac tcggccgctg gcgccgtccc agttcggcca    6360
gtcgagcgat tcgacgccgg gaatcggcga attgcctgcg cccaggttta ctgcgcggcg    6420
gtgatccggc tcgatcaact gagcgatgtc gcgcttcatg ccgagtttga acaggttttg    6480
aatatccatt tttctctcca ggttgctgct agtaaatgtc gctgttgatc ttgaatccat    6540
gctcagcgcc gtcgttgtag tcatactcgg catagctgtc gcagtaatcg ttcaaatgtt    6600
gaatgatacc aagaacgtcg ttcgcggcct tgtgccgttt cgcggcgatg gtcttggcga    6660
tgctgtcgcc gacttccagg gtttcggccg tccggcggtg gatcagaaga cgactccaaa    6720
gatagagccg gacgcgacga atgatgtcgc gatggcgctc caatcgaact tccaactctt    6780
caagttcttg ctcgcgagat ttgatgactc gtcgaagctg atgaactttc agttccaaat    6840
cgtccttagt agccatattt acctcagaaa gggaaatcgt ctggaactcc aggaagctcg    6900
acgattgttg ttgagcctga tcggtctaga atgcatccga ccgagccagc cctgtgggga    6960
tagggcctac acgaactata acaggtaact tccatgacta ttcgccaggt cgatcctcca    7020
caccatctac aaattggcgg tcgcttcgac tttagttttc gttcgtccag gacggcgcgt    7080
ctgtcgcagg aaaggcagcg cgccttaacc gacgtaacca tgggtatagt cgatcattcg    7140
gatgagttca tcatcctctg attctctcga cttcagaccg cccaaagagt ccgactggcc    7200
```

```
gtagcatttc gcatcgatat ccatcgaaga caggaatcct gccgatactg cggagatatc    7260
aactttgtcg ccggccttct tgaaaccttc gcactcagca tcaagggcca caatcgcact    7320
cgcggccatg ttcgcatgac ttatgaggtc ggggaagatc acaggaactt cacgcgacat    7380
gccacggacc gtcatcttca ggactacata cttcatactc actatccctt ttgtatgtga    7440
ggaaagaatt tgctgttttc aggatggtgg aagcgctcgg ccgcaggcgg tctttcttcc    7500
ggacattgaa tcgtcgaagg cgggaaaacc gcgccggcga taatcgccgc gaggagtgca    7560
gcggatgtcg acatccagag ggcggtttcc aggctcaccc gaacttccgg acggcgcggc    7620
ttcattcgct ccaccctctt cccggttcat aggatggtag actgccgccg cgaacccagt    7680
tgtcccacat atggttcaga ccagtcggtg gctggggcgg cgaactgtag aatccgggag    7740
tctcagtgct gctcaggaaa taaggagtgc aaacggcctg gacggccagt tggtgccgct    7800
cccacatctt atcaatcgct cttagcatga cgtcttcgca ctgagcctta ctgtcgaacc    7860
gtctgctagt atggtccggt atctggacac atccgtctcc agtgcaaagg aaagcagtag    7920
caatccatac ggtgatactc gccatttcgt caccctcttt agttgatgag cagagtctat    7980
tccatctgct cgccaggagt aaagcgcttt tcgtcgggat aaatgccgat gatgtctgcg    8040
tcgagcatcc aaatgtccac ggacggatcg tcgctgctga tttgatatag gttgtacagc    8100
tcccgtccgc cgacagcacg ctcgcctcgc ggctcaaccg ccagaacctt gccatgtcct    8160
tctccgtgct cgtccaggta tatgacgtga tcaccgactt catagctttc ttttgtaacg    8220
aggcgtgaac gcgagctgtt ctgcgattcc actacccagg aatccagcac gccgcctttc    8280
atgtcgcgaa acaatcttgc cgatttgtcg caatcgaata cgcccagaac ttcgccgtct    8340
ttcaacacga tatgtacgat tggcaaaaga gtattcatgt ttaatctcca ttggttgata    8400
attagagtct aatctgccga aaagttcccg taaagaatta ttttctcata actgattagt    8460
tgcaactgtt aacctgatgt atatgtttga atctcttttg aacgtttgat gtttccccta    8520
taataagcgc acacagccaa caaccacgtg gaactacaat gtttaaactt tcctggatat    8580 tcggcgcaa aaaggataat gctgcctgtt ctgaatcggc gccggagaaa gtcgcacaaa    8640
tccctcagca cgatccgctc gaccccatga tcaagctggg aaggattcgc ggctggaacg    8700
tcgagccgga gaaagccccg gtaattcgta gcgtgaaaga tttcctggag ccgggcctat    8760
ctgtagcaat ggatagtgcg tatggtgatg gaccaactcc ggcagcgaag gctgctgcgg    8820
gcggccagaa tccctatgta gtcccgacta tgttgcagga ctggtacaac tcccaagggt    8880
tcatcggata ccaagcttgc gcaatcattt cccaacactg gttggtggac aaagcttgtt    8940
ccatgtctgg ggaagacgca gcacggaacg gatgggaact caaatcggac ggcaggaagc    9000
tatccgatga acaaagcgcg ctgatcgccc ggcgcgacat ggagtttcgc gtcaaagaca    9060
accttgtcga actcaacaga ttcaagaacg ttttcggcgt tcgcatcgcg ctgttcgttg    9120
tggagtctga cgatccggac tattacgaga accgttcaa cccggatgga atcacacccg    9180
gctcctacaa gggaatctcc cagatcgatc catattgggc gatgccgcag ctcactgccg    9240
actcgacggc cgatccgtct tccgaacatt tctatgagcc ggacttctgg atcatcagcg    9300
gtaagaaata tcaccgaagt cacctagtag tcgttcgcgg accgcagccg ccagatatcc    9360
tgaagcctac atacatcttc ggcggcatcc cgctcaccca gagaatctat gagcgcgtgt    9420
atgcagcgga acgacggcg aacgaagccc cgctgcttgc catgtcgaag cgaaccagca    9480
ccattcacgt tgacgtggaa aaggccatcg cgaatgagga cgctttcaat gctcgcctgg    9540
```

```
cgttctggat cgccaaccgt gataaccacg gcgtgaaagt tctgggaatt gacgaaggca    9600
tggagcagtt cgacacgaac ctggccgact tcgacagcat cattatgaac caatatcagc    9660
tggtcgcggc catcgccaag actccagcca cgaagctcct cggcacttct ccaaaaggat    9720
tcaacgccac tggtgagcac gaaacgattt cttatcatga agaactggag tccattcaag    9780
agcacatatt cgacccactt ctcgaacgtc actatttgct tctggcgaag tcggaagaaa    9840
tcgatgtgca gctggaaatc gtctggaatc ctgtagactc cacgtccagc cagcaacaag    9900
ccgaattgaa caacaagaaa gccgctaccg acgaaatcta catcaactct ggcgttgtgt    9960
ctccggatga agttcgcgag cgtctgcgcg acgatccgcg ttccggctac aaccgactca   10020
ccgacgatca ggcagaaacc gaaccgggca tgtctccgga aaacctggcc gaattcgaga   10080
aggccggtgc acagtcggtc aaggcgaaag gcgaagccga gcgagccgaa gcccaggcgg   10140
gagccgtaga gggcgcaggc ggcccggttc ccgccgctcc acgcgcgact aagcctctcg   10200
cgaaggcggc cgaggaaggg gccagcgagg ccgctgaacc gccgtcgcgg ccggacccca   10260
aggccgagct gcggaacttg ttggtcgatc ttttgtcgaa gctccaagac ctggacgaca   10320
ttaaggcgcc ggacggcgta gacatagagc acaatgatgc gcctggctta agcgcacgt    10380
ccaaacctgg cgtgtctggc atggagcctt cagtgttttc gtccaaccgc atcgtcgggc   10440
ctcgtgatca ttcggaactc cagagaatca aggtgaatgg aataaccacc ttgatcgaaa   10500
atccgcgcgg aagcattcgg caaggaaagg atgggagttg gcgagttcag atgaaacacc   10560
actatgggtt catcaaggga acgaaggcg ctgatgggga tgaagtcgat tgcttcgtcg    10620
gtccgaatct gggatccaaa cgggtcttcg tcgtcaacca ggtgaacaag gaaggtcagt   10680
ttgacgagca caagtgcatg ctcggcttca acaacatcaa cgatgcgaag tctggatatc   10740
tgtcatgctt ccgcccaggt tgggatggtc tcggctccat ccatgaagtt gacctacccg   10800
cttttccgtcg ctggctggcg aacggcgaca caaccaaacc gtttggaggc gagtgatggc   10860
attcaaggcc tccaaaaagc gcgaacgccg ggcacctctt ccggtcggaa gagggaagcc   10920
cataattcca tcggcaggaa tcgaggcctg gtatcgaaag cagatgaagg atatttccaa   10980
gctcatgatc gccgactatc gaagcgagat tgagaaggca ctgtcccagc ctgcggccga   11040
acggttcttc gccagcgacg aatccgttaa cgtcctgttc aagatgaccc ttcgaagcct   11100
acagcagcga tggagccgca tttttgaagg tttcgcggcc aagatcgccc cggagttcgt   11160
caaccggacc gaagaagccg ccactgccgc gacccttcac agcttgtcgg tggccggcgt   11220
cgatcagcca cgagctgcgt ataatgagag cgtcaggaac accctggagg ccgcaaccaa   11280
ttacaatcat actctcatca ccaagatcca agaggaagtc cacgagaaga tttacacatc   11340
agtaatgctg tctctgactt ccccgaatcc ggaagagcaa ggaacttccg gcataactaa   11400
cgcacttcgc aaagtcggga agttttctga agatcgaatc gaactcatcg caagagatca   11460
aacaagcaag ctttacagtt ctctgagcga tgagagaatg gcggaaaatg gagtcgagga   11520
gttcgagtgg ctacactctt ctgccggcaa gactcctcgc cacacccacc tggagaaaga   11580
tgggaagaga ttcaagctga atgaccccag actttgggag ggtccgaaag cagaccaggg   11640
gccgccagga tgggcgatta actgtagatg cagaaagata ccagtcattt gacatcgata   11700
ggagcgctat atgccgttag ttcatggcac ttccaatgag gctcgttctg aaaacatcaa   11760
gcgggaaatc gaagcggta aggacccaaa gcaggctgcg gccatcgctt actccatcca    11820
gcgcagtgag aaagggaaga cggcgaaaga ttgttcgcct gagctcgtcg ccgatcttcg   11880
cgccctggtg gactctctgt cgaggctcgt gaaatgaacc gcaagacgtg ccggcgccga   11940
```

```
ctcgtggtcg atgtaatcag ggccaatatt cacggcggat tcttcagcct gaagtttgcc    12000
gccatcgatt tggcaatcat cggcgtcgcc atcttgatgg cttttggccg ataatgctga    12060
gaaaatctgg attctgacta aaaattctag tccggatagc cgcaagttac cgtttacgga    12120
aaatagcagt aatttggaaa gcctactgcc gcgaggcttt aacagagcca gttcctaatt    12180
tccgatttag ccgcatgctt caaaagtata tagcctgtga aattagaagt aacgttacaa    12240
tagaattcat ctataagtaa cgttataata taacgtcaat ctatatgctc tagacgtatt    12300
gaaattcaat ttttaatcgg taaattggta atttgaatta gtttagaagt tgaaagtctc    12360
gcggcagtag gcttagacaa atcccgtcaa gtttccgaga ccaaattacc ggattttcgc    12420
ggctgaggaa actggtaatt agatcataat acaaattata atgtaagtta acagtcgcgg    12480
ctacatctaa ttattgttcc gcttatttac ccttggatgt actgcgtata taatacagcc    12540
atagtccacg actcttcgaa ttaacgatgg caaagtcgaa aagaaaaatt gacgaaaatg    12600
gatatatgac catcgagggc tgcccgatca gctcttatgg cgttttccag tattctgctg    12660
gtcaactcgg tcttccgggc gatccgacgc ggattgtcaa cgtatatcgc ccggagtctg    12720
ccgtcagcga tccggagtac atcgaatctc tgaagaatct cccgttgatc gacgagcatg    12780
agatgctgtc gggattcgac gacgatgacg acagtgtggc ccccgaagac aaaggggtgg    12840
agggcatcat cacatccaac gcttactacg aagccccatg ggcacgcggc gatatccgca    12900
tctattcccg caacatgcag aatcagctgg aaaggggcaa agaagacctg tccctaggct    12960
atagttgccg ctacactgag caacccggca tctggaacgg aacgccttat gaagtcgtcc    13020
aggacaagat gcgcggcaac cacattgccc tggtaaaaga gggtcgtgtg ccgggggcca    13080
gagtattgga tggtctgtgt tttgaccatc tcagttttga tttcagacca tccgatgagg    13140
gtaatgaaat gagtctcaag aaagccaagc ggaagccccc tgtccagcgc gtagggcaag    13200
ctgctgactc ggcggtcgaa gagttgcgcg ccctgtggcc gaagctatct gcgtctgtcc    13260
agaagttcct gggcgaagaa gagcaggagc cggagcatca ggaaggcgca gctccggccg    13320
aaccgaccga cagcgagcac ctgaccgagc atccgactct ggaaggtgcc cagaaggatg    13380
acgaagagca ggaagaggag ccttccgttg tcgatccggc cgtggccgcc gtcgagccgg    13440
agcatcaaga aagcgccgca tccgaaatgt ccggtgaagg cgaagtcgcc gaactgatct    13500
ctcaggtcaa agccattctg gctcgactgg agggcacggt agccgaaggg gcagacgaag    13560
agcatggcga aggtcaagat gtcgtcgagg gcttggagga gcagagcagc ctcagcggct    13620
cgcaaaccgc cagcgacgat ggtggtgaga gcaaggataa cagcgaggaa cttcctgaaa    13680
tggcacagaa gaacgcgcaa gatgctgcaa ttcgcggtct ctatcgcgac attgctgcta    13740
aagatcgcct ctacaagcgt cttagctccg tggttggtgc gttcgatcac cgagctatgg    13800
actcggctga agtcgctgtt tacggcgtga aaaagctgaa catcagctgt gcgaagggcc    13860
aggaagctct ggcgctcgac atgtacctga aaggcgtcga agcctcgcgc ggcgcggcca    13920
gccgtcaatc gaaagcccag gattcggccg gttctgctcc gcagtgcgcc gagctggaca    13980
gctacctgaa gggggagtaa ctcatgttcc agaaacaagt ttaccgccag tacactcctg    14040
gttttccggg cgatctgatc gaggacggcc cgaagcgggc gcggccgggt cgaatcatgc    14100
ctctgtctgc cgtaaatccg gctgccaccg ccaccggccc caaccgcatc agtcgcgctt    14160
tcggttacgc cggtgacgtc agcgccctcg gcgaaggtca gccgaagacc atcgcggctc    14220
gcgcttctga agtcgtgatc ggcggcgcca acttctttgg tgtcctcggt catccgaagc    14280
```

-continued

```
actatgcgct gttcggttcg gccggagact ccctggctcc cagctatgat ctgcccgatg    14340
gcgccgaagg cgagttcttc gacatggcca ccggcctggt cgtcgaaatt ttcaacggcg    14400
ccgcaaccgc cctggacctg gactatggtg acctggtcgc ctatgtacca aacaacctgc    14460
ctaccgccga caacgcgctt ggcctgccgg ccggcgccct ggttggcttc aaggctggct    14520
ccatgccgac cggcttggtc cagattccca acgcacgcat cgttaacgcc atcagtctgc    14580
cggcccagtc ggcggggaat ctggttgctg gcgttaccat cgtccagctc acgcagtaag    14640
gaggcgtcat gagccagatc agcaagaccc attcgcgcct cgcaggccgc aatgcgaaac    14700
ctttcgacct gaaaaacatc accaatgacg ccgtggcgtc tctgcgccgc atcggcctgg    14760
tattcgatca cgccgtcgtc caggaccaga tcaaggcctt ggcgaaggcc ggcgcgttcc    14820
gctccggctc ggccatggac agcaacttca ccgccccgt gaccacgccg tccatcccga    14880
ctcccatcca gttcctgcag acctggctgc cgggcttcgt gaaggtcatg accgctgcac    14940
ggaagatcga cgaaatcatc ggcatcgata ccgttggctc ctgggaagat caagaaatcg    15000
tccagggcat cgtggagccg gccggcactg cggtggaata cggcgatcac accaacatcc    15060
cgctgaccag ctggaacgcc aacttcgaac gtcgcaccat cgttcgtggc gagctgggta    15120
tgatggtggg cacccctggaa gagggtcgtg cctcggccat ccggctgaac agcgccgaaa    15180
ccaaacgcca acaggcggcc atcggtctgg aaatcttccg caacgccatc ggcttttatg    15240
gctggcagag cggcctgggc aaccgcacct atggttttct gaacgatccc aacctgccgc    15300
cgttccagac cccgccgagc cagggctggt ccactgccga ctgggcaggc atcatcggcg    15360
atatccgcga ggccgttcgc cagctgcgta ttcagagtca agatcagatc gatccgaagg    15420
cggaaaagat caccctggcc ctggccacca gcaaggtgga ctacctgtcg gtcaccacgc    15480
catacggcat ttcggtttct gactggatcg aacagaccta tccgaaaatg cggatcgtgt    15540
ctgctccgga actgtcaggc gtccagatga agcccaaga gccggaagat gctctggtgc    15600
tcttcgtcga agacgtgaac gcggccgtcg atggaagcac cgatggcggc agcgtgttca    15660
gccagctggt acagagcaag ttcatcaccc tgggtgtcga aaagcgggcg aagtcgtatg    15720
tggaagactt ctccaacggc accgccgtg cgctgtgtaa cgtccgtgg gccgtggtgc    15780
gctacctcgg catctaaccg atgcctattc accaaaggcc gggtttccgg cctttgttca    15840
ctctgactct gactcggttg taggggccgg ttagggcata attactagga ctacgccaat    15900
gactgtttac atcgtttccg ccatgactca atccgtgtct acaatgcgt atgacacctc    15960
tgatccgtcc aatcctcgcc tccagcgaaa gattctgatt cgtggccgcg ccggcatcgc    16020
atccgaaact tccggcttcg gcgacatgat ttccgacgcg gccgggcgtc cgatctggac    16080
cccgcagggc gattgcactg ccgtgagcga ttcggatttc gagctgcttc aggccaataa    16140
gattttcatg cgtcacatgg ataagggcta tctgcgagtc gtgaagacag acatcaccag    16200
tgaccaccag cggattgcca aagagactcg caccatggag cgcgatggat tccagcctct    16260
ggacgctgct cgtttgcagc agaaaatcaa ggttaccacc gccagcgctt cccaggaaca    16320
agagttccgg attttaaccga gggttttcggt atggtgattt tcgacgaaaa taagttttcgc    16380
acgctgtttc cggagtttgc tgatccagcc gcttatccgg acgtgcgcct gcagatgtat    16440
ttcgacattg cgtgcgaatt catttctgat cgcgattcgc cataccggat tctcaacggc    16500
aaagccctgg aagcatgcct gtatcttctg actgccacc tcctgtcgct gtccacgatg    16560
caagttcagg gcgcggctgg aggtggcgtc acagcaggtg ggactcaagg cggtttcatc    16620
accagcgcta ctgtcggcga ggttagcgtg gctaagctcg cgcccccggc caagaatggt    16680
```

```
tggcagtggt ggctgtccgg gacgccttat ggccaagagc tgtgggcgct cctcagcgtc  16740
aaagcggtgg gcggattcta catcggaggt cttccagagc gccgaggctt ccggaaggtt  16800
ggaggaacgt tctggtgatc cctggtgcga atcttctgcg aatggccttc ggggtcatcg  16860
gtactcaaat tgtgaaatat cgcaagtttg agcagcgagt gaagaatgat caagctcagt  16920
acgtttccat gttcgaggag cctttcgacc tggcagcgtc tgtccagcga gtccgacgcg  16980
atcagtatgt ccagtttaat ctggagttcc aacggaatta tgttatgatc ttcgccaact  17040
ttgagatggt tgacttggat cgcgatgtgg ccggtgacca gttcctctgg accggaagag  17100
tttttcagct ggagtctcaa ggctcctggt tttatcaaga cggctgggga gtttgcctgg  17160
ccgtggatat cggtgcggcc aagctcactg atgacgggaa accgactttc taggtgatgt  17220
atgtttgacg gcgaactgat agcgaaaatg gttgtcgagc tgaatgcggc gatgacatct  17280
gctcaagagg ctttgcagtt cccggatttt gaagtcgtcc agaaagctca gccgacccaa  17340
cagggaacgt caaccaggcc gaccatcttt ttccagaaac tgtttgacat tcctcgcggc  17400
tggcctgcca ccgattggca cctggacaac aaggctcgca aatatgtaga ataactcga  17460 cagcatgtag agacgacttt ccagattagt tcccttcatt ggcagaatcc tgaaataact  17520
cacgtggtta cggcttccga tatcgccaac tatgtgaggg cttatttcca agctcgatcc  17580
acgattgagc gcgtaaagga actggacttc ctcattcttc gcgtgtctca aatttccaac  17640
gaagcattcg agaacgataa tcaccagttc gaattccacc caagttttga catggttgta  17700
acttacaacc aatatattcg cctgtacgaa aacgcagcat attcggccga tggggtatta  17760
ataggcatat gagtctgagg cgcgattcag aactaatcgc cgcgcacctc cagatgttaa  17820
gagccatgcg cggcaggtcc gtttcggccg gatggtattc cacggctcga tatcctgaca  17880
aggcaggcgg atcggtcgga atacaagtcg cgagaatcgc acgtctcaat gagtacggcg  17940
gaactatcga ccatccgggc gggacaaggt atattaggga cgccattgtt cggggccggt  18000
ttgttggcgt tcggttcgtc agaaacgact ttccgggaga aaccgaggta actaagcctc  18060
acagaattac catcccggct agaccgttta tgcgatatgc ttggaacttg ttttccgcag  18120
atcgcgccgc aatccagaac cggatagcca tgaggctggc cagaggacag atcactccag  18180
atcaagctct tgcccagatc ggcctggcgt tggaaggata catagccaga agcatcagga  18240
ccgggccatg ggtggctaac tcagcatcta cggtcaggag aaagggattc aacagaccgc  18300
tggtcgatac ggcgcacatg cttcaatcga ttagcagcag agtaacataa ccaggagatc  18360
atccagtgat cagtcagagc cgttatatcc ggatcatttc gggcgtaggc gcaggcgctc  18420
cggtcgcagg ccgaaagctg attctgcgcg tcatgactac caacaacgtc atcccgcccg  18480
gaatcgtcat cgagttcgac aacgccaacg cagtcctgtc atacttcggc gcgcagtcgg  18540
aagagtatca gcgggctgcg gcttatttca gttcatcag taaaagcgtg aattcgccgt  18600
ccagcatcag cttcgctcgc tgggtaaaca ccggcatcgc gccgatggtt gttggtgaca  18660
atctgccgaa gaccatcgcc gatttcgccg gcttctcagc aggggttctg accatcatgg  18720
tcggcgcggc cgaacagaac atcaccgcca tcgatacgtc cgctgcgact tctatggaca  18780
acgtggcgtc gatcatccag accgaaatcc gcaagaacgc cgacccgcag ctggcccagg  18840
ctaccgttac ctggaatcag aacaccaacc agttcacctt ggtcggcgcc accatcggca  18900
ccggcgtcct ggctgtggcg aaatctgccg atccccagga catgtccact gccctcggct  18960
ggtccacctc caacgtcgtc aacgtcgccg gccaggctgc cgatcttccc gacgcggccg  19020
```

```
ttgccaagag caccaatgtc agcaacaact tcggttcgtt cctgttcgcc ggtgcgccgc   19080
tcgacaatga ccagatcaag gccgtgtcgg cctggaacgc ggctcagaac aaccagttca   19140
tctacacggt cgcaacttcc ctggcgaacc tcggcactct tttcaccttg gtgaatggca   19200
acgccgggac cgccctgaac gtgctgtcgg cgactgctgc caacgacttc gtggagcagt   19260
gccccagcga gattctggcc gccaccaact acgatgagcc gggcgcttcg caaaactaca   19320
tgtactacca attccctggc cgcaacatca ccgtttccga cgataccgtt gcgaacaccg   19380
tcgacaagag ccggggcaac tacatcggcg tcacccaggc caatggccag caactcgcgt   19440
tctaccagcg cggcattctg tgcggcggtc cgaccgatgc ggtggacatg aacgtctatg   19500
ccaacgaaat ctggctgaag tcggctatcg ctcaagcgct cctggacctg ttcctgaacg   19560
tcaatgcggt tccggcgagc agcactggcg aggcgatgac cctggcggtg ctgcagccgg   19620
ttctggacaa ggcgacagcc aacggcacgt tcacctacgg caaggaaatc agcgccgtcc   19680
agcagcagta catcacccaa gtcaccggtg atcgccgcgc ctggcgtcaa gtccaaaccc   19740
tgggttactg gatcaacatc accttctcca gctataccaa cagcaacaca ggcttgaccg   19800
agtggaaggc caattacacg ctgatctatt cgaagggcga tgccatccgc ttcgtcgaag   19860
gatcggatgt gatgatctaa tggtttgcgg cggactcgat ccgccgcgac cttccataaa   19920
tggagtgagg aataaacaat gatcaacatt tctgcgttcg gctcgatctg ccagttcacg   19980
gcaagtagaa ctttcccgaa cggattcacc gtcaccgagt tgccgacga tgcggaccc   20040 atcgacagcc cgccgttcac tgcggccgat accggcgtcg gcctcaacgg tgacatggta   20100
gtctggaacc gggcgaacat cctggaagtc gtcgtcaacg ttatcccgaa caccgagggc   20160
gagcgcaacc tggcagtcct tctggatgcc aaccgcaccg gaaaggacaa gtcgggcgct   20220
cgtgatgtcg tcggtttggt cgtggcgatg ccggacggca gcaaaatcac ctgcaccaac   20280
ggcaccccaa tcgacggcgt tctgatcaac gcggtggcaa gcgtcggccg tctgaagacc   20340
aagccgtatc ggttccgatt tgaaaaagtg atcaaagccg gtactagctg atgaagaaaa   20400
ttccgctgac agcagtcccc aatcaagcga tctcatttaa cgccggtagc agctattgga   20460
agattcgcct gtaccagaac atggacatga tgaatgccga tatcagccgc gacggcgtga   20520
tcgtttgcca tggggtccgc tgcttcggcg ggattcctct tctccagtac agccatcagt   20580
accgacctga ctatgcaat ttcgtcttcg accgcgacgc cgattggaca ttgttcggcg   20640
acggcatcaa cctgttctat ctggacggcg ccgaattcgc cgagtatcag gcgcttgcca   20700
cgaggaaaga atgagcacat caacgatcag aaccgggacg aacaacgata tccttttgga   20760
cgacaatgga aacatggtta tcctcaggga tgtcgaagcg tgcgcccagg acgttcgggc   20820
ggcgatgctc atgcgcaccg gcgaaaacat tttcgatgtg aactccggcg tgggatattt   20880
cgaatacatc ttctcgccgc agaaaagcta tgatgacgct cgcaaatcca tcgcggacgc   20940
aattttatcc tcaccggatg tgaccggcat cgagcagctt gacatcgaca taaccgggga   21000
agtcttcggc gtcgatgcga aagtcatcac catccacggg cctgttacca caggagtttg   21060
aaatgagtac catccgcatc caatacgcca acggcaccca actgttcctg gacggcaaaa   21120
atccgccgcc cctggacccg ctaccctcgt ttaaccgtc tgtcgaagat ctggaaggcc   21180
tggaccgcga aagaacacc gacaagggcg actcctctcc ggccggtctt cccgttcccc   21240
cggtaaacgt cgattcagat gtcgacaacg gcggaaccat cccggctccg gtatcgaccg   21300
acgctgctgc ggccgaatcg gccccggaag gcgcccagga agctcctgca gcaggccaag   21360
gcgacgagaa aggcgccgag gaagcccga ctacagcccc ggtagaaaag gccgaggaaa   21420
```

```
cggcctcgcc ggccgctgaa gaggaaaccc cggctcccgc caatgccacc tctcgcaaaa    21480
ccaccagcaa gtaaggactc gacatgatca acgtcagcgg cttcggcacc ggaattgtaa    21540
tagtttccgc ctcatcgttc ccgatggggt tttccttgtc gaagttcgct gatgatgaga    21600
gtccgatatc ctccaaagag ctggagccgt tcggatatga gatgctttat gacggtggcc    21660
tattcgcctt tgacaaggct gctcctctgg aagtatctgt atccgtcatc gcagggagcg    21720
aggatgatat taaccttcgc atccttctca attccaaaaa gggatcattc agatttcttc    21780
cgggaatcat cccggacatg acgactctcg tggccactct tcctgatggc ggccgcaccg    21840
ttctgtccaa tgggactatc atcaagggtc cggccatcga caccatacag aacaccggac    21900
gacgcaaagg caacacgtac acttttgttt tcggtagcta tcttggcgcc cagactgctc    21960
gtcaagccat ttctaacgtt atccaatcgg tactggaggt ggtctgatgt tagggatttt    22020
caccagcctc ctaagttcgc gatcttttc gattgtggac caaaacacaa accagctagt    22080
tgctgcggat ttgaggataa gccgggtcaa cacccggttt tcttctgtag ggcaacgcca    22140
catgctggaa gatggtacga ccaagatgga ttccagaacg atccacccta tggaaatcat    22200
cgtcgaagta ttttgccctt caattgatgt cgtcgatcag atcaatcaat tgctcctgga    22260
tcgcgacaca ctgtacaaag tcatcactcg cggcatggta ttcgaacgga tgatgtgtac    22320
cagcgaagcg ctcaatcaga ctccggatat gatatcggcg actcctgcgc ggctgacatt    22380
ctcccaagtt ctcgtccaga atcccaagcc tataatgttc agaaatgcag gggactcttc    22440
tatgatcgac cgagggctgg ccctagctga agacgtggtt ggctcggccg gcgatctgtt    22500
cgactacgca gtgaacggcg tccagaacgc cgcagacttg ttctgaggtg ccaattgaac    22560
tctttcctca agtctattct caacacgcct actctcacca tacgcgatga tgtcaccaaa    22620
cttcctgtct ggaagagtct tcaagtcaag aaagtggaaa tttactcgcc ggcttccgta    22680
gtgtcgaaac ctctggcgac gaaagaccag acggaagctc aagtgtacac cgaagctctg    22740
gacattgatg tgaagaatgg aaagatcatc caaccggtgc gactccgcat caatgctatc    22800
tgtccggacc tgtccaccgt tgaaagtatc atgaacgctt tcaatgataa cacctcgact    22860
ttcgctatca cttctaagtc gatattggcc gataaaatgg ccatcatgac gctcgatgta    22920
gatcagtcgc cagacatgtt gaacgcggct gagatcaata tggaattcga gcaggttgag    22980
cctccagtat tgaatgaatt cgatcctgcg ttccctcaag atagtccgac ttatgggta    23040 cagattcaat ctcttttctga tgctaatttg ctggatttgg gcgccatcgg cgattcgata    23100
tcttcggccg caaaatcgct atataatcgc gtgaccagct acttctgagg atgtatcatg    23160
cttgaaatca atcttcccga tggccgtcaa actcgcgtac aaatcgaggc gtggtcggca    23220
ttggatggct gggaactcca gcgccgtttc gtcgaattcg ctgtcagcca agattccgac    23280
ttccgccgct cttcaccat ggaaatcctg ggctatgcga aagtgctgct tggcgacgac    23340
gacaccggta ttccgctgac cactgcgcg gtcatcaaca accacctcgg ccactggaag    23400
aacgtggaac tggttttcaa ctctgttctc aagcacaatg gcatcgaccc ggccacgcac    23460
gccgaccggc cggactattg gaacaagtc ggatcgcaga tggccatcgc atttctggcc    23520
gaggcgtcca agctcattgg tccagcaatg aagatcgccg aaggactcgc caacaagccg    23580
gagtgattca tgtctagtga tttggatgaa ttcatacttc ggtatgaggc cgatactgcc    23640
agagccgagc gcaatctgga gcgcctccag aaccagatca ggcgcgtgaa cagcgcatcg    23700
acgagtggcc ttcaggattt gcgccacttc gcagacggcg cggccactga actcggccga    23760
```

```
gtcgttccgc agatcgattc tgtgacgagc gcgattcgcg ggatgaacgc gcaactggcg   23820
ataggcgcca ctggcgtggc cctggtcgcg gccggcgtca aggcgttcat gaacaccagg   23880
gaccagtaca accagcaacg catccaggcg atggatatcg catcgcccc ggcgcgactg    23940 gaagagtacc agcggaagtt tgctcgccag tctggaggca cgatcagccg cgagcagggc   24000
gcggaaatga caaaaaatct ggccgacact ttccggcgag cttatcgcga tatcggacgg   24060
gtcggcccgg aagcgcgaat tctgcgtatg gccggcgttg atgtcgggag cttccaaaag   24120
ggcatgcggc cgctcaacga catcattact gatctggcca cgaaaatggc caagctgaag   24180
ccggacgaaa tttctgccta cgctgatgcc cttggcgtct cgcgagacta cctgagcacc   24240
ctggctaaga tcggcccagc catgggaaaa gtcaccgaga tgacgactgc ggaactccag   24300
tccagggtcc agggcgagtc caacattcag aaattcaacg atgctctggc gaatctcaac   24360
cagacgttca ccaccctgga aaaccgagtc ggcgaaaagc tcgcgcctgc gttcaccaag   24420
ctgatcgaaa tcatcgacaa gatagtccag gctattccca atgaagtgga agaattcgcc   24480
aaggacacca aagcccgctg ggatgacggc atcaccggaa aggctacggt tggtggtgat   24540
atcctttccc ttctcagccc tggcgccctg ctaggccgcc tggcctcctg gggaactcgg   24600
cgtgggatgg aagaggcagg cctgatcgac aagtcgaagg ttcccggcgc tcaaaccagc   24660
gaagacctgg ccaagaaaca agaagaccag gacaaggcta ctaagtccat gaaagagcta   24720
gagaagctgg ctgaccagac cacgaagtct accaatgatt ttgcggtggc gatcaacatg   24780
ttcagtggcg cggtatcgtc gttcgcgaat gccgttgacg agcgccaagc ttgggcagcc   24840
tgggcggggg aaattggtcg ggcggtcggt atgggaagca ccgcgccgac ttcgcgggcc   24900
accggcgtct atccgcacgc gatctatgat cagtcgaaga gtggcgcggc cggacaggtc   24960
ttcggcgagc caatcggcgc ccagtctctt cgcaatcgca tgttctcgcc gcagcgcaag   25020
gccgaaccgg tcaccgttcc atcgtacatc aacgatatca tcaaagatgc ttcgaagatg   25080
tacaacattc ctgagctgga catcaagaaa ctcatataca ccgaaagccg attcaacgcc   25140
agggccacca gcgaagccgg agctaaaggc ctcatgcagc tgatgccgga aatcgccaag   25200
gcgtatggta tcactgacgt atatgaccct cgccagaaca tcctcggcgg aacgcgccta   25260
ctgcgggaaa acctagatcg agcaaatggc gacatgcggt tggccttgac ctactatcat   25320
ggcggactcg atccgaagaa ctggggccca aggactcgcg catatccggg tttggtaatg   25380
agcgctccaa tcgagctgat ggaagaggct cagcgcaagc agaaggctgc ggccatgacc   25440
gtcgccaacg agacgttcgc cccggaaggc ggcgacatgg acattcgtcc ctatgatggc   25500
gggcgactgg aaacccagca ccagggcaag aaggaagatg agcgccgcga agcccgtcga   25560
tatgacgaca gggttgtgcg accggaaatt cgcatcatcg accgcatgcc agaccgcagc   25620
gacggcgaaa tcctcaagat gtctagacgt caagaggccg accgggcaga ttctggattc   25680
cggaagttcc cgaatcaagt tcgcggcgag accaagcaga acatccaggc tcaactcact   25740
gcaggagcca tcgcgcaagt gatcggcgtt aaccccaacc agatcatgcg ccgcgaaatc   25800
agccgttctg acttgctgtt cggatacaac caagccatcc tgggcaagca acaggagatc   25860
aaggccgccg cgaccgaagc caacaacgta ttcctgtctc cagccaagct tgccgaagcc   25920
acggccaagg tgaacgccgc atcgcgagaa atggatattc tcaggacgta cggcgagcaa   25980
cttctgaaga gcgctccaga gcgcggccag gagctgacca tcggtcggat cgacatgttg   26040
gtcaacgtca ccgcgcgcgaa ttctccggaa gaggctcgtg agatattcag caagcagact   26100
gcagaccagc tgactacggc aatccaggac gctcaaaacg attccgcaac taagatactc   26160
```

```
tactgatgaa aaagagaatt ctgcgagtaa cattcaacat gccttatgga cccgaagtca   26220
tccgcgaaga tctggatgtt cgggtccgga ttatgaaggc tgcgttgcgg attcagaacc   26280
gggcgacgat ggaaattttc ggcctcacca ctcagctgcg cgagtctctt ctgtcgcagt   26340
tcaccgcgtg gaagcaccgg caacgtcaag tgggcaggga gatgaattg atgatcaagg    26400 tgtcggtgga agccggctac tctgaccagg ggcgcgagca agtttccaga gtctttgtcg   26460
gcgaagttgc cattgtcgat atcatttctc cgccacctga cattggaatc cgcatccagt   26520
gctataccag gcaaatcgac aggacgaaga ccattcggaa tatgccgccc gccaacacga   26580
cgtttgtcaa gttcgtcgag tggggcgcga acgaaatggg attgaacttc atctgcgata   26640
ccagttacaa cgatcaagtt ctgaagaatc cgggccggtc tatcactgtc gcgtcggcaa   26700
tcctggcgtc gattcaggat atgtacatgc cggacgtggc cgcgttcgtc gatgatgaca   26760
tattgatcgt gaaggaccgc gataaagtca ttcgtccgga tgaggtgacc aacgtcaact   26820
cgtttgttgg aattccatct tggtctgaat ggggcgtgga attccagtgt ctgtttgagc   26880
catcgattcg tgtggctgga ggcgtagcgg tcgaatctct catgaatcca agtgttaatg   26940
gtaactatgt aataactgct ctggaatacg agttggccag tcgggatcgg ccgttctata   27000
tcaaagtcat ggggagtcca gcagcataat ggccagggaa atcaaatcat tcaacatgtt   27060
cggagttcac tatacttcgc ggcaattctc tgctgtcgat gggctcagca tgatgtcgga   27120
aattcagaac gtgccgccag aagaattgct caagggtact gatgtattgg cgcatccgga   27180
agaccatccg gaaggcatct ggcttccatt gactgctgcg aacatcaatc tttatgtcgt   27240
tgatcgagcg aaagtaatag ctcccgtaca agttcttgca cttctgtccg aagtggtaat   27300
cgactggaac tttggttttc tcaaagactg gaccggagtc aagattccat ccagatttgt   27360
cgaagatatc aaaagcgtga agacggcaca ttcaccttct gtagttgcga gcttggtcgc   27420
gaacggctca gcctctatgc gcgagttgga agagtattat tcgactcaag atgcgtttaa   27480
gatgatagac atcatgacgg cgaagagcgt gaacgaggcc ttggcgtccg aagcatcgca   27540
caacagaatc aaaaagggat aattcctaac cgggcctggg aaggctatac tagacctgcc   27600
aaatcagagg cttttcccatg tccaatattt ctctaacatc cgcaaaagct cccgacagga   27660
cgcgactgat cgccgctctt gacgctcggt cgcggcggga tgctctagat ttcgaagtaa   27720
tgataccggc tcaggttgtt caatatgaca gggccgagaa tatcgcgacg attcaacctc   27780
tcatcacctg ggttgacacg gaacacaacg ccgtccaaag gcatcagctg gttgatattc   27840
ctgtaatttc catgggggct ggcggcttcc acataagttt cccgattcag caaggtgaca   27900
taggctggat ttatgcggcc gaccgcgaca cgtctcagtt cctggagtcg ttgtcaatgt   27960
cgaagccgaa caccggccgc atccataagt tcgagcatgg cctgttcatc ccggacgtat   28020
tccgtcgata caccatcaat tccgaagatt cggccgctat ggtcatacaa tcgacttccg   28080
gagcgaccag aatttcgatt cgcggcgaca acatcaagat cactgcgccg tcgaatgtca   28140
ccgtggatac tccgcaggcg aatttcactg gtgatgtgac tatcgctaac actctggttg   28200
taaacggtat caacgtgaac aaccacggcc acctcgaaaa caacccgcct gatgccggaa   28260
cgaagggcgg catgattgct taaggagaat ttcatggcaa gttttgattt ttctgattta   28320
acagcggggg ggtgtaatgg ctaactacaa ctacatcgtc gatactggtg tgatagtcgc   28380
agataccgcc gacgttctga gtgacgttga agccgagttc cgcgccgccc tcggtgccaa   28440
tatcaacttg gccgcgagca ctccgcaggg atcgcttgtc gcggccgagg ccatcgcccg   28500
```

-continued

```
ttccagtgtc atgcggaatg aagcgcgaat tgccaatacc ataaacccga acgtttcatt   28560
cggaacgttc ctggacgcga tctgtgcctt gatggggatc gagcgcggtt ctgacctgtc   28620
aaccttcggc tatggagttc aagtcaccgg ccgcagccaa acccgcattt ccaacgggtc   28680
tagggtccag actccggccg gcgcgatctt cacagtgatg agtgatgtca cgattcctgc   28740
tggtggtgtc gcgaccatcg atatcaaatc gcaggagtat ggcaacattc ctctgccggt   28800
cgggaatctc atcatcatcg acggaacaat tggctggtcc ggagcgaaag tcatcgcctc   28860
cactcgcgtc gatccgggca gccgccaaat gagcgatgca gagttgaaga atgcccgcgt   28920
taatcgattg gccatccaag gccgcaactc gactatggcc atcaaggcgt atgtgagcgc   28980
cgttccaaac gtcacgtcgg tgaacgtaat cgagaacaac accggcgccg ttcaagtggt   29040
gaatggagtc tcgtttaccc ttccgtatgc tgtttgggtc tgcgtcgccg gaaacccgga   29100
taaacaagca gtcgccgatg cgttgtgggc cgcccataac ggcggaactc catgggacta   29160
tggtgcgacg aacaacgcg tcccggtgga cggtccgaat ggcgttcctg tgcgcgatcc   29220
ggcgtccggt cgaaagtatg tcgtgaagtg gaccactcca attatgtacg atggatatgt   29280
taacgtaaca gtccagcaag gttcctcctc tgtagctccg gaagccattc agaacgcagt   29340
ggtcaattac gcccagggga aagtggaagg ggaagagggg ctggtggtgg gcgcgagcct   29400
gtcggcattc gaagtcgccg gcgccatcgc tcgcgaaatt cccggcatct acatcaaact   29460
ctgccaggtc gcgtgcgtcg cggctggctc gccggctccg gctccgggcg atttcacttc   29520
ggaatacgtc atgagcgcat tcggccaggc taccatttcc gttggtaacg ttcgggtgac   29580
tttcgtatga ctctgcctgc gtacaattcg gacatccaac aagctctgaa atggctccat   29640
aaccaggcgc ctggaatcac cggcctgatc cagagaaagg cgcaatggta tgacagattc   29700
agccgccaat tctgggccaa ctgggagcgc gacgttttcc acttgaaaac tgccaacccg   29760
ttcggcctca tggtgtggtg catcatcctc ggcacgccgt cgaaaggatt cggcctatat   29820
ccaaaaaaca gttcttgggc attcggtcgg ctacgccaga acttcatcta tagcggtaca   29880
caagttccgc caccggcaga cgcatcgccg ggcggcaact tctacggtgg cggcaatgcc   29940
gaaattctca acttggacga aatcaggaaa gtgcttcagc taagatatgt agcgctgatt   30000
tcgaacggct cgattgcata tatcaatcgc atgcttcgct acatattcaa tgatgatgag   30060
ccgtgggacg aggcgaccgg tctgtacttc tatctcatgg actcaaccgg cgaggatggc   30120
cctgtggaga acttggccat atatcggaaa gattgggaag gtatggtgct gttgtacagt   30180
tcgcccagaa cgaaccatgt gctgacatcg acccctgcca gcgacgccga ttggccggga   30240
gtcgatccgg ccgcgagcgg ccgtccggta acggtcgaaa cggcgtccgc tacggccccg   30300
gacggctccg ctacggtgtg caagcttact aagccggccg ggagtaccgc ttacgtctcc   30360
gcgccgatag atgggccgct ggggtccggt agcactgtaa cgttctcgtt cttcgcgaaa   30420
gccggctcca cccgtttcat tgcaattcag tcggctgccg atttcccccag tcgagccgat   30480 gccgttttcg acctggattc cgggcacgtg atcagcgatc agatgttgga cagcagcgtg   30540
gtaagcgccc gaatgattcg tctggagaat ggctggtggc gttgcgttct cacgaccaag   30600
accgtcagct cttcgttccg cgctgcttac gtcgcgccgg cagaaaccaa cttcagctgg   30660
attgattcta attcaagtat ggcgattgac gtgcttatct ggggcgctca gatcgaactg   30720
ggtgatactc caaccggata cttggagact accggggcgc ccgtaaccat caccgattat   30780
gtcttgcaga atgcccagac cggaacggtc gagttcaccc agccccttcc gattggagta   30840
gaagcgtatt ggactggcga ctggaaaggc gggtctgcga ccgagccggc cagattcgcg   30900
```

```
gtaggggatg ggactcaaga tacattcaat ctgtccagtc ctgcatacat aggcctaccc   30960
actagtgggg cattcaagtt agaatacaga gttggtccgg cgcttaattt gtcgccgcaa   31020
ttgatcaacc tcatgaatga ccgggcggtc ggtatcatgc cgacttgcgc cggttgcgat   31080
gtaaaagtca ttcaggagta atgacgtgat cacacccgaa ctgatcccca gtccgtttgc   31140
tgcgcagggc gacaaagacc cgatcccgca gacctcttcc actggctttg ccaaccttcg   31200
cgatggctac acgccggact acgaaatcag tctggagtcg aacaacccgc aggccaaagc   31260
ggtcgagcgg aaaattcaaa accaactctt cttcatcgcg acccagaacg cacaggcgtg   31320
gcagcggcaa atggcgccgc cgtggtttca gggcatgccg gcggctacg  aacagaatgc   31380 agaagtcgtg cgcgtcggaa atgacggcat aatgcgtcgc tatcgttcca tggtgaatgc   31440
caatgcgagc gaccctctta gcagcacgac ttgggaagaa caacccgcct ggtcggtgat   31500
gcgctccagc atcccgatgc cggctggagg cccaggccta tcttctggcg gagaagtcat   31560
cacgactggc cgcaacttca acgatttgtt gaatgggacg tgggagttct tctctgattc   31620
agtggttatc gcttctcaga atgccccgt atatccggcg tccgctggtg ccgctgctgg    31680
catgttggag gcgaaatctt ggatatccgg gtccaatacg ttctgcgttc aacgctacac   31740
tgaccgcgtc gggaacgtcg ctgtgcgcgg gcttaatgcc ggggcatgga ccaactggat   31800
gtatgctgta aacgtcatgg ccctccaaca aggtcgagtg acctatggag tcgcggccgg   31860
cccggcgaac gcttacacgt tgacgctcgt tccgcagctc caaggcggcc tggtggacgg   31920
catgatcctt cgggtcaagt tcaacaccgt gaacaccggc gcctctacca tcaacgtctc   31980
cggactcggc gccaaagcca tcgtcggcgc ggccaacttc cctctcactg gcggcgaact   32040
tggccaagga ctcatcgctg agcttgtctt cgacgcagca ggcgaccgct ggaggattct   32100
ggcaggcgcg ccgcgcatcc aagtgggcaa cgcagatcag gactaccagg cccccagctg   32160
gaaacaggtg aaggactatg tagcgtccca aaagctcacc gaagtggatt gggccgatgt   32220
cgtcaacaag ccgaacgtcg ccatccaaga caccacgccg tggttcgcca atctggagct   32280
gtctgacgct cggcctttca tcgattttca tttcaacaac aaccgcgcca aagacttcga   32340
ctatcgcttt atctctgagg ctgatgggtc gatggcattc tattctcgcc aggggtctgc   32400
cggtcctacc caggacatcc tgttcagcag gtcgaatgta acattcctcc agccgcgact   32460
ggatgttgcg aaaaacctcg catacatcgc gaactctggt cctctttggc agaacaccac   32520
tgccgatcag cctggttgga aattcacctt cgcacaaggc gtggacgcca acaacaacgc   32580
ggtgatagca gtcaatacca ccaatcctga cggctcttat cgctcgcaaa tcatgcgatg   32640
ggactgggcg tccacgaacg tcatattcaa caatcgccct ctgtttgctg acaatacgt   32700 tccttgggac tccggaaact tgatccagc caccaagctc actgtcggga ctaccaacaa   32760
catttcggga ccgaccggaa ttcgcaatac caccagcaat accggaaata tgaacacctg   32820
gggctccagc tccacaactg catcgtatgg aaacgcagct cttcaaatct tcggcagagg   32880
gggtggcgag cctgcggcca tctacttcga caactcccaa accggctggt atttgggtat   32940
ggacaaggac ggccagctga agcgagcagg ctggtcgctc ggcaataact cctatgtggt   33000
caccgacgag tcgaatattc gtttccacgt gaattccatg gctggcactc cggtatgggg   33060
cggaaatgaa ttctgggggc cgtggaactt caacccgaac accaagctga ccattaaagc   33120
cggcacgcag gaaactagca gcactgcgat attcagcgga acgatgccgt tcgccccaat   33180
cgcgtctctg tcagactatt cccaggcgcc gttgacggtt acaactcgc cgactggtcc   33240
```

```
atctgctaag cctgccgtca tcgcgttcat tcgccctggc aactgggag cgttcttcgg    33300 catcgatacc gacaacaagc tgaaatgggg cggcggatcg ctcggcaaca gctccaggga   33360
gatcgccgat tccagcaaca tcatgaatct ttgggcggcc aacccgaccg cgccgtcctg   33420
gaacggccaa accgtttggc gatccgggaa ctttgatccg gcaacgaagg tggatttgaa   33480
cgccgcgaac gccaccaacg gcaacatgat cttcaaccgc atcgccggaa ctggcagcgg   33540
gatcgcctct tcaggccgcg tcggcgcaat cagcctccag aacggcgcaa cggcaggcgc   33600
ggccgcagcc gtaacattcg agcggggcgg tggtttcttc gtcaacttcg gtttggacac   33660
cgacaacgtt ctcaaagtgg gcggcggaaa cctgggggcg aacgcctatc ccatcatcca   33720
ctccggcaac tacaacaact acatcaacca ggcgctggtt caggtgggtc ttggcggagt   33780
cggttcctat ggcatctttg cggttctgga cattgccgct ccaaccgcga ccgttcaacc   33840
gggagtggtt gtggacggtt ccattctcat ctactcgtct tgcgccgcaa actacaatag   33900
cggtcaaagg cctgccggaa cttggcgctg catgggatat gtagtcaacc gggatgccaa   33960
cactcctgac tccgcgaccc ttttccagcg agtgacgtaa aatgaaatgg acgcggatca   34020
gaaaccctcg ttggctggat gaaacaaaca tccacgccat ggtgactttc gaggggatcg   34080
gggaagttcc tttcaccgcc aatccgcacg acgtggaggc ccacgaagg gccatccacg    34140 ctgcgatcct atccggggcg cacggaccta tcgccccggt cgatgcgaag cgggagcagg   34200
ccttgcaggg cgctatacgg gccagggaaa agcgggctat ccttcgtgat acccgctggc   34260
ccatagatcg tcacgacgag cagaggcggc tgggtatcga acccacggat ggacctgggc   34320
tgatcgcagc ccttgtttac tggaggcagc agattcgcga ttggaatagc ggggatcggc   34380
cgcgacttcc catggctttg aaaacaatgt tcaaaaatca ggagtactga tgaaaataac   34440
gaaggatatt ttgatcacag gaaccggatg caccacggat cgggcgatca agtggctgga   34500
tgacgtccag gcggccatgg acaagttcca catcgagtca ccgcgagcca tcgcggccta   34560
cctcgccaac atcggcgtcg agtccggcgg actggtaagt ctggtggaga atctcaacta   34620
cagcgctcaa ggattggcca acacctggcc tcgccggtac gcagtagacc cgcgagtccg   34680
cccgtatgtc ccgaacgctc tggcgaaccg cctggcccgt aacccggtcg ccatcgccaa   34740
caacgtgtac gcggatcgca tgggtaatgg atgcgagcag gatggcgatg gttggaagta   34800
tcgcgggcgc ggcttgatcc agctgaccgg gaagtcgaac tattccctgt tcgccgaaga   34860
ctccggcatg gacgttctgg agaaaccgga gcttctggaa actccggccg gcgcgtcgat   34920
gtcttctgcc tggttcttct ggcgcaatcg ctgtatcccc atggcggagt ccaacaactt   34980
ctccctggtc gtgaaaacca tcaacggcgc cgcgcctaac gatgcgaacc acggccagct   35040
ccggatcaac cgctatatga agaccatcgc cgcgatcaat caaggctcct gacattccac   35100
ccaaagaaaa ggccgcttat tcagcggcct ttttgctttc tggctttgcc tcttcagcca   35160
tcttgacctc gaccggcgcg gcggactcct cctgagttac cgaatccaca tagttcccta   35220
gtgaactcag aacgccgatt aacagcgctc ttactacctt gtccttgact gtctcgccta   35280
tgatcttggt cagaacggat atcaactctt cccggagtct tgggctgatt cttggccgaa   35340
agcgcttgcg atgctctttg cgtttcatgt ttagtcctct gtctgcggtc ttctcctcac   35400
cccgataatg gcttggggat gcgctgtgtt agtcggaagg gtcgggcgct attataaccc   35460
gtcgaaaatg ctcgcgctta actgtttaac gatacgcacc gcgatactaa atcgccttct   35520
ttctggccaa ggaactctgg cggcctggtc cggtctaagg cctaatttgt cgacattaaa   35580
acgagaaaac ccggatcgcc tgtaggacaa ggcgtccggg tttatttcga tctagtgtac   35640
```

```
gctagaatca gtggcttccg ccccaaccgt ccagccagca atcgaagacg gcgtgtctcg   35700
gcttgtcctt ggcgccatgg gagaagtgct tgaaccggat gacctggccc ttgagatact   35760
ccctgtcatt ccagcggcgc tgtttctcgt cgtgggtcag gctggaggcc gacacgttga   35820
aggtgactcc aggccacaga cgttcgttgc ggcagacgaa cgcaccgacc attccggacg   35880
gcgacaggtt ttctgcgtgg ctggagcggg ccgtgtggcc aagttcattg atgaaagctt   35940
cattgttgtt gtgcatcaac tcttccacgt cgatgatctc agcttcatcg tagtcgtatc   36000
gcttgacttt cacacagtgc ccttccttgg cagtcgagcg accgaacttg tacagtccat   36060
cagcgcgctt gcccatggac ccttcgaatc ccagcatcgt gtggcggcgc tcgacttcgc   36120
tgaactgttc gatggaagtc accagttcct gctcgaccag gtgaatcctc tcatagccga   36180
ggcagttacg caggaagttc acgcgctcgg tcgccctggc taggcgctct tcggtcggtg   36240
cacgatgatc ggtgaaatca tcgaacacat ggaaagacca gtccggctca ccgctgtggc   36300
ggcgaagatc gccggacgac ttctggaaaa ctttcgggtc gctgatgtcg ccgcagacca   36360
gctcgccgtc caggccgttg aacagtttat cgctgaggta ttcgtagatc gattgattgt   36420
tctgccgctt gagttgacga gtcagcgcct cgccttcgaa tacgaagcag cgaaatccat   36480
cgatcttcgg cgagaaatac atcggcagtt ggccttccag cagcttcggg tcaaaattcg   36540
atgcgagcat gggtttcata cagttctcca gaaaagaagc ccggcgaacc gggctaaatg   36600
gcggtaagcc ggctcagatg gtttcgttgg cgtggttcag ttcggccatg atcgacgcat   36660
agagctcatc cgactccttg atgaacacgc cgtcgtacat gacgcctttg cgatccttga   36720
tggtgtcgta ggcagcagcg tagcaggcga gcatggtggt gtcatgctct tccgtcacgt   36780
cgaacagagt catggcggcc gataccaggc tcttgatggc caacccatga tttccacgtg   36840
ccagagcgcc tgccagatcg ccgaggcgct gcaaatcgtc gccgtaggtg ggatgtactt   36900
cgccgctctc gatgaaggcc gacagatgat cgaacagatt ttcgccgagt gcgcggcca    36960 tgatcgtggc aaccaccatt acgtcgccga tgccatcttt cacatcgacc gggttgttct   37020
gaacccaggc ttcgcatact tctgcgaact cttcgaccaa cttcaggaat tgatctttcg   37080
cagacgagcc tttgatcagg ttacggtcgg aagcccattt aaccaccagg tcgtgaagtt   37140
cgcggctcat gatttgttcg atgttcattc tttcgattcc ttctgtatt gggatttgac    37200 tgcgttgatg atgacgccg tgctctggcg cgatccgtcc ttggttgtgc caaaatagaa     37260
ggccataaca gacttcagtt cggcgaacca atagccgatg atggtgccga tggcgacaga   37320
ggaagtcggg tccatcagcg cctcgcggcc gaaggtgaag attgcgatga tgatgagaat   37380
ggagcctgtc agaagagcga atgtaatcgc cgggcgaacg aaatcgttct gctgcgcggc   37440
aagcctcctc gccgaatccc tgtctgccgc ctctgcggcg aactggctaa gctcggcctg   37500
gagctgattc tgctcagact gaaggcgatt ttgttcggct tgaatcgcaa gctcctggag   37560
acgaacgcgc tcgcgctct ggagttcggc gaggcgcgct agagcttccg gattcgcgtc    37620
tagagcgctc gcgactgagg ctgggtcggc cttcgacccc agcgccgtcg cgacgatagc   37680
gccaacggcg gcgcctgcag gcccacccag gagcgacccc agagccgggg cagccgcgcc   37740
gatcttacta cctatgtctt tccagtccat ttcgactcct caaaagaaag gcgccattac   37800
agcgcctttc tccggccggt gatttagaac tcttcggctt cggtcgcatc gccgacgcca   37860
ccggcgtcac tgcgaggctg ttcctgcttg ctgtagtcca ccttcacctc gccgccgacg   37920
aacgacttgt acaggtcggc cgcagccttg aagtgatccg ggttcttcac caggccttcc   37980
```

```
agctcgaact ggacgccgga ccagctaccc ttgtcgttcg acatgcctac ggtggtcata    38040
cggaccaggt tggcgaaagt cggcggggtg cgcaggccct gcggggtctg aaccttttc     38100 tgggacagcg cggtcatgag cttcttcgag gccttgatct gcgaagacga cagggagatc    38160
agagcctggc cgaaatcgcc ggtgtccgga tcgatgacga tgacgtaatg accacgggtg    38220
tcggcgaagt agtcagactt cttgtcgctg accgaaccgt cttcgttcgg cgcgtacagg    38280
cgtccttcga cttccttcac cttggtcggg tctttcatca tttccttgaa gtcttcgacg    38340
ctgatggcgc ccttgaaacc gccctcggcc tcgcgaccgg cccagcggat gaactcgcgg    38400
cggtacgcgg ccggaatgat cagcaggccg gtcttgccgt cgtaaaccct gccggtgacg    38460
gtattcagga acatgccggc cttcgcgccc tcgatgtact tcggatcgtc ttcatcgacc    38520
tgcggagaca tcttctgcag aacctggatg aaggggatgg cataggactc ggcatcggcg    38580
ccttcgaagc ctgcgccgtc atacgatccc aaatccatga agtcgggaac ttcggtagtt    38640
gcgacggcgc cgccaccggt ggcaacttct acggccttgg tttcttcggt tgcttcggaa    38700
gtttcggttt tcttaccagc catgttaggc tccttgtttg tcgaatttca gttatcgcta    38760
actgtgggtt tataataacg gaagttgcaa ctaagtaaag caaattacat atcaagattt    38820 gctcttttc accttcggtt tcgtgatctt ggcctctttg tattcgtgta cgccgatgaa     38880
atctggcagc tcttcgccct tctccaggta ctcgcgaccg aacgcctgga gggtctggta    38940
atggacatcg cggttgatgg tggcgtcata gccggcttcg atgatggcct cggccgcctt    39000
cttcgcatct tccatttcgc cgcgaccgaa ttcggccaga accttggtct tgatgatgcc    39060
gtcgttgtcg gtttcttcca gccacttcca gaacttcgat ttgttctctt ctttgacgga    39120
aatgatggcc ttcggctcga ctttgaccgt gcgaccgtca gccagagtag tggtcttttg    39180
accaagctcc tccagcagct ccggaatggt gttgcgcttg agggttttca gctcctcttc    39240
cttttcggcc agcgcctttt gaagatcgag gatttcgacg tccagctgcg aagccttgtc    39300
caccaggttc agcagtcgat ggccgatgtc ggtggcttca accgccattt catccatgac    39360
gccaaaatag tcgatttcgc ccggcgcgtt ctctttcaag tattccggga tttcaagctc    39420
ttgctctttc atgtccgcct ccaacttagt gatgttccct tacttgaacc aagtattgag    39480
tagatattat gccgcatctt ccttgatacg gctactgatt tacatattaa atttcgtcgc    39540
gagtgctaac gtcagcctca aacacgccat caacgacata acttgccagg ttgcgtttcc    39600
actccaagct gacctggatt ttctcgtcga tggaatccag acagatcagg tcgaagtaca    39660
gaaccgagtt gacggtgccg attcgatgat ttcggtcttc ggactgcatc cgcagctcgt    39720
tgtcttcgtc ggtcgtgtag tagatggcca cgtctgcggc tgtgagcgtg atcccgatcc    39780
ctgctgcggc cgggttgccc aggaacacct ggacgcgctt ggcctggaaa tcgtcgatca    39840
attttttccg ctcggcctct ttggtctcgc cgtagtaggt gccaaacgaa atcccttggg    39900
cctccaaata cgccttgatc tggtcgattt cctgaatgcg catggcccag acgatgatgg    39960
aacgctccgg gtcttcctcc agcagaccct ccagaagatc agtaaacacg gcgaatcgcg    40020
ggttgtcttc gggcggcagg atcaccggct caccatagac gttgatatag ccggacgcca    40080
cttgcttgag tttcgagcgc gctgccgcgg catcgaaaga tacatcaagc atgaaatctt    40140
cgttctggag aacaaagtgg tagtcttctt ccacgcgctg gtaaaccttt cgttgctcag    40200
gcgacatttc gaagtatatg cgcttgtaca ctttgtccgg caggaatggg agtgcttctt    40260
tcttcgttac acggaaactg tgcggctcga tcagggaccg cagcttgtcc aggttccgga    40320
ataccgggcg cccacactcg tctttttcga ccagttgcgg cggcatggtt tgcttccctt    40380
```

```
ccagcttgcg catgatagcg atcattcgag gatcgtcact gggcaccaag acggaaaatt    40440
cggccacaaa cgcccgatag gatttagtcc ccagaattcc attccgcaag aattggaact    40500
gcatgaacaa atcggtcggt gcccgcgtca gaggagttcc ggaaaggatg cgacgggcca    40560
cggccttctc gcccagcttt acgatctttt tcgcacgctt ggcttgtggg tttttgatcc    40620
tcgttgactc gtccacaatt gcgcaaactt tgaatgtatc aaggaatcgc tcgacctcat    40680
catagccagc ctggtggttg attgcatcaa cgttgatggc gaagacgcga agaactttt    40740 catctgcgaa cgtctcggaa tacagacggt ccaagcgcgc cctggccttt ttggaagtcg    40800
gtcggccgcg ccaatccacg ctcaaagtct tgatcgcgac gtgggtggga atctcgcgca    40860
gaatccagtt ggtgtggacg cctttggggg cgacgatgag cagcgcgtcc acgcgccct    40920 gtaggaagag gcgaacggca tcagccaaag tcgtccaagt cttcccggtg ccctgctcca    40980
tcaggtatgc gaagttccgt tgttcaggg acgctgccag ggcattgaat tggtgctgca    41040
tggcctcggt cttcatgccc ttgacggat atgttttggc tttcatttgt tctccaaatc    41100
ggcgaggaac tgaacaatgt tatccagtcc ttctgcatag ctcgcaactt ccaccaagtc    41160
gcggctgtta agctcgaaca aatcgaacat aggattcagc agcagccaat cggttccgat    41220
cttggccagg acgaagcccc ggccaccca gccgatccgc tcccgaagaa aagggatttg    41280
cccaggttcg aaacatctgg ccattgggca ggtggaagcg cgtttcggcc actcctccaa    41340
agccttgaac tcgacccaga actggacacc tcgacgattc aggcagatcg aatcggacat    41400
gccagaccgc cgcgtctcca gaaagtcgat caggattcgg ccgagcgagc gctgcttaaa    41460
cgcattcgcc gctttcgttt cgcgatcatt catcaccttc gccctctttg gaaactttct    41520
ctgcttgcgc tgccaacttt gacttctcgc gctcggtcaa tatccgcttg acggccttca    41580
cgatgaacat gtcgatgccg ctgagcctcc atcctttgat caggaaccaa gcgccggtcg    41640
gcgtcccttc agcaatctgc tttccgtatt gcagatattt ttcaggccga attctgaaac    41700
gtatcggctg atcaaccgag tcatcaacgc acatgatgtc gagaaactgc gactggccct    41760
tgtacaccgg gttttccct tgatcagccc tcttcttctg gcgaatcggt tcgttctcat    41820
cagacagaac tttttcacc atcttgacaa tgaccagacc atcatctcca tcgcggatat    41880
cccgaatgtt ctgaatgggg tttccggaag ttactccaac cagctccgga ttgtcataag    41940 catgaccca gagcgtgtga gcttcgttca aatctgcgaa ttgaacttca gaattcgaca    42000
gactcgcggc gactttctcc caatcctgaa gcgtcttcag gtgggtgcct gccagctctt    42060
tatattgagc cttcagctcc ttaagatcgg ccttcaactc cttcagatcg gccttcaaca    42120
gtttctccag ttctttgtct tggctgattt tcgccgaaag aatctgggct tccagagctg    42180
ctacatcagc agccttgtcc tcaacatcct gtgccgatat cggcaattg ccagggcga    42240 tcctcgcggc cttgacttcc tcgcgaagac gcaggaaccg ctcggccttc gccgggccga    42300
agcctttggc gttcatgatg ccgccgatca agcgtccatc cgccactacc cagttaagtt    42360
cggaatgctc cgggtccagg gccgtatatt ctacgccttc cttggccaat tcgcgaagta    42420
tggacacagt ttgctggtcg tctttcgccg cccgaagaca cgcggccgcg tattccaggc    42480
gatgatatcg cttcatgtag caggtccagt acgtcaccac agcgtagctg accgagtggg    42540
agcggttgaa tccccaggcg ccgaacgtta ccatttcctg ccaaacacgg tgagcatcgt    42600
ccggggcgac gcctatggtc ttggcgccct cgatgaacaa ttcccggcgc ttgttgaaaa    42660
attcttcgcc ctttcgcgca gacatggctt tccgaatcgc cgacgtttgt tcccagtcga    42720
```

-continued

```
actgcccaat gtccttcaca atggacatga tctgttcttg gtacaggaaa actccatatg    42780
ttccagacag atactgctcg acctgcggga tggtataggt cacaggctcg cgaccggcca    42840
cgcgctcgat gtatttggtg gccatgcccg aagacaacgg gcctggacgg gcgagcgccg    42900
ttatgtggtc gatgttttcg aacgcggtga tattgatcgc attggcgacc gagcggacgg    42960
cctggccttc gaactggaag atgccggaca tcttgtcttc gttgagaatg tccagaaccg    43020
ccttgtcgtt caacggcaag tcgtacagct cttgcgccgt cacgcaatta gcatcttgga    43080
tgacgcccag agttcgaagc ccgagcgcat cgatcttgag aagattcaga tattctgaat    43140
cgggcttgtc gagctgcgcg acaccttcag aagttaccgt gcagaagtcg atgacttcat    43200
cgttgcagac caggatgcct gccgcgtgga ctccagagtg ggatgggtga atttcgaggt    43260
cgcccatgca ggcggacgca atctcatact tttcacggaa gtcgcggccg ggttgagttt    43320
tttcgaaagt gtcctccaat cctttttcat atcgttcgtc cgccgatgta tattcgatga    43380
tcgagttttt gatgttgtcg gtatcgtgga aggggatgcc gaagcgtttt ccgacgtgag    43440
cgataaccga cgcggccttg agtgtgttga tgttacccaa cttcacaacg ttccaagtgc    43500
catacttctg ctggagatat tcgaacacta gatagcgatg ggtatcggcg aagtcgatat    43560
ctatatcggg aagatcggac cgggaaatgt cgataaagcg ctggaagaga aggcgatgag    43620
ggagcgggtc aacctcggta atgccaagga gatagcagac caaagagccg gccgaagagc    43680
cgcgagctgg accgaccagc atgtgcttct ggcaaacgc gaccagatct gccacgacca     43740
ggaagtagct gtcgaaatct ttcagctgaa tctgcttgat ctcttcttgg aatcgatcct    43800
catactcctg ggtccattcc ttgatgtggc cgcgactgag gcgtaggct tgcccctcgc      43860 gagccagagc gacgatatca ccatccaagt ggatcatcgg cgccttcgcc agtttcacat    43920
ccgccaaccg ctcgactacc gcacgagtat tggctgcggc agtatcgaac tcttcgcgag    43980
tcatgatgtg gcgtaaacgg ctccacagct cctcttcggt ggcgatgtgg cgaaggccga    44040
ccgattcccg caccttccag gccgacgcga aatcagcatg gtcgatggac ggcatgtcgt    44100
tgtaagaggt aattaccacc ggctttccga atgccctggc cgtctccata gcgccgtgcg    44160
cggcgaccat cgacgcggga ttgatgtcaa tgtagtcgat tccggccaga tccagatggg    44220
cataggcctc gccagcgaat tgatgacgc cgtcagcttc ctggaattct tgcggagtca    44280
atccttgatt ctggaccgac ttggaagtca agcggtagaa cttcttggtg tccttggcga    44340
gcacccaggc tttgagcttc agctctttct cgccatcgtc ggcgcatttg atcgggattt    44400
ccatgccgaa tccgcgaggc agttctgcct tggtagcggc ttgttcccaa cggacgtggc    44460
cccatgttcc atcatcgacg atggcgacga atggggattc gatctctttg gcgcgctcga    44520
tgatctccgg gaatcgacca tatgcggcgc cgtaggagta accagagcga acgcggagct    44580
gagggaaaga catcatgcgg cctccattgc ttgatacgcc cgatacactc ccatgcgctt    44640
gcagacttcg tggagcagcc gcacgtcgtc gagcgcccgg tgtttctgta catatggtcc    44700
gcagtagtgc tcataaagat gttgcagccg catgcgtgg ccgaacaacg cgccgactc      44760 ttccacagta cagatatcga gcgatgggaa attgacttcg tccaggccga acttgccgcg    44820
agccagatcg caggtcagca tgaacttatc gaatggcagg ttgtgggcaa tattcgcgtc    44880
ggctctggaa aagaagtcgc gaactttctg gcgctgatcg aggaaagatg ggtgcttgac    44940
caggtcttcg ttcttcaacc cggtgatctt ggtgatgatt tcctcgataa cgattccagg    45000
attgcagatg aactctactt catccaaaat cttttcgcca tcagttatca cgccggcgaa    45060
ttcgatgatt ctcggctgct ttctcagact cacccctttgg tggaacggga gtcctgtggt    45120
```

```
ctcagtatcc catacagcga atatcatgtt tgttccctct tatgtcgaaa ggccggctgc    45180
tttcgcgacc ggcctgagga gtataccgcg acggctgaag atttacgcct tctgtccgtc    45240
tttcggcgtg atgcggccgg agcgcatggt ggcgtgaaca aacgccgaat agttgatcga    45300
gtccaaggcc gaatcggcat ccttgaaccc gctattcgcc aggcgagtga gtttacccac    45360
catgtgcatc acgaacaggg cgagtcgatg atcatcggcg gtcttcgcca ccaggccgtt    45420
cgggaagagg atttccatga tctttccgta catcagatca ttgcgaccat aggtgctctg    45480
gcgggcgcgg aagacttctg ctgcggcgta cagattgttg agaacatctt ccgcgaaatc    45540
atctggatgg gaatcatctt cgcccggcca gacggattcc atggcgaacg gcgcggcgtc    45600
ttcggtcggg tcttcggact gagccgtttc agcgagcgga gacggggctt cgcaaacgc    45660
ctcgtcgagg gtaggggcgg agttcggggc ggccaggaac ggctcgcctg ccatgtcgtt    45720
gggcgcgcta tcgggtcgc tatcggccgc gacggcgaag aacggcgcat cgcaaccttc    45780
caggttcagg atgtaggagt cgatccccag gctattgtag gcatcgatga tgtcctggcg    45840
atcatcgaac gccgcgacga tcttggtgac gccttcgatt ttcttcagga tgtcgagcgc    45900
gactgcccgc ttgaactgag gcgccggctc ggtgttacca tacggccgca tgatgagttc    45960
atactcgcga tgttcggcga tgccgagttc gcggtggagc ttggccctgg tctggaaaaa    46020
gtggttgtcg gttcggccgg tgacgaagaa aatcatgagg tcggcgtcga tggcattcct    46080
gatgcgacct acagcgtgcg ggttgagagt gtccttgtcg agacgagaat gatactcgtc    46140
ccattgccgt tccaaggcga agctcttgcg gtggctatcg tcgaatacgc agccgtccag    46200
gtcgaagatg atgatgccat tctttggttt gcgttccata ttcagatttc cttactggtt    46260
gctttctggg tgacggtttt atcgatgaac gtcccatcag aagtgaggcg gaaaacttcg    46320
ccattctgga tgaaatcgaa cgattgcacg ttcatcgtga tgcgaatgga ttcgctgccg    46380
ttggtcactt cgacttgtgc gatgtcgcca actttctcga caatgatctt catgttacat    46440
ggacttccca ttgacggcca cagggttggc ctcttgtttt tccgatcccc agaaatcgcg    46500
gcgcagttct tcctgctcgg ccgagcgatc catccagggg cgatagaact tgcactggta    46560
gataggttcc aacggaacat caatcacagg aatctgacct ggctttgtct ccagagcggc    46620
catgaaccgg tcataggatt tctgctggat ttcctcttca ttcatcacct tcgacccata    46680
gcgcgggaag gcgcaggagc cggtggcgac gcagtgcggc tggagcaggc tgtcgaacat    46740
aggatagact tccagaacca gccggcgcat ttcgcggaat acttcctgat attcaccctg    46800
ggtccgaacg cacaggcgaa ccttcgccat gtcgctgaga gtccgcagat tgaacttggc    46860
cgcgatcttc gtttccatgt tggaagggat gatggcacga gcgtcctgga gcgacgcgcc    46920
ggcctccaga agcttctggt agctggtttg cgcgtcggca atggcgtcat gccacagacg    46980
gttcagctct tcgcggacat ggtaggtcgg gtcaggctcg ccatttaccg tagccggttc    47040
gtcgaattcc cagcggaagg cttccggctg aacgacggcg ctgatttcca gagcgcgact    47100
ggtttcctgc tgataagccc cggtacgagt ccgaacgagt tgatgggtga agttcttgct    47160
gacaccctcg atctggaaaa tgaagtccac gaactcgaac ggcgagcgga tggtgtccag    47220
catgtacttc cagtggtcaa gcttttcggc ctcggtcatg gtcgccgggt cttggccgcg    47280
catgcgagtg gatttcgtcc ccaggagaag ttcccaggcg ttctgggtgt aactgatcag    47340
agaaattttc atcagaaatc ttccggaatt ggcgtgaagt ggaatttttt ggttagagcc    47400
agggccaggc cttgggcttg ctctttacga aggccatact gctctatctc ttccttgagc    47460
```

| | |
|---|---|
| agttcgcagg cctccagacg cgactcatac tcttcagcct cctgaacgga tgagaaaacg | 47520 |
| gttccaccag aggttcggta cacaagttca atcgacatga tgacctcagt agcagcggat | 47580 |
| gatttcggcg cggatatctc gacggtcgag gtagtgctca cgaatcttat cgcgggcgcg | 47640 |
| ctcggcctct tctcgactgc cgaacgacag gttgaacgaa gtgaaaggct tatcgtccag | 47700 |
| ttcagcgccg gtttgataca ggatgcctac cagaacgaaa gacggcgcgg tcttcggctg | 47760 |
| ctggtcggct tgcatttcga gttcgaggaa ggacatagga acctcttcag gatgatctgg | 47820 |
| tgcgtaaatt aatagcgctc ctgctgagca gctacggttt ccggctcgta gatgagcatg | 47880 |
| tcaacgattt ccgggcactg gcctttcacc cagtcgatgg ccgcgaccag tgtggtggaa | 47940 |
| gcggagaaag agaaagtgcg gtaagactca tggatgtacg gcgaccccat cgaatcgcgc | 48000 |
| tcggtcgtgc gagaaatgac tgctttgata ttaacgatcc ggcccatctt cggcctccac | 48060 |
| tttagcgatt atatctgaca ggctcagctt ctcgccattc aggaaataac tggcgcgaaa | 48120 |
| cttcctgtca ccctctggcc cgacgatccg ggccgttatg gtgagactcc cgccgccaag | 48180 |
| ggcatcggtg tccctgaaga aagccagcag cgcccgcttg agcgctgcct cgcgaggatc | 48240 |
| gacggccatt aacctaccac gttccagccg tgctgagcgc accaaaccgc accggcccct | 48300 |
| gcaggaaggc tattcagaag gaacacagga gtcaggcggc cgtcctcggt catatggatg | 48360 |
| aagtagcggg cgccttcacc gagccactcg gccttggcga tagcgcgttc gagattggcc | 48420 |
| ttggtggcgt aggttttggt gtggttcttg tcggtggaga aggttacttc gcgggccatt | 48480 |
| tgtcgattcc ttttggttga agggtttcgc gtttcgatga gggaatatta cgcccacctg | 48540 |
| atccagaagt aaagcacttt tgtaaattac ttcacgaaca tccgcttggc cttctgataa | 48600 |
| gacgaagaag tcatcaggcg ctcgatgacg tccatgtccg aaaccagatc gtccagaagg | 48660 |
| acgttgcgcc aggtagcgaa ccggccgagc gagaagatgc cggcttcatg ggtgagattc | 48720 |
| cagatcatgg attcgcgctc gtcgcggccg agcggaacga ttttgccttt ggtctggatg | 48780 |
| gtcggctcgc cgtcctcgat tagctgtttc cttctgatcc cgaaggccgc gcagacttca | 48840 |
| tccaggtccc atgccggatt ccattcgatg gtttcgatct caccatcagc gttctccaaa | 48900 |
| acgccattcg cgacggattc cacgatcaga gtatcgccgg tgatggacgc gcgaaatgtc | 48960 |
| ccgaagtcgg gactggggaa ataaacggtc tggaagacgt cacaagggat ggaaagcttg | 49020 |
| tatcgactca cgatgatgga tgttcctttg ccgaatgacg ggtcgatacc caggtccatc | 49080 |
| cccgcagcag ccaggttggc gcggaacggc gcggtgctta tgacattcac atggtcatct | 49140 |
| tgccggcgaa ggtactggaa gaaagaggcg tcgaaaggac ggctccaagt gatacgattc | 49200 |
| gcaagcttag ccaccagctt ctcatagtag tcagccggtg cgatccaacg cttttcagtc | 49260 |
| gccagattcc agatggaccg gtccgacagg ccgcccgtta ctttcctgga gtacatgttg | 49320 |
| cagtggtcga tgcgcggctg ggaaatgaac tcgccgtcga tgtagatagc tttgtgtaca | 49380 |
| gtgacttcgc ggaacgggat accggtgagt tggccaatta ctggcgagcg gaatcgcaag | 49440 |
| agggcgttgt gacgctcctt gttctccggc gtcgccgcgt cgatgatttg gcttgagga | 49500 |
| aagcgatgcg cggcgatcag tccggcgagt ccagcaccta cgatgatgac tttctgatca | 49560 |
| ggaatcatga tttgttcctt ctgaatgtac aaaacttgag aggataaaaa agggaccccat | 49620 |
| tttcatgagt cccttgaaga gctagacgat tcagtctcag aagagcggcg gcttactctt | 49680 |
| cttcaccatc ggaaccgtcg gcgccctgat cttcaccgtc gtgctcctgg ccttcatcac | 49740 |
| cggccttctc gtcatcgccc tggccagctt cgtcttcctt cgaagcgatg gcaaccagat | 49800 |
| cgacccagcc catgacttcc agcttgctca gatagctgcg aaccgaggct ccatacagca | 49860 |

```
ggtgtgccac tttctcgccg aaagcttcga tttctaccgg ctcaccgacg gcgcagttct    49920
cgttgatgta ggcaaacacc ttgccgcgaa tcgaaatggc ctgcggggtg ccatggccgt    49980
cgccggtcgg gatgaagtgg gtggcgcggg ggcgacgcga gccgttggac ttcagttctt    50040
cacgacgggc ttcggccttc gcacggcgct cttcctgctc ttccttgcgg cgctgcttct    50100
cggcttcgcg ctcggccttc ttctgctcgg ccaggcgctt gcgctcttct tcacgagcga    50160
ctttctgagc ttcctgggcg gccttcttct cttcggcctt tttggctcgc tcggcttcct    50220
tctcggcctt cttctgctcg cgctcggctt ccttggcctt cgccttctcg gcctgctcgg    50280
cttccttcgc cttggccttt tcagcacgct cggcctcctt ggcggcggcc ttttccttcg    50340
ccttctcggc gcgctctgct tccttcttct cacgctcggc cttgcgcttc tcttcgcgct    50400
cggctttctt ctgttcggct tccttggcct tggcctcggc cttctcggcg cgctcgcgct    50460
ctttacgttg acgctcggcg gccttctcgg ccttgcgcag ggcggctgct tgttccttgg    50520
tcagctcttc gccttgggtc tgttcgttct ggtccatgtt cttactccgg gaatgtttga    50580
aatgatggct tattggcctg tgagaggatt atctctaaac taattgaaga agggaatacc    50640
tttcgcctga acttctctaa atattttcct ttcgggaaag tccagactcc agggaactta    50700
tttatgttag cgaagttttt aactcttacg caaaaacaac aagtattcaa ttgcgcgagt    50760
tatcccagta tacatcaact gactataagg gatggacggc aagttttctt ccaacatggc    50820
gacccgtttc cattccgatc cctgcgactt atggaacgtc atcgcccagc cgaagtcgaa    50880
tccgccaatg gccttctgtg cctccagccg cacatcttcc tcaaccgaaa agctaagagg    50940
attgaacttc acccagcgct catagttcgt gccgataatg cgaactttgg caaacagcat    51000
ttcatccggc tcgtcatcat cttcttggcc ttcggggacc ggcttgaagt ccagcagaat    51060
tgcttgctcg ccgttcatga tgccatattc gtgctggttc ccggtgcaca ccagcttctc    51120
gccgatttcc ggttgtacac ccttgtagcc gaggatgcgg cgcgccctgg cgttcaaacg    51180
gcggcgagta ttgttgtagg cgcaaaggat cacgccatca tcgtccaaga acgtccgcat    51240
ttcgtcgtcc gacatgtcga atccggcccg taccaggatg tcgtcatact cgcggcaggg    51300
taggcgcttg ccctggcgga cgaacatcga cgcccgaacg atattgccgg cgttgcgctc    51360
gatttcggtc atgatggtgt cacagctgtt ctcatggaaa atctggacgc gcgcacagg    51420 aggaacttgg ccaaagtcac caatctccag aaccggaatc cggtgcgaca gcaagcgctc    51480
ttcatcccac tcgccgatca tggacgactc gtcgagcacg accaacttcg gcttctcgtc    51540
gagcgagtct ttgttggcaa acatgatttc gccgtcttca tcttcaccaa tcggccgata    51600
gatgaagctg tggagggtcc gggcattggt gcagcccttc tcgcgaagcc gcgctgctgc    51660
tttcccggtt ggcgcgacga agactgtcca gtccatcgag cagcaaagtt cggcgattat    51720
cttcgcgatg gaagtcttac cagttccggc gaaaccagcg agtctataga cctggcggcg    51780
gtgcgctcga tcacaccaac cgcgatacca gtccacaacg gaattgatcg cgtcgatctg    51840
ctgactgttt ggtcgaaagc cgaatcgctc ttcgatctga tcgacggtga agttagatgc    51900
tgacatattt gcgttctcca acgctaggtt taattgaatt gaggctcagt ttaagcaagc    51960
cgtccacaga ccatccagta tcacgacgat acttgcggcc gtgcggatcg acatagaagt    52020
ttttcgtgcg gcgcagcaga acataatgcc aagcggcgcc gagcgcgtgg actcttcctt    52080
tatatgggaa ggccttcgcc tgctctgcgg cctccttggc cccagggagc cagcggacgg    52140
tcgaaaggac caggaccgcc cccttaatag cctgggaagc ggcgcggccg tcctttgggc    52200
```

```
tatagcgatg tctatcgaag tctacccagt ggtggttgcc gcgccggagc ttgaccgttc    52260
gggatcgccc ctcgaacacc acagtgcctt cgtgagttaa aatatgttcc gccatcgaat    52320
gttcctttat aacgtacagt tatgctttac ctctgcgcag gaagagtata ctatcagctg    52380
actcgccaaa gcgagcgaat ttaatccaac tttacttcgg caggaaagtg gccgatacta    52440
gcgccgccgc ctgtactgcc ctccaaaaca gaggatacat taaatgcaag aatgcaagat    52500
ttaccgcgac caactcccgg tcggtaaccc gaatcccaat gtcgacaaga cccgcgaccc    52560
gaaccttaag cccggtttcc tgcgtcgcag tcgcgagctg acccggcgc tggccgttcg     52620 catccgtcgc gagctgatcc acgccgaagc atccgacttg gccaaggccg gatgggtcaa    52680
ttcacagtcc agcctttatg gatcgaaagc cttcccgcgc cattccgtcg ttcgcgtgac    52740
cggagttccg gaagatggag ctttcatcgg catgctgatc ggcttcatcg agcatcgcga    52800
gcatggcgaa tgggcggtca tggaagccgg aacgaaagaa ggcggcgccg tcattattcc    52860
agtcgatcac atcatgcgag cgtcattcgc cgaagccgaa gagttctctg aaaagtggga    52920
gcggaacctg ggatggcgtc tgctgcgcca gctccgcgag tgcggcgccc ttgccggac    52980 tgaagacgag tttctgcggc ggatcatcaa tcgatacgtt cgtgatcgca cgatcctcga    53040
tcaccacaaa gtcggcgcgg acaaaatcta cactgatgca gtgctcaaaa gcatcggcga    53100
aacatggccg aagattcctt cggggaaatt cgtcggacac cgagtcgcgc agctcctgat    53160
cggccacaag ctaggtcgag cggggaccat cctgaatgac ctggtggact tcttggagaa    53220
gttcgcggcc gggcgcgata agttctcaa catcgccatc tgtaattgag gtgaatggca    53280
tgtataataa accgactttg aatcaccacc atcaaaccgc attgttatat ctgtataaca    53340
atcccgatca gccggccttc acagacccca acaatcaggc gctaaatgaa cttcggcaga    53400
tggggtatgt aaaggcgaaa aaattcgaaa actgggcagg caccggccat cttaggatgg    53460
aatggacgct caccaaggcc gggattgagc gcgtcgaagt cgggtttctg gggaagtgcg    53520
ccgcttgcaa gggaatcggt cagacgttgc ttcgggggaa gtgtactgtt tgcaatggcc    53580
gcggccaggg gtggatcagc gaatggtcgc agaagccaat cgaagataat cctcaaatcg    53640
tcccaaagtt cgaaaagaca gatgcgaatc ggctagcaga cgccattgaa gaaatcgccc    53700
ggctggaaaa ggcactggcc gaatccgaaa agcgcgggag cgaactggcc gcgagctatt    53760
gcgatggcgt gatcggcgat gaatacggcc atcctcattg tcgttataaa gtggagcgcg    53820
acgccgccct ggccgaagtc gagcgcctgc gagaatcaaa aggcgatccc tctggcagct    53880
tcgacagatg tatgaagatg atgtacgagc gagacgagaa agcaaaacag ctggaagtcg    53940
ccctggccag ggtcgcggag ctggaaacgg ctctggcacc attcgcagcg gttgcccaac    54000
cacagccgtg cacgcaacca caggcccatc ctgctcgctg tggttgcgag cggtaagtgc    54060
caagtaagga gttcatgtaa tggaacataa gaaaccttca ccagtagatg gagtcatcat    54120
gaccagcctc gacgttctcc ggaaagcgaa gcccgaagca caggacgagt atgccgtgtc    54180
catgttcgca acggcgattc gccagaaact gcaacgctcc cgcgataaag gccgaggcgg    54240
ctggatcgac tgcgacgaag atattctgat caacggattc gccgaacatg cgctgaaggg    54300 aaaatgagaac aacctcttgg acctggcgac gttcctgatg ttcatgtggg tgcgcggcat    54360
cgatgatgcg aagattcccc cggcgctcga aaaggcgcga cagcacaaga tcatggaagc    54420
ctggagtcga atccatgaag atggcctaaa ctccgccaga aaggcgagtg ctgcgcgaca    54480
gttcgtggaa gtgcctcgac gcaagggcg cccgagcga cttgcatgaa gcctcacgaa     54540
ataagactgg cacaggccga agagttcctg cgcgaactcg gccgagggat tccggacgac    54600
```

```
gaacgggtaa tggtcggcta cgctgaagag gccacagtcc aaaccgacga gaacggccgc   54660
aagctcaacg ccggctggtg gcccgtgccc tggaaggaag gcaagtacat caattccaga   54720
tccaacgcat atgcctgtat ctcgtcgtcc atcaagacgc caaacccgaa gaccggccag   54780
atgcgatact ggcgcggcga ggcctctttc ggccacggcc tggcgttaat ggtcgatgac   54840
atcggctccg gcaaagggtc caagggcgac ttcgaccgcg acgagttccg cgagcgccta   54900
gagccgaccg cgattgtgga gacttcgccg aacaactacc agttctggta tttcttcaaa   54960
gagccgatgt cccacatgct ccagttcaag gcgctgctct attcgttcgt ggaccaggtg   55020
ctaaagaaag gcggcgacaa caccgtcaag gacgtcagcc gttacggccg gatgccattc   55080
ggcttcaaca caagcgcgg gaaagacggc aagttcaaat atgccgacga aaacggcaag   55140
cccgaactcg tgcgactgtt cagtgccgac tattccaagc gctactcgcc agaagagatc   55200
gcccaggcat tcggcgtccg catcatcatg ccacagatga agaaggtgga gataaaccgc   55260
gacgattggt tgtatgacca agtatggttg aagtatgccg agcacatctg cacgaaatac   55320
aagatgggag aagcggcagg cggccaggtc cagcagaata tgtccggcaa ataccgcatc   55380
cgctgtccct ggggcgacga gcacaccaac ggcgatcctt tcggcgcata ctttcgcgga   55440
ccgatacctg gcgccgagca cgaatatgtg ttcggatgcg ggcacgatac ttgccgcaaa   55500
gagcatcgac ggacatgggc ggccttcacc gatgaagtcg tgctacccta tatcgtcgaa   55560
caattggaaa gaatcaacca ccgtcacatc ggtgaggagt agacaatatg caaaacgatc   55620
ctggaatcct gatcacggcc attggcttgc tgttcctcgg ccttatcatc ttcttcgaag   55680
gcctaaaggg atggaaaata caagtcgcaa acttcctcgc gtcgcttctg tgctttttct   55740
tcggcctttc tgctttgacg ttctggttcg tcgttgcgtt tgacgtattt taatcgacga   55800
acggtacaga aattttcgga tggggacgga acttattagc tatgccggtt taggtaggag   55860
ataatagccg tcccttttcgc ctcaatatgt agaggcaatg ttgaatccga tcatgtaaag   55920
cagaaggcgg caaacctaac atgattatcg acgaagataa tatttttgat gatggcgaat   55980
cagggtccag tgagtttgat ctcacacaga tagaagatgc tggaatggac cctttgatga   56040
ccgccgcaag taaagcggcc gacgatgcga ttgcgaggaa tgagacgtac cgagcacaaa   56100
aggcagcaaa gtatgccgag gcgtatgcgg aaccagattt gaagaagcga gcgcgattgc   56160
tgatgctcga tcaggccttt gatcttccgg tcagccggct ggtgaaagga ccgttcgatg   56220
acttcatcac caagtacagc tcgacttcag acagcaacta cctcgcggtc tatgacacgt   56280
tgttctgtaa gggcgacgga accgtccac acccgcactt cgacgagttt cgcggccggc   56340
tggtggacca tcgcggcgtg gcgttcaaca acaagaccct cgatccgatt gacctgatgg   56400
gcgccctcgc ggctgcggcc ttggacgatc cctcgattaa gaagacgatt gagacttgct   56460
gcgtttgggc gcgtcgatat cgccgcaact cgctgatcga gacgtttgag aagaagatac   56520
cggattggga cggcgaagag cggatcgaaa cgctgctgat cgacttgttc aaaccgttcg   56580
acaccgagct taaccggatg gtgagcaagt atttctggct gagcttgtac tgccgcatca   56640
actaccctgg aatctcggcg ccgatctcgt tggcgttgat tggtgggcag gatgcgggga   56700
aatcctattt cggcctgctg atctgcaaag aactgtctgg cggtcgcgat ctggctccag   56760
tccagctcga tctgagccga cacgaccaga cgccattcct gcgcaatatc accggcaact   56820
cggtcattgc gaacgtcggg gaatgtccg gcttcaaaaa gggcgacatg gagcgcatca   56880
aggagttctt ggttcgttct tcggatacat tcgaccagaa gtttgagccg ggagaaacga   56940
```

| | |
|---|---|
| tcaagcggca atggatcacc atcatggacg gcaacggata cgatggactc cagcgggacg | 57000 |
| actccggcaa ccgtcgattc tatccgatgt tcgtggcaca acttcccgac gaagatggaa | 57060 |
| agccgaactg ggttaagccg ggcgatggta atgaaccgtt caaggtggac ttcaccgact | 57120 |
| tcggccgcaa attctggcaa gcgatggctg aatgccgcgc atggatcgaa gagcatggtg | 57180 |
| tcgatggata cctggatatg gtgtcggaag cgaaccgcga agtgcagaag ttctctattt | 57240 |
| cggaaatgga gaatgcgcgt ggcgtggttc gtgatgacac gattgatatg tatctgatca | 57300 |
| acgtgctgat cagttgcgag ttcgaagaga tcaagcctgg caggaattca agaatcctg | 57360 |
| gatggagagt tgacactgta gccattctga atggttcga catcctcgcc aggaagaagc | 57420 |
| cgatttctcg tcaccttact ccgcacttga aggcgctggg atttgtcccg aataagaacg | 57480 |
| gcctgaatgg atggtgctta cctgtcgata aggttgcacc tggatggacg aagggtatgc | 57540 |
| atatgacact gccgccgttc aatgatgcgc ttgtgtactt gctgagaaag ggcgacccgg | 57600 |
| acatcactga tgaggctgca atgacaaaga ttcgggcggt acgggccgag cgagctaaga | 57660 |
| ttttgggcga ggatttctga tgtagtggtg gagtgtactt ggactaggcc gccttcgggc | 57720 |
| ggtcttttct ttggtgcggc gtacattcga tttcggtggc ggccgagtga gattcggaag | 57780 |
| ctatccggta attaggatgg gatggtgtg gcgtattgtg gaaagttcgt ggatggtgga | 57840 |
| tcgagaattt tgtgtggtga gggggtggat tatggaaaat cgacgattct gactggatt | 57900 |
| ttggggtcgg ccgcgtcgag cttaccggta atttacgaaa ccaggaatta gggtcgagcc | 57960 |
| ttagtgccgc gtgggcttga agcgcttttcc cggatacttt ccggattcgg aagcagccgc | 58020 |
| aaaactatac tacagcgaaa atcgattgca caatcctaat agaaaaaatc tatcacggac | 58080 |
| gttacctatc tttaaaatta ataaaattaa tagtaatttg gtaatttggt atactttagt | 58140 |
| atttgaaagc cttgcggcac taagcctgta cacttcccgt caagtttccg attccgctca | 58200 |
| actcgcggca gggtcgccgg aaacttccgg acttacaatc catgggtcgc ggcaacacca | 58260 |
| cggcggacta agcggcaagt gccaaaactc gacgaacgga accggaaatt tgggagcgcg | 58320 |
| acagaatagc tcagctggac atatttctaa cattcgattt aacactcaat ccaaacactc | 58380 |
| accaccatcg tctcccacca acagccgact cgaccctcac ccaccagcag accgcccata | 58440 |
| taacatccta taacaccacc taacactcat tcaccatcaa acccacccag acctacagcc | 58500 |
| cacccacaag cagcccatag acgcgatccc tggcccata gtacaatcgc gccatactca | 58560 |
| gtgtcgcggc agagcaccag gggccatccg ccaaccaagc caccacgacg actccagaat | 58620 |
| cgaactccag ggacgcagca acaaatgacc gccaaattct acagccccga cgatttagtc | 58680 |
| acgccacagg aattcgcaga cccgcatttc gcggcgatca accaaaagcg attcgacctg | 58740 |
| tacatcgacc tgcgcgtcca aggctacagc tcctggcggg tcttccgagc catctggggc | 58800 |
| gaggagcata tggacggtcc cgctcaggcc cgcatcttcg cgatggagtc caatccgtac | 58860 |
| tatcgcaagc agttcaaggc caagttgaac gcgaccaaaa cgtccgactt gtggaatcca | 58920 |
| aagacggcgc tccatgaact cctccagatg gttcgcgacc caaccgtcaa ggattccagc | 58980 |
| cgtctgtcgg ccatcaagga gttgaacgtt ctggctgaaa tcacgttcgt ggacgagtcg | 59040 |
| ggcaagacca ggatcggtcg cggcctggcc gacttctacg catcggaagc cgaggctcag | 59100 |
| accgcgaccg tcgctgctgc ggccgaagcc aatggatatg tgccggaagg tgaagaggga | 59160 |
| gatttcccgt ctccgtctcc ggaaccgacc gaggaagacc gcgccaaccc catttagaca | 59220 |
| taaaataaca tcattctagg cccgaatcgg accgaactaa ggcgaaggta gcgggaaggg | 59280 |
| acgaaaaacg attctagggc ggttctagga agttgacgcc taaccctcag aaactacaaa | 59340 |

```
ccccggactc tagttcagaa tccggggttt tcttttgggg ttcttattcg ccagtttcga   59400
tgatttcgaa gttgtatttg acgccttcgt gctcgaaggt caacttgcct gccgctttca   59460
gttgcatgcg gaatcggatg cacttagagg aaggcaaacc gaactcgatg aaggctgcgt   59520
tgcaggattt gaactctccg cgcttgcctt tcacggtgac cgctacgcca tgacgctcgg   59580
tgcgcttgcg ggcaacttct gggtcttttcc aggagttggc tatggctgct gacaggtctt   59640
tggtctcttt ggttttctcc ggcgcgttct tcgcctcttc gcgcattttc cggatttctt   59700
ccagcgcttc ctcttcggtg atttcttctt ccggcttcag attctcttcg gccttctctt   59760
ctgccttctt cttggaagtg cgggttttgt aaacctttgc cggggcttcc tcttcctgga   59820
aggcttcttc ctcggccggc agagcattca ggatggcgag gcagcgacgc tcagcagtct   59880
tgcggtcaga gaaacgcttg acggtcgcat cggcgttgtg ggcgttgtag aaggcgacca   59940
gttctttcat ttctgcgtcc tggatgtcgc cgaaggtttt gatggagttg gtcatttttgc   60000 gatcctctgt tttggaagat ttcgtttggg cttcagtttg tcgccccgtt gaaagagatt   60060
atgcctaggt cgatgctgcg tgtctacatt tatttagcag aatgatggtg aacccgacga   60120
acggtcgtcg gatgtgaaaa caccgcagag caggctgcgg tgtttgttgg cgttggggtg   60180
atgtcagaaa gtcgggacgg tgataggctc gatgggcgga tcgccgggcc tgtcgttgtc   60240
cgatgcgggc gccgggctgg aagggatcgc acccgaccga agcgccagcg attccgactg   60300
cctgcttacc tgtggagctg gaggagccgc tggtgccttt ggagggattg gaggcaggtc   60360
atttcgaccc ttgaccattt gcagaggttc tggaagatcg ggaagcgcgc cagcgatttc   60420
gccatacgtc cgcgccggat cgtcgccgaa catttcggcg gatcggttat ctttgacgat   60480
ctggctgatg gccgtcacat cgccgcccgg ttctgcagga tcgatgccca cgaatggagt   60540
ggtcacgcag cgcatgttcg gatgggtagg cagatttttc agaacgatgg agtctgccca   60600
gacatacgga ttcttgtggt tgccgggtcc gtggctgatg atctcggcag gaatatggcc   60660
gttcatggtg agccattccg ccatcccttg ccgagtcagc gggcttacca cgatctggcc   60720
agtggactct ttggcgatgg cgaacagatc accgaattcg aatccaatga ttgtgtagtt   60780
ggacctggac tcgccgacga aagccagagt ttcgatgttg tggtggatat cttgttcttc   60840
ccagatgtaa agcatgatgc gctcctcaat aaggctgctt gttgtattcg accagagaca   60900
taccggccgg aactttgaag cggacgtatt cgatcatcat cgccgtgcga cgccgattcg   60960
tgccagactc gtcattgacg aagagttcgc actgatgcgg aatgactcgc gtcaccaggc   61020
cttcgccttt cgagccgtag aacttgatgt aggctgcgac gcctcgcgtc atgttcagac   61080
ggatcgtttc gcagagtcgc tgcgcggccg acgcgctgga cagatcggtc ggactgaccg   61140
tcacccagta atgccacctt tgttctttat cggacataag ctgccctcca atgagaaagc   61200
ctctgccgag tcgcataggc tggttgttgt tagtcgcgct tcaacagaac gactttgtca   61260
tatgcgcgat atttaccgcg ccagtcttcc cagtagtcgc cggccgggca ggtaagctcc   61320
agggtgattt cgtcgcgcca gcattcgaca gaaaggacaa ttgccttgtt cctggctgcg   61380
gaatccgccc tgagcttaat cagaatttcg tcgccagttt tcaactcatc aactctcaca   61440
actttggcca tgacacactc ctgtttgaag aggcgcggcc ggaaccaacc cagccgcgcc   61500
gatggattaa cgtttgtgaa ggatggacac tgcgtccacg tcgaggatgc tgatggtacg   61560
gcgacggcgc ggattgctgc gttcatggat gcgaatcagg ttcgcaactg gagcttcgtc   61620
caccacccat acatcttccg gcttctgcgt ccggagcagg accgtcactt ctgcgttctg   61680
```

```
ggcgaggccg ttgcagatga acgtgaactt ggacgaggga gttctgtaca tgtcgagatt    61740
ccttttggga cttcgggtcc ggcttttcag tcggtgaaga gattatgcct gatcatcacc    61800
gtcgagtaaa gcacttatgg accaattctc cagttaaatg gaaccaaagc gcggtatcgc    61860
tgatcgctac gcttccacgc catggcsc tt cttgctcaca gacttcgaac cacaagctaa    61920
tttccatcct ggccaggact cggccgaagg attcgagccg acgccggctg ccaggatgt     61980
cgacattcac ccgtcgatta atttcgtacc ggcgaccgtt gatgacgaag accaggcgca    62040
gggtgcgtcc gtccagacat tcccagtatt tggtttcata ccgaagccag tagcgcttgc    62100
cagccgggcc taccatggtc atttaatcga tgctcctggc cgcgccacgc ggtccggtcg    62160
gcgggacggg atcgaaccga cccaggatgt agtcgggccg gcgcgcttcc tgaggacaca    62220
cggcgagaag gcgccatcct gcgtccaggg cagactggag ttcgtccgtg cagcagtctt    62280
ccttgagcag cagacggttg acgttctgga gattcggacc aggtatggcc gatcctgtga    62340
gtgagttcca accttcgacg ccgtgcacca tctgcggttg gttgatgtag ccttcggacc    62400
tgccagccaa ccggcttgcg gccagctcca ggcgctccag catgggtcgc agagcggctt    62460
ccgggtcaac gtcgtcccag agaaggacca ggttgatgat ggtgtacgga tagtccttgt    62520
ccagatccca ggccgaagcg gtcaggcggc ccaggccgat tcattacac ataacgggaa     62580
cgtcgttgct ccaggtggac ggctcccagt tccgctcacc aggattcccg attgttacgc    62640
cttccaggtt ccccaggaga acgtggagct tgctgacata ttccgcctcc aaggctttcc    62700
gctcttcgtc ggtctggttg tggcgataga aggatggagg gctgactttg gcatggtaga    62760
gtttcatgat tgttccttta tgtagggttc aacttcaaag aatttcgtcg cagaacttct    62820
cgaaaggact ccgccttttc ttctcgcagg cggcacaggt gatttccagg gccggaatct    62880
cgttataggt cttgccgaag tacagccagc gtttacatag gcttcgaccg tccgccatga    62940
agaagtgagc ttttcgagca gcgccgggtt gcgcccagcc gctcggcatc ttactggact    63000
tgttcatgcg gtctccctct tcggctcagg aatccatggt gtgatttcgt ccgcccattc    63060
cccatcgatg aacatcaagg acagaagacc atagcgcccg aagctgaagc ctacatagaa    63120
cgatccgggt tccacttcca tgctggcggt attgcgttct tcgatcatct ggaaatcgaa    63180
cattgcatag ctcataccat caccatgtcg atttcattga tgaagaaatg gacatcgaca    63240
ccatcggcgc ggccggtgta acgcagccga gtcgtcccat caatgtgggc ttcctcgacg    63300
ccgatgactt ccaggatggt gtcgttgcaa tacagcttga cgaacatctt gatgccggag    63360
ccaatcgcct cgaaggcaat ctgcttgtac aggtcttgct tgatcatgct ttacgctcct    63420
gtttgcggat gtattctgcc ctgacttcgg cttcgaattt cgcccaaagc gcgttgtcga    63480
ctggacccca gggaccggtc tgagttccgt ccaccggtgc gaacttgcca ccggcgcggc    63540
gatatttgga cagagttttc aggctgatga tcttctcatc ttgggaatcg aattggacta    63600
tcatttgacg tacttcccga agtagcaggt gtggaggatt ccaggccctt tggagatagc    63660
cttcagcttg atgccgaaat tcttgatcgc ccagtccaga tcgtggtgat agaactcgat    63720
gatgttgacg atttgaccgg cgctgtagtg gatgacgcga accttgccgt tccagcggaa    63780
atcttcgcgg ctgtttacgg cctcgacttc gatggtgtcg tttctgccga tggtccattt    63840
ggagctagtc atgtcgcaat cctcttttg gagtgtttcg cgtttcgatg aggannnnnn      63900
nn                                                                   63902
```

<210> SEQ ID NO 2  
<211> LENGTH: 66024

<212> TYPE: DNA
<213> ORGANISM: Bacteriophage P1777

<400> SEQUENCE: 2

| | | | | | |
|---|---|---|---|---|---|
| cgttcgacga | cttcatcacc | aagtacagct | cgacttcaga | cagcaactac | ctcgcggtct | 60 |
| atgatacgtt | gttctgtaag | ggcgacggaa | ctgtcccaca | cccgcacttc | gacgagtttc | 120 |
| gcggccggct | ggtggaccac | cgaggcgtgg | cgttcaacaa | caagaccctc | gaccccattg | 180 |
| acctgatggg | cgccctcgct | gctgcggcct | tggacgatcc | atcgatcaag | aagacgattg | 240 |
| aaacttgctg | cgtttgggcg | cgtcgatatc | gccgcaactc | gctgatcgag | acgtttgaga | 300 |
| agaagatacc | ggattgggac | ggcgaagagc | ggatcgaaac | gctgctgatc | gacttgttca | 360 |
| aaccgttcga | caccgagctt | aaccggatgg | tgagcaagta | tttctggctg | agcttgtact | 420 |
| gccgcatcaa | ctaccctgga | atctcggcac | cgatttcgtt | ggcgttgatt | ggtgggcagg | 480 |
| atgcggggaa | gacttacttt | tcaatcttga | tctgtaaaga | gttgtcgagc | gaccgaaagt | 540 |
| tatcgccggt | ccagcttgac | ctgagccgtc | atgaccagac | gccatttttg | cgcaatatca | 600 |
| ctggcaactc | ggtgatcgcg | aacgtcggcg | aaatgtccgg | cttcaaaaag | ggcgacatgg | 660 |
| aacgaattaa | agagttcctg | gtgcgatccg | atgatacttt | cgatcagaag | tttgaaccag | 720 |
| gcgaaactat | cagccgacaa | tggatcacca | tcatggacgg | caacggctat | gatggtcttc | 780 |
| aacgggatga | gtcaggaaac | cgtcgatttt | atccaatgtt | cgtggcgcaa | cttcccgacg | 840 |
| aggatggcaa | gccgaattgg | gttaaaccgg | gcgatggaaa | tgaaactttc | gcgcgttgact | 900 |
| tcaccgactt | cggccgcaaa | ttctggcaag | ccatggctga | gtgccgcgcc | tggattaagg | 960 |
| cgaatggcgt | ggagggatat | ctcgatctag | ttcgggcgac | caacaacgaa | gtccagaaat | 1020 |
| tctctatttc | ggaaatggag | aatgcgcgtg | gcgtagttcg | tgacgatacg | attgacatgt | 1080 |
| atctgatcaa | tgttctgatc | agttgcgagt | tcgaagagat | caagcctggc | aggaatgcca | 1140 |
| agaatcctgg | atgagggct | gataccgtcg | ccattctgaa | atggttcgat | attctcgcca | 1200 |
| ggaagaagcc | gatttctcgt | caccttactc | cgcacctgaa | ggcgctggga | ttcatcccga | 1260 |
| ataagaacgg | cctggctggt | tggtgcttac | ctgtcgataa | ggttgcgcct | ggatggacga | 1320 |
| atggcatgca | cacgacgttg | ccgccgttca | atgatgcgct | tgtgtacttg | ctgagaaagg | 1380 |
| gcgacccgga | tatcactgat | gaggctgcca | tggcaaaaat | tcgggcagtc | cgggccgagc | 1440 |
| gagccaagat | tttgggcgag | gatttctgat | gtagtggtgg | agtgtacttg | gactaggccg | 1500 |
| ccttcgggcg | gtcttttctt | tggtgcggcg | tacattcgat | tccggtggtg | gccgagtgag | 1560 |
| attcgaaagc | tatccggtaa | ttagggtgag | gtggcgatgt | tgcattatgg | aaagttcgtg | 1620 |
| gagggtggat | cgaggatttt | gtgtggtgat | tgggtgaatt | gtggaaaatc | gccgattctg | 1680 |
| actggatttt | tggggtcggc | cgcgtcgagc | ttaccgtgaa | tttacgaaac | caggaattag | 1740 |
| ggtcgagcct | tagtgccgcg | tgggtttgaa | gggcttaacc | ggatactttc | cggtttcgga | 1800 |
| tgcagccgca | aaagtatact | acagcgaaaa | tcgattgcac | aatcctaata | gaaaaaatct | 1860 |
| atcacggacg | ttacctatct | ttaaaattaa | ttaaattaat | agtaatttgg | taatttggta | 1920 |
| aactttagta | ttgaaagcct | cgcggcacta | atcttgtaca | tatcccgtca | agtttccgat | 1980 |
| tccagccagc | tcgcggcagg | gtcgccggaa | acttccggac | ttccaatcca | tgggtcgcgg | 2040 |
| caacaccacg | gcggactaag | cggcaaggac | caaaactcga | cgaacggaac | cgggaatttg | 2100 |
| ggcgcacgac | aaaatagctc | agctggacat | atttctaaca | ttcgatttaa | cactcctctc | 2160 |
| aaacgctcac | caccatcgtc | tcccgccaac | cgccgactcg | atcctcaccc | accagcagat | 2220 |

```
cgcccgtata acatcctata acaccaccta acactcattc atcatcaaac ccacccagac    2280
ctacagccca cccacaagca gcccatagac gcgatccctg gccccatagt acaatcgcgc    2340
catactcagt gtcgcgacag agcaccaggc cccatccacc aaccgagcca ccgcgacgac    2400
tccagaatcg aactcaggga cgcagcacca aatgaccaaa tactacagcc ccgacgatct    2460
agtcacgcca caggaattcg cagacccgca tttcgcggcg atcaaccaaa agcgattcga    2520
cctgtacatc gacctgcgcg tccaaggcta cagctcctgg cgggtcttcc gggccatctg    2580
gggcgaggag catatggacg gtcccgccca ggctcgcatc ttcgcgatgg agtccaaccc    2640
gtactatcgc aagcagttca aggccaagtt gaacgcgacc aaaacgtccg atttgtggaa    2700
tccaaagacg gcgctccacg aactcctcca aatggttcgt gacccaaccg tcaaggactc    2760
cagccgtctg tcggccatca aggaattgaa cgttctggct gaaatcacgt tcgtggacga    2820
gtctggcaag accaggatcg gtcgtggttt ggccgacttc tacgcatcag aagccgaggc    2880
tcagaccgcc accgtcgctg ctgcggccga agcaatggc tatgtgccgg aaggcgaaga    2940
gggagatttc ccgtctccga cgccggaacc gaccgaggaa gaccgcgcca accccatta    3000 gacataaaat aacatcgttc taggcccgaa tcggaccgaa ctaaggcgac ggtagcggga    3060
agggacgaaa aacgattcta gggcggttct aggaagtcgt agcctaaccc tcagaaacga    3120
caaagccccg gactctagtt cagaatccgg ggctttcttt tgggcgcctt attcgccagc    3180
ttcgatgatt tcgaagttgt atttgacgcc ttcgtgctcg aaagtcattt tgccagccgc    3240
cttcagctgc atgcggaagc ggatgtgttt cgaagaaggc aggccgaact cgatgaatgc    3300
tgcgttggtg gaccggaact cgccgcgctt gcctttgaca gtcacagcca cgccatggcg    3360
ctgagtgcgt ttcttggaaa cttccgggtc tttccaggag ttggcgatgg ctgccgacag    3420
gtctttggac tctttggctt tctccggagc gttcttggcc tcttcgcgca tcttccggat    3480
ttcttccagc gcttcctctt cggtgatctc ttcttcaggc ttcagattct cttcctcggc    3540
cttctcttct tccttcttct tggaagtgcg ggttttgtaa accttggccg gggcttcctc    3600
ttcctggaag gcttcttcct cggccggcag agcattcagg atggcgaggc agcgacgctc    3660
agcagtcttg cggtcagaga aacgcttgac agtcgcatcg gcgttgtggg cgttgtagaa    3720
ggcgaccagt tctttcattt ctgcgttctg gatgtcgccg aaggttttga tggagttggt    3780
cattttgcga tcctctgttt tggaagattt cttcgggct tcggtttgtc gccccgttga    3840
aagagattat gcctaggtcg atgctgcgtg tctacattta tttcatcaga tttatcgcaa    3900
agccgacgaa cggttgtctg atgtgaaaac accgcagagc aggctgcggt gtttgttggc    3960
gagggcgatg gtcaagcgaa cggatcgccc agcatatctt cagacggggc acgttgcata    4020
tcgcccagct tgtctttgtc agttgccgga ctggacggga tcgcgccgga ccgaagcgac    4080
agagattccg actgcctgct cacctgcgga gccggaggag ccggaggagc cggaggagcc    4140
ggaggagccg gaggagccgg aggagctttt ggcgcagtag gggcaggcgg gaccggcagg    4200
cctggaggag ccatcggcgc catgggcggt tctggaagat caggaagact cggcgctatg    4260
ctgccaaagg accgctgcga ctgctgcgcc ggattgtcgc cgaacatttc ggcggatcgg    4320
ttgtccttga tgacttgacc tatggccgtc ttgtcgccgc ccggctctgc cggatcgaag    4380
cccgtgactg gcctggttac gcatcgcatg ttctgatggg tcggcagatt tttcagaact    4440
atggaatctg cccagacata cggattcttg tggttgccgg gtccgtggct gatgatctcg    4500
gcaggaatat ggccgttcat ggtgagccat tccgccatcc cttgccgagt cagcgggctt    4560
accacgatct gaccagtgga ctctttggcg atggcgaaca gatcaccgaa ttcgaatccg    4620
```

```
atgattgtgt agttggacct ggactcgccg acgaaagcca gagtttcgat gttgtggtgg   4680
atgtcttgtt cttcccagat gtacagcatg gttcgctcct caataaggtt gcttttggtg   4740
ttcgaccaga gacatgccgg ccggaacttt gaagcggacg tattcaatca tcagcgccgt   4800
gcgacgccga ttcgtgccag actcgtcgtt gacgaagagt tcgcattggt gcgggattac   4860
tcgcgtcacc aggccttcgc ctttcgagcc gtagaacttg atgtagaccg cgacgcctcg   4920
cgtcatgttc aggtggaccg tttcgcagag tcgctgcgcg gccgacgcgc tggacagatc   4980
gtttggactg accgtcaccc agtaatggcc actttgttct tgtcggaca taagctgccc    5040 tccaatgaga aagcctctgc cgatccgcag aggctggttg ttgttagtcg cgcttcaaca   5100
gaacgacttt gtcatatgcg cgatatttac cgcgccagtc ttcccagtag tcgccggccg   5160
ggcaggtaag ctccagggtg atttcgtcgc gccagcattc gacagaaagt acaatcgcct   5220
tgttccttgc tgcaccctct gcggcatctg ctctgagctt aatcagaatt tcgtcgccag   5280
ttttcagctc atcaactctt acaactttgg ccatgacaca ctcctgtttg aagaggcgcg   5340
gccggaacca acccagccgc gccgatggat taacgtttgt gaaggatgga cactgcttcc   5400
acgtcgagga tgctgatggt acggcgacgg cgcggattgc tgcgttcatg gatgcgaatc   5460
aggttcgcag ctggagcttt gtcaaccacc catatatctt ccggcttctg cttccggagc   5520
aggaccgtca cttctgcgtt ctgggcgagg ccattgcaga tgaacgtgaa cttggacgag   5580
ggagtcctgt acatgtcgag attccttttt tggacttcgg gtccggcttt tcagtcggtg   5640
aagagattat gcctgatcat caccgtcgag taaagcactt atggaccaat tctccagtta   5700
aatggaacca cagcgcggta tcgctgatcg ctacgctccc acgccatggc ccttcttgct   5760
tacatacttc gaaccacaag ctgatttcca tccttgccag gactcggccg aaggattcga   5820
gccggcgccg gctagccagg atgtcgacat tcaaccgccg attgatttcg tatcggcgac   5880
cgttgatgac gaagactagg cgtagggtct gtccgtccag acattcccag tatttggttt   5940
catgccgaag ccagtagcgc ttgccagccg ggcctaccat ggtcatttaa tcgatgctcc   6000
tggccgcgcc acgcggtccg gtcggcggcg caggatcgaa ccgccccagg atgtagtcgg   6060
gccggcgcgc ttcctgagga cacacggcga gaaggcgcca tcctgcgtcc agggcgtact   6120
ggagttcgtc cgtgcagcag tcttccttga gcagcagacg gttgacgctc tggagattcg   6180
gaccagggat ggccgagctg gtgtgcgagt tccaaccttc gatgccgtcc accatctgcg   6240
gttggttgat gtagccttcg gacctgccag ccaaccggct cgcggccagc tccaggcgtt   6300
ccaacatggg tcgcagagca gcttccgggt caacgtcgtc ccatagaagg accagattga   6360
tgatggtgta cggatagtcc ttgtccagat cccaggccga agcggtcaga cggcccaggc   6420
cgatttcatt acacatcacg ggaacgtcgt tgctccaggt ggacggctcc cagttccgct   6480
caccaggatt cccgattgtt acgccttcca ggttccccag gagaacgtgg agtttgctga   6540
cgtattccgc ctccagcgct ttccgctctt cgtcggtctg gttgtggcga tagaaggatg   6600
gagggctgac ttttgcatgg tagagtttca tggcggttcc tcggttttg aaggcttgaa    6660 cgttagagaa tggtgtcgca gtatttctcg aaaggactct ggcgcttctt ctcgcagatc   6720
gcgcaggtga tttccaggtc gggcagctcg ctgtaagtct tgccgagata cagccagcgc   6780
ttgcacagac tgtggccgtc cgacgtgaag aagtgagctt tcgagcagc gccgggttgc    6840 gcccagccgc cttgatcgtt tttgcgcttg ctcatgacga tatctcctct ggatcgggaa   6900
tccatggtgt acgttcagtc acccaaactc catctacata gatcaggact gacagagcag   6960
```

```
tcgcgccaaa cccgaagcct acatagaatg aaccgggatc gatttccatg gtggcgctat   7020
tggtggtgct attgcaatcg acttcaaagt cgaatagcga atgaccaatc ataccatcac   7080
catgtcgatt tcattgacga agaaatggac atcgacacca tcggcgcggc cggtgtaacg   7140
cagccgagtc gtcccatcaa tgtgggattc ctcgacgccg atgacttcca ggatggtgtc   7200
gttgcagtaa agcttgacga acatcttgat gccggagcca atcgccgcga aggcgatctg   7260
cttgtacagg tcttgcttga tcatgctttg cgctcctgtt tgcggatgta ttctgccctg   7320
gcttcggctt cgagcttcgc ccaaagcgcg ttgtcgactg gaccccaggg accggtctga   7380
gttccgtcca ccggtgcgaa cttgccaccg gcgcgacgat acttggacag agttctcagg   7440
ccgatgattt tctcttcttg ggaatcgagt tgggcgatca cttgacacac ttcccgaagt   7500
agcaggtgtg gagtatttcc aggcctttgg agatagcctt cagcttgatg ccgaaattct   7560
tgatcgccca gtccagatcg tggtgataga actcgatgat gttgacgatt tgaccggcgc   7620
tgtagtggat gacgcgaatc ttgccattcc agcggaaatc ttcgcggctg tttacggcct   7680
cgacttcgat tgtgtcgttt ctgccgatgt tccatttgga gctagtcatg tcgcaatcct   7740
ctttttggag tgtttcgcgt ttcgatgagg taactatacc tcagtcacct catcgagtaa   7800
agcactttcg aacagattat tgaaatttct tgaagacaga tcaatcggac gcgtcatcga   7860
tatcgaacgc cgagcgcgcc aggttgatga tctctggcca ggtcaaggtg aaggctttgc   7920
cgtcatcacg aatgataatg ggagtccgca gcggctcgcc caccagcatt gtgtaggtat   7980
gtttctcgcc ggatgcggag ccgatgcggg tgcttaaggt gagcggggat tctttgtgta   8040
cggtgccgat cattgtttcg ttcctcggtg atgcccggag aatcgggctc gttggattag   8100
gctttgccgc gacggattgt tacgccgcat tcagtagtca ctcccttagc ggcaggatcg   8160
cgaacaagat aagcacaggc ggctttgaca ttcagagttc gggttacgcc gagttttgcag   8220 gaaagatcgt tcccttcttc gtcccacaga tgggcgatgc gagaggtaca gccttttttct   8280 acttcggctt ctacagttac ggactggtca atgttgaata ccggcatcgc tttctctccg   8340
aggttgttcc gtttcaatga ggtgactata cctaagtcac ctcattgagt aaagcatttt   8400
cttcagatta tctgaaacct tttgaagtca ggaactgccg ccagagccag tcgatgtgtt   8460
cgttgcagta acgctcgcca tcggacgaca tagccagagc accatccttg atgccgaacc   8520
gggtaacggc gagccattcg aatccgaact ggagcgttcc tgggcgaggg atatgggaca   8580
tggcgtattt ctgcacggtc agtgatcctc agaaggtttc gcgtttgcga tagccgctac   8640
tttctgcata ccgaggcgat agaaatcggc ttctttcctg gctttggtaa gctgctccat   8700
ggcgtcgcac gccgtcttgt gctgggaatt ggcgttcttg atgctgccgt ccaggctctt   8760
gtctaactct cccgaagag ccttctgcga tgctagctcg gcctccaaat cctggattct   8820
gagttgaagc tggcggttct gctcggcgac cttgtcttcg cgggctacga agttctgcag   8880
gcggtcgaca agacgagtat tttcgcgcac cagctgctgt ttggcgactt tggtccttcg   8940
cagttctgct cgcaatgcgg acaactccag cgcatgcaga tcgcgtccg attcttgcga   9000 ctctgcggcc tgcttattgc gcagatagta ttgcccagcc gcgaaggcga gcagtgctcg   9060
gtctgtatcc ttaactgtct tggccatgaa gtgggctcga tacagaggcg cgaacttgca   9120
ggcgtctggg tcccaggcca gattatcggc cacaggccag aatgcgcgaa agcttttcgc   9180
atcgacatgc gccttgaccg tctgcgatgc gcccgactct tcgcagatga tttccagagg   9240
gacataaatg gcgttcttga tgcttcggaa agaaatggtg gacataacac aatcctcata   9300
agaagtcgcg gccgggacca tcctggccgc gcatcgtaat cactcttcgc cttcgtccgc   9360
```

```
gctcagccac tcttcgaagg cgaaattcac cttcgactcg acccaatcct gcagctcatc   9420
ggcgaactcg tcactgtcga tgtccatggt gattcccata acttccatgt tccatagcgc   9480
ggcattcagt tcgaactgca ccatctgctc gccatcgact tccagcagga tgcggtctgc   9540
gacttcatag tcgtctacat cgaacagatg gccgcccgcc aggaggtgct gtacgaaagc   9600
ttcatcgagg ttggtgactt cgatctggac ttgtttggtc attttcgtat ccttacttag   9660
cggctttgaa ttgggctttg aggttggcca gttcagcttt cagatcgatc atcgcctgac   9720
cgcgcaggcc ttccatttca gcctcgctga ttgcgatctt ggctgcgcgg attttgtcgt   9780
tgatttgatc tttagtcatt tttcggcttc cttttgtttg aagggtttcg cgtttcgatg   9840
aggagattat gccgatagtc agaatggaag taaagtgtct gagtgaagaa atttctgtac   9900
accgacgaac ggttgcgctc gaccgtctgc tgcggtgtcg atatactcgg cctattgcga   9960
acaatggact gattaaatgt tcaagctcaa tcctgcactg cgagcggtct ggcgaactcg  10020
tgcccgttac aaagtcatct atggcggccg ggcgtcttcg aagtcgcacg acgctggcgg  10080
tatagccgtt ttcctcgcgg ccaactacaa gctcaagttc ctctgtgctc gccagttcca  10140
gaaccgcatc agcgaatcgg tctacacatt gatcaaagac aagatcgaaa actcagagta  10200
taatggcgaa ttcatcttca ccaagaactc catcaagcac aagattaccg gctcagagtt  10260 cctgtttttat gggatcgccc gtaacctgtc ggaaatcaag tccaccgaag gcatcgacat  10320
tctctggctt gaggaagctc actatctgac ccaggagcaa tgggaagtca tcgagccgac  10380
catccggaaa gagaactcag aaatctggat catcttcaac ccgaacgaag tgaccgactt  10440
cgtgtatcag aacttcgtgg tcaagccccc gaaagattcc tgcgtcaaga tgatcaactg  10500
gaacgaaaat ccgttcctca gtgagacgat gctcaaagtg attcacgaag cttatgagcg  10560
cgaccgggag caggccgagc acatttatgg cgggattccg aagactggag cgacaaatc   10620 cgtcatcaat ctcaagttca ttcttgcggc catcgacgcc acaagaaac tcggctggga   10680 gccggccgga tcgaagcgca tcggcttcga cgttgcggac gacggcgagg atgcgaacgc  10740
aactacgctc atgcacggca acgtcatcat ggaagtggac gaatgggacg gcctggaaga  10800
tgaactgctc aaatcgtcca gtcgcgttta caacctggcg aagatgaaag cgcatcggt   10860 cacttatgac tccatcggcg tcggcgctca tgtcggttcg aagttcgccg agttgaacga  10920
tgccagccca gacttcaaac tgatctatga cccattcaac gcgggcggcg ctgtcgataa  10980
gcctgatgac gtctatatga agctgccgca cacgacgatc aagaacaaag accacttcag  11040
caacatcaag gcgcagaagt gggaagaagt cgcgacccga ttcaggaaga cttatgaagc  11100
ggttgagcat ggaaaggttt atccatttga cgaattgatt tcgatcaact ctgaaacgat  11160
tcacccggac aaaactaaatc aactgtgtat cgaactttcg tcaccgcgca aagacctgga  11220
catgaacggc cggttcaaag tcgagtccaa gaaggatatg cgcgagaaac gcaaaatcaa  11280
gtcaccgaac atcgctgact cggtgattat gtccggcatt ctgccgatcc ggaagcccaa  11340
aggcttcttc gacttctaaa catagaaaag cccggatcgc tccgggcttc gggtcttact  11400
cggtgcggtt cctggcgctg agtgtcgacg caacggcctc gccgactccc agggcttcct  11460
ggccggccgc gagcgcttcg gcttccgact cgacgatgaa atcatcacct tggccatcgc  11520
ctggcggaac ctcgaccagc acggcttctt cgccttcgaa ccgcaggtca taggtctttt  11580
cgacggacag accgtaacga gcgttgagcg cgtcccagag ctgggcctca taggtccgca  11640
ggtcttgcag agctttctgg tggctgagca tggccatgtc aacggcccgt tgcagggttt  11700
```

-continued

```
cgtccaggac gttgaatcga atgcgaagag aacgaatccg ctcgacgact tccgcatcca   11760
ctacatgtct ttcgatcatt gcttttcacc tttgctgaat gtaacgttgt agccgttgtc   11820
ggccaggtag gtcagggcgc cttcgaagga agttccgacg aggtgcttta gcttcatttc   11880
gcgttgcgcg gccagccaga atgcagttcc ggagaactcg gcgcggcctt cggccaagac   11940
cctgccatca ggcccggcga tccgtacatt gacggaagat agcttgatcg gcatcagtga   12000
atacctccac tggcttgcga cggcatgctt tcggcgcgag cagcttgcca gtccgggcag   12060
ggacaggctt ggcggacgcg ctccagctcg tcggcatcca tgacatagag cttcccatcg   12120
gcagtgtcgt gtgccatggc gatgttcggg aagtcggtgg cgctcaggcc ggcgacagcg   12180
cggatttcgt cccagagcac cagatgctcg gcattcaggc gggcggcgag cgcttcatgc   12240
tctttagcga cgcgcgccat gaactcgtcc atccggaatg cgaattccgc atcgatggca   12300
cgggccgagg ccatggagct gagtcgaatc ggttctttct tcatgatgat tctcttttgg   12360
ttggtggttg ttcgctgccc aggcctattc acggcctggg cagcacgatg aagatgaaca   12420
caaaggctgc aaacgccaat agcgttccgg caagcatttt ggaatgactc tgcatctcag   12480
cgtactgctt agtggacatt ccgtgctgcg ccgcctcggc cgcgaagcgg gctttcgcct   12540
cgataacttc cgggcgcagc gacaggacat attctaaggc ctcttcccgc gcttttcgg    12600 cctcgaccga cctagggtcg cgggccgaga cttcgctgtg ccctggcctc gcgggatggg   12660
cttgcagcga tggagggagt tcagccgcca cgactccata gtctgcgcag gcccaagcga   12720
tcccgatgag gatcgcgagg atggattgga cgattcgcag catcactttg tcgctaggga   12780
agttcatgat caatcctcca ccgaccgaac gatttccatg ttacgcccgg cattggcccc   12840
tgcattgaag gcgcgccgac cgtcgctatc gtccagacgc atgagcttgg cgacattcga   12900
cttcttgtag ccaggatcgc cgaaatgttc gtgaaccgca gcttccttca ccacaaccag   12960
agacgttccg gcagaagata ccagctccat acgcttcctg gtgatggact gaaggcgata   13020
gctgatttcc tgggtcgcgg ccagtttgaa ttgcgcggca acctttacgt tgaaacgttc   13080
gtacccttga gccttctgat actcccgaca tagacgatca atggcctcga ccagggagtt   13140
gaacatattc accgccagct caacgtccga cttgtagcct ttgaagcgta cggcatgacc   13200
ccagcgcttg gtagtgcttc cgtcgcgggc gcttctggat gccttagccg atgctctgtg   13260
gttgttgatg ccaccggcga aatccatgat gcagtcattg tacgtcgcca cggccactga   13320
gaaaaacttc atccagttcg ggattgcgga atagtaacga gtggcaattt gctcatcgaa   13380
ctcttcgcga atctcgccgg tagcttcgaa gtcgtgaagg tcatatttgt ccttcaactt   13440
cttcacacgc tcggctgcga tggccgcttc gtgcggactg gaagagtcgg ctgccatggc   13500
ggtcagtttg cggatgcggt cttttcgcct tctcgatggct tccggagtga attcgttctg   13560
gtcggtcatg gtcggttcct tttgtctgaa gggtttcgcg tttcaatgga gctattctgc   13620
cttcactcag aatggaagta aagcactttc ttccactatt tcggcatcga ctggaagaaa   13680
ttccagatcc aatcacctgc taccagcaag aggatgaggg cggcaaagaa caggacgacg   13740
gccgcgagct gtgcgccagg cttcagcttg ggatggctga gctttggttc tgcgggaacg   13800
gattgagtgc tggcgctgcg accgtcttct cccaggccgt agccgatgcc gcattcacgc   13860
gcctggagcg gcaccaggga tttcagatac tcggtctgct tttgcgactc ttcgtagatg   13920
ccggcgacgg cgaaccagag ggcgaacacg acggacgtac acacaaccca ggcgccggtc   13980
agcaggaggg ccagcgggcc gatgacgaag acggtagcag ccaggacgat tgcgccgccc   14040
cagatgatga agccggccag accattagtg atgtcgacac agaacttttt cattttcaga   14100
```

```
ttccttcggt tacgggatgg aggggatttg aaactctgcg ccgccgagaa catcaatgac   14160
gacctcccag agcgtcggaa cagaccactg gtaacggtcg aagtcggttt caggatcgac   14220
gcccagcgtc acataggaag tggcaggcca tttatgaaca ctgcctttcc gcatgagagt   14280
cgccacgcgg ccgtcaccga gcggattcgt cctgtgcgga acgtacgcag acatcgaata   14340
ttgctgcccg gcgtcgacaa caaatctttg cctctggcgc agacatacag agcccacagg   14400
attccagccg cgaccgccgc aagcctggcg agccgaagaa tgctcataac cttcgtgagt   14460
catttcgccg aggcaagccg agcgatcctc gtaatagttg atgttctcca tcgatccaac   14520
cagcaccaga gactcgaaat cgaatcgatg atcgtggatg ccgagtgat tgaagcaaag    14580 ccgacgcggc agctccgggt gccaaacatg gaggcgaccg gccggaagtt ggacctgaat   14640
gaaccccagg ccgtgcagag tgatcttgtc cttcatcggg tcatggacgg tgctcatgga   14700
taatcctcag tagcagaaat gtattgtgag agttacgatt gacaagccgg tcgcccatag   14760
aagggcgaac caggccatgg ctttgattgt cgtgtagatc atccgaagaa ttttccggca   14820
cagatcgggc caatgcccat ttcgatggat gcgtggttgg tcaactcgcg accgcagcag   14880
gagcactgac cagtcttccg accgtaggcg actgccgatt ccatcggctt tcgaacatc    14940 ttcagaacgt cgtcgtgctc agtatcggtg cagtcgcgac tcttgatgaa tttgccattt   15000
gtgatccggc cgaggtagat gtcgcccagg acgtacaggc taccgcgtt ccggctgtga    15060 gcgctagcct ctttcacgac aacgatgagc ggctcctcgc cttcgccagc taggcggatt   15120
ttcgggcgct tgataccaga ctcttttcgcc ttctcaaacg ctttctcgat gccggaaatg  15180
tccagagtcg gcgcagcagc ttcctgcgcg gccactttct cgcgatactt ggcgaggttt   15240 tcgatgcgc gcttcgcagc agcgatctga ttttctgtca aggagccgta tttatacaac    15300
gactcctgaa ggctctgagc gaagctgaag gaatttccag tccaccactc gatgatatcc   15360
gggtgcgcgg cttcgaaagc cttaattttg aggtcgcgtt cttgcgcagc gctacagatt   15420
ttctcggcgc gcttttctgc cgccttggca cggctcttgg cgcgctgctc cgggctggtt   15480
ttgtactctt tgtatccgac accgccgcag gcaaagcagg cgcgaccata agatgaaggg   15540
ccacggtaca ggccggtgcc tgcgcatttg gtgcacttgt cgcgatacag cttcacttcc   15600
ttccgggagt tcgggcgggc gcccatggac acatcttcca gcgtcttcgg cgcttcgtca   15660
gtgatcgcta cggtagcgaa gtcatcgccc aggtcttcga agcctgtgaa cagattctct   15720
gctgcgttca tatcgattct cctgtttgga aagttcgttt cgatgagttg actatacgcc   15780
agaaatggaa aaacggtagc gatttctcac taccgttcgt cgggtcgaag acaatcaata   15840
aatgtcgcta ttgatctcga acccatgctc agcgccgtcg ttgtagtcgt actcagcata   15900
gctgtcgcag tagtcgttca aatgctgaat gatgcctaga acatcgttcg cggccttgtg   15960
ccgtttcgcg gcgatggtct tggcgatgct gtcgccgact tccagggttt cggccgtccg   16020
gcgatggatc agcagacggc tccaaagata gagccggacg cgacgaatga tgtctctgatg  16080 gcgctccagt cgtccgtgca actcttcaat ttcttgctcg cgagatttca ctactcgtcg   16140
aagctgctga acttccagtt ccaaatcggc cttagtagcc atgttcacct caaaaaggaa   16200
aatcgtctgg gactccagga agttcgacga ttattgttga gcctgatcga tccagaatgc   16260
atccgaccga gccggccctg tggggatagg gtctacacga actataacag gtgacttccc   16320
tgactattcg ccaggtcgat cctccacacc atctgcaaat tggcgggcgc ttcgacttca   16380
gttttcgttc gtccaggacg gcgcgtctgt cgcaggaaag gcagcgtgcc ttaaccgacg   16440
```

```
taaccatggg tatagtcgat cattcggatg agctcatcat cctctgattc tctcgacttc    16500
agaccgccca agagtccga ctggccgtcg catttcgcat cgatatccat cgaagacagg    16560
aatcctgccg atactgcggt gatatcaact ttgtcgccgg ctttcttgaa gccttcgcac    16620
tcagcatcga gggccacaat tgcactcgcg gccatgttca catgactgat gaggtcgggg    16680
aagatcacag gaacttcacg cgacatgcca cggaccgtca gcttcaggac tacatacttc    16740
atactcacta tccctttgt atgtgaggaa agaacttgct gttttccgga tggtgaaaac    16800
gctcggtcgc aggcggtctt tcttccggac attgaatcgt cgaaggcggg aaaaccgcgc    16860
cggcgataat cgccgcgagg agtgcagcgg atgtcgacat ccagagggcg gtttccaggc    16920
tcacccgaac ttccggacgg cgcggcttca ttcgctccac cctcttcccg gttcatagga    16980
tggtagactg ccgccgcgaa cccagttgtc ccacatatgg ttcagaccag tcggtggctg    17040
gggtggcgga ctgtagaatc cgggagtctc agtgctgctc aggaaataag gcgtgcaaac    17100
ggcctggacg accaattggt gccgctccca catcttatca atcgctctta gcatgacgtc    17160
ttcgcactga gccttactgt cgaaccgtct gctagtatgg tccggcatct ggacgcagcc    17220
gtctccagtg caaaggaaag cagtagcaat ccatacggtg atactcgcca tttcgtcacc    17280
ctctttagtt gatgagcaga gtctattcca tctgctcgcc aggagtaaag cgcttttcgt    17340
cgggataaat gccgatgatg tctgcgtcga gcatccaaat ctccacggac ggatcgtcgc    17400
tgctgatgtg gtacaggttg tacagctccc gtccgccgac agcgcgctcg cctcgcggct    17460
caaccgccag aaccttgccg tgcccttctc cgtgctcgtc caggtatatg acgtgatcgc    17520
cgacttcata gctttctttc gtgacgaggc gtgaacgcga gctgttctgc gattccacca    17580
cccaggaatc cagcacgccg cctttcatgt cgcgaaacaa tcttgccgat tgtcgcaat    17640 cgaatacgcc cagaacttct ccgtctttca acacgatatg tacgattggc aaaagagtat    17700
tcatgtttaa tctccattgg ttgataatta gagtctaatc tgccgaaaag ttcccgtaaa    17760
gaattatttt ctcacaactg attagttgca actgttaatc tgatgtatat gtttgaatct    17820
cttttgaacg tttgatgttt cccctataat aagcgcacac agccaacaac cacgtggaac    17880
tacaatgttt aaactttcct ggatattcgg gcgcaaaaag gataatgctg cctgttctga    17940
atcggcgccg gagaaagtcg cacaaatccc tcaacacgat ccgctcgacc ccatgatcaa    18000
gctgggaagg attcgcggct ggaacgtcga gccggagaaa gccccggtca ttcgtagtgt    18060
gaaagatttc ctggagccgg gcctatctgt cgcaatggat agtgcgtatg gtgatggacc    18120
aaccccggcc gcgaaggctg ctgcgggcgg ccagaatccc tatgtcgtcc gactatgtt    18180 gcaggactgg tacaattccc aagggttcat cggataccaa gcttgcgcaa tcatttccca    18240
acactggttg gtggacaaag cttgttccat gtctggggaa gacgcagcac ggaacggatg    18300
ggaactcaaa tcggacggca ggaagctatc cgatgaacaa agcgcgctga tcgcccggcg    18360
cgacatggag tttcgcgtca agacaacct cgtcgaactc aacagattca gaacgtttt    18420 cggcgttcgc atcgcgctgt cgttgtgga gtctgatgac ccggactact acgaaaaacc    18480
gttcaatccg gatggaatca cgcccggctc ctacaaggga atctcccaga tcgatccata    18540
ctgggcgatg ccgcagctca ctgctggctc gacggcagat ccgtcttccg aacatttcta    18600
tgagccggat ttctggatta tcagcggtaa aaaatatcat cgcagccatc tagtagtcgt    18660
tcgcggaccg cagccgccag acatcctgaa gcctacatac atcttcggcg gcatcccgct    18720
cacccagaga atctatgagc gcgtgtatgc ggcggaacgg acggcgaacg aagccccgct    18780
gcttgccatg tcgaagcgaa ccagcaccat tcacgttgac gtggaaaagg ccatcgcgaa    18840
```

```
tgaagatgct tcaacgctc gcctggcgtt ctggattgcc aatcgcgata accacggcgt   18900
gaaagtcttg ggtactgatg aaagcatgga gcagttcgac acgaaccttg ccgacttcga   18960
cagcatcatt atgaaccaat atcagctggt cgctgccatc gccaagaccc cagctacgaa   19020
gctcctcggc acttctccaa aaggattcaa tgccactggt gagcacgaaa cgatttctta   19080
tcacgaagaa ctggagtcca ttcaagagca catattcgac ccacttcttg aacgccacta   19140
tttgcttctg gcgaagtcgg aagaaatcga tgtgcagctg gaaatcgtct ggaaccctgt   19200
ggactccaca tccagccagc aacaagcaga attgaacaac aagaaagccg gaccgatga    19260 aatctacatc aactctggcg tcgtgtctcc ggatgaagtg cgcgagcgtc tgcgtgacga   19320
tccgcgttcc ggctacaacc gactcaccga cgatcaggcc gaaaccgaac cgggcatgtc   19380
tccggaaaac ctggccgaat tcgagaaggc cggtgcacag tcggccaagg cgaaaggcga   19440
agccgagcga gccgaagccc aggcgggcgc cgtagagggc gcaggcggcc cggttcccgc   19500
cgctccacgc gggactaagc ctctcgcgaa agcggccgag gaaggggcca gcgaggccgc   19560
tgaaccgccg tcgaggccgg accccaaggc cgagctgcgg aacttgttgg tcgatctttt   19620
gtcgaagctc caagacctgg acgacattaa ggcgccggac ggcgtagaca tagagcacaa   19680
tgatgcgcct ggcttaaagc gcacatccaa acctggcgtg tctggtatgg agccttcggt   19740
gttttcgtcc aaccgcatcg tcgggcctcg tgatcattcg gaactccaga gaatcaaggt   19800
gaatggaata accaccctga tcgaaaatcc gcgcggaagc attcgacaag gcaaggatgg   19860
gagttggcga gttcagatga acaccacta cgggttcatc aagggaacga aaggcgctga    19920
tggggatgaa gtcgattgct tcgtcggtcc gaatctggga tccaaacggg tcttcgtcgt   19980
caaccaggtg aacaaggaag gtcagtttga cgagcacaag tgcatgctcg gcttcaacaa   20040
catcaacgat gcgaagtctg gatatctgtc ctgcttccgc ccaggttggg atggtctcgg   20100
ctccatacat gaagttgacc tacccgcgtt ccgtcgctgg ctggcgaacg gcgacacaac   20160
caaaccgttc gggggcgagt gatggcattc aaggcctcca aaaagcgcga acgccgggcg   20220
cctcttccag tcggaagagg gaagcccata attccatcgg caggaatcga ggcctggtat   20280
cgaaagcaga tgaaggatat gtccaagctc atgatcgccg actatcgaag cgagattgag   20340
aatgcactgt cccagcctgc ggccgaacgg ttcttcgcca gcgacgaatc cgttaacgtt   20400
ctgttcaaga tgacccttcg aagcctacag cagcgatgga gccgcatttt tgaaggcttc   20460
gcggccaaga tcgccccgga gtttgttaac cggaccgaag aagcggccac cgccgcgacc   20520
ctgcacagct tgtctgtggc cggcgtcgat cagccaagag ctgcgtacaa tgagagcgtc   20580
aggaataccc tggaggcagc aactacttac aaccatactc tcatcaccag gattcaagag   20640
gaagtccacg agaagattta cacatcagta atgttgtctc tgacttcccc aaatccggaa   20700
gagcaaggaa cttccggcat aacgaacgca cttcgcaaag tcgggaagtt ctctgaagat   20760
cgaatcgaac tcatcgcaag agatcaaacc agcaagcttt acagttctct gagcgatgag   20820
agaatggcgg aaaatggagt cgaggaattc gagtggatgc actcttctgc cggcaagact   20880
cctcgccata cccaccctgga gaaagatggg aaaaggttca agctgaatga ccccagactt   20940
tgggagggtc cgaaggccga ccaggggccg ccaggatggg cgattaactg taggtgcaga   21000
aagataccaa tcatttgata tcgataggag cgctatatgc cgttagttca tggcacttcc   21060
aatgaggctc gttctgaaaa catcaagcgg gagatcgaag ccgtaaagaa cccaaagcag   21120
gctgcggcca tcgcttactc catccagcgc agtgagaaag ggaagacggc gaaagattgt   21180
```

-continued

```
tcgcctgagc tcgttgccga tcttcgcgcc ctggtggaca ctctgtcgag gctcgtgaaa    21240
tgaaccgcaa gacatgccgg cgccgactcg tggtcgatgt aatcagggcc aatattcacg    21300
gcggattctt cagcctgaag tttgccgcca tcgatttggc aatcatcggc gtcgccatct    21360
tgatgacttt tggccgataa tgctgagaaa atctggattc tgactaaaaa ttctagtccg    21420
gatagccgca agttaccgtt tacggaaaat agcagtaatt tggaaagcct actgccgcga    21480
ggctttaaca gagccagttc ctaatttccg atttagccgc gtgcttcaaa agtatatagc    21540
ctgggaaatt agaagtaacg ttccaataga attcatctat aagtaacgtt ataatataac    21600
gtcaatctat atgctctaga cgtattgaaa ttcaattttt aattggtaaa ttggtaattt    21660
ggattagttt aggagttgaa agtctcgcgg cagtaggctt agacaaatcc cgtaaagttt    21720
ccgagaccaa attaccggat tttcgcggct gaggaaactg gtaattagat cataatacaa    21780
attataatgt aagttaacag tcgcggctac atctaattat tgttccgctt atttacccct    21840
agatgtactg cgtatataat acagccatag tccacgactc ttcgaattaa cgatgacaaa    21900
gtcgaaaaga aaaattgacg aaaatggata tatgaccatc gagggctgcc cgatcagctc    21960
ttatggcgtt ttccagtatt ctgctggtca actcggtctt ccgggcgatc cgacgcggat    22020
tgtcaacgta tatcgcccgg agtctgccgt cagcgatcct gagtacatcg aatctctgaa    22080
gaatctcccg ttgatcgacg agcacgaaat gctgtcggga ttcgacgacg atgacgacag    22140
cgtggccccc gaagacaaag gggtggaggg catcatcacc tccaacgctt actacgaagc    22200
cccatgggct cgcggcgata tccgcatcta ttcccgcaac atgcagaatc agctggaaag    22260
gggcaaagaa gacctgtccc taggctatag ttgccgctac actgagcaac ccggcatctg    22320
gaacgggacg ccttatgaag tcgtccagga caagatgcgc ggcaaccaca tcgccctggt    22380
aaaagagggt cgtgtgccgg gggccagagt attggatggt ctgtgttttg accatctcag    22440
tttttgatttc agaccatccg atgagggtaa tgaaatgagt ctcaagaaag ccaagcggaa    22500
gcccctgtc cagcgcgtag gcaagctgc tgactcggcg gtcgaagagt tgcgcaccct    22560
gtggccgaaa ctctctgcgt ctgtccagaa gttcctgggc gaagaagagc aggagccgga    22620
gcatcaggaa ggtgccgctc cggccgaacc gaccgacagc gagcacctga ccgagcatcc    22680
gactctggaa ggcgcccaga aggacgacga agagcaggaa gaggagcctt ccgttgtcga    22740
tccgccgtg gccgccgtcg agccggagca tcaagaaagc gccgcatccg aaatgtccgg    22800
tgaaggcgaa gtcgccgaac tgatctctca ggtcaaagcc attctggctc gactggaggg    22860
aacggtagcc gaaggggcag acgaagagca tggcgaaggt caagatgtcg tcgagggttt    22920
ggaggagcag agcagcctca gcggctcgca aaccgccagc gacgatggtg gtgagagcaa    22980
ggataacagc gaggaacttc ctgaaatggc acagaagaac gcgcaagatg ctgcaattcg    23040
cggtctctat cgcgacattg ctgctaaaga tcgcctctac aagcgtctta gctccgtggt    23100
tggtgcgttc gatcaccgag ctatggactc ggctgaagtc gctgtttacg gcgtgaaaaa    23160
gctgaacatc agctgtgcga agggccagga agctctggcg ctcgacatgt acctgaaagg    23220
cgtcgaagcc tcgcgcggcg cggccagccg tcaatcgaaa gcccaggatt cggccggttc    23280
tgctccgcag tgcgccgagc tggacagcta cctgaagggg gagtaactca tgttccagaa    23340
acaagtttac cgccagtaca ctcctggttt tccgggcgat ctgatcgagg acggcccgaa    23400
gcgggcgcgg ccgggtcgaa tcatgcctct gtctgccgta aatccggctg ccaccgccac    23460
cggccccaac cgcatcagtc gcgctttcgg ttacgccggt gacgtcagcg ccctcggcga    23520
aggtcagccg aagaccatcg cggctcgcgc ttctgaagtc gtgatcggcg gcgccaactt    23580
```

```
ctttggtgtc ctcggtcatc cgaagcacta tgcgctgttc ggttcggccg gagactccct    23640
ggctcccagc tatgatctgc ccgatggcgc cgaaggcgag ttcttcgaca tggccaccgg    23700
cctggtcgtc gaaattttca acggcgccgc aaccgccctg gacctggact atggtgacct    23760
ggtcgcctat gtaccaaaca acctgcctac cgccgacaac gcgcttggcc tgccggccgg    23820
cgccctggtt ggcttcaagg ctggctccat gccgaccggc ttggtccaga ttcccaacgc    23880
acgcatcgtt aacgccatca gtctgccggc ccagtcggcg gggaatctgg tcgctggcgt    23940
taccatcgtc cagctcacgc agtaaggagg cgtcatgagc cagatcagca agacccattc    24000
gcgcctcgca ggccgcaatg cgaaaccttt cgacctgaaa aacatcacca atgacgccgt    24060
ggcgtctctg cgccgcatcg gcctggtatt cgatcacgcc gtcgtccagg accagatcaa    24120
ggccttggcg aaggccggcg cgttccgctc cggctcggcc atggacagca acttcaccgc    24180
cccggtgacc acgccgtcca tcccgactcc catccagttc ctgcagacct ggctgccggg    24240
cttcgtgaag gtcatgaccg ctgcacggaa gatcgacgaa atcatcggca tcgataccgt    24300
tggctcctgg gaagatcaag aaatcgtcca gggcatcgtg gagccggccg gcactgcggt    24360
ggaatacggc gaccacacca acatcccgct gaccagctgg aacgccaact tcgaacgtcg    24420
caccatcgtt cgtggcgagc tgggtatgat ggtgggcacc ctggaagagg gtcgtgcctc    24480
ggccatccgg ctgaacagcg ccgaaaaccaa acgccaacag cgggccatcg gtctggaaat    24540
cttccgcaac gccatcggct tttatggctg gcagagcggc ctgggcaacc gcacctatgg    24600
tttcctgaac gatcccaacc tgccgccgtt ccagaccccg ccgagccagg gctggtccac    24660
tgccgactgg gcaggcatca tcggcgatat ccgcgaggcc gttcgccagc tgcgtattca    24720
gagtcaagat cagatcgatc cgaaggcgga aaagatcacc ctggccctgg ccaccagcaa    24780
ggtggactac ctgtcggtca ccacgccata cggcatttcg gtttctgact ggatcgaaca    24840
gacctatccg aaaatgcgga tcgtgtctgc tccggaactg tcaggcgtcc agatgaaagc    24900
ccaagagccg gaagatgctc tggtgctctt cgtcgaagac gtgaacgcgg ccgtcgatgg    24960
aagcaccgat ggcggcagcg tgttcagcca gctggtacag agcaagttca tcaccctggg    25020
tgtcgaaaag cgggcgaagt cgtatgtgga agacttctcc aacggcaccg ccggtgcgct    25080
gtgtaagcgt ccgtgggccg tggtgcgcta cctcggcatc taaccgatgc ctattcacca    25140
aaggccgggt ttccggcctt tgttcactct gactctgact cggttgtagg ggccggttag    25200
ggcataatta ctaggactac gccaatgact gtttacatcg tttccgccat gactcaatcc    25260
gtgtcttaca atgcgtatga cacctctgat ccgtccaatc ctcgcctcca gcgaaagatt    25320
ctgattcgtg ccgcgccgg catcgcatcc gaaacttccg gcttcggcga catgatttcc    25380
gacgcggccg ggcgtccgat ctggaccccg cagggcgatt gcactgccgt gagcgattcg    25440
gatttcgagc tgcttcaggc caataagatt ttcatgcgtc acatggagaa gggttatctg    25500
cgagtcgtga agaccgacat caccagtgac caccagcgga tttccaaaga gactcgcacc    25560
atggagcgtg atggattcca gcctctggac gctactcgcc tgcagcagaa aatcaaggtg    25620
accacagcca gcgcttccca ggaacaagag ttccggattt aaccgagggt ttcggtatgg    25680
tgattttcga cgaaaataag tttcgcacgc tgtttccgga gtttgctgat ccagccgctt    25740
atccggacgt gcgcctgcag atgtatttcg acattgcgtg cgaattcatt tctgatcgcg    25800
attcgccata ccgattctc aacggcaaag ccctggaagc atgcctgtat cttctgaccg    25860
cccacctcct gtcgctgtcc acgatgcaag ttcagggcgc ggctggaggt ggcgtcacag    25920
```

```
caggtgggac tcaaggcggt ttcatcacca gcgctactgt cggcgaggtt agcgtggcta    25980
agctcgcgcc cccggccaag aatggttggc agtggtggct gtccgggacg ccttatggcc    26040
aagagctgtg ggcgctcctc agcgtcaagt ctgtgggggg attctacatc ggcggccttc    26100
cagagcgtcg aggattccgg aaggttggag ggacgttctg gtgatccctg gagcgaatct    26160
cctgcgcatg gccttcgggg tcattggcac tcaaattgtg agatatcgca gtttgagca    26220 gcgagtgaag aatgatcaag cccagtacgt atccatgttc ggggagcctt tcgacctggc    26280
agcgtctgtc cagcgagtcc gacgcgatca gtatgtccag tttaatctgg agttccaacg    26340
gaattatgtt atgatcttcg ccaactttga gatggttgac ttggatcgcg atgtggccgg    26400
tgaccagttc ctctggaccg gaagagtttt tcagctggag tctcaaggct cctggtttta    26460
tcaagacggc tggggagttt gcctggccgt ggatatcggt gctgccaagc tcactgatga    26520
cgggaaaccg actttctagg tgatgtatgt ttgacggcga actgatagcg aaaatggttg    26580
tcgagctgaa tgcggcgatg acatctgctc aagaggcttt gcagttcccg gattttgaag    26640
tagtccagaa agctcagccg acccaacagg gaacgtcaac caggccgacc atctttttcc    26700
agaaactgtt tgacattcct cgcggctggc ctgccaccga ttggcacctg gacaacacgg    26760
ctcgcaaata tgtagaaata actcgacagc atgtagagac gactttccag attagttccc    26820
ttcattggca gaatcctgaa ataactcacg tggttacggc ttccgatatc gccaactatg    26880
tgagggctta tttccaagct cgatccacga ttgagcgcgt aaaggaactg gacttcctca    26940
ttcttcgcgt gtctcaaatt ccaacgaag cattcgagaa cgacaatcac cagttcgaat    27000
tccacccaag ttttgacatg gttgtaactt acaaccaata tattcgcctg tacgaaaacg    27060
cagcatattc ggccgatggg gtattaatag gcatatgagt ctgaggcgcg attcagagct    27120
aatcgccgcg cacctccaga tgttaagagc catgcgcggc aggtccgttt cagccggatg    27180
gtattccacg gctcgatatc ctgacaaggc aggcgggtcg gtcggaatac aagtcgcgag    27240
aatcgcacgt ctcaatgagt acggcggaac tatcgaccat ccgggcggga ccaggtatat    27300
tagggacgcc attgttcggg gccggtttgt tggcgttcgg ttcgtcagaa cgactttcc    27360 gggagaaacc gaggtaacta agcctcacag aattaccatc ccggctagac cgtttatgcg    27420
atatgcttgg aacttgtttt ccgcagatcg cgccgcaatc cagaaccgga tagccatgag    27480
gctggccaga ggacagatca ctccagatca agctcttgcc cagatcggcc tggcgttgga    27540
aggatacata gccagaagca tcaggaccgg gccatgggtg gctaactcag catctacggt    27600
caggagaaag ggattcaaca gaccgctggt cgatacggcg cacatgcttc aatcgattag    27660
cagcagagta acataaccag gagatcatcc agtgatcagt cagagccgtt atatccggat    27720
catttcgggc gtaggcgcag gcgctccggt cgcaggccga aagctgattc tgcgcgtcat    27780
gactaccaac aacgtcatcc cgcccggaat cgtcatcgag ttcgacaacg ccaacgcagt    27840
catgtcatac ttcggcgcgc agtcggaaga gtatcagcgg gctgcggctt atttcaaatt    27900
catcagtaaa agcgtgaatt cgccgtccag catcagcttc gctcgctggg taaacaccgc    27960
catcgcgccg atggttgttg gtgacaatct gccgaagacc atcgccgatt tcgccggctt    28020
ctcagcaggg gttctgacca tcatggtcgg cgcggccgaa cagaacatca ccgccatcga    28080
tacgtccgca gcgacttcta tggacaacgt ggcgtcgatc atccagaccg aaatccgcaa    28140
gaacgccgac ccgcagctgg cccaggctac cgttacctgg aatcagaaca ccaaccagtt    28200
caccttggtc ggcgccacca tcggcaccgg cgtcctggct gtggcgaaat ctgccgatcc    28260
ccaggacatg tccactgccc tcggctggtc cacctccaac gtcgtcaacg tcgccggcca    28320
```

```
ggctgccgat cttcccgacg cggccgttgc caagagcacc aatgtcagca acaacttcgg   28380
ttcgttcctg ttcgccggtg cgccgctcga caatgaccag atcaaggccg tgtcggcctg   28440
gaacgcggct cagaacaacc agttcatcta cacggtcgca acttccctgg cgaacctcgg   28500
cactcttttc accttggtga atggaaacgc cgggaccgcc ctgaacgtgc tgtcggcgac   28560
tgctgccaac gacttcgtgg agcagtgccc cagcgagatt ctggccgcca ccaactacga   28620
tgagccgggc gcttcgcaaa actacatgta ctaccaattc cctggccgca acatcaccgt   28680
ttccgacgat accgttgcga acaccgtcga caagagccgg ggcaactaca tcggcgtcac   28740
ccaggccaat ggccagcaac tcgcgttcta ccagcgcggc attctgtgcg gcggtccgac   28800
cgatgctgtg gacatgaacg tctatgccaa cgaaatctgg ctgaagtcgg ctatcgctca   28860
agcgctcctg gacttgttcc tgaacgtcaa tgcggttccg gcgagcagca ctggcgaggc   28920
gatgaccctg gcggtgctgc agccggttct ggacaaggcg accgccaacg gcacgttcac   28980
ctacggcaag gaaatcagcg ccgtccagca gcagtacatc acccaagtca ccggtgatcg   29040
ccgcgcctgg cgtcaagtcc aaaccctggg ttactggatc aacatcaccl tctccagcta   29100 taccaacagc aacacaggct tgaccgagtg gaaggccaac tacacgctga tctattcgaa   29160
gggcgatgcc atccgcttcg tcgaaggatc ggatgtgatg atctaatggt ttgcggcgga   29220
ctcgatccgc cgcgaccttc cataaatgga gtgaggaata agcaatgatc aacatttctg   29280
cgttcggctc gatctgccag ttcacggcaa gcagaacttt cccgaacgga ttcaccgtca   29340
ccgagtttgc cgacgatgcc gatcccatcg acagcccgcc gttcaccgct gccgataccg   29400
gcgtcggtct caacggtgac atggtagttt ggaaccgggc gaacatcctg gaagtagtcg   29460
tcaacgtcat tccgaatacc gagggcgagc gcaacctggc agtcctgctg gatgccaacc   29520
gcaccggaaa ggacaagtcg ggcgctcgtg atgtcgtcgg tctggtcgtg gcgatgccgg   29580
acggcagcaa aatcacctgc accaacggca cccccatcga cggcgttctg atcaacgcgg   29640
tggcaagcgt cggccgtctg aagaccaagc cgtatcggtt ccgatttgaa aaagtgatca   29700
aagccggtac tagctgatga agaaaattcc gctgacagca gtccccaatc aagcgatctc   29760
atttaacgcc ggcagcagct attggaagat tcgcctgtac cagaacatgg acatgatgaa   29820
tgccgatatc agccgcgacg gcgtgatcgt ttgccatggg gtccgctgct tcggcgggat   29880
tcctcttctc cagtacagcc atcagtaccg acctgactat ggcaatttcg tcttcgaccg   29940
cgacgccgat tggacgttgt tcggcgacgg aatcaacctg ttctatctgg acggcgccga   30000
attcgccgag tatcaggcgc ttgccacgag gaaagaatga gcacatcaac gatcagaacc   30060
gggacgaaca acgatatcct tttggacgac aatggaaaca tggttatcct cagggatgtc   30120
gaagcgtgcg cccaggacgt tcgggcggcg atgctcatgc gcaccggcga aacatttttc   30180
gatgtgaact ccggcgtggg atatttcgaa tacatcttct cgccgcagaa aagctatgat   30240
gacgctcgca aatccatcgc ggatgcaatt ttatcctcgc cggatgtgac cggcatcgag   30300
cagcttgaca tcgacataac cggggaagtc ttcggcgtcg atgcgaaagt catcaccatc   30360
cacgggcctg ttaccacagg agtttgaaat gagtaccatc cgcatccaat acgccaacgg   30420
cacccaactg ttcctggacg gcaaaaatcc gccgccctg acccgctgc cctcgtttaa   30480 cccgtctgtc gaagatctgg aaggcctgga ccgcgaaaag aacatcgaca agggcgactc   30540
ctcgccggcc ggtcttcccg ttcccccggt aaacgtcgat tccaatgtcg acaacggcgg   30600
aaccatcccg gctccggtat cgaccgacgc tgctgcggcc gaatcggccc cggaaggcgc   30660
```

```
ccaggaagct cctgcagcag gccaaggcga cgagaaaggc gccgaggaag ccccgactac   30720
agcccctgta gaaaaggccg aggaaacggc ctcgccggcc gctgaagagg aaaccccggc   30780
tcccgccaag gccacctctc gcaaaaccac cagcaagtaa ggactcgaca tgatcaacgt   30840
cagcggcttc ggcacaggaa ttgtaatagt ttccgcctca tcgttcccga tggggttttc   30900
cttgtcgaag ttcgctgatg atgagagtcc gatatcctcc aaagagctgg agccgttcgg   30960
atatgagatg ctttatgacg gcggcctatt cgccttttgac aaggctgctc ctctggaagt   31020
atctgtatcc gtcatcgcag ggagcgagga tgatattaac cttcgcaccc ttctcaattc   31080
caaaaaggga tcattcagat ttcttccggg cagcatcccg gatatgacga ctctcgtggc   31140
cactcttcct gatggcggcc gcaccgttct gtccaatggg actatcatca agggtccggc   31200
catcgacacc atacagaaca ccggacgacg caaaggcaac acgtacactt ttgttttcgg   31260
tagctatctt ggcgcccaga ctgcgcgtca agccatttct aacgttatcc aatcggtact   31320
ggaggtggtc tgatgttggg gattttcacc agcctcctaa gttcgcgatc ttttcgatt   31380
gtggaccaaa acacaaacca gctagttgct gcggatttga ggataagccg ggtcaacacc   31440
cggttttctt ctgtagggca acgccacatg ctggaagatg gtacgaccaa gatggattcc   31500
agaacgatcc accctatgga aatcatcgtc gaagtatttt gcccttcaat tgatgtcgtc   31560
gatcagatca atcaattgct cctggatcgc gacacactgt acaaagtcat cactcgcggc   31620
atggtattcg aacggatgat gtgtaccagc gaagcgctca atcagactcc ggatatgata   31680
tcggcgactc ctgcgcggct gacattctcc caagttctcg tccagaatcc caagcctata   31740
atgttcagaa atgcagggga ctcttctatg atcgaccgag ggctggccct agctgaagac   31800
gtggttggct cggccggcga tctgttcgac tacgcagtaa acggcgtcca gaacgccgca   31860
gacttgttct gaggtgccaa ttgaactctt tcctcaagtc tattctcaac acgcctactc   31920
tcaccatacg cgatgatgtt accaaacttc ctgtctggaa gagtcttcaa gtcaagaaag   31980
tggaaattta ctcgccggct tccgtagtgt cgaaacctct ggcgacgaaa gaccagacgg   32040
aagctcaagt gtacaccgaa gctctggaca ttgatgtgaa gaatggaaag atcatccaac   32100
cggtgcgact ccgcatcagt gctatctgtc cggacctgtc caccgttgaa agtatcatga   32160
acgctttcaa tgataacacc tcgactttcg ctatcacttc taagtcgata ttggccgata   32220
aaatggccat catgacgctc gatgtagatc agtctccaga catgttgaac gcggctgaga   32280
tcaatatgga attcgagcag gttgagcctc cagtattgaa taaattcgat cctgcgttcc   32340
ctcaagatag tccgacttat gggtacagag ttcaatctct ttctgatgct aatttgctgg   32400
atttgggcgc catcggcgat tcgatatctt cggccgcaaa atcgctatat aatcgcgtga   32460
ccagctactt ctgaggatgt atcatgcttg aaatcaatct tcccgatggc cgtcaaattc   32520
gcgtacaaat cgaggcgtgg tcggcattgg atggctggga actccagcgc cgtttcgtcg   32580
aattcgctgt cagccaagat tccgacttcc gccgctcttt caccatggaa atcctgggct   32640
atgcgaaagt gctgcttggc gacgatgaca ccggcattcc gctgaccacc gcggcagtca   32700
tcaacaacca cctcggccac tggaagaacg tggaactggt tttcaactct gttctcaagc   32760
acaatggcat cgaccggcc acgcacgccg accggccgga ctattgggaa caagtcggat   32820
cgcagatggc catcgcattt ctggccgagg cgtccaagct cattggtcca gcaatgaaga   32880
tcgccgaagg actcgccaac aagccggagt gattcatgtc tagtgatttg gatgaattca   32940
tacttcggta tgaggccgat actgccgagg ccgagcgcaa tctggagcgc ctccagaacc   33000
agatcaggcg cgtgaacagc gcatcgacga gtggccttca ggatttgcgc cacttcgcag   33060
```

```
acggcgcggc cactgaactc ggccgagtcg ttccgcagat cgattctgtg acgagcgcga   33120
ttcgcgggat gaacgcgcaa ctggcgatag gcgccactgg cgtggccctg gtcgcggccg   33180
gcgtcaaggc gttcatgaac accagggacc agtacaatca gcagcgcatc caggcgatgg   33240
acatcggcat cgccccggca cgcttggaag agtaccagag aaaattcgtt cgccagtccg   33300
gtggaaccat cagccgcgag cagggcgcgg agatgaccaa aaatctggca gacactttcc   33360
ggcgtgctta tcgcgatatc gggcgagtcg gcccggaagc gcgaattctg cgtatggccg   33420
gcgttgatgt cgggagcttc caaaagggca tgcggccgct caacgacatc attactgatc   33480
tggccacgaa aatggccaag ctgaagccgg acgaaatttc tgcctacgct gatgcccttg   33540
gcgtctcgcg agactacctg agcaccctgg ctaagatcgg cccggccatg ggaaaagtca   33600
ccgagatgac gactgcggaa ctccagtcca gggtccaggg cgagtccaac attcagaaat   33660
tcaacgatgc tctggcgaat ctcaaccaga cgttcaccac cctggaaaac cgagtcggcg   33720
aaaagctcgc gcctgcgttc accaagctga tcgaaatcat cgacaagata gtccaggcta   33780
ttcccaatga agtggaaagc ttcgcgaagg acaccaaatc ccgttgggaa gatggagtgc   33840
tcgggaaggc gaccgttggc agtgatatcc tatccctcct cagccccggc gccctgctcg   33900
gtcgcctggc agcgtggggg actcgtcgcg gcatggaaga atcagggctc atcgacaagg   33960
acaaggttcc cggcgctcaa accagcgaag acctggccaa gaaacaagaa gaccaggaca   34020
aggctactaa gtccatgaaa gagctagaga agctggctga ccagaccacg aagtctacca   34080
atgattttgc ggtggcgatc aacatgttca gtggcgcggt atcgtcgttc gcgaatgccg   34140
ttgacgagcg ccaagcttgg gcagcctggg cggggggaaat tggtcgggcg gtcggtatgg   34200
gaagcaccgc gccgacttcg cgggccaccg gcgtctatcc gcacgcgatc tatgatcagt   34260
cgaagagtgg cgcggccgga caggtcttcg gcgagccaat cggcgcccag tctcttcgca   34320
atcgcatgtt ctcgccgcag cgcaaggccg aaccggtcac cgttccatcg tacatcaacg   34380
atatcatcaa agatgcttcg aagatgtaca acattcctga gctggacatc aagaaactca   34440
tatacaccga aagccgattc aacgccaggg ccaccagcga agccggagct aaaggcctca   34500
tgcagctgat gccggaaatc gccaaggcgt atggtatcac tgacgtatat gaccctcgcc   34560
agaacatcct cggcggaacg cgcctactgc gggaaaacct agatcgagca aatggcgaca   34620
tgcggttggc cttgacctac tatcatggcg gactcgatcc gaagaactgg ggtccaagga   34680
ctcgcgcata tccgggtttg gtaatgagcg ctccaatcga gctgatggaa gaggctcagc   34740
gcaagcagaa ggctgcggcc atgaccgtcg ccagcgagac gttcgccccg gaaggcgcg   34800
acatggacat tcgtccctat gatggcgggc gactggaaac cccagaccag ggcaagaagg   34860
aagatgagcg ccgcgaagcc cgtcgatatg acgacgggt tgtgcgaccg gaaattcgca   34920
tcatcgaccg catgccagac cgcagcgacg gcgaaatcct caagatgtct agacgtcaag   34980
aggccgaccg ggcagattct ggattccgga agttcccgaa tcaagttcgc ggcgagacca   35040
agcagaacat ccaggctcaa ctcactgcag gagccatcgc gcaagtgatc ggcgttaacc   35100
ccaaccagat catgcgccgc gaaatcagcc gttctgactt gctgttcgga tacaaccaag   35160
ccatcctggg caagcaacag gagatcaagg ccgccgcgca cgaagccaac aacgtattcc   35220
tgtctccagc caagcttgcc gaagccacgg ccaaggtgaa cgcagcatcg cgagaaatgg   35280
atattctcag gacgtatggc gagcaacttc tgaagagcgc tccagagcgc ggccaggagc   35340
tgaccatcgg tcgaatcgac atgttggtca acgtcaccgg cgcgaattct ccggaagagg   35400
```

```
ctcgcgagat attcagtaag cagactgcag accagctgac tacggcaatc caggacgctc    35460
aaaacgattc cgcaactaag atactctact gatgaaaaag agaattctgc gagtaacatt    35520
caacatgcct tatggacccg aagtcatccg cgaagatctg gatgttcggg tccggattat    35580
gaaggctgcg ttgcggattc agaaccgggc gacgatggaa attttcggcc tcaccactca    35640
gcttcgcgag tctcttctgt cgcagttcac cgcgtggaag catcggcaac gtcaagtggg    35700
catgaaagat gaattgatga tcaaggtgtc ggtggaagcc ggctactctg accaggggcg    35760
cgagcaagtt tccagagtct tgtcggcga agtcgccatt gtcgatatca tttctccgcc     35820
accggacatt ggaatccgca tccagtgcta taccaggcaa atcgacagga cgaagaccat    35880
tcggaatatg ccgcccgcca acacgacgtt tgtcaagttc gtcgagtggg gcgcgaacga    35940
aatgggattg aacttcatct gcgataccag ttacaacgat caagttctga agaatccggg    36000
ccggtctatc actgtcgcgt cggcaatcct ggcgtcgatt caggatatgt acatgccgga    36060
cgtggccgcg ttcgtcgatg atgacatatt gatcgtgaag gaccgcgata agtcattcg     36120 tccggatgag gtgaccaacg tcaactcgtt tgttggaatt ccatcttggt ctgaatgggg    36180
cgtggaattc cagtgcctgt ttgagccatc gattcgtgtg gctggaggcg tagcggtcga    36240
atctctcatg aatccaagtg ttaatggtaa ctatgtaata actgctctgg aatacgattt    36300
ggccagtcgg gatcggccgt tctatatcaa agtcatgggg agtccagcag cataatggcc    36360
agggaaatca aatcattcaa catgttcgga gttcactata cttcgcggca attctctgct    36420
gtcgatgggc tcagcatgat gtcggaaatt cagagcgtgc cgccagaaga attgctcaag    36480
ggtactgatg tattggcgca tccggaagac catccggaag gcatctggct tccattgact    36540
gctgcgaaca tcaatctta tgtcgttgat cgagcgaaag taatagctcc cgtacaagtt     36600
cttgcacttc tgtccgaagt ggtaatcgac tggaattttg gttttctcaa agactggacc    36660
ggagtcaaga ttccatccag atttgtcgaa gatatcaaaa gcgtgaagac ggcacattca    36720
ccttctgtag ttgcgagttt ggtggcgaac ggttcggcct ctatgcgcga gttggaagag    36780
tattattcga ctcaagatgc ctttaagatg atagatatca tgacggcgaa gagcgtgaac    36840
gaggccttgg cgtccgaagc atcgcacaac agaatcaaaa agggataatt cctaaccggg    36900
cctgggaagg ctatactaga cctgccaaat cagaggcttt cccatgtcca atatttctct    36960
aacatccgca aaagctcccg acaggacgcg actgatcgcc gctcttgacg ctcggtcgcg    37020
gcgggatgct ctagatttcg aagtaatgat accggctcag gttgttcaat atgaccgggc    37080
cgagaatatc gcgacgattc aacctctcat cacctgggtt gacacggaac acaacgccgt    37140
ccaaaggcat cagctggttg atattcctgt aatttccatg ggggctggcg gcttccacat    37200
aagtttcccg attcagcaag gtgacatagg ctggatttat gcggccgacc gcgacacatc    37260
tcagttcctg gagtcgttgt caatgtcgaa gccgaacacc ggccgcatcc ataagttcga    37320
gcatggcctg ttcatcccgg acgtattccg tcgatacacc atcaattccg aagattcggc    37380
cgctatggtc atacaatcga cttccggagc gaccagaatt tcgattcgcg gcgataacat    37440
caagataact gcgccgtcga acgttactgt ggatactccg caggcgaact tcaccggcaa    37500
tgtgactatc gctaacaccc tggtcgtaaa cggcatcaac gtgaacaacc acggccacct    37560
cgaaaacaac ccgcctgatg cccggacgaa aggcggcatg gttgcttaag gagattttca    37620
tggcaagttt tgattttct gatttaacag cgggggggg ttgtaatggc taactacaac     37680
tacatcgtcg atactggtgt gatagtcgca gataccgccg acgttctgag cgacgttgag    37740
gccgagttca gcgccgccct cggtgccaat atcaacttgg ccgcgagcac tccgcaggga    37800
```

```
tcgcttgtcg cggccgaggc catcgcccgt tccagtgtca tgcggaatga agcgcgaatt   37860
gccaatacca taaacccgaa cgtttcattc ggaacgttcc tggacgcgat ctgtgccttg   37920
atggggatcg agcgcggttc tgatctgtca accttcggct atggagttca agtcaccggc   37980
cgcagccaaa cccgcatttc caccgggtct agggtccaga ctccggccgg cgcgatcttc   38040
acagtgatga gcgatgtcac gatccctgct ggtggtgtcg cgaccatcga tatcaaatcg   38100
caggagtatg gcaacattcc tctgccggtc gggaatctca tcatcatcga cggaacaatt   38160
ggatggtccg gagcaaaagt catcgcctcc actcgcgtcg atccgggcag ccgccaaatg   38220
agcgatgcag agttgaagaa tgcccgcgtt aatcgattgg ccatccaagg ccgcaactcg   38280
actatggcca tcaagtcgta tgtgagcgcc gttccaaacg tcacgtcggt gaacgtaatc   38340
gagaacaaca ccggcgccgt tcaagtggtg aatggagtct cgtttaccct tccgtatgct   38400
gtttgggtct gcgtcgccgg aaacccggat aaacaagcag tcgccgatgc gttgtgggcc   38460
gcccataacg gcggaactcc atgggactat ggtgcgacga caacggcgt cccggtggac   38520 ggtccgaatg gcgttcctgt gcgcgatccg gcgtccggtc gaaagtatgt cgtgaagtgg   38580
accactccaa ttatgtacga tggatatgtt aacgtaacag tccagcaagg ttcctcctct   38640
gtagctccgg aagccattca gaacgcagtg gtcaattacg cccaggggaa agtggaaggg   38700
gaagaggggc tggtggtggg cgcgagcctg tcggcattcg aagtcgccgg agccatcgct   38760
cgcgaaattc ccggcatcta catcaaactc tgccaggtcg cgtgcgtcgc ggctggctcg   38820
ccggctccgg ctccgggcga tttcacttcg gaatacgtca tgagcgcatt cggccaggct   38880
accatttccg ttggtaacgt tcgggtgact ttcgtatgac tctgcctgcg tacaattcgg   38940
acatccaaca agctctgaaa tggctccata accaggcgcc tggaatcacc ggcctgatcc   39000
agagaaaggc gcaatggtat gacagattca gccgccaatt ctgggccaac tgggagcgcg   39060
acgttttcaa cttgaagacc gccaacccgt tcggccttat ggtttggtgc atcatcctcg   39120
gcacgccttc gaaagggttc ggcctttatc caaagaacag ttcttgggca ttcggtcggc   39180
tacgccagaa cttcatctat agcggtacac aagtcccgcc accggcagac gcatcgcctg   39240
gaggcaactt ctacggtggc ggcaatgccg aaattctcaa cttggacgaa atcaggaaag   39300
tgcttcagct aagatatgta gcgctgattt cgaacggctc gattgcatat atcaatcgca   39360
tgcttcgtta catattcaat gatgatgagc catgggacga ggcgaccggt ctgtacttct   39420
atctcatgga ctcaaccggc gagaatggcc ctgtggagaa cttggcagta tatcggaaag   39480
attgggaagg tatggtgctg ttgtccagtt cgcccagaac gaaccacgtg ctgacatcga   39540
cccctgccag cgacgccgat tggccgggag tcgatccggc cgcgagcggt attccggtaa   39600
cggtcgaaac ggcgtccgct acggcccgg acggctccgc tacggtgtgc aagcttacta   39660
agccggccgg gagtaccgct tacgtctccg cgccgataga tgggccgctg gggtccggta   39720
gcactgtaac gttctcgttc ttcgcgaaag ccggctccac ccgtttcatt gcaattcagt   39780
cggctgccga tttccccagt cgagccgatg ccgttttcga cctggattcc gggaacgtaa   39840
tcagcgatca gatgctggac agcagcgtgg taagcgcccg aatgattcgt ctggaaaatg   39900
gctggtggcg ttgcgttctc acgaccaaga ccgtcagctc ttcgttccgc gcggcttaca   39960
tcgctccggc agaaaccaac ttcagctgga ttgattcgaa ttccagcgcg gcgattgacg   40020
tgcttatctg gggcgctcag atcgaactgg gtgatactcc aaccggatac ttggagacta   40080
ccggaacgcc cgtcaccatc accgattacg ttctgcagag cgcccagacc ggaacggtca   40140
```

-continued

```
agttcacaca gcctcttccg accggagtag aagcgtattg gactggagac tggaaaggtg    40200
ggtctgcgac cgagccggcc agattcgcag taggggatgg gactcaagat acattcaatc    40260
tgtccagccc tgcatacatc ggcctaccca ctagtgqggc gttcaagcta gaatacagag    40320
ttggtccggc gcttaatttg tcgccgcaat tgatcaacct catgaatgac cgggcggtcg    40380
gtatcatgcc gacttgcgcc ggttgcgatg taaaagtcat tcaggagtaa tgacgtgatc    40440
acacccgaac tgatacccag tccgtttgct cgcagggcg acaaagaccc gattccacaa     40500
acctcctcca ctggcttcgc aaaccttcgc gacggctata cgccggacta cgaaatcagc    40560
ctggcgtcga caacccgca ggccaaagcg gtcgagcgga aaattcaaaa ccaactcttc      40620
ttcatcgcga cccagaacgc acaggcgtgg cagcgacaaa tggcgccgcc gtggtttcag    40680
ggcatgcctg gcggctacga acagaatgca gaagtcgtgc gcgtcggaaa tgacggcata    40740
atgcggcgtt atcgttccat ggtgaatgcc aatgcgagcg accctctcag cagcacgact    40800
tgggaagaac aacccgcatg gtcggcgatg cgctccaaca tcccgatgcc ggccggaggc    40860
ccaggcctat cttctggcgg agaagtcatc acgaccggcc gcaacttcaa cgacctgtta    40920
aatgggacgt gggagttctt ctctgattca gtggttatcg cttctcagaa tgccccgta     40980
tatccggctt ccgctggtgc cgctgctggc atgttggagg cgaaatcttg ggtgtccgga    41040
gccaatacgt tctgcgtcca acgctacact gatcgcgtcg ggaacgtcgc tgtgcgcggg    41100
cttaatgccg gagcgtggac caactggatg tatgcggtaa acgtcatggc tcttcaacaa    41160
ggtcgggtca cctatggagt cgcggccgga tcggcgaacg cttacacgtt gacgctagtt    41220
ccgcagctcc aaggcggcct ggtggatggc atgattcttc gggtcaagtt caacaccatg    41280
aacaccggcg cctccaccat caacgtctcc ggactcggcg ccaaagccat cgtcggcgcg    41340
gccaacttcc ctctcaccgg cggcgaactt ggccaaggac tcatcgctga gcttgtattc    41400
gacgcagcag gcgaccgctg gagaatcctc gcaggcgcgc cacgcatcca agtgggcaac    41460
gcagatcagg actaccaggc ccccagctgg aaacaggtga aggactatgt agcgtcccaa    41520
aagctcaccg aagtggattg ggccgatgtc gtcaacaagc cgaacgtcgc catccaagac    41580
accacgccgt ggttcgccaa tctgagctg tctgacgctc ggcctttcat cgatttcat      41640
ttcaacaata accgcgccaa agacttcgac tatcgcttta tctctgaggc tgatgggtcg    41700
atggcattct attctcgcca ggggtctgcc ggtcctaccc aggacatcct gttcagcagg    41760
tcgaatgtaa cattcctcca gccgcgactg gatgttgcga aaaacctcgc gtacatcgcg    41820
aactctggcc ccctttggca gaacaccaca gccgatcagc ccggctggaa attcaccttc    41880
gcacaaggcg tggacgcgaa caacaacgcg gtgatcgcag tcaataccac caatccggac    41940
ggttcctatc gctcacagat catgcgatgg gactgggctt ccacgaacgt catattcaat    42000
aatcgtccgc tcttcgccgg tcaatacacc ccttgggatt ctgggaactt taatccttcc    42060
accaagttga ccgtgaatgc cacgaaccaa atcgccggcc cgaccgggat tcggaataca    42120
aacggcaaca ccgcaacat gaacacatgg ggttccggtt ccacaacggc atcctatggt     42180
aatgctgcca ttcaaatctt cgggaaaggg agtggtgagc ctgccgcgat ctatttcgac    42240
aactcccaga caggatggta tctggggatg acaaggatg acagctcaa gcgggccggc      42300
tggtcgctcg gcaataacgc ctacgtgatt accgacgaat ccaacattcg tttccacgtg    42360
aattccatgg ctggcactcc tgtttgggc ggaaacgaat tctgggggcc gtggaacttt      42420
aatccgaaca ccaagctgac catcaaagcc ggcacccagg aaactagcag cactgcgata    42480
ttcagcggaa ctatgccatt cgctccaatc gcatcgctgt ccgattattc tcaggcccct    42540
```

```
ttgacggttt acaacgcgcc aaccggtccg tctgcaaaac cggccgtcat cgcgttcatt   42600
cgtcctggta actggggagc attcttcggc atcgataccg acaacaagct gaaatggggc   42660
ggcggatcac tcggcaacag ctccagggaa atcgccgatt caagcaacat catgaatctt   42720
tgggcggcca acccgaccgc gccgtcctgg aacggcaaaa ccatttggcg atccgggaat   42780
tttgatccgg caacgaaagt ggatttgaac gccgcgaacg ccaccaacgg aaacatgatc   42840
ttcaaccgca tcgccggaac tggtagcggc atagcttcgt ccggtcgagt cggtgccatc   42900
aacctgcaga acggggcgca ttcggggcaa gcggcagcag tcactttcga gcggggcggc   42960
agtatcttcg tcaacttcgg cttggatacc gacaacgttc tcaaagtagg tggcggaaac   43020
ctgggggcag atgcctatcc ggtcatccac gccgggaact acaataacta catcaaccag   43080
gcgctggttc aggtgggtct tggcggagtc ggttcctatg gaattttcgc ggttctggat   43140
tatgccgctc caaccgcaac cgttcaaccc ggagtggtcg tggacggttc cattctcatc   43200
tactcgtctt gcgccgcaaa ctacaatagc ggtaaaagac ctgccggaac ttggcgctgc   43260
atgggatatg tagtcaaccg ggatgccaac accccctgact ccgcgaccct tttccagcga   43320
gtgacgtaaa aatgaaatgg acgcggatca gaaacccacg ttggctggac gcggtaaaca   43380
tccacgccat ggttactttc gaggggattg gagaagttcc tttcaccgcc aatccgcacg   43440
acgtggaggc ccacggaagg gccattcacg ctgcgatcct gtccggggcg cacgaccta   43500 tcgccccagt agactcgacg cgggagcagg ccttgcagga cgctatacga gacagggaaa   43560
agcgggctat ccttcgcgat acccgatggc ccatagatcg tcacgacgag cagaggcggc   43620
ttggtatcga aaccacggac gggcctgggc tgatagcagc ccttgttcac tggaggcagc   43680
agattcgcga ttggaatagc ggggatcggc cgcgacttcc catggctctg aaaacaatgt   43740
tcaaaaatca ggagtattga tgaaaatcac gaaggatgtt ctgatcaccg gaaccgggtg   43800
caccacggat cgggcgatca agtggctgga tgatgtacag gcggccatgg acaagttcca   43860
catcgagtca ccgcgagcca tcgcggccta cctcgccaac atcggcgtcg agtccggcgg   43920
actggtaagt ctggtggaga atctcaacta cagcgcccaa ggattggcca acacatggcc   43980
gcgccggtac gcagtagacc cgcgagtccg cccgtatgtc ccgaatgctc tggcgaatcg   44040
tctggcccga aacccggttg ccatcgccaa caacgtgtac gcggatcgca tgggcaatgg   44100
atgcgagcag gatggcgatg gttggaagta tcgcgggcgc ggcttaatcc agctgaccgg   44160
gaagtcgaac tattccctgt tcgccgaaga ctccggcatg gacgttctgg agaaaccgga   44220
gcttctggaa actccggccg gcgcgtcgat gtcttctgcc tggttcttct ggcgcaatcg   44280
ctgtatcccc atggcggagt ccaacaactt ctccctggtg gtgaagacca tcaacggcgc   44340
cgcgccgaac gatgcgaacc acggccagct ccggatcaac cgctacatga agaccatcgc   44400
cgcgatcaat caaggctcct gatattcgcc caaaagaaaa ggccgcttat tcagcggcct   44460
ttttgctttc cggctttgcc tcttcaacca gcttgacttc aaccggcgcg gcggactctt   44520
cctgagtgac cgaatccaca tagttcccta gtgaactcag aacgccgatt aacagcgctc   44580 ttaccaccctt gtccttgact gtctcgccta tgatcttggt cagaacggat atcaactctt   44640
cccggagtct tgggctgatt cttggccgaa agcgcttgcg atgctctttg cgtttcatgt   44700
ttagtcctct gtctgcggtc ttctcctcac cccgataatg gcttggggat gcgttgtgtt   44760
aatcggaagg gtcgggcgct attataaccc gtcgaaaatg ctcgcgctta actgtttaac   44820
gatacgcacc gcgatattaa atcgccttct ttctggccaa ggaactctgg cggccgggtc   44880
```

```
cggtctaagg cctaatttgt cgacattaaa acgagaaaac ccggatcgcc tgtagggtaa    44940
ggcgtccggg tttatttcga tctagtgtcc gctagaatca gtggcttccg ccccatccgt    45000
ccagccagca atcgaagacg gcgtgtctcg gcttgtcctt ggcgccatgg gagaagtgct    45060
tgaatcggat gacctggccc ttgaggtatt ccctgtcatt ccagcggcgc tgtttctcgt    45120
cgtgggtcag gctggaggcc gacacgttga aggtgactcc aggccacaga cgttcgttgc    45180
ggcagacgaa cgcaccgacc attccggacg gcgacaggtt ttctgcgtgg ctggagcggg    45240
ccgtgtggcc aagttcattg atgaaagctt cattgttgtt gtgcatcaac tcttccacgt    45300
cgatgatctc agcttcatcg tagtcgtatc gcttgacttt cacacagtgc ccttccttgg    45360
cagtcgagcg accgaacttg tacagtccat cagcgcgctt gcccatggaa ccttcgaatc    45420
ccagcattgt gtggcggcgc tcgacttcgc tgaactgttc gatggaagtc accagttcct    45480
gctcgaccag gtgaatcctc tcatagccga ggcagtgacg aaggaagttc acgcgctcgg    45540
ccgccctggc taggcgatct tcggtcggtg cgcgaggatc ggtgaaatca tcgaacacat    45600
ggaaagacca gtccggctca ccgctgtggc ggcgaagatc gccggacgac ttctggaaaa    45660
ctttcgggtc gctgatgtcg ccgcagacca gctcgccgtc caggccgttt aacagtttat    45720
cgctgaggta ttcgtagatc gattgattgt tctgccgctt gagttgacga gtcagcgcct    45780
cgccttcgaa tacgaagcag cgaaatccat cgatcttcgg cgagaaatac atcggcagtt    45840
ggccttccag cagcttcggg tcaaaattcg atgcgagcat gggtttcata cagttctcca    45900
gaaaagaagc ccggcgaacc gggctaaatg gcggtaagcc ggctcagatg gtttcgttgg    45960
cgtggttcag ttcggccatg atcgacgcat agcgctcgtc cgactccttg atgaacacgc    46020
cgtcgtacat gacgcctttg cgatccttga tggtgtcgta ggccgcagcg tagcaggcga    46080
gcatggtagt gtcgtgctct tccgtcacat cgaacagagt catgacggcc aataccaggc    46140
tcttgatggc taatccatga tttccgcgtg ccagcgcgcc ggccagatgt ccgaggtgct    46200
gcaaatcgtc gccgtaggtg ggatgaactt cgacagtctc gctgaagacc gatagatgat    46260
cgaacagatt ttcaccgagt tgcgcggcca tgatcgtggc aaccaccatt acgtcgccga    46320
tgccgtcttt cacctcgact ggtttgttat aaacccaggc ttcgcaaact ctgcgaact    46380 cttcgaccaa cttcaggaat tgatccttgg ccgaagagcc tttgatcagg ttccggtcgg    46440
aaccccattt aacaaccagg tcgtgaagtt cgcgactcat gatttgttcg atattcattc    46500
tttcgattcc ttttggattt gggattttac tgcgttgatt atggacgccg tgctctggcg    46560
cgatccatcc ttggtggtgc cgaagtagaa ggccattacc gacttcagct cggcgaacca    46620
atagccgatg atggtgccga tggcgaccga ggatgttggg tccatcagag cctcgcggcc    46680
gaatgtgaag attgcgatga tgatgagaat ggagcctgtc agaagagcga atgtgatcgc    46740
cgggcgaacg aaatcgttct gctgcgccgc aagcctcctc gcagaatccc tgtcggccgc    46800
ctctgcggcg aactggctaa gctcggcctg gagctggttc tgctcagact gaaggcgatt    46860
ttgttcggct tgaatcgcaa gctcctggag acgaacgcgc tcggcgctct ggagttcggc    46920
gagacgcgct agagcttccg gattcgcgtc tagagcgcta gcgaccgagg ctgggtcggc    46980
cttcgacccc agcgccgtag cgacgatagc gccaacggcg gcgcctgcag gcccacccag    47040
gagcgacccc agagccgggg cagccgcgcc gatcttacta cctatgtctt tccagtccat    47100
ttcgactcct caaaagaaag gcgccattac agcgcctttc tccggccggt gatttagaac    47160
tcttcggctt cggtcgcatc gccgacgcca ccggcgtcac tgcgaggctg ttcctgcttg    47220
ctgtagtcca ccttcaccct gccgccgacg aacgacttgt acaggtcggc cgcagccttg    47280
```

```
aagtgatccg ggttcttcac caggccttcc agctcgaact ggacgccgga ccagctaccc   47340
ttgtcgttcg acatgcctac ggtggtcatg cggaccaggt tggcgaaagt cggcggggtg   47400
cgcaggccct gcggggtctg aaccttttc tgggacagcg cggtcatgag cttcttcgag    47460
gccttgatct gcgaagacga cagggagatc agagcctggc cgaaatcgcc ggtgtccgga   47520
tcgatgacga tgacgtaatg accacgggtg tcggcgaagt agtcagactt cttgtcgctg   47580
accgaaccgt cttcgttcgg cgcgtacagg cgtccttcga cttccttcac cttggtcggg   47640
tctttcatca tttccttgaa gtcttcgacg ctgatggcgc ccttgaaacc gccctcggcc   47700
tcgcgacctg cccagcggat gaactcgcgg cggtacgcgg ccggaatgat cagcaggcc   47760 gtcttgccgt cgtaaatctt gccggtgacg tgttcagga acatgccggc cttcgcgcct   47820
tcgatgtact tcgggtcatc ttcatcgacc tggggagaca tcttctgcag aacctggatg   47880
aaggggatgg cataggactc ggcatcggcg ccttcgaagc ctgcgccgtc atacgatccc   47940
aaatccatga agtcgggaac ttcggtagtc gcgacggcgc cgccaccggt ggcaactgct   48000
acggccttgg tttcttcggt tgcttcggaa gtttcggttt tcttaccagc catgttaggc   48060
tccttgtttg tcgaatttca gttatcgcta actgtgggtt tataataacg gaagttgcaa   48120
ctaagtaaag caaattacat atcaagattt gctctttttc accttcggtt tcgtgatctt   48180
ggcctctttg tattcgtgta cgccgatgaa atctggcagc tcttcgccct tctccaggta   48240
ctcgcgaccg aacgcctgga gggtctggta atggacatcg cggttgatgg tggcgtcata   48300
gccggcttcg atgatggcct cggccgcctt cttcgcatct tccatttcgc cgcgaccgaa   48360
ttcggccaga accttggtct tgatgatgcc gtcgttgtcg gtgtcttcca gccacttcca   48420
gaacttcgat ttgttctctt ccttgacgga aatgatggcc ttcggctcta cttttaccgt   48480
gcgaccgtcc gccagagtag tggtcttctg accaagctct tccaacagct ccggaatggt   48540
gttacgcttg agggtcttca gctcctcttc cttttcggcc agcgcctttt gaagatcgag   48600
gatttcgccg tccagctgcg aggccttgtc caccaagttc agcagtcgat ggccgatgtc   48660
ggtggcttca accgccattt catccatgac gccaaaatag tcgatttcgc ccggcgcgtt   48720
ctctttcaag tattccggga tttcaagctc ttgctctttc atgtccgcct ccaacttagt   48780
gatgttccct tacttgaacc aagtattgag tagatattat gccgcatctt ccttgatacg   48840
gctactgatt tacatattaa atttcgtcgc gagtgctaac gtcagcctca aacacgccat   48900
caacgacata acttgccagg ttgcgtttcc actccaagct gacctggatt ttctcgtcga   48960
tggaatccag acagatcagg tcgaagtaca gaaccgagtt gacggtgccg attcgatgat   49020
ttcggtcttc ggactgcatc cgcagctcgt tgtcttcgtc ggtcgtgtag tagatggcca   49080
cgtctgcggc ggtgagcgtg atcccgatcc ctgctgcggc cgggttgccc aggaacacct   49140
ggacgcgctt ggcctggaaa tcgtcgatca atttttcccg ctcggcctct ttggtctcgc   49200
cgtagtatgt gccaaacgaa attccttggg cctccagata cgccttgatc tggtcgattt   49260
cctgaatgcg catggcccag atgatgatgg agcgctccgg gtcttcctcc agcagaccct   49320
ccagaagatc agtaaacacg gcgaatcgcg ggttgtcttc gggcggcagg atcaccggct   49380
cgccatagac gttgatatag ccggatgcaa cttgcttgag cttcgaacgc gctgccgcag   49440
catcgaaaga tacgtccagc atgaagtctt cgttcttgag aacgaagtgg tagtcttctt   49500
ccactcgctg ataaaccttc cttgctcag gcgacatttc gaaatatatg cgcttgtaaa    49560
ccttttctgg caggaatggt aatgcctctt tcttcgtgac ccggaagctg tgcggctcga   49620
```

```
tcagggaccg cagtttgtcg agatttcgga atactggtcg tccaagatcg tctttctcga    49680
cgagctgagg ggggactgta ctcttcccat ccaatttgcg catgatggcg accattcgcg    49740
gatcgtcgct gggaaccaga acggaaaatt cagccacgaa cgcccgatag gatttcgtgc    49800
caagaatgcc atcgcgtagg aattgaaact gcatgaacaa gtccgtaggc gctcgcgtca    49860
gaggcgtgcc agaaagtatt cgacgtgcca cggccttctc gcccagcttt acgatctttt    49920
tcgcgcgttt tgcttgtggg tttttgatcc tcgtggattc gtcaacaatc gcgcacactc    49980
tgaacgtctt gaggaatcgc tcgacttcgt catagccaga ctgatggttg atggcatcga    50040
cgttgatggc aaagacccgg agaactttct catcggcgaa cgtctcggca tacagacgat    50100
ccaaacgcgc cctggccttt tggaagtcg gtctgccgcg ccaatccacg cacagagtct    50160
tgactgcgac gtgagtagga atttcgcgca gaatccagtt agtatgcacg cctttggggg    50220
cgacgatgag cagcgcgtca acccttcctt gcaggaagag cctaactgag tctgccaaag    50280
tagtccatgt cttcccggtg ccctgttcca tcaggtaggc gaaatttctt ttgtttaggg    50340
aagctgccag ggcattgaac tggtgctgca tagcctcggt cttcataccc ttgactggaa    50400
aggttttggc tttcatttgt tctccagatc tgcgaggaat tggatgatat tgtccagtcc    50460
ttctgcatga ctcgcgactt ccaccaggtc gcggctgtta agatcgaaca gatcgagcat    50520
gggattcaga agcagccaat cggttccgat ttttgccagg acgaagccgc gaccacccca    50580
gccaatccgc tcccgaagga aagggatttg cccaggctcg aaacatcttg ccattgggca    50640
ggtggaggcg cgtttcggcc actcctccaa cgccttgaac tcgacccaga actggacacc    50700
tcgacgattc aggcaaatcg aatcggacat accagaccgc cgcgtctcca gaaagtcgat    50760
caggattcgg ccgagcgagc gctgcttaaa cgcattcgcc gctttcgtct cgcgatcatt    50820
catcgccttc gccctctttg gaaactttct tagtttgctc ttccagtttg gccttctcgc    50880
gctcggtcaa tatccgtttg atggccttca cgatgaacat gtcgatgccg ctgagcttcc    50940
agcctttgat caggaaccaa gagccggtcg gcgtcccttc ggcgatctgc tttccgtatc    51000
gcagatattt ctcaggcctg atacggaatc ggatttgttg atcaaccgaa tcatccacac    51060
acatgatgtc gaggaactgc gactggcccc tgtacaccgg gttttccct tggtcagccc    51120
tcttcttctg gcgaatcggt tcgttctcat ctgacagaac tttcttcacc atcttgacaa    51180
taaccaggcc gtcgtcgcca tcgcggatat cccgaatgtt ctgaatgggg tttccggaag    51240
ttactccaac cagctccgga ttgtcataag catgaccca gagcgtgtga gcttcgttca    51300
agtctgcgaa ttgaacttca gaattcgaca gactcgcggc gactttctcc caatcctgaa    51360
gcgtcttcag gtgggagccg gccagctcct tatattgggc cttcagctct ttcagatcgg    51420
cctttagctc cttcagatcg gccttcaaca gtttctccag ttctttgtct cggctgattt    51480
tcgccgaaag aatctgggct tccagtgctg ctacatcagc ctcctttacc tccacatcct    51540
gcgccgatat cggcaattg ccagggcga tccttgcggc cttgacttcc tcgcgaaggc    51600
gcaggaacct ctcggccttc gccgggccga agcctttggc gttcatgatg ccgccgatca    51660
ggcgcccgtc cgccaccacc cagttgagtt cggaatgctc cgggtccagg gccgtatatt    51720
ctacgccttc tttggccaat cgcgaaggga tagacacagt ttgctggtcg tccttcgccg    51780
cccgaaggca cgcggccgcg tattccaggc gatgataccg cttcatgtag caggtccagt    51840
acgtcaccac agcgtagctg accgagtggg agcggttgaa tcccaggct ccgaaagtca    51900
ccatttcctg ccacacacgg tgagcatcgt ccggggcgac gcctatgtc ttggcgccct    51960
cgatgaacaa ttcccggcgc ttgttgaaga actcttcgcc cttttcgcgca gacatggcct    52020
```

```
tccggattgc cgatgtctgc tcccagtcga actgtccgat gtccttgacg atggacatga    52080
tctgttcctg atataggaag acgccgtacg tccctgacag atattgctcg acctgcggaa    52140
tggtataggt cacaggctcg cggccggcca cgcgctcgat atacttggtg gccataccag    52200
aagacaacgg acccgacgg gcgagcgccg tgatatggtc gatgttttcg aacgcggtga    52260
tattgatcgc gtttgcgacc gaacgaactg cctgcccttc gaactggaaa atgccggaca    52320
ttttgtcttc gttgagaaca tccaggaccg ccttgtcgtt caaaggcaag tcgtacaact    52380
cctgcgcagt cacacagttc gcgtcctgga tgacgcccag agttcgaagg ccgagcgcat    52440
cgatcttgag gagattcaaa tattccgaat ccggcttatc gagctgcgcg acgccttcag    52500
aagttaccgt acagaagtcg ataacttcat cgttgcagac caggatgcct gccgcgtgga    52560
ctccagagtg ggatgggtga atttcgaggt cgcccatgca ggcggacgcg atctcatact    52620
tttcacggaa gtcgcggccg ggttgagttt tttcgaaagt gtcctccaat ccttttccat    52680
accgttcgtc cgccgacgta tattcaatga tcgagttttt gatgttgtcg gtatcgtgga    52740
aggggatgcc gaagcgcttt ccgacgtgag cgataaccga cgcggccttg agcgtattga    52800
tgttgcccaa cttcaccacg ttccaagtgc catacttctg ctggagatat tcgaacacta    52860
gatagcgatg ggtatcggcg aagtcgatat ctatatcggg aagatcggac cgggaaatgt    52920
cgataaagcg ctggaagaga aggcgatgag ggagcgggtc aacctcggta atgccaagga    52980
gatagcagac caaagagcct gccgaagagc cgcgagctgg gccgaccagc atatgcttct    53040
tggcgaacgc gaccagatct gccacgacca ggaagtagct gtcgaaatct ttcagctgaa    53100
tctgcttgat ctcttcttgg aatcgatcct catactcctg ggtccattcc ttgatgtggc    53160
cgcgactgag gcgtaggct tgcccctcgc gagccagagc gacgatatca ccatccaagt    53220
ggatcatcgg cgccttcgcc agtttcacat ccgccaaccg ctcgactacc gcacgagtat    53280
tggctgcggc agtatcgaac tcttcgcgag tcatgatgtg gcgtaaacgg ctccacagct    53340
cctcttcggt ggcgatgtgg cgaaggccga ccgattcccg caccttccag gccgacgcga    53400
aatcagcatg gtcgatggac ggcatgtcgt tgtaagaggt aattaccacc ggctttccga    53460
atgccctggc cgtctccata gcgccgtgcg cggcgaccat cgacgcggga ttgatgtcaa    53520
tgtagtcgat tccggccaga tccagatggg cataggcctc gccagcgaat tgatgacgc    53580 cgtcagcttc ctggaattct tgcggagtca atccttgatt ctggaccgac ttggaagtca    53640
agcggtagaa cttctttgtg tccttggcga gcacccaggc tttgagcttc agctctttct    53700
cgccatcgtc ggcgcatttg atcgggattt ccatgccgaa tccgcgaggc agttctgcct    53760
tggtagcggc ttgttcccaa cggacgtggc cccatgttcc atcatcgacg atggcgacga    53820
atggggattc gatctctttg gcgcgctcga tgatctccgg gaatcgacca tatgcggcgc    53880
cgtaggagta accagagcga acgcggagct gagggaaaga catcatgcgg cctccattgc    53940
ttgatacgcc cgatacactc ccatgcgctt gcagacttcg tggagcagcc gcacgtcgtc    54000
gagcgcccgg tgtttctgta catatgggcc gcagtagtgc tcataaagat gttgcagccg    54060
catgcggtgg ccgaacaacg gcgccgactc ttccacagta cagatatcga gcgatgggaa    54120
attgacttcg tccaggccga acttgccgcg agccagatcg caggtcagca tgaacttatc    54180
gaatggcagg ttgtgggcaa tattcgcgtc ggctctggaa aagaagtcgc gaactttctg    54240
gcgctgatcg aggaaagatg ggtgcttgat caggtcttcg ttctgcaacc cggtgatctt    54300
ggtgatgatt tcctcgataa cgattccagg attgcagatg aactctactt catccaaaat    54360
```

```
cttttcgcca tcagttatca cgccggcgaa ttcgatgatt ctcggctgct ttctcagact   54420
caccctttgg tggaacggga gtcctgtggt ctcagtatcc catacagcga atatcatgtt   54480
tgttccctct tatgtcgaaa ggccggctgc tttcgcgacc ggcctgagga gtatatcgcg   54540
acggctgaag atttacgcct tctgtccgtc tttcggcgtg atgcggctgg agcgcatggt   54600
ggcgtgaaca aacgccgaat agttgatcaa gtccaaggcc gaatcggcat ccttgaaccc   54660
gctattcgcc aggcgagtga gtttacccac catgtgcatc acgaacaggg cgagtcgatg   54720
atcatcggcg gtcttcgcca ccaggccgtt cgggaagagg atttccatga tctttccgta   54780
catcagatca ttgcgaccat aggtgctctg gcgggcgcgg aagacttctt ctgctgcgta   54840
cagattgttg agaacatctt ccgcgaaatc atcgggatgg gaatcatctt cgcccggcca   54900
gacggatgcc atggcgaacg gcgcggcgtc ttcggactga gccgtttcag cgagcggaga   54960
cggggctttc gcaaaagcct cgtcgagggt aggggcggag ttcggggcgg ccgggaacgg   55020
ctcgcctgcc atgtcgttgg gcgcgctatc ggggtcgcta tcggccgcga cggcgaagaa   55080
cggcgcatcg caaccttcca ggttcaggat gtaggagtcg atcccaggc tattgtaggc    55140
atcgatgatg tcctggcgat catcgaacgc cgcgacgatc ttggtgacgc cttcgatttt   55200
cttcaggatg tcgagcgcga ctgcccgctt gaactgaggc gccggctcgg tgttaccata   55260
cggccgcatg atgagttcat actcgcgatg ttcggcgatg ccgagttcgc ggtggagctt   55320
ggccctggtc tggaaaaagt ggttgtcggt tcggccggtg acgaagaaaa tcatgaggtc   55380
ggcgtcgatg gcattcctga tgcgacctac agcgtgcggg ttgagagtgt ccttgtcgag   55440
acgagaatga tactcgtccc attgccgttc caaggcgaag ctcttgcggt ggctatcgtc   55500
gaatacgcag ccgtccaggt cgaagatgat gatgccattc tttggtttgc gttccatatt   55560
cagatttcct cgctggttgc tttctgggtg acggttttat cgatgaacgt cccatcagaa   55620
gtgaggcgga aaacttcgcc attctggatg aaatcgaacg attgcacgtt catcgtgatg   55680
cgaatggatt cgctgccgtt ggtcacttcg acttgtgcga tgtcgccaac tttctcgaca   55740
atgatcttca tgttacatgg acttcccgtt gacggccaca gggttggcct cttgtttttc   55800
cgatccccag aactcgcggc gcagttcttc ctgctcggcc gagcgatcca tccaggggcg   55860
atagaactta cactggtaga taggttccaa cggaacatca accacaggaa tctggccggg   55920
cttcgtctcc agagcggaca tgaaccggtc ataggatttc tgctggattt cctcttcatt   55980
catcaccttc gacccatagc gcgggaaggc gcaggagccg gtggcgacgc agtgcggctg   56040
gagtaggctc tcgaacatag gatagacttc cagaaccagc cggcgcattt cgcggaatac   56100
ttcctgatat tcaccctggg tccgaacgca caggcgaacc ttcgccatgt cgctgagagt   56160
ccgcagattg aacttggccg cgatcttcgt ttccatgttg gaaggaatga ttgcacgagc   56220
gtcctggagc gacgcgccgg cctccagaag cttctggtag ctggtttgcg cgtcggcaat   56280
ggcgtcatgc cacagacggt tcagctcttc gcggacatgg taggtcgggt caggctcgcc   56340
atttaccgta gccggttcgt cgaattccca gcggaaagct tctggctgaa cgacggcgct   56400
gatttccaga gcgcgactgg tttcctgctg gtaagccccg gtacgagtcc gaacgagttg   56460
atgggtgaag ttcttgctga caccctcgat ctggaagatg aagtccacga actcgaacgg   56520
cgagcggatg gtgtccagca tgtacttcca gtggtcgagc ttttcggcct cggtcatggt   56580
cgccgggtct tggccgcgca tgcggtggga cttcgttccc aagagcaatt cccaggcgtt   56640
ctgggtgtaa ctaatcagag aaatcttcat cagaaatctt ccggaattgg cgtgaagtgg   56700
aatttttcgg tgagagccag ggccaggcct tgggcttgct ccctgttaag gccatactgc   56760
```

```
tctatctctt ccttgagcag ttcgcaggcc tccagacgcg cctcatactc ttcagcctca   56820
tggacggatg agaagacggc tccatcagag gttcggtaca caagttcgat cgccatggtg   56880
acctcagtag cagcggatga tttcggcgcg gatgtcgcga cggtcgaggt agtgctcacg   56940
aatcttgtcg cgggcacgct cggcctcttc gcggctgccg aacgacaggt tgaacgacgt   57000
gaaaggctta tcgtccagtt cagcgccggt ctgatacagg atgcctacca gaacgaaaga   57060
cggcgcggtc ttcggctgct ggtcggcttg catttcgagt tcgaggaagg acataggaac   57120
ctcttcagga tgatctggtg cgtaaattaa tagcgctcct gctgagcagc tacggttttcc  57180 ggctcgtaga tgagcatgtc aacgatttcc gggcactggc cttttcaccca gtcgatggcc  57240 gcgaccagtg tggtggaagc ggagaaagag aaagtgcggt aagactcatg gatgtacggc   57300
gaccccatcg aatcgcgctc ggtcgtgcga gaaatgactg cttttgatatt aacgatccgg  57360 cccatcttcg gcctccactt tagcgattat atcggacagg cttaacttct cgccattcag   57420
gaaataactg gcgcgaaact tcctgtcgcc ctctggcccg acgattcggg ccgttatggt   57480
gagactcccg ccgccaaggg catcggtgtc cctgaagaaa gtcagcagcg cccgcttgag   57540
cgctgcctcg cgaggatcga cggccattaa cctaccacgt tccagccgtg ctgagcgcac   57600
caaaccgcac cggtccctgc aggaaggcta ttcagaagga acacaggagt caggcggcca   57660
tcctcggtca tatggatgaa gtagcgggcg cattcaccta gccattcggc cttggcaata   57720
gcgcgttcta gattggcctt ggtggcgtag gtcttggtgg tgttttttgtc ggtggagaag   57780 attacttcgc gggccatttt gtcgattcct tttggttgaa gggtttcgcg tttcgatgag   57840
ggaatactac gcccacctga ctcagaagta aagcaatttg tgtaaattac ttcacgaaca   57900
ttttcttggc cttctgataa gacgaagaag tcatcaggcg ctcaatgacg tccatgtccg   57960
aaaccagatc gtccagaagg acgttgcgcc aggtagcgaa ccgaccgagc gagaagatgc   58020
cggcttcatg ggtgagattc cagatcatgg attcgcgctc gtcgcgaccg agcggaatga   58080
ttttgccttt ggtctggatg gtcggctcgc catcttcgat gagatgcctt ttcctgatgc   58140
cgaaggccgc gcaaacgtaa tccatatccc agtcgctgtc ccattcgatg gtttcgattt   58200
taccatctaa agtctccact atcccccttag tgatggattc gacgatcaga gtatcaccgg   58260
tgatggacgc tcgaaacgtt cccactttag gaccagggaa atacacggtc tggaagacat   58320
cacaggggat ggaaagcttg tatcgactca cgatgatgga ggttccttca ccgaatgacg   58380
ggtcgattcc caggtccagc cctgccgcag ccagattggc gcggaacggc gcggtgctga   58440
tgatattcac gtggtcatct tgccggcgaa gatactggaa gaaagaggcg tcgaaaggac   58500
ggctccaagt gatgcggttc gctagcttag ccaccagctg ctcatagtag tctgccggtg   58560
cgatccaacg cttttcagtc gccagattcc agatggaccg gtccgacagg ccgcccgtta   58620 cttttcctgga gtacatattg cagtggtcga tgcgcggctg ggaaatgaac tcgccgtcga   58680
tgtagatagc cttgtgtaca gtgacttcgc ggaacgggat gccggttagt tggccaatca   58740
ctggcgagcg gaatcgcaga agtgcgttgt ggcgctcctt attctccggc gtcgccgcgt   58800
cgatgatttg ggcttgagga aagcgatgcg cggcgatcag tccggcgagt ccggcaccta   58860
cgatgattac tttctgatca ggaatcatga tgtgtccctt atgagtgtac aaaacttgag   58920
aggataaaaa agggacccat tttcatgagt cccttgaaga gctagacgat tcggtctcag   58980
aagagcggcg gcttactctt cttcaccatc ggaaccgtcg gcgccctgac cttcaccgtc   59040
gtgctcctgg ccttcatcgg ccttctcgtc atcgccctgg ccagcttcgt cttccttcga   59100
```

```
agcgatggcg accagatcga cccagcccat gatttccagc ttgctcagat agctgcgaac    59160
cgaggtgccg tacagcaggt gggccacctt ctcgccgaag gattcgattt cgaccggctc    59220
accaacggtg cagtgctcgt tgatgtaagc aaacaccttg ccgcgagtcg agaaggcctg    59280
cggggttcca tggccgtcgc cggtcgggat gaagtgagtg gcgcggggc gacgcgagcc     59340 gttggacttc aggtcttcgc ggcgggcttc ggccttcgcg cggcgctctt cctgctcttc    59400
cttgcggcgc tgcttctcgg cttcgcgctc tgccttcttc tgctcggcca ggcgcttgcg    59460
ctcttcttcg cgtgcggctt tctgggcttc ctgcgcggcc ttcttctctt cggccttctt    59520
ggcgcgctcg gcttccttct cggccttctt ctgctcgcgc tcggcttcct tcgccttcgc    59580
cttctcggcc tgctcggctt ccttcgcctt ggccttttca gcgcgctcgg cttccttggc    59640
ggcggccttt tccttcgcct tctcggcgcg ctcggcttct ttcttctcgc gctcggcttt    59700
gcgcttctct tcgcgctcgg ctttcttctg ctcggcttcc ttggccttgg cttcggcctt    59760
ctcggcgcgc tcgcgctctt tacgttggcg ctcagcagcc ttctcggcct tgcgcagggc    59820
agcggcttgt tccttggtca gctcttcgcc ttgggtctgt tcgttctggt ccttctgttc    59880
catgttctta ctccgggaat gtttaaaggg atggcttatt ggctgtgag aggattatct     59940 ctaaactaat tgaagaaggg aatacccta gcctgaactt tcctaaatat tttctttcgg     60000
gaaagtccaa actctaggga acttatttat gttcgagaag ttcctagctt ttacgcaaga    60060
acagtaagta ttcgattgcg cgagttatcc cagtatacat caactgacta taagggatgg    60120
acggcaagtt ttcttctaac atggcaaccc gtttccattc tgaaccctgc gacttgtgga    60180
acgtcatcgc ccagccgaag tcgaatccgc caatagcctt ctgcgcctcc agccgcacgt    60240
cttcctcgac cgaaaagctc agagggttga acttcaccca gcgttcatag ttcgtgccga    60300
taatgcgaac tttggcgaac aacatttcat caggctcgtc gtcatcttct tgcccttcag    60360
gaactggctt gaagtccagc agaatggctt gttcgccgtt catgatgcca tattcgtgct    60420 ggttccagt gcacaccagc ttctcaccga ttcctggctg cacgcctttg tagccgagga     60480
ttcggcgagc gcgtgcgttc aagcggcggc gagtattgtt gtaggcacaa agaatcacgc    60540
catcgtcgtc caggaacgtt cgcatttcat catcagacat atcgaagccg gcccggacca    60600
atatgtcgtc atactcgcgg cagggcaggc gcttgccctg tcgcacgaac atcgacgccc    60660
gaacgatgtt gccggcatta cgctcgattt cggtcatgat ggtgtcacag ctgttctcgt    60720
ggaaaatttg gacgccgcgc acaggaggaa cttggccaaa gtcgccaatc tccaaaaccg    60780
gaattcggtg cgacagcaag cgctcttcat cccactcgcc gatcatggac gactcgtcga    60840
gcacgaccaa cttcggcttc tcgtcgagcg agtctttgtt ggcaaacatg atttcgccgt    60900
cttcatcttc gccaatcggc cgatagatga agctgtggag ggtccgggca ttgatgcaac    60960
ccttctcgcg aagccgcgct gctgccttcc cggtcggcgc gacgaagacc gtccagtcca    61020
tcgagcagca aagttcggcg atgatcttcg cgatggaagt tttaccagtg ccggcgaatc    61080
cggcgagtcg atagacctgg cggcggtgcg cccgatcaca ccaaccgcga taccagttca    61140
caacggaatt gatcgcgtcg atctgctgat tgtttggccg aaagccgaat cgctcttcga    61200
tctgatcgac ggtgaaacta gatgctgaca tatttgcgtt ctccaacgct gggtttaatt    61260
gaatcgaggc taagtttaag cacgccatcc acagaccatc cagtatcacg acgatacttg    61320
cggccttgcg gatcgacata gaagttcttc gtgcgccgca gcagtacata atgccaggca    61380
gctcccagcg catgaactct tcctttataa gggaaggcct tcgcctgctc tgcggcctcc    61440
ttggccccag ggagccagcg gacggtcgaa aggaccagga ccgcacccatt gacagcctgg    61500
```

```
gaagcggcgc ggccgtcctg tgggctatag cgatgtctat cggggtctac ccagtggtgg    61560
ttgccgcgcc ggagcttcac cgtccgggat cggccatcga acaccacagt gccttcgtga    61620
gtaaaaatgt gttccgccat cggatgttcc tttataacgt acagttatgc tttacctctg    61680
cgcaggaaga gtatactatc agctgactcg ccaaagcgag cgaatttaat ccaactttac    61740
ttcggcagga aagtggccga tactagcgcc gccgcctgta ctgccctcca aaacagagga    61800
tacattaaat gcaagaatgc aagatttccc gcgaccaact cccggtcggt aatccgaatc    61860
ccaatgtcga caagacccgc gacccaaacc tgaagcccgg tttcctgcgt cgcagccgcg    61920
agcttgaccc ggcgctggcc gttcgcattc gtcgcgagct gatccatgcc gaagcatccg    61980
acttggccaa ggccggatgg gtcaattcac agtccagcct ttatggatcg aaagccttcc    62040
cgcgccattc tgtcgttcgc gtgaccgagg ttccggaaga tggagctttc atcggcatgc    62100
tgatcggctt catcgagcat cgcgagcatg gcgaatgggc ggtcatggaa gccggaacga    62160
aagaaggcgg cgccgtcatc attccagtcg atcacatcat gcgagcgtca ttcgccgaag    62220
ccgaagagtt cgccgaaaag tgggagcgga acttggggtg gcgtctcctg cgccaactcc    62280
gcgagtgcgg cgccctggcc gggactgaag acgagttcct gcggcggatc atcaatcgat    62340
acgttcgtga tcgcacgatc ctcgatcacc acaaagtcgg cgcggacaaa atctacactg    62400
atgcagtgct caaaagcatc ggtgaaacat ggccgaaaat tccttcgggg aaattcgtcg    62460
gacaccgagt cgcgcagctc ctgatcggcc acaagctagg tcgagcgggg accatcctga    62520
atgacctggt ggacttcctg gagaagttcg cggccgggcg cgataaagtt ctcaacatcg    62580
ccatctgtaa ttgaggtgaa tgatatggaa gatttgggaa agcccagcat tccggagttc    62640
gagaagatcg acgccaaaaa actttatgag gctctggaga cgattgcgga gctagagaag    62700
aagtgggacg aatccgaaaa gcgcacacgc gatctggcag aagtggaacg gccagaggta    62760
gtcggctatc gcagcgcggc ttctcgcatg gtctatgaaa aggactatgg actgcagaat    62820
cctgagtcga tgatgcttgt ctcccagcac gaccgcatag tcgggagct gctgactgca    62880 ttaacctcga tgactgaggc gcgcaatcgc tacaacaacc tatggaattg cgctggtaac    62940
cgcctagctt tggcgcaagt tgaaatccgc aaagtaacat ccgagcgcta cgcagccctg    63000
gccaggatcg ctgagctgga aaaggaattg gccgaatccg aaaagcgcgg gagcgagctg    63060
gccgcgagct attgtgacgg cgtagtaggc gatgaatacg gccatcctta ttgtcgttat    63120
aaagtggaac gcgaagtcgc gctggccgaa gtcgagcgcc tgcgagaatc aaaaggcgat    63180
ccttctggca gcttcgacag atgcatgaag atgatgtatg agcgagacga gaacgcaaaa    63240
cagctagaat tcgccctggc cagggtggcg gagctggaga agaactggc gatggcacgc    63300 gacgcagcag caaagggtga tgctgcccgc cacgctgctg gcgcatgga aatggagatt    63360 catgagctga agacgaagct ggccgagctg gagaaacaag agccggtggc atgggagcc    63420 ttccatttcg gcgggaagcg cgacggcaag ctgtatgcgc aatgcgaaac tgaggctcag    63480
atagaggcgt atatcctcga catgcaccga agcagcgact cattgacgct caggaaaggt    63540
tccctctaca ccgcgcctgt agtccaggct caacccagcg tgcctgatgg gtggaaaccc    63600
gttccgatgg aaccgacgcc gcaaatgaca ttcgtcggcc agtccctgcg ttatgactcg    63660
gtaaacagca tcggcgagat ttaccggcaa atgctcgccg tagctccctc acccatcgat    63720
ccggctgcgc atcctcagcc gtgccaacaa ccacaggccc atcctgcccg ctgcgggtgc    63780
gagcggtaag tgccaagtaa ggagtttatg taatggaaca gcagaaacct tcggaagtag    63840
```

```
atggagccat cgtcatgacc gatctcgata ttcgcattct tcgaaaggcg aagccagaag   63900
cgcaggacga gtcgccgtg tccatgttcg caacggcgat ccgccagaaa ctgcagcgct    63960
cccgcgataa aggccgaggc ggctggatcg actgcgacga agatattctg atcaacggat   64020
tcgccgaaca tgcgctgaag ggaaatgaga acaacctctt ggacctggcg acgttcctga   64080
tgttcatgtg ggtgcgcggc atcgacgatg cgaagattcc cccggcgctc gaaaaggcgc   64140
gacagcacaa gatcatggaa gcctggagtc gaatccatga agacgcctg aactccgcca    64200 gaaaggcgag tgctgcgcga cagttcgtgg aagtgccacg acgcaagggg cgcccggagc   64260
gacttgcatg aagcctcacg aaataagact ggcccaggcc gaagagttcc tgcgcgaact   64320
cggccgaggg attccggacg acgaacgggt gatggtcggc tacgcggaag aggccacagt   64380
ccagaccgac gagaacgggc gcaagctcaa cgccggatgg tggcccgtac cctggaagga   64440
agggaaatac atcaactcca gatccaacgc ctacgcctgt atatcgtcgt ccatcaagac   64500
gcccaacccg aagaccggcc agatgcgcgta ctggcgcggc gaagcctctt tcggccacgg   64560
cctggcgttg atggtcgatg acatcggctc aggcaaaggg tccaagggcg acttcgaccg   64620
cgacgagttc cgagaacgac tggagccgac cgcgattgtg gagacttcgc gaacaacta    64680 ccagttctgg tatttcttca aagagccgat gtcccacatg ctccagttca aggcgctgct   64740
ctattcgttc gtggaccagg tgctaaagaa aggcggcgac aacacagtca aggacgtcag   64800
ccgttacggc cggatgccat tcggcttcaa caacaagcgc gggaaagacg gcaagttcaa   64860
atatgccgac gaaaacggca agcccgaatt ggtgcgcctg tacagcgccg actattccaa   64920
gcgctactcg ccggaagaga ttgcccaggc attcggcgtc cgcatcatca tgccgcagat   64980
gaagaaggtg gagataaacc gcgatgactg ggtgtatgac caagtatggc tgaagtatgc   65040
cgagcacatc tgcacgaaat acaagatggg agaagcggca ggcggccagg tccagcagaa   65100
tatgtccggc aaataccgca tccgctgtcc atggggcgac gagcacacca acggcgatcc   65160
tttcggcgca tactttcgcg gaccgatacc tggagccgag cacgaatatg tgttcggttg   65220
cgggcacgat acttgccgca aagagcatcg acggacgtgg gcggccttca ctgatgaagt   65280
cgtcctgccg tacattgtcg aacaacttga acgcatcaac cgccgccata tcggcgagga   65340
gtagtaacta tgcaaaatga tcctggaatt ctgattaccg caatcggctc attgcttctc   65400
ggccttctcg tcttcttcga aggcctgaat ggctggaaaa taccagtagc gaactttctc   65460
gcgtcgcttc tgtgcttctt cgtcggcctt tctgcttaa cgtgctggtt cgtcttggcg    65520
tttgacgtgt tttagtcgac gaacggtccg gaaattttcg gatggggacg gaacttatta   65580
gctctgccgg tttaggtagg agataatagc cgtcccttc gcctcaatat gtagaggcag    65640
tgttatatcc gatcatgtaa agcagaaggc ggcaaaccta acatgattat cgacgacgat   65700
aacattcttg atgacgaatc ggggtccagt gagtttgatc tcgcgcagat agaagatgct   65760
ggaatggacc ctttgatgac cgccgcaagt aaagcggccg acgatgcgat tgcgaggaat   65820
gagacttacc gagcgcaaaa ggcagcaaag tatgcagagg cgtatgcgga accagatctg   65880
aagaagcgag cgcgattgtt gatgctcgat caggcctttg atctcccggt cagccggttg   65940
gtgaaaggac cgttcgacga cttcatcacc aagtacagct cgacttcaga cagcaactac   66000
ctcgcggtct atgatacgtt gttc                                          66024

<210> SEQ ID NO 3
<211> LENGTH: 45333
<212> TYPE: DNA
<213> ORGANISM: Bacteriophage P1792
```

<400> SEQUENCE: 3

```
tcaaaaggaa gaaggaatct taagagccta taggtctatt atactacatt ttggatacct      60
tgtcaagtac tttttgatat ttctttgata atcacatgat ttacccgacg aacggtatga     120
tagggttcta taggtatacc ctaagactac ccttcgtagg ttgctggtaa ggggtaagtg     180
gcatagggtt cccttgatcc aggttctata ggtataccccc tagactacct ctgtttgcta     240
tgtcctggcc tattgcccct ttatccagta atataccaac aggtatcgga ggttgccttt     300
gatccagggc ctataaccgg gggttacccc aaaagtctat tttatcctcc ggtgtatctg     360
gggaatatcc ccccaggagt cccccagata aagtgggggt ggcctatccc caggggtata     420
gcccctagcc cctccctagg ataccatggg attagtccgg gggtcaaccc cttgagatac     480
cgttcatcgg gtggaccccta gggtattcat aagaaaaatc ttagggtatt cagggggtgg     540
atcgggggga atatccctta gactcccccct tgacagtctg ctggctaatc tgatactcaa     600
gacttctatg tccgggggat agcgcccag ggtatagccg aaaggctgta tgaaaaacca     660
gtagacaacc ccgtaaagaa tatggcgtaa tggcgccgcc ttgagggaaa ccgataggca     720
ccggggggaaa ccccagggggc ttgacaaaacc ccgcggaacc gggtctaatg gcccccacgt     780
tctacctagg ccaccatccc tcaagtctac ggacacatgc gggggctgcc aaccaagggg     840
gaatgcctaa gtcacccaag tgtaaggccg gcaggcatcg gggggttgaca agggataggg     900
gaagcggtaa gatggccccc aagtcaacgg cataacgtgc atgactcctt cgggattagc     960
gtagccttga caataagcgg atgtgttgat ccggggcggt gtagatagggg cgccttgttt    1020
atatcctaac tacaaagcta tgactctagc cgataggatt ggtccaccac gtaaatacag    1080
acggaccact tagcaacaag tcgagagact ataaagcgcg atattgacaa gccaagccta    1140
aggctctaac ataggcaccc gtccccagcc atctacggat ggttgagata caagcccca    1200
ggtagggcag gcattgggga atgccgatag tttaagctag accattcaac aaccgagtat    1260
cttaggtcta accaatcccc ccggataacc cgcttgattg cggacccagg aacggcggtt    1320
agactattga aaaaggttgg gtcaaaaggg tagccatccg agtccctact actagcttat    1380
cgtgactggt atgcgagagt cctttgggca agacgcatcc ctacctaaca ggtaaggtta    1440
ctccctacga tagccatccg gctccctctt acaagtaacc tcggagttag gtaggatata    1500
ttacaaagga ctaacccttt gcaatgtatc ctctagaggg aattaaagtg aaaggcaaac    1560
cgaaacaaag gaccgcagta tacaaggcg gtcgcaagac tgctaaaact gatatccatc    1620
gcaacaatcg gaagtcggtc tttggtagcc cacgtctggg gcgtaacccc cttgacattc    1680
tccttaactc ctgaaacaaa aggaaatact tatgaaaact gtactcaccg cagacaaaat    1740
cctcggcaag gatcagatca ccgctggtct ggtagctctg aaatcgttca acaaggcttg    1800
gaacgaagcg acccaacaac tggcggcctc ggctaccgta ctggctcacg agcatggtga    1860
tgttcgggct atccgtgcga tgctggccat gatgccgaag ggcgctaaga ccaacagcct    1920
gcgccgctac ttcgagcgct acgcaccggt caagtggtcc gaactcaaga aagagttcaa    1980
gttcgacggc aacaaacagc acaagggcgt tcgccggggg gaaaccgaag aagacttggc    2040
attgttctcc ggcatcctga cacccactg gtccgactgc ggcccggcgg aaaccgctga    2100
caatttcaag ccgatcgatc tccaggcacg gctcctgcgg ctggtcaagg actgcaacaa    2160
ggaactggac agcgagttca aggaccagtc caaggtaact gctgaccagg tgaatcagct    2220
gaataccctg ctgcgccaga tgttccccaa cggcgaggcg gcctgatgcg agtagtgggt    2280
```

```
ggcgcttggt tcttccccaa ggttactaag cgcacccctc accagcaacg aatccgaaag    2340
tatctgtcca tggtaaaccg tgggcaggta tctagggcca agcggtacgc tgaaaggcat    2400
tgcctatgat ggccaggggc gtactatgac gcgccccagg tctatcccta gagtgcatgg    2460
taggtccgtg cattgtagcg atagactatc aggaggtttc catgggttac tgtatctttg    2520
ggcaggctcg ttccatccaa gatcggggtt atgtgtctgg tttctgcgat gcaagggtag    2580
gctggcaagg gggtattgtt taccgctgga tattcaagga cggtaaattt gcctgcggtg    2640
tctactctac ggatggtatc cgtctgagcg tctgcgggtg ggtcaaatga agtcacccta    2700
cgaagcggcc cacgaaaggg cactcatggt taatcggttg cagaagctca cgaggatgct    2760
gcgggttcac cccgatccca gtggaagca agaacaacag gaattgatta agaggttgaa    2820
gaaatgacta tcgctatcgt ggtgtcttgc gtaggcatcg atacttctt cttccgtgac    2880 tggaaggaag agatgggtat caactgaccc aactgatgag gccatggtga ttcctggccg    2940 aaaccccac cggacctatg gtcgcaggct ggggagtctt gggaaatcag caaaggaaac    3000
catcccgtga aacgcaacga ctatcgtaag gttagccgca acatgcaagc tatcgaggca    3060
atcgaccgca agattgccaa ggtaactcgt gagttgacca actacagcgg caatcacctt    3120
ggtaaaaccc tggagttgaa caagctccgg gcaaagcgtg catcgctggc taagaacagg    3180
gcgcggtaat gtcatggaag tatattgcat gtgccgccat acgctcacgt tccaatgggt    3240
tgttgctggt agcgtgggtg gttctcttcg tcctgtcctc gaccttggac agcatccatt    3300
ttgcatcgtg aggtagtcct atgaatatca aggtgtggcc acgcaacgga gtaaccctca    3360
gttctctggt taagtcccaa accttccgta taaatgaggg tgtgtacatg gtctgcgaac    3420
tccgcagcat caggatgcag ggtgaatctg atgaggttgc cgttgttaac cttaagactg    3480
gcaacgtcat ttacatgcct ccagtgagtc tggtatacc agtaactgcc gagctgaatt    3540
gctacgaggt gtaacatgaa actccaatac aacatgatta ccagtaagat caaggttgcc    3600
tcttgggatg atctggagtc ggggcgtctg tacatccgcc aggacgagga cggggctgca    3660
aacccgcgtg tctttatgta catggaagtt gcagatgaat tcttcatcgt ggatatcttc    3720
ggtggacccg tgggtgccgt atacttcagc ggcgatgttg actgcgggtt ctaccccgtg    3780
accatcaagg ctgcgtccat cgaagtccat cggttcggcc caccggccta gggtgtgtac    3840
tatgacgctc gcccgataca tctaccactg gttggtatcc aaggttgtca tccgtcgata    3900
ccagcctaac cccaaactgt accccaactg gtccgttact catatccgtg tgtcgatctt    3960
cggcaaacgt gcaggtatcg tctatgaaat ccactgaacc acaagtctat tggttggcca    4020
gtcccgatgg tgaattccac ctgaaggtca tcaacttcgg ccagttcatc accgaaaccc    4080
tttacgaact cggcattccg gtggaccaca aggttcatcg ggtccactga ggtgaccc at    4140 gacaaacact accttcactg tagcagcaac ccgcccccgg aacgaccttc acatcagtaa    4200
gcgggcggat ggggtttatg tgaacccctaa aaactctggc gatattgcct tcctcaagga    4260
aggtaataag gttgtcgtcc tcagccagag cgggttcagc atcctcgaag cccagaccat    4320
gcccaacatc ggggaactct acccggctaa ggaggtccat gtatccgcca aggtgtgggg    4380
accgtatgaa gagtaaacca atgatcggcc agataatggc ccaggagcgt cgcatgaagc    4440
gtcgggtaga gaaacgagag ttcaacatga ctcatcagga aggcccccag gagcccgtg    4500 gtgagcttgg tttcaccctg gcagccgtag gtgtggagtc gagccgatcg gcttacctgc    4560
ggcacgccag ggaggctatg atccaatctg gtgagccttg cccccactgt atgccagtct    4620
tcggtcccaa agagggccgt tgctgcaact gcgcgaggga ctggtgatgg atttcggtaa    4680
```

```
tctttggtgt ctcttgggcg tccatcggta caaatggtcc gcagcaaatg atgacatacc    4740
tcctgataat cccagcgatc ctggcctaca tgtcggtagc cctcatcaag tcaaccaaac    4800
gactaatcaa aggagattac taatgcaccg cagagacttt ccctcctgct gtaccgcaaa    4860
aatctacatc ggcatgggcc cctcgggtac cgctgaccat tacgccggcc tcgcatccaa    4920
cgggttcagc ccccgtggtt tcgcccagga actgatcggc gccatccgtc gtgagtacaa    4980
cgagggccac ggtacgatgg tcttcacggt gaacagcgag caggtggtag cagataccat    5040
cctccgccgc atgggcagcc actacaaccc ctgggcatcc agcgacaacc actcgaccaa    5100
ggtccgggtc cacgtcatca acgtgcaagc tgcggcggag atcctcatct accacggtgt    5160
ccccggtact gtcgagcact cggaatacct cgacaagctc tgtaaaggtc tgtaacatct    5220
aggccttgac attctgctgg aagtgtggta ataaccttt aaggtgtccg gggttgctct    5280
tatacctata ggataccttta gggtctacct ttatctctta cttattattt gaggtatcaa    5340
atactcaaga tgtatacccg gactatgctg gtggctatcc ccctgtgggt tctttacctc    5400
ctcgtcctcc cctacctgat gacctcggat tcaacctcgg ctagcgccct gggtgccggt    5460
ctgatggttg catccatctt ctatgggctc ttcttcttga agtacctgta caactacagt    5520
aagcggctgg agaaaaaggt caagactttg ggggtgggaa atgggtgagt cgaaggaacc    5580
tatcgtcagc ttcgagaagt tcatgcaggt catgtatgac cgagacgagt acgccaagcg    5640
cctggaagta gcaacggcca agatcgagga gctggagaag tccttggcaa tggcactcga    5700
cgcagcagcg aagggtgatg atgctcgcca tcagtgcggc ggaatggaga tggagatcca    5760
ggaacttcgt gatgaattgg caggactgaa aaatgaagta aaggcgagta agcctcagca    5820
tgtcaccct catttctggc gacaacgggg gggtggtcga atctttgtgt caggtaactt    5880
taacctggac accgagacga taccttcat ctgcctggag actggccaaa gctgggacat    5940
tcaggagggg cgggtagagt atatcttcga gttactcccc aagggccata ccttcacggt    6000
ggaggtctga tgtactatga cgaacagcaa tggggaccgc acccaagggc gccgccggtg    6060
ttaccgtacc agtgaggtaa cttcggacat atatgacgcg atctacaata tcccagcaat    6120
cgctggatcc cccaagaggc caccggatga tgattgggta tactacctcc tgatggtagt    6180
cctcttcatc agcttgtgca tggccttcct tactcccctc atcaccagca aggatacagc    6240
ctattaaagc caaagtcttc tacgagcgac tgaaaacctc cggcgagctg accctgaatg    6300
gcggcatcta caaggccacc aaggttcctg cgccccacaa gggtaagcag cagcgtcgcg    6360
gccccttcta agaggtcgct agtaataccc ctagtattcc tgtcctgggg gtattgctgg    6420
ataactcaac aaaggagaaa acaaatggca cgtatcaagt acgccttcgg tatgaagtcc    6480
aagaatggcg aggataaagc cctcaaggtg atgacctcta cctcctgctt cggtacaatg    6540
gaaggtccgg taacccacgg ctataagctc gacggttgga ccttcatctg ctcccgccga    6600
agcaagaagt tcatcgatgt actcaacaag tgtacccaag gtgaactcaa gaccatcacc    6660
atcggaggca aggccttcaa gatcccgaag gtccacttct ggtcttacga aagcaaggcc    6720
aaggattccc ccttcgagaa gtattctaac gggacggaaa tgatttcccc cacccatcac    6780
ggaaaggaag gggtctgcgg tatctacttc aaccccaagg tacacaccct ggattcctgg    6840
tacccccatca tgaaattcct cttcaagatg atctccagcg gactcgacta ccaaggtcgt    6900
gaagaggagg ttcacctgaa gcttgctgag aagcatggct tctggaagtc ctacctcgca    6960
atgtccttcc acgggctgat agccaatggc tacaccgggt atccgatctc caactacatg    7020
```

```
ttcagtagtg attgggatga tctcaagaag ggagatatcc acatccaatc cgctgacgag    7080
tctatccgat tcggtcgttg gatgcccaat cgggatgccc caggtggacg cgagtgggta    7140
aggggcacac cctggcggtc tgaattcctg aagattcagt tggacaaggt ggaggtggtt    7200
accatagccc ctcagccaac cgtcttcgga agaaagatc cctacatgac cgtagatagc    7260
gaggtgggag ggttcctacg gcttactccc actagctgtg aaaaacacgg agtggtaatg    7320
ctggggatta tgggtgaaat taactggggt cgtgacataa aggatatctt actggccctc    7380
gaagacttca tcgagaaaaa cttctgacaa ccaaggagaa atcaaatggg aatgtatgca    7440
gcccataatg tgtactatga cgccgagggc tctattgtac accaatactc ggtcaagagc    7500
atgaccgaat atacaaactg cttcggagcc tattgcgacc ggacctccgg cgttagtggc    7560
gaccggtggg ttaccggggt tggccacctg ctggtatcta cccacgagaa tacctctggt    7620
aaactggtgg agttcttgaa cagcgatctg gtcaacagga ttaccgacgg tggtattctc    7680
tcggcttcca tcgactggcc tacccgttgg tgggattaca cgatgacct caagaaccta    7740 agtgatcccg accacttctc tcccccagga cgccggcagg cagtgtatgt acgggtggac    7800
ctcaggaaga acgcatcggc catcatctgt gccctccgaa tgggcgatcg cttgtggtgt    7860
gtaggtgatt ccatgcgtcg ctatacccag gaaaaccggg ataaggtcct gggatgcaat    7920
gcagagatcc tcaccctcgc ggcttgtgcc caggtaggta gcactgctca ctgcgacagc    7980
tatcctgcca tgttcccggt gactgccggt gaataccggg aaggatgcga gagtcacgga    8040
tgggaagtgt atgacagcta catcagcgaa gtcatggatg gtatcgtagg tgggtacaag    8100
gagatcacct acttcgatat caagagcatc catgggcgga ctcgcgaaga gttcaaggac    8160
aaactcaagc atcacgacgc tgagttgtgg caagggtata ccaaggacga ttacctgatc    8220
gaatgcgacg ggctcgaagg tgtacacaat gatcggatcc tctccatcat ggcacctatc    8280
actatcgacg taggtgacca aggtcgggaa aggtctgaga ccgtacccac cagtccctac    8340
agcatccccg aaatcctcga aaaactggag actatgcaat gaacaacgca atcccctga    8400 tcggtgcaga tcccgaagtt ttcgtcggct acgaccgtaa ccccagagc gtcatcggct    8460 tcatcggtgg aaccaaggaa gccccttgg ctgtagccgg tggtgccgtc caggaagaca    8520
acgttcttct ggagtacaac atcgacccgg ccagcaccaa ggaagagttc gtgaagcgta    8580
tcgtttccgt tcgactcctg ggtgcccaga tgctccaccc cttcggcatg aacatcatcg    8640
agaacctgtc ctctcacctg tacgacgagg aactcctccg cagcttcggt ccccaggctt    8700
acgtcttcgg ttgcgagccg gactacaact gctggactcg tcgtcagaac gtgatgccga    8760
aggatgcccc tccgaccctg cgcactgctg gcggccacgt ccatatcggc ttcagccaca    8820
tcgagcgagt taccaaggct accacccgcg aggtcatgca gatgtgtgac tacctcctgg    8880
gcctggcctc tgtcatcctc gatggtgaca cccagcgtaa gaagctgtac ggcaaggctg    8940
gcgcaatgcg ctataagccc tacgcgcgcg agtaccgtag cctgtcgaac ttctggatct    9000
tctctgtaga cctgaccgag tgggtctatg aaatggcagt acgggcttac acctccaagc    9060
acctcctgga ggagtacaag tccatcgtat ctggcgatga agtccagcga atcatcaacg    9120
agaacgacgg cgccgcggcg gtagctgcac ttaaagcgct gggggtggta tatgaatgac    9180
ctgaataatc gccatcggtt ggccggggac ttcaacatgt actactcctc cacctatgcc    9240
ttcttccggg tggacggaga gcctcgggta gtgtacgtgg acgataccga gtccattggt    9300
gacgaccgtc aattcgacgg gtttcgtctc cttggcaacg tgtatcgccc cgacggcagt    9360
aactactacg gaggggttgt ctacagcgag gtagaaagcg tgcggccctc cagtgggtac    9420
```

```
tatgacgtct ttggtcgtgg ggttcgtgat acctatgtat ccttcctcgt gaacaaccgt   9480
acccagcgca agggtgtaga tccccggaac atcttgctga atcatggcca acaggctatc   9540
accggcgaaa tgatgatccg aatcttcacc caggccgagg aaatgatctc tgctccctcc   9600
caccgggact tcttcatcaa ggatggggtt gtccactgga agggcgtgaa ggtcggccag   9660
atggtggatg ggcggctgtc cgcagatgaa caattcaaga accaggagga cttgctatgt   9720
cagttattgg cacacagata gggttccata agaaccagat catcgccccg gaacaccacg   9780
aggaacttcc tgcggttgct tccttcgggt tcgaagtcga actggaaggc ctcaacaact   9840
ggccagaagt ggatgggtgg gatctgaagg gtgacggctc tctgcggggg gtatggagt    9900 atgtcttctc cggtcccgcc tctggccaga gggcaatcac tcgggttgaa tcctttgtaa   9960
gtgcgatgga agaaacccct ccggctccta ccttccgatg ctccacccac ctgcacatgg  10020
atatgcggga cgtagagtgg ccggtgtacg aacgaacggt cctgacttac atggcattcg  10080
aggatgtttt cttcgatcac tgccagccat atcgtcggga tagtaacttc tgcatcccgt  10140
tcttcagcaa cgactggttg gcccagacct tcggtcgccg tatcctggcc ccggaaggtg  10200
accgagagaa agtcttgggt cttacctcct ggcccaagta ttcggccttg aacctccagg  10260
taacccacaa cttcgggtcc atcgagttcc gtggtgctca cgccctgact actcgacagg  10320
aaatggtagg cctgatgcag cgtatgttgt gtctcaaggc cttcgccatg gctcacgcag  10380 aaaccccct ggaagagttc ctcaaggtgc tctccgaggt gaatctccgt gatgtgttct   10440
tcctgggggt atctccggac tatgaaatgt ctccgggtgg tcgtgaaatg gggatcgcca  10500
gtgctactct cgcggtggca accatgggct ttgttcgctc cggggtagat cctctggagg  10560
atgaacagaa ccgtcagcgt cgtctccggg agcaggaacg tgagcgtcag agggctttgg  10620
atcgcaggct gcttttggct cgatctacta cctccagact actcgatggt gcagcagagc  10680
ggtacaactt ggcaatggtc ccaggtaccc aggttcgact ggatacgcg attactgcgg   10740 taacttctct gcgtcgtatt ggtcaccaag tgcgtgtacg agaccttctg gaggaccaag  10800
aggctcttca agatgccttc gtactgctca tggataaccc gcagcacctt cagcgccata  10860
ccggcgtaac aatcgaacca gatatgtact aaggagaaat acaatgtgtg gattggtagg  10920
cttctgtgcc acaactaacg cgagtgataa cgaaatcgct cttctcaaat ccctcctggc  10980
cgtggatatt atccgtggtg ctcacgccac cggtttggcc aagatcgacc cggttaagaa  11040
cgaggtagga attcacaagc gggcagtaga tgcctacgac ttcctggctg atcctgaaac  11100
caaggagttc ctggacaagg gtcgggctcg catctacatg ggtcacaacc gttacgccac  11160
gatgggcgac aagacggacc atggtaatgc ccacccttc caggtagacc acatcaccat   11220
ggtacataac ggaaccgtag atacctgggg cctgcacctg ctggacggca atgataagta  11280
caacgtggat ccaacatgc tgtgcgctac cattgccaac cacggtgcca agaagacgtt   11340
cgaggagaag ttctctggtg ctgctgcggt tgtctggtgg gattccaagg aacgtagcct  11400
gaacttcatc cgtaacgagg atcgtcctct gttcatggcg gttaccacca ccgggaccat  11460
cgtatgggca tcggagcctg ggatgctcaa ggttttcctg gagcgaccca atgctaagat  11520
ccgcctgcgt tctcctatcg ctgaactgaa ggccgaagtc ctggtaacta tcccgttcac  11580
ggaggccgga gtgcgaaagg gtgcagaacc ccagaccact ccggtcacgt ttctggacct  11640
cccgattccc gaaagcgaaa ggcaagcagc ggcatggtgg agtcgttacg tcggtgtctc  11700
ggactacgat gactacagcc gaagccaagg cagccaagcg ggaacgaaag gcagccaagc  11760
```

| | |
|---|---:|
| gggctcgtcg tatggaacgt ctggcgatgc gtacgcaagg aacaccctcc ggatcaacaa | 11820 |
| caacctcgac gcagcaggta gcaccttcaa gcaccggcaa ctcgtcacct tcgatgttgt | 11880 |
| caagatcgag gcctacgcaa acggcagcga gtacggaact gtcactggaa tcgagcgtga | 11940 |
| agaaaacctt ctcatcgaag ctcatggcat caacgtcgcc aaggtccacg gatacaccgt | 12000 |
| cctccgaggg agtatctcca atgcctactt catcggccaa gaccgtgatc tcaaggttac | 12060 |
| tgtcgaggat ctggcggtaa gctgcctgga cccaaagcat cggccgactc ctggggagac | 12120 |
| taccccagtg ttgaggattg aacgatctc atcggagacg aaatcccatt ctaaacccag | 12180 |
| ggttcaagtc ggcggcacct cggggaacac ccctccggcc aacatcacct accccctgaa | 12240 |
| ggtgcaaggc cacaccttca acaacgtgca tgtctttcgg gacttcgtgt cccagggatg | 12300 |
| tgcatcttgc gggaagatcc caaccgcata tgaccagcgt aatcgtcatc tgacggtata | 12360 |
| cgaaggtgcc aagttcactg gtagcctgga tgagtgcgag ttcatctgtg gtgagtgtgt | 12420 |
| aatcgaaaat aaataggagg tcaaaatgac ccaagtaacg atgaagcgtc aagtagtgat | 12480 |
| ccagatggag accgacgcaa cccgtaagta tcccttctcc cgtgacaccc tggacaagat | 12540 |
| ccagtcgatt cgtcgagtca aggagcagga actcaatgat gccaacccgg acgaggaatt | 12600 |
| cctggtaccg gccccggtag tcattgcgga agctatcgac cgactcttcg aagactactt | 12660 |
| cgagtaaggt agtgcgttag taatagtccc tggccgaccc atgccggttc ctaagatgcg | 12720 |
| tacatgggat ctaacttagg attccagggg ctattgctgg cttcactacc ctcaacagaa | 12780 |
| acaggagatt tgccatgttc tatatctata aggtgcccg ccctctgct ggtgctgtag | 12840 |
| cccttcgtaa cgccctgggt gctcgaatcc ttcgctccga ggggtctacc tatcggggtc | 12900 |
| gtgcgggtac tgcggtaatc aactggggta ccgttggtgc agaggctcac cgactccggg | 12960 |
| atattgcccc tgtgttcctc aacgacccgg cagttgttca ccgctgctct aacaagctgg | 13020 |
| agttcttccg ccacttcgag gccaatgctc cccacctgat tcctcgttgg accgagcgct | 13080 |
| gggaagatgc cttgggtgta ctcaatatct ctggtcgcat gtatgcacgt accgatctga | 13140 |
| acggccatag cggtcgtggt atccatctgg tgtgtactgt caacgatgca gaagttgctg | 13200 |
| caatcgatgc tctccgtaga cagggccact acccggtaca catctacggt cacacccaca | 13260 |
| tcccggatgt tatcaccagg gcacaactgt tcacccaggg aatcgtcggt aagcgtaccg | 13320 |
| agtttcgagc ccatgtgatc cgtggggaag tagtacttct ccaagtcaag ctccgccgtg | 13380 |
| ttgccaatga aatggtgacc aacgaaggac aaagcatcgt tcgtaacgta gctggcggct | 13440 |
| gggtctacgg ggttaacgat gcaatggacc gtgatggtgc tgagcaggct atgtcggcag | 13500 |
| cggcagaggc tatccaggta gctggactgg acttcggtgc agtagatatc atcttccagc | 13560 |
| acgccactgg ccgggccttt gtcctggaga tcaacaccgc cccaggtctg gacgctgaag | 13620 |
| gcagcgccct ggaggcatac gtcaagggct tcagcaaaat cttcgaggag actatctaat | 13680 |
| ggctgttcgt gttttcgttt atggtactct cctgtcaggt ttgtacaacc actaccttct | 13740 |
| ggaaggggcc gagttcatag gcaatgctgt atcctgcgca cggggtctaa tgtactccgc | 13800 |
| tggcggcttc cccatcctct ccttcgcctc ccgtgctgac ctcatcgtag gcgaaatctg | 13860 |
| gcaactcccc gagggcgaag cggggatga atgctggag aacctggatg ccctagaggg | 13920 |
| ttatccgggt tggtatgatc gtaccctcaa ggatttccga atcaatgggg aacgcatcaa | 13980 |
| ggccctggtg taccatcagg atagccacat ggcgatggat atcgtcaagg atggcgactg | 14040 |
| gaaggcacac ctggcaaaac gacaaggagc agtataatga cgaaatgac cgtagacaaa | 14100 |
| gcagtagaag tctaccgcga tactccgaat acattcggac accaagagct acatgcccag | 14160 |

```
aagatgcttc tcaaggagat cctgggcctt gtagcttccc agcgacacct ccaagactct    14220
atcgaggtct ccaagattcc ggaggcctcg gatagtcccg agaccagcta cggtgggtac    14280
tgtgacgaat ccattggcat tcgcttcatg tgggagcgac tgaagaaaat cgaggatcgt    14340
cttcgggaac tggaggaggt ctacggtacc ttcgtaacaa ctccttataa aaccctaccg    14400
ggcaacgtga atgctgtacc aagcctggtt ctcaagagtc aactggaggg gtaagtgaag    14460
aagatcatcg gtgatacggc ttgtccgggt tgccgagcta aggtgggga taaaacagga    14520 aatcacctca tcttgttcgt tgatacagaa aagggtactc ggttcggaag ttgtaaccgt    14580
tgtggtcact acgaagtcct cgaagagggt ttcaaggtgc cagagcgtaa ggagaaatcc    14640
gaggaggata tcatccatga agtcaacgaa gtccttgagt atccaattaa agccctcgat    14700
actcgaaaga tcagcaaatc aatcgctgaa cggtacgggg tacgtgttgg tctatcacaa    14760
gagaatggtg aggacgttat cgagcattac tatccacgca ctcgcgaagg ggagtaccga    14820
gcgttcaacg tccgaatcct agaacctaag gctttctact accgtggaag ccccaagggc    14880
ggtgtagacc ccttcgggta taacaccctt cggcataagg atatgggaca cctgcggtta    14940
gtcatctgcg aagatgaact gtcggctatg tctgtggccc agatcatgga gtcgaaactc    15000
ccggagaagt ggaagcatct tcgtcaggca tccattagct ggtcctcggg tgttggttct    15060
gctgacgggg acattgcgtt ccttaaggag tctggtgtac ttgagcggtt caacgaggtc    15120
atctattgcc acgatgcgga cgacgaaggc cgtaaatcag tagaaaaggt acgtgccctg    15180
taccccgagt gtaagtttgt cgagctcccg ctgaaggatg ctaacgacat gctcatgcgt    15240 aatcggggg atgaggttta ccagatgata cgtttcggca gcaaggtcaa gtctccggac    15300
tgttccgtta ctgtcgatga ggtatacgct gaggctctgg aaccccccaa gtggggcaag    15360
agttacccgt gggaaggttt aaccaaccta acctatggtc agcgggatgg tgaaatcatc    15420
ggggtaggcg gtggtactgg tatcggtaag accctgttgg cccacgagat tgctgcctgg    15480
aattgcattg agcacgggga gaacgtaggg acattcctgt tggaagagca ggtagccatg    15540
acccttaaga atatcgcggg gaaggttgcc aacgtgccct tccaccgacc ggatatcgag    15600
tgggatgagc aagcctttaa agatgctgct ggtaaactcc gtggcaaaact cttcatgtgg    15660 aagaacaagg gtcagaacga ttgggatcat atcaaggagt gtattcgctt ctgggctgta    15720
gccatggatg tgaagactat ccttctggat aacatgaccg ccatgaccaa ccaccttagt    15780
ccttctgaaa tgaacacgga gatagcccgt atctgtacag aactcgcagg gatggccgac    15840
gagctaggac tgcggatctt catcttctcc caccttaacc cacccaaggg taaccgtacc    15900
cacgaggagg gcgctgaagt aaaggaaagc cagttcactg gttcccgagc tatgcagcgg    15960
tggtgtcagc ttatgatcgg cttcgagcgg aacaagcagg ctgacgggga agagaagcac    16020
gagagtcgaa tccgtgtaat caaggacagg aactacggta acactggcct agtgttcacc    16080
aagtataacc ctgagacggg tcgcttggtt gagcgcgagg gcagttacga cgaggtacct    16140
gctgacgatg acaccccaat ttgattacgt gatctatgac cttgagggg acggcctctt    16200 caatacggtc acaaggcttt ggtgcgctgt tgttgtagac attccgactg ggtagtccg    16260 gggattccgg cccgaggaaa tggatgtgtt ctacaggatc atcgcccatg caaagttcgt    16320
agtcggtcac aacatccttg actacgacaa ccgggtcctt gagaaacttc atgggattat    16380 catacccca gatcgaagct acgacacctt ggttgcatcg aggttgactt ggccagaccg    16440
accccagggt cattccctgg gtgcctgggg tagattcctg aagtgtcaca agggtgattt    16500
```

```
taacgacttc tccaagttct cagaagaaat gtttgagtat tgccttcagg atggagtggt    16560
cagtcacgca ctgttcaact acctcctccg ggtactcggc atgacttggc aagagcttgt    16620
tgaatggagg actgtagatt ggctaaaaag cgagtgagga actacaagcg tgaaagggaa    16680
ctggctattc gacgcggcga aacgggcgtt gggtctaagt ctggagatgc tcagcggcac    16740
cgagcccgcc gaaaggtgga aaagcgtctt ggaaggaaac tcggagccga cgaggttgtc    16800
gatcatatca aacgtgttaa agatggtggc ggtaacgggg attctaatct ccgcgtccgt    16860
agtcattctt ctaacgctgc tgatggtggt cgtgtgggca atcgtaaggc caaaggcatt    16920
cgtaagaaaa agtaactaag gaggggcctt cgggcccccg aggactctct atgttcaatc    16980
gaaagcttag catcagtaac atcctcagtt ccttcgataa ggttctggtg aacctgaaga    17040
ccttcatcca agagtcttcg gaggaatctg agcgcatcta caacgagatc agcctgctca    17100
aagctgagcg tacccaggtc atgcaggaca acctgaaggc ccagaaggta ctggctaatc    17160
tcgaagagct tctgggaggt aagaatgaag aagtatcggg ttaacgtggg gttccaggac    17220
accaaggtgt tcactgcgga cttctatcga atagaactgg atatcattcg gttctactcg    17280
ggtgattctg atgccaaccc attgaccgtc cgggcctatg aggttgggc tgtccgtgga    17340 tgggtttctg tggaggagat taacgatgga gagtaagaag gaaagcctgg aggatcaggc    17400
acggaaggag attgccctgg agaaggagtt ctctggtagc tggggtggcc ccgagatcga    17460
tgctgatgac ttccccttgg gtagtgcctg tggcctagat cccgaggtct gcgagtcatg    17520
cagctgagtc agtgcgcatc atagcaggag atatctggtg agtatcctag cgcaagtgct    17580
tgtcatcttc tggagtgcat tcttccaggt attcctcctg ggattgaact ctaagctgct    17640
ccgggatgac aagatcaagg ctgggttcgt agtgtcttgg tgtatcacgc tggctcagtt    17700
tgcttacatc aaggcggtag cctcctccca cttggatatc ggatggttta tcttcgtgtc    17760
cgggtgggga ggtgctattg ggattacctc tgctcaatac ttctacaagt ggtatgacag    17820
agttttccac agatagtctt gacaaatcca gcaaagtgtg atataataac cttaaggtgc    17880 cggggggttgc tttacccccta taggagatac aaatgagtga ccatgtaagc tactccaaac    17940
atgtccgtgg taagtacctg tgtaatatgg cttctgccct acataagagc atggaggtac    18000
aaaggactaa catccggaag ttcctcagca gtccccacat taccctacgg agaagcgtc    18060 gggtgttcct gagcctgcca gagggattcc tgggggtgag ctacttcaca ggctctcatc    18120
ttaacctgag ttcctactcg gatcgtcgaa acgcccggat tcgtgacaag gatatgagcc    18180
tctacgatga cttctacgtg gacaggggcg cccagctgga ccctcgggat gtcctgctta    18240
cctcccaaga ggagaagaag tgggggtttc aattccttaa gaagaggcgg ggtggtgtct    18300
tcaacctgtc cgacgaagag ttgagcgatg ccaaggatat ccagcgcaag cttgacctgt    18360
cctggtacct ggtggacctt gcctgtgagc gtgggtgttc ctacttcatt ttcgactggt    18420
gataacatga gcaagatcaa gagtgttctc atggagcggg tagatgactt cctgctcaag    18480
caagttgctg tagcgttctt ggaacagcaa tggcgactgg accgaagcgg aaccgtggac    18540
tacctctcct acctggaggg tatctccgac gaggcagtgg aggtagtcat agagaatctg    18600
gcggagcgtc ttaagggga ttaagtggat tggagaaagt cactgttcgt tgagcacaag    18660
gtagctgata tcatcagtcg ccagagtaaa cgtggagtcc acttcaagac tcagcgggcc    18720
aagtggctga tccatgtgct taccgaacga atcctcaaga ttgaccttga ggccgtcccc    18780
cagatgccga tgatgatcgt aaaggctggg gccttcagca agccattcct aaagagtggt    18840
aagccgaacc aaaggctcca gtccttatgg caacgtcttg ggcacttcga ggtatctgga    18900
```

```
ccattcactg caatcgagta catacccttc gaccttggta agactgccaa gttcaaggat    18960
tggatgctgg atcagggatg ggttcctgac caatggaaca tcaaggatat tactgtcggc    19020
actgatggca agaagctacg tggatccgac cttaatgaat ccttgaacaa gtacattgaa    19080
gacctccgac agagtaaatc tggacgactc cgaatgaagc tccagggtat catccctggt    19140
aagactacaa tcggagaggt caagagaaag ctagaaaggc aacgaaaggt actaacgact    19200
cctaagatga ctgaagagtc gatggatacc gtccagggag acctgggaaa gctggtgatg    19260
cagcgaatgg tttgggccca ccgtcggtcc ctcttgcagg ggctggtaga tcaggtgagg    19320
cccgatggac gcctagaggg gagtgctaac ccctgtgcaa cacctacggg ccgtatgagg    19380
caccgtgtag tagttaatat ccccgctgct cgttctccct ttggaccaga aatccgaggg    19440
ttgttccagg ggacacctga tgccggtgaa tggaaatgga ctgtcctccg ccagacatt    19500 ggagagaacg aaagggttag gcccttcact aacatcgtgg aggaactcaa gaaaggtaag    19560
tggaagcctg taggaaagca caagatatac gtcccagcga atcaaatgat cttcgtgggc    19620
tatgatggtg ctggactaga gcttcggatg cttgcatcct acatcaataa cccagagtac    19680
accaaagagg tggtcgaggg tgatgtacac acggccaacc agatagccgc agggctccca    19740
acccgtgacg atgctaagac cttcatctgt gagatatgga tgacttgggg gaaacccctc    19800
gattaaaact gggtgaactc agggaaccct ttaatatggg aatcctgagc caagacactt    19860
gacatttccc gtagaatgtg ttatactgat attttatggg aggtgtttat gaagtaccca    19920
aatggatggt ttaagattaa gaactgtaga aagtgctcct cggagttcca gcctactgcc    19980
cctagccacc actactgctc agacgagtgc aaggagtggg gtaggatcaa tgcctactac    20040
accagagtct atggactcac gtatgatgaa gtaagggcta tggctgatga acgagaccac    20100
aagtgtgata tctgcgggga aagggattc ctgatggact cctctaagca cattgcattc    20160
ttagtcgttg accactgcca tgcaactggt aaggttcgtg gactcttgtg tcacaactgt    20220
aacagagcat tgggactgat gaaagattct ccagagcttc ttcggaaggc tgctgagtat    20280
cttcaagtgt aaggtgcaga gactattatg taggacccaa gcgggttcga agcgcccagc    20340
ccctggaaga cagggtgatg atatagtccg atccccaggg gaaaccttgg ggcagccgag    20400
aggcgggcca gtagtagcga cactggttga acttttgatg cgttcatcta cggtgctggg    20460
gatgccaaga tcgggactat cattggaggc accagggcag acggggctag gctccgggcc    20520
cagttccttg aggctaaccc tgatcttgct gcattgattg agagggttaa gcaggaagcc    20580
gagagaggtt atctcgaagg gctagacgga cggaagctaa ccatgcgacg ttctgagtct    20640
ggcgacgtga tgatccataa ggcattgaac accctcctac aagcggcagg tgcaattgtc    20700
atgaagtggg ccatggtgct cctagatgaa cgggtccgga ggttgaacct tcgggcttgg    20760
aaagtcctgg atatccatga cgaaggtcag tgggaatgcc acccagagga tctcattgcg    20820
ctacgtggac agatggaaat ctgtgtccgg gatgctggag ttctccttgg ggttaactgt    20880
cctttggcta gtgattccat cgctggtcgc tcgtggtatg acacacactg atacatctgg    20940
gggttgactt tcagcccct ttgtggtata ataccttctt ccctacgaga ggtttaagat    21000
atgtctaaga aagtatccca acgattcacc ttccgtgtag cgaagctgat cttcccctac    21060
atcgtaactc cggacaccga gtacggtgaa gtctaccaag taaccatctg cattccgacc    21120
aaggaagagg ccgacaatct ggtacagcag atggagtcca aggatgcccg actgaagggt    21180
accatcaagt accaagagcg tgacggagag tacctgttca aggtcaagca gaagaagcac    21240
```

```
gtggattgga tgcaagacgg tgagcgcaaa tctgccgtga tgaagccggt ggttctgacc    21300
tcggacaaca agccgtatga tggccccaat ccgtggggtg gctctactgg tgaagttggc    21360
atcctgatcg agacccaaaa gggcccacga ggcaagggta ctatgacggc cctgcggctg    21420
cgcggtgtac gactccacga gatcgtatcc ggtggtgacg gtgaggacga tccgctgttc    21480
ggtggtgcct tcaccgagga agagcccgag gatgtattcg acgaggtgtt cgatgacgaa    21540
gacgctccta tctaaggggt tgggggatca cgaggcgggg gtatgcccac ggggctgccc    21600
ctactgctta atcgaattcg aaagagtgtg gggtgtaagg gtggtcagtt ctacagctgc    21660
atctaataat aaagtagagg tcgatcctaa tggaatcaag ccgggtgagc cgggcgctaa    21720
acttgatagc ggcaaggtgg atgttggaat catcttcgaa gcgttcccga gggctctata    21780
tgcagtggca caagttgcta acttcggagc cagcaagtat agtcgcgggg gttggaggtc    21840
tgtcgagaac ggagtccagc gatatgatgc tgccttcggg agacacctcc ttgagcgaca    21900
caagggtgag gctttggacc cccaaagtaa actaccccac cgataccacg aagtgtggaa    21960
cgctctagca tccctggaac tagtcattca gcaagaggag gactccaatg gaacttctgt    22020
tggatccaag ggctaagact gttcctagca actactctgt aaaaggcgtt gatgtagacc    22080
tggggcttcc cccaggctac agcctaacgg aggaagctat ggacaaggcc aagcgtcaag    22140
agagtgaata ttacgactgg aagggctacg aagcactggt taatccggtg gtagagcacc    22200
cagagtatcg agccaagggt gaagcctttg ccctccgtgt attctgggaa gagaagctca    22260
aagagtctca ggtcgtagaa gaggtaacgt aatgattgct ggtatcgatg gtgacgttct    22320
taggtatgag ctaggccacg tggctatgtc gaaggaacac atcttcgata tccaggtgga    22380
gaagccatgg cctgaggaag aagtccacaa gctcgtcgat gataaagtcg aacaaattat    22440
caaaagggtg aatgcagatg agtgtgaaat ctaccttact ggccaaggaa attttaggct    22500
ggagcttgcg aaaatcaagc aatataaggg tactcgaatc ggtcttgaaa agcctcatca    22560
ctgggaaacc gtgtcagcca gacttaagga caagtgggga gcaatcactt tccacgtat    22620 cgaggctgat gactggctcg ggattcgagg gactgaagag ggagataact ttacagcgtg    22680
ttctagagac aaggatatcc gccaagtccc aggatgctac cattacagtt ggccctgtgg    22740
agattcccag ccggagttgg gaccgttcca gttgatggt cttggaagag tctccgcttc    22800
ttggagaatg tatggcgtta aaaagccgca gaaatcatgg aagcttgagg caacggtac    22860 ggcattcctc tacgggcaac tccttgttgg tgactctgtg gataacatac caggcctccc    22920
agggacggga ccaaagacag cggcagattt gcttggggag ctttctagtg agagagatct    22980
cttcgcagct tgcgcttacg cctaccaaca gaagtacgga gataattgga aagagtacct    23040
tctggagaat tttcgtctcc tctacctcat tcgggaccgc tcttggcttg atattcagca    23100
gtccggtaac gagtatcact gctcactgaa gaaacattgg gagattccct atgacgatga    23160
agaaatattc tattgaggaa gcacagaaaa tctgtgaagg cctcttttgag atccttgagg    23220 gtcttaactt tactgactac aaggtcgctg gtggtttcct tcgggatgca gacaacgggg    23280
ttgcacccaa ggatatcgac ctgtatgtcc gtaggcccta tgtggaggac cccactgata    23340
ctcggcgtag tcgcttttggc ccacggttga tccctgtga tgacgatacc ctagaggtag    23400
aggtcactcg gttctacaat aagctgggcc acaagaaagt ccggtgtagg actggggata    23460
agcctgatgg gtatcctgcg gggtttgatg tgtgggaatc cattggtgtt gacctacccg    23520
tcaaccttgt cgtgagtact cactcccatc cagcagagtt cgatgtagga ctgtgtgaga    23580
ttgcatgctg gcccataagt atccgtggac tgaaatctca aatctaccgt tcaagggctt    23640
```

```
atgagtttga taaagaagag aagtgcatta ctcttaaccg agtcctagac cctcttctgg   23700
atcattctca acccctaact gacaatcaag ttgaaaaggt tgtctctcat atccaacgta   23760
tcaaactgaa gtatccggag ttccgggtgt gcctggggga ttggatctgg cttctggttc   23820
gggctaattc tatcctgact gaagggacac tctcggttat ctggaagctt caagaaggag   23880
ggctcattgg caaagcaggg gagattcttc agacccaaac tgaagtcatt gattgggacg   23940
aagtacgaca gcgaaaccga gaagatcgtc cacgagacga tgccctggat gcagttcaag   24000
ccagacccgg tgagctacgt catacagcac aagtacaagc ccgacttcaa ggtatcgacc   24060
tcacaacctt gtggatcgac gaagcacctg ctggtcgagg tcaaggggta cttccaggaa   24120
gcctcggagg catctaagta catctgggtg agggaggctc tccccccaga tactgaactt   24180
gtgtttatct tcgagcgtcc taacacagct tgccattggc ttagtaagcg taaagatggc   24240
acaaagcaat ccatggcgga atgggccgaa cgtaatggct tccgctggtt tactctagag   24300
actttcaagg agtccttccc taatgagtaa gaagtataat gaagacactc tcgtcattgc   24360
ggacacccaa gttcgatccg aggtcaacat cgatcacctc gggaaccttg gggagtggat   24420
cgcacgtaac cgccccaagc gaattgttca tattggggac cattgggaca tgcccagtct   24480
gtcaagctac gaccgtggta ccgctaagat cgaaggccgc cgagtcctcg ctgacataca   24540
agctggtaat gatgcgatgc gagttctgct cgaccctctt cgccgcctac agcaacacca   24600
agcgggttgt aagaagcgta tctaccgacc agaaatgcac ttcttcatcg gaaaccacga   24660
ggagcgtatc aagcggtatg aaaattctaa ccctgctctc caaggtttta ttgggtacga   24720
tcattttgat ctgtccgatt ggattgtcca tgatttcctc gacgtgggtg ttatcgaagg   24780
tgtcgccttc gcccactact tctacaatcc caacagtggt cggccatacg gcggagtgc   24840 cgagcatcgc ctcaataaga tcaagcgcag cttcgtccaa ggccacgaac agggattcaa   24900
gtaccacatc gaggcagtag gcaagaagcg aatccacggg cttgtagtcg gtagcttcta   24960
cactcacgat gagtcctaca aagggcccca gggtaacgac cactggcgag gtgtagccct   25020
cctccggaac cacaaggacg gagagtatga cctcaagctg atgagtgtgg aggagttcct   25080
gtgagtaagt tcttgccaga cctgtactac attaagtctg agcatgactt cggtcaacgg   25140
gggttggcgt ttaagacgcc gatctccgca gaactctggc tggatatgaa gtttgggaaa   25200
ggtggtgctg aggatgggct tagacgaggg atgtattcca tcgaagtcct ggagatcctc   25260
tacatcccca gcgttcacct tccggatatc ttggggtaat ctatgaaaga tcgagtggga   25320
cgtaagctag aggtagggga cagtgtagtc ttcctggtcc acaggaacac ctcctcccat   25380
ctagccattg gcaccgtcga tgggtttacc cccaagatga ttcggatcaa atgcccgacc   25440
atgagttgga ctattgacgc tgagtatgtt ctaagaagca gtgacaaggt ggtgtactat   25500
gacaaaggct gaactggaga aagcacttga agagacgcaa agcgctcttg cgaaggctga   25560
ggcgaaggcc ttttcctttg aagaactggc tgaagaagct aaaagacaga ttgaattcct   25620
cgaagggatg ctagacctag tagaccttag ggcttctgta ttctacggag attggagggg   25680
ttatgcagaa agatcaaaag gtaagggtg gattccttg gacctacatt gcggtagcag   25740
ccttgtttgc cctgctggtt tatgtaggat atagctgact gatgttactc ctgaccctgg   25800
gagaaatatc cagactcctc atcgatgtat tatcttgggc aggttcactg taggtatcca   25860
tcgagtaacc aaaaaaaagg ccccaagggt atcatcccaa ggggccttat ctttagctcc   25920
gtagagcgtt cagcagtgtg ttgaacttat caacgagtgc ctcgtgagta tccgtatagg   25980
```

```
aagccacggg gatctcaact accttaccct tgacgtaagc cgcaatggct gcatctaggc    26040
cactcacttc gctagccttg ggtttccagt tacctggttt agcctcgcta gccttagcac    26100
ctacctccag aagctcaggc ttcccctcaa tatcctccca tttcactggc tcaaagtctt    26160
tcgggccaat gacttgtcga agggtccat cttcattacg tacagcaata gccttcgatt     26220
gaataacgaa tacactgttg ccgtcgttgt cagcgatata acctgccata atctaactcc    26280
taattaaact gccgatttga aggtacccac ggtaccaccg aaaggataca ctcggacagt    26340
gcattcccca aattgaccat cagtctccgt ctgattaccc ttagcatacc aagccttgtc    26400
cggagataca gcgaacttga tcttagctgt agacccttgg ataaagtgga agtgacaacc    26460
tggggttaca tccggaccaa gagtaacggt aatatccgta gtcccctggg acatgaagaa    26520
ccaaccagac tgctgcttag taagggtaat gttctgggtg agttgctggg tgttgacaac    26580
gttaccaccg aggtgagtag tcaccagtcg gggatccagg tagttctgtt gaagagaacc    26640
aatgttcttc acaggaccac gcatgtcgtc aaactgctcg ataatgtaat ccccgatggt    26700
accaccgttt tggtcatccg ggccaatcac gtgcttaata gccacgtaaa cacccaggtg    26760
ttcccgtcga gggtctactc ggaattcact accgaatgca gtaccgcaag gtgcctcaat    26820
catggtctca gagaacagac caatcacgtg gccagggtca cggttaccac ccgaggtttc    26880
tccaggagca cccacgaggg tattgaccag gacagagggg ataacggcct ctgagggatt    26940
ctccgggaag gaggctgtaa cgttctctac taccagggct gcgttctcct taactgcata    27000
atagtcaggg aggaactctg tagcggtaac gatgttagta tttacccgac cggcatccga    27060
ggtaatctca atgagatcac catcggcatt acgtcggaag acttttggaa catcaaccac    27120
gtaggcacgg ccaccaggac cagcggcatc agtttctaca taagttgcca tattacttct    27180
ccttaaagat ccagagcatc ttccatcgct tccataccgg caacgaaagg acgtgctgga    27240
gtttgcttat acaagaactt ccagatttca cctgcggatg ggtcatcccc aaacgaagcg    27300
atagttttac caacagccat agcaccctca gttgcagcac cagctactgg acccaagact    27360
acctctgcgg gggtagtccc tcgacggtaa cccgtcagca tgtcgtagat catagaagcc    27420
tggagtggca tctgttgcat cactacgtcc atcatccgtt gttctggact acgggtatcc    27480
tctcggctag acccaccgaa cttagccatc tgacggagtt catcctggat gtaacccaga    27540
ctcatcatca gaccaagagt gaaggctaca cctgcggcac ccataccagc gttggtccaa    27600
gaaccagcga agtgtgggct cagtcgtcta cggaacatcg gtaggatgat gttaccatag    27660
gctgctgggt aacccttcaa gagggagaac atctgaacgt ttccgttgct catccacata    27720
ggcttatcag cgaaggtggg gtctaggact acctgatcta caaaccgacg catggccaaa    27780
gtcttgacgt tgttagccat caggacttca gatggagtag ccggggagat caacttgagg    27840
gcatcctgct ggctaccgat gttaaccccc atttcccgaa gctgagcaac cttcagagca    27900
ccattggcag aactgaaagg gagacctgcg gctagatcca tcaggttgtt ctgatagacc    27960
cgcttagcag tctctgttgc aaatattcgg ttaacatggg ttaggatgga caagccgttg    28020
atgaggaact gaccacggat cgccttttgg atggtagagt taaacacctc agcaccaacc    28080
cgatcagcca tcagagaagt agcagaagcc agggtgtggt tcatatcact cataaaccga    28140
ccggtctcag actttggaac cccactgtag atcctgcggg ctgcttgcct tactacctca    28200
cccatagttg ggagtacagc cccaagggta ggcataaccc ccgccttagc gaagggtagg    28260
ctgaactcgt tcagggtcga gaaaccgcg agtggaagtc ttgagagcac gagggcaccc    28320
gacgtaacag ccgctagctt cttaaggtta gggtctttga tacgaccgtg cataccatta    28380
```

```
taggcatcca ccaggtcata catccgatcc acctcttcct tggtaacccg tttaccagcc    28440
cgttgagcct cagctacagc agaagcgatc ttagcgttag ccttctctcc gttgatacca    28500
aacctttcgg taaaggcaat ccggtgggaa gccccttcga agtagtctcg gatttcctgg    28560
agacgcttct taggagtatc attaagagaa tacttattga ggatctcctg aggtacggag    28620
ccaaaggccc ggctttcttc cagttgacca tacttaggta ctgcatcgct ttgggcgaac    28680
cgtccacgta gggtatctgg gtcaccctgg atacgatagc gagggtctac ttcccaagcc    28740
ccggtctgct ggttctgagt aaccagtcgg ttaacctcag gggcagtgtt accacgagta    28800
tcatccgaga cttctgccag ccagttggct acagcatctt cagcagcttg tcggctctgg    28860
aagtacggag tgatatcgtt caggaactct ggggattgaa ccttctcagg ggacagccca    28920
aagggcatat agttggggat agtaccaacg gacattccac cacggttaac agcctcattc    28980
cttacgtcat ccatcaaagc acggagacgg gtagcttctg gggtattgac acctgcggat    29040
gtatctgaga taatcctgtc gatctctttc gaagacttac cctcgaagat gttatcgagt    29100
tcagagttcc acttacctgc ctggagttcc tgatcctcaa agatagtctt accagaggct    29160
cgcttaccac tcatatcagc cctgaaggtc tcagagaact cacgggcgat aggagaagcc    29220
ttagcaagtg gctccaggag ggacgtagct tcgtttccta gggcatccca ggctttcttg    29280
accgtacccc taggctcaag ctcagaagcc ttaggagggg ccgcagggtc gttaggatca    29340
actacggcag acccagctga gtcctgatta cgtcccaggg tgtccaatcc cgaggataca    29400
gcaccaccgg cagtacccat agctgtacca gtgaaggcag ccgtcaggag gttatccatg    29460
aactgctctg gggtttgtac ctgccctact gcatcatacg cgatagtgtc ctggagcgcc    29520
tgctgggcac cagaggtaac accttcagcc acaccagaga ctacagcgtg tttaccagct    29580
tgggttacag cctcaatggc ggtctgctta ggtagacccg attggaccaa catctggtaa    29640
gcgccatctt taccgatgtg cttgaggagt ggggcagcga taacaccagc acccgcagtg    29700
tctagtaccg agaggccagc accaccgagg actgcggtcc atgggttgct ttgatcgggg    29760
tctagttcct tcatctggtt actcagggca cctacgttga tacccatgga actcaggaag    29820
gaaccaatga gcgctccacc catacgacct ggggccccaa agacagagcc agccttagca    29880
cctgcggcac caccagcaag tacagggggcc atcgaaggga gagcctctac aatgttattc    29940
ttaaggaacg acccgatgga tgggatatct tggatatcag cgaaagaccg aacatcaggg    30000
gttccgtact gtgacgcttc ctgagcattc tcctcggcca tctgtgtgcc gtagtctttc    30060
aggtagtcac tgccagtcag ttcaccaagg gtagcaatag taccaccgat gttagactgc    30120
atggtatcaa ccccacgacc aatcgcagag ctaatagaat tagggtcagc cggagttact    30180
agggcactca ggtctggggc aggctcaggg gtagtagggg ctacttcctg gggtgcctct    30240
tcgataacct ctggctcatt caaggaagcc aattcagcgg ctacgtcgag gcccttgacc    30300
tcagccagtt ccgcatcaat agcggccttc agttctggag aaagagccat aagtcacctt    30360
ctagttgctg gaaagagaat aggctcttaa gatgtatctt aggatactaa ccttcttagt    30420
aagtaagtca aaaggaagaa ggaatcttaa gagcctatag gtctattata ctacattttg    30480
gatactttgt caagtacctt ttatcgggtt ggggcaggat agtccaaatc agcaccaaac    30540
caattacccg taggttgcag cttagcagcc tcccgctgga taatacccac tgggttagcc    30600
cccggattag cccgaagttc atttcggaca gtctgggcaa tagcctgttg ggcagtctta    30660
ctcagcttct taccacccag agcctgagaa ccgttgactt cactcaggat accaagggcg    30720
```

```
tccttagtag taacagcttc acctcgggct gccttagctg ccgcttgacg tgcctgagcg   30780
ctgatcttag cagttttgag gcgtacagca gaactaagct gggcattctc ttgagacata   30840
tcctggccac gtcgagtagt ttcagcctgt agctgggccc gttggttagc caggtcttgg   30900
ccacgtcggg tcaactccag attagcccta tctacagcag cctggttgac ccacttatca   30960
aggacgccct cagtcttacg cttggtttgc tcaagggtcc cttccttaac tttcaggttg   31020
ccctccccaa ggcgtacatc agcagcatcc ttagccacct tacgctccag atccttttcc   31080
ttgatctgac gatcagcagc tgcggcagcc atcttctgct ggttgatccc agcctgtagg   31140
ttacgatcca gttgacgctc ataggaagca gcgaacatat ccccggcttt accagtcttg   31200
tctagggccg aagccagaag accagtacca atgagagcgt aagatacata acgagacagg   31260
tcatcattat ccatagtcct catctgggtc aactcttcgt tcacccggtt cttaagctct   31320
tggggtttaa gctctacacc ttctctctgg gcatcagcct caactacagc ttgggccatt   31380
tcaggacgac ttacagcacc agtacgaaga ccctcggctg cacccgtttg gatgacctgg   31440
cgattagcct cctcctcatc tgctacagca gcaccagcct cggaagccac ctctggggtg   31500
atctcaggct cgatagaggg ttggttaggg gttaccccat aggacaacag accggccccc   31560
gtagggcctc ctgtggcgtt ctgggctgca cgttggccta cccctgggc ccattggtta   31620 gcctcttgag caacctcggg acccatgttc tcaaccgctt ggctagcctg agccatttct   31680
tctgcacgag tacgctctgc atccccgagt tctcctgggg ttacagcggc ttgtacacct   31740
acagagatag gaccaccgag gatacctgcg atacgaccca aggcaccgcg accagtagct   31800
tcagccgcag gtgcaacctc ttgggctgca cgggaccaac gctctgggtt ctccagggct   31860
gcctgagcag cacgacggac acgatcagga atacctgagc cctctacagc cagcggcagt   31920
ttgttccttg cgattcgcgc catgtccagt tcattctgag cagcccggag gatgctaggg   31980
cgaattgggg acccttcata agccatgctg gccataggat taacctccaa atagtttact   32040
taggattcca gactttggct gctgtccgaa accgagttct tctgcgctag gaaggattcc   32100
cactcccgct cccataccctg ctgcaacttc cgctgcgcct cgttcgcttg ctcctctagc   32160
cccctcgaca gaaaagcttg gtactgtttc tgaagaaggc tcacttcctt gcccgaggag   32220
agccgcgagt gctgctccgc ccattgcgcc aaaagggttt gattgtccac tagactctcc   32280
cgattgcatt gtcccaaggt gggtggggcg gtaggaacct tgacggctca actgtacccg   32340
ctcctgccca ccacctatat tctgtcctat agcgaacagc ttctgaggaa gggaggccat   32400
tagaacagaa ggccccgac cctaccacca gcattcatac caacagaagc acccgctggg   32460
ccaccgaaga gagcacccaa ggaagcacca ccgagagcac ccagggcaga cccgaggcca   32520
ccaccaccgc caccacccga agaagtagtg acattggttc ccccatatc gccggagata   32580 agctccttat aggcgaggag gtcgttgagg ctgacgttat tctcataggc ccacttctgt   32640
agagccccgt tgatttcctg ctgctcctgg ttctgaagca tgctaccagc atctacctgc   32700
atggcattac cagagccgag gcccttagca atagccgaca ggttacccag ggtattcaac   32760
ctattctggt tgtaagcctg ctggtcttgg aaagccaact gggaagcgtt attctgttga   32820
ttctgaagca gcctagcgt agcaataccc tcggctacac ccgctcggga actaccatac   32880
tgaccagcgt tggttgctcc tgcccgcagg tctggacgta ccgtagtgtc gaagtcccat   32940
tgcatctgtt cgttggctgc accaatggca ttcgccaagc cagttttgtt gggatcgtaa   33000
ggaccaaggt aatcagccag agagctaaca cctgagctac ccaggagaga ctgaagggca   33060
cccccgagac cacccagccc ttcgattcca ctaagctgga gagcattttg gtcagccacc   33120
```

```
gggtcaaagt tcggatcgcc cccgtaattg gggtcaaagc ccccgttatg tagccaatca   33180
ctggcacccg agagtagttc attatagtta ccttgctgat agggtgtgga cactgaggtg   33240
gtcttttgct tcttactacc acccttgtaa gcccgagaat ctagagcatc ctctacacca   33300
aaccccatca ggcgttttac gttaaattgg aggaagttca tctggagtta cctcacgata   33360
gaaggatacg gagtcttcgg tgtacccgag tttctctagg gtaggcttcc agccccgacg   33420
accttcgcat tggataaacc gacagttaac tcgttgggcg aactgtccga ggaagtcgtc   33480
tacctccgag taatctaccg gggtttcatt cccaggcatc tttccactcc agaagaagtg   33540
taggatgttg cccaagggggg cctgggatac ttggatgact cccgcgtacc cactctcttc   33600
ctggtagaag acataggcct cataattaac cagggaatgc accaagtgct caaagtccca   33660
gaacttaccc aagtcagtcc tgttaaaagc acgggctagg gctggaacta cggtcgggag   33720
ggagtctata ttctcacgag taatcaaatg aatcatggag tcaccaccag ggggaatgtg   33780
aatgtacccc cgaagactgc tccttgggga attccttgga ttagaacacg gccattagct   33840
gtgatcttaa acattgcttg gttaaccaca ccagtctgaa tagtagccct gttgagaaca   33900
tcaaagactt gatccaacgg aggtgcgtta gggtcagacg gaggtggata agtaatagtg   33960
ctctgcgctg gtatgatgct ggagtaagcc gggataaaca actcagcagg aggccaatac   34020
gcctggggaa gatccaggac agtagctcca ttagtgtagt taccaccaga catgagcatg   34080
gttatccaca cttcatcctt agcagtgttc atcctatagg cacaggtacc catcggctga   34140
tggttgttct gtggggtaaa taggataaaa tcccccggca ggtccttggg tttagtacct   34200
gcgagtctcc attggttatc caagtcgtaa tgatagatgc cggatactgg acctaccact   34260 ccggggggcaa aatactttac agtccctggc ttgagcttct taggggggctc catagagacc   34320 ccccagtagc cgtcagctag gtcattaaga gtctgtccaa ccctaacgaa ttcttcatta   34380
aggaagggca gcagttcctc ctcttcctgt ggtggaatcg aagggctgta cttttgactc   34440
atcgcatacc tgccttcggg gccatttcaa tagtgtatcc gttgaagtac cagtcaccct   34500
ctgaggagaa gtcgaacttc aaggctatgt accggcccac atgtttagtg tcaatcttat   34560
agtcctggcc aatccggtat gggtaggggc ccttccaccg aataccagaa ccttgtacct   34620
gagcattacc aacccagatg ttgcaggtgc cgttacccgt gatatgcggg atgatagcac   34680
tcacagtctt catcattcgg tcatccccaa gatagatatc ggatctctca agggtactaa   34740
cgaagttctg cccagagaat gtagagttat taccgaagag gaacaacttc ttatcctgga   34800
aagacgagaa gatcatactg gacttttctg ggttataaga gccttcaccc cagaccgaag   34860
tatcggtatc ccaggggttg gggtcgtcat cccagaggtt agacaccttt ggatcgatga   34920
tcccgtaggc tccactgaga acgttgggaa ggtctcggat actccaagtg ttttccttcc   34980
agttccagat gatagccctg tcgcagtgct tacctggctt agacctagtg aagagtagc   35040 atacccacat ttcagtattc acgtggtctg caattacgaa ggtccgttga tagttgtcag   35100
ggttaatatc cgagaagaag aacttacgga cctgagcatc aataacagac tgcttctgca   35160
caccgttgtg gacatatacg tcaccgtggc ctactacaaa gtggttacca tcgaactcta   35220
ttgcacagtt gggtccgagg ataccctacgt cgttaaacag ctgctggaac tggaagatga   35280
acaatccacc gatataccgc atggagtata cagagtcttc cttgtagatg atgaaagagt   35340
cacgaagctt cacaccatcc acgatagcac cattggtatc agccaaggtg ttctgaccag   35400
catctttagt ggggtccgtt gggtcccaag atgcaggtac accaccagca tcagccgagg   35460
```

```
tactccacca gaccatctgt ggcatttcta cagagttact tgtagcgttt aagccaacca    35520
ggaagttctt aaaagactta agcctcttaa aagtagtatt cgctgggaag ttagggagca    35580
ccctaaaggt tgattctgac ggtggaagat gatgaggagg gttaacccca tcgttagcaa    35640
agattacccc gttgaacgat cctacagacc atctgttagt tatactagca gcgtaaggtc    35700
ctggggatac atcgatgatt gtagtcccgt cggctagata caaccgttgt tcagaacaca    35760
ggagccaata ggggatgtta ttccggatga aaggaaacat atccaagatt ggggcctggg    35820
ctgtatcaaa gataggcgta tggcccagag ccttctgagc cttgccgttc ttaaaccgga    35880
cgttgttccc gaaggaccat ttctccagtg gcaggtcagc gggggcgata tcggtcacaa    35940
tccccgtagg gttcttgacc tcttgtctct ctagggccat tgtatacctc agttcttaat    36000
gatgaagaac acagaacaga acggtgggat attacccaac ggcatgttga tctttactgc    36060
atggttgtga gtctgacctt gaccagcagg gccagtctca aggttggtat tggctgcgtt    36120
accagagcca cccgtcagag caccagagtc acccgcagaa ccggtgaggg tagtagcccc    36180
tcgggatctc caagtgtggg tgtgcgatgg gatttgggct agggtaaggg cagtcccttc    36240
agtgaaccca tcccatacga tgttagcgct accacctcta gtccctacag cctgggaaga    36300
accatcgata ccccaaggga atgcaccaat caggttaggg acgggaaccc cgttagaggt    36360
agtacctacc ccattgcaca acttccaacc tgctgggatc tgagctagtg acccagccca    36420
catgataacc atcccaggtt taacatactg ggttgtatca gcgactgcgt ttagctgggc    36480
tgccgttaca gtgacagcct gagaaatatt ggggaaggtg ttcttaatag cactcttaat    36540
gagacgcagg tggtcatccc caaaggattt cagatcagag ccggtagggt tcgtaggcac    36600
caactggtta atgtaagttg cgacctcaag acccattctt ggcctccttt atctcttctt    36660
tcatttcttt tcgggtgaca taccgctccc caaagattgc catagaaatc tggagatcgc    36720
tcaccgcttg ggtgagcttc tccgtggcct ggatgtttct ttcaagcaga gcctgattaa    36780
cattctgacc gacaaccgag gaacctaccg tcactaccga ggatacgacc agggcactga    36840
cgatgctgcc caggttatca gttagaagtt gcatcctccg tcttctcctt aaggttgtct    36900
tccaggactt ttacgaactc gtcgtcaacc ttagagttag tcttctccgc cagagcctta    36960
gcaccagtca cgatggactt agcgattacc ttggttggga agagggtagc cagaaggttg    37020
attgcgaggg ttttttagaaa gataggcatc tgaatctcct taacgttcaa tgtctttgat    37080
cgccagtcga gtgctagcga agtcagcggc attctcctcg ttctggagtt ccataacagc    37140
ccgttcgagt ttctgacccc agaactggga ccgagcttca tccatggtgt acagataaat    37200
ctgctcaagg acaccataga gataaatctg cggatacttc gtcagagccc aagtcgttgg    37260
gttagcgagg cttagctctg ggagtacagt ccagtagttc acaatgaacg gggcaccgtc    37320
aggaacaacg gggaatactc gccagaagtt acccaaccga gtgtagtagg ttacaccctg    37380
aggttggtag ttgtagttaa cataatgggt gaaggtatcc tgggtgatgt actgaagagt    37440
acgtccaccg ataagggagt caccgtgat agatcgtaga gcaacaaagt gctcaggtat    37500
ctcaatgcca ccaccgaagg ccattaggat ttcgaagtgt tcgttctccc tcacccgtag    37560
caatcggtta agacggtcag tggtattacc aatgaacaac atcagaagtt cttgggtaag    37620
atcctgacgg tcagaccact ggatagcggc gatagcgaga tcagttacgt tgttgatcgt    37680
agccattcat tacacccgtg cctcagaggt ccgcatccga tagttatctc ggtcattaag    37740 ccaacggta aatcttgcgg catggtctgg gtcacaaccg atcaggttaa gatcgatggg    37800
accaccttca gacatggggc gattccgtag ggcctctaca acaaccaggg ggatacttgc    37860
```

```
taccttgcgc atattatcct ttcggttact gttgacaccc gagtggcgct cttcggcgtt    37920
agcggacagg attgactcaa catcttgagt atcctttcgg ataaagagcc caaggtcttc    37980
gtcaattgca taagtcgatt ggatactcat gatgtacctc ctaaggggaa acaaagggcc    38040
ccgaagggcc ccgttgggtt agacctgggc tacaacgtcg cggatcagag caccggactt    38100
ctcgttgttt acacgcaggg tgtactcaac cagcagttgg cgcttctcgc tgtcaccggt    38160
cttagccagt tcatgctgga agaacggacg caggtagcag agggcgtgca tcttcggatc    38220
aaagatgaac atggtgtttt cgtggaacca gcggttggca cgaatggtgt acttaccgaa    38280
gtcactctcg tagacgtcca cggtctgcgc aatgcggttg tccgaggcat ccagggtgat    38340
ctcagttgca cgacccttca tgttcttgct gatggccttc ttgatcgagc tcgaagtctg    38400
gatcgagtta gcctgaccac cgttgcgcca gatggcctca gaggcattca ggagcatgtc    38460
ttcggtcaga agacggaggt caccagcggt accagtgtcg gaaccatcac cagttggcag    38520
ggtaccgtta gcacctaccg aaccgttggt cttgtagtag gcaaagatgt ttgccatctg    38580
acccggagta gtggtgttac gctggatctt agcctgaggg gcaccgacca tggcgtattc    38640
catgtccagc ttcagttcct tcgacttctt agccagctga tacgccagtt cgttcttacg    38700
accagccttc ttgaccttat ctgcggtacc ggtgacttgc agggtctcgt ccgagatttg    38760
gcagtagttg ttcaacatgg tggtgaagct accagccttg atggttgcat cctcaccttc    38820
cactcgggtg ttcttacccg gctggcggag ttcatcagtc tgccactcgt gggtgatagc    38880
ggtagctacg ccccttgccga tagcagtcat gaacggggtg tcatagggtg cgatgttgta    38940
gatgatatcg ataaggtctt cgcgcttacc gttgatctct acagtcgaga cggcattagt    39000
tggagttgcc ataagttacg tttccttcta ttagaaaata tcgagagagg agaagagagc    39060
agcagcggct tcaaccgact ggtctttcct cagattagcg cgggcagctt taacccgctt    39120
agaaccctct gaggcttccg acctacgagc agcaggttta actgcggcag gtagttcagt    39180
ctcctccttc ttctctaggg cagccttgcg acggacctga gattcagccc acttacgtgc    39240
tgcatcgagt acagccagtt ggcgggcatc agatatccct cggatctcat cctcggagta    39300
tccaatcgat ttgccgtaag acacgatctt gtcaccccaa gactcatccg tagtcatttc    39360
cgggataagt ttcttggcta gctctgtctg acgcttaacg taggcagagt ggacaatctc    39420
ggctcgcttc tcttgcatag ccttaatgtc gttacgacgt ttgataagag cctgggctcg    39480
gtctcgggct ccagggcttc ccagtcgaag ggtttgatac ttctctgggt cctgggcctt    39540
aagctgctcc cagtttacat tgtcatactg attagcacca gcaatagcgg taacagcata    39600
ctgctcaagc tcggccagta gattagagcg ttcagcatca agctcttcga atttagctgc    39660
atactgatcc tctagttcag cttgtcgagt tacaaactct tcattgcgaa ggtagccact    39720
cttaagctct tcgaagttaa cctcgtagac ttcatcccca atcgggatct caaagagttt    39780
atcctcagga tcttcctcgg actcaacctc ggggtcttcc tcagaacctt cttctggttc    39840
ctcctcggac tcaacctctt cggtgtcctc tggagtacct tcatctacta cctcttcctc    39900
ctcttcttcc cctacgactt taccatctac ggtttcatca ccgggggcca ggaggtcatc    39960
accgagcaaa tctccgaagg cttccgctgc ctcgaattca tccatgcctt gattctcaag    40020
gtccattact tatactcctt tagagtgatc gaatccagga tagcctgaat acgaagttgt    40080
acgcggttga gggcatgtag ttcgtggtag atggcctccc tggactctga atccttaggt    40140
gccgtggact tccactctcc ctcgatctct tcttggacaa tacggaaaag ctcaggaaga    40200
```

| | | | | | |
|---|---|---|---|---|---|
| acgttctcac | gtaccatctg | ttgtgccgca | tcagtcagca | ctagactata | gccaaaacgt | 40260 |
| tctcccaaga | ttatttcctc | actgccttcg | agggcttctt | agtctcaggt | accttaccgt | 40320 |
| ctccgatata | agcagcccga | gcctgagttg | cctcaagatg | atactccgct | tcgttacgag | 40380 |
| cccgttccca | agtgaaacga | tcacgctcaa | gttgtagttc | cgcttcctta | agggccattt | 40440 |
| ctctctgctg | aaggacagcc | tcttgcttct | tcagttcgat | ctcagccagt | ctgatctgag | 40500 |
| cctctacctg | cttcatctgg | gcctccgctt | gcttagccat | agcgtccgat | tgggcacgtt | 40560 |
| gggcatcagc | ttgggctttg | atatcttcag | gcttaggttg | tgcttccttc | tgctctctga | 40620 |
| tggccttagc | ccgttgagct | tcaggagaat | ccggggttagt | ccagaagcga | tccgggtctt | 40680 |
| tgtacccagc | gttctctgtg | acttccttaa | ggatgttgta | aagattctgc | tcagagacaa | 40740 |
| ggaccccgag | acctccaccc | ccgactacag | cctgggccat | ttcccagata | cgcatcaggt | 40800 |
| ggagcatctg | ctggtctttg | ttcatgttgc | caataccaac | ggtaaccgtc | aggtcggatc | 40860 |
| tctctcgcca | gttggcaggg | ttaatagcaa | cccacttgcc | tcgtagctgg | aagacctctt | 40920 |
| cctgattctg | gtacttgatg | gcatggtcat | gcagaagttg | gaacaaacgc | ttaacaccag | 40980 |
| tctctgcaaa | catccgggca | atcaggtcaa | tctgttgctc | agcagcagtc | atcaactggt | 41040 |
| ttacactcat | agccgcttgg | ttagagtgca | gggtgttttg | gtctagacct | cgggtacggt | 41100 |
| cagtgatacc | tgtccgctta | cctctgtctg | cctctagtcg | atccagcatc | ccatagactt | 41160 |
| ccccagacaa | ctgaggggtc | tccaggggca | tgatggaatt | catggcctta | actcgaacaa | 41220 |
| taccagctgc | ctcgttggtc | agcaagtctt | cgaggttcac | ctgaccgtcc | aagaccacag | 41280 |
| atcggccctg | gttagtacgg | tagatgttat | ccatgatgtt | ccgcatgaga | accgaacgga | 41340 |
| tctcttgaat | gtctcggatc | ttatcgtaga | cactcatccc | gtggaactta | tgggcaattc | 41400 |
| gataggcatt | caggtcagcg | aagggacggc | aatcccaagg | ctcgttgctg | ataatgtagt | 41460 |
| caccaacgta | caggatacgg | cgcaactcag | agataccatc | cccatctacg | tcaagaaggg | 41520 |
| tgtagcactc | agaggcccat | acctcacggt | tggcttcagc | atcatcccca | gagttgtact | 41580 |
| ggagttggcc | agtcatatcg | aagttatcac | gtaccaacct | ttctggctga | ctatcagaga | 41640 |
| attcatactc | atcgtatgga | agctcatcta | gtacatcctc | gggaacaccc | aagagccgca | 41700 |
| ggtcacttac | ggtatacttc | tcacggtgac | agaggaagcg | tgcatcatca | atacaggtag | 41760 |
| ccaaccgatc | aaccaggaag | ttctcaggct | tgatacaggt | gactttaatc | tctcgcttct | 41820 |
| tcttgtcctt | gcgaattta | atactgtagg | ttccatcctc | gtccacactc | tgtgctagaa | 41880 |
| tctcagtgtc | tggatcagcc | aggatatccg | ctaccatttc | ctcagagaga | ccagagaatc | 41940 |
| gttcgaaggt | agggttcagg | acctcttcta | catagacctt | tacaacaccg | gtcttcatca | 42000 |
| tcagagtgtc | ttggaaccag | tcgaacatta | ccttgaaccc | ctcgttctta | cgcatgaaga | 42060 |
| ggtagttcac | atactcagtc | tcttgctctg | cctgttcaac | atcttcggca | gtctgaggtt | 42120 |
| catacttaac | tacttgaccg | cctgacgtga | ataccttcat | aagagaaggc | ataatccagt | 42180 |
| ctacagtctc | ttgaacgtcc | ctagatacaa | tcgcggactt | cccagggcgc | tcgttaccga | 42240 |
| agggctctcc | gaagtaatac | ttcagggcct | cagaacgctg | cttggaaagt | tccgaagagt | 42300 |
| tgaaatcaag | ggcgtcgtta | acaagttggt | ctagatgacg | aagtacctgt | tcatcatcca | 42360 |
| taggcttaat | cttgcgacga | cgcttagcca | ttagacaata | ctcccaaacc | aatcagggt | 42420 |
| caactttgca | gtatcactcc | tgtagtatcc | actgtttcgt | acagcaccag | gacgtgcatg | 42480 |
| ccgggaagcc | atcaacaggg | cataccgggt | agcgagatc | atatcgtcgt | ttctgtcgat | 42540 |
| aatctttccg | tcctttcggt | ggtacatttt | catttctttt | aggaagttcg | tacacgtatt | 42600 |

```
aaacaccttc agatcaccat tctccatacg ggtcaacatc cagttaacgc cgaactctac    42660
agagttaccc ccgtgtttac catcaggacc tgggggggttg ctgaagggtt cataaacaac    42720
attgaggttg tggtcatcct tcaggaggtc tacgaagcga cgacctgagg tagctccatc    42780
atgcttaaac gcatcgtggg ggactacaac agggatctgg tgaccaccct tgaggtagat    42840
agcatcagcg tgcatgccga gggtttcgcc agattcactt cgttcatcat acaggtaata    42900
cttgtccttc tctgcatccc aggctacaca ggcgatagcg ttagggtggt caaaccctag    42960
gtcgatacct ataatcctgt ggaagtggtc cgggatatca aaaggctcac atacgaactt    43020
ctcttccaga atggggaaga ctacaccaga tccgagcata ggaacaccct cggccctcat    43080
cctgcgttct gctggagagt ataccgagag tagctgctct ttaacttctg gactgaggtg    43140
tggggcgtct tcccagcttg catggacaag gaactgacca ggtttaagat cctggaggaa    43200
gtccttgacg atctccgtca gaccatgctc tggggtaaac gtcagatata caataccccc    43260
agtagtagcc gttcgggtta cacactgggt ataaatatcc ttgggcatt cctcatcgag     43320 ccagatgacg tcgatggcag tacccatgaa tttgtcctgg gacatttcgt aggacttgaa    43380
gataagggac gagaggcccc cggaggcatg cttaacaact actgcttgca cacatccggg    43440
tttaccttcc ctacgaatcg tctctacgat atcttccttg gggatcatcc ccgttccaaa    43500
agcctcaggg ttcttccagt cacctagtag ttcggactga agaatatccc gagtggtatc    43560
cgtggagatc cccgccgccc agcagttcac tggacgatca tactttctac cagtccacca    43620
ctcagggtag cgaccggtga ggtggcaggc catgataaag gccccggtgt aggttttacc    43680
acagcggtta ccagtcatag ccagcaactg ggcgcagttc gaggaagctg cgataaactt    43740
ctcttgccac ccataaggag tgtactggtt catgcggaaa tacttctgcc gctccgccaa    43800
ctccctgact agattccgta ccgctcttg ggtatccatt agaccacctt gtcacctact      43860
gttgatgcac gccacaggc ccgttggagg tcccttacgc gcactggagt ttgtttagcc      43920
cagagactat cttctgcctc ccatgcagcc tcgtcaaacc ttccggattt cagaagattc    43980
cacgtcttgg ggaacttctt cgtccacgct gtacccagct ggaagttgac gctaacgagg    44040
gcatcgaata gctctggagt gcaaaaaggc agctgagata cttgcccttg ggctgcatca    44100
taggctgcct tactatcttt ctctagccaa gtctctgctc gtgctagggt aatcggtccg    44160
tcttccccag ggagttgcaa gtggccataa ccaccagtta tcttcccgag ggagtctttg    44220
taccacttta gtaccaaccc ctctcttcgc ttgattagat caaggtactt aagaggctgg    44280
gaaagaaatg actttagcca actctggctc ttcgtcgaga attcgtcgaa cttcactgat    44340
tagatcctct gcggacatat cttccacatt cttagtagta agctccagtt tctgcttagc    44400
tccgaagcct ccacgatcca ggatatcctg ggccgccttg aggcgaatcc cacctttctc    44460
ttctgggttg ctagcgatct ctacaaccac acgaagcgcc atgggacgt gactcccgat      44520 gcgctcagag ataaaggcgt tgatgtattc ggcatgcttt cgatggtatg cagctacgtt    44580
gcgttgcgca tgattaggag agaacccagc ggctatatat gcttgggttt tgttcatacc    44640
atctgccaga gcctcacaat agaggtctag cttttcttta gcagaaagag gagcagcccc    44700
aatcgagaca acctttttcgt ctgacataca ctgctccgat ctctctaaat ggtcaccccg    44760
gtaggactcg aacctacgac ctcctgtgtc caagacaggc actctaacca actgagctac    44820
gaggagttaa tggtggtcga aggaaggaat tgaacctcta gcctaaggcg tccgggttac    44880
aaccggatgg tagtagccat ctacctctac aacgaccttt gttggcgacc catgtcggat    44940
```

```
tcgaaccgac ggcttctccc tagacagggg agcactctaa ccgctgagtt aatgggccat    45000
aatggctggg acgtagggc tcgaacctac gacctgagag ttaacagctc cctgctctac    45060
caactgagct acatcccaat gaattctaaa ggttaatttc tcaaccttat aatactatta    45120
tatcacactt tttctatttt gtcaagccct tttttcatct ttttattttt tagtcgcaag    45180
acccggattt gttagggttt ttgctggaat ggggaagggg ttcttaagac tatcttaaga    45240
taaccttaag gtaactaacc ttcttagtaa gtaagtcaaa aggaagaagg aatcttaaga    45300
gcctataggt ctattatact acattttgga tac                                 45333

<210> SEQ ID NO 4
<211> LENGTH: 44884
<212> TYPE: DNA
<213> ORGANISM: Bacteriophage P1797

<400> SEQUENCE: 4
ctaaccttct tagtaagtaa gtcaaaagga agaaggaatc ttaagagcct ataggtctat      60
tatactacat tttcgatacc ttgtcaagta cttttttgata tttctttgat aatcacatga    120
tttacccgac gaacggtatg ataggggttct atagatatac cctaagacta cccttcgtag    180
gttgctggta aggggtaagt ggcatagggc tcccttgatc caggttctat aggtatacct    240
tagggctacc tctgttctct atgccctggt ctattgcccc tttatccagt aatataccaa    300
cagttatcga agggtgcctt tgatccaggg cctataaccg ggggataccc caaaagtcta    360
ttttatcctc cggtgtatct ggggaatatc cccccaggag tcccccagat aaagtggggg    420
tggcctatcc ccagggtat agcccctagc ccctccctag gataccatga gactaacccc     480
aagatcaacc cctagggata ccgttcatcg ggtggaccca agggtattca taagaaaaat    540
cttagggtat tcaggggtg atcgggggg aatatccatt gataaccct tgatccccta      600 ttgacttccg ttgatacct atgttaatca agactgtct atatccgggg gtttgctggg     660
ggactgatag tccataggct gtatgaaaaa ccagtagaca accccgtaaa gaatatggcg    720
taatggcgcc gccttgaggg aaaccgatag gcaacggggg aaaccccagg ggcttgacaa    780
accccgcgga accgggtcta atggccccca cgttctacct aggccaccat ccccccttgcc    840 gcagtgctat ccgggggctg ccaaccaggg aagagcgccc aagtcgccca agtgtaaagc    900
cggcaggtat cggggttga caagggatcg gtgaagcggt atagttcgcc ccacgtcaac    960
ggcataacgt gcatgactcc ctcgggatta gcgtagcctt gacaagcaag actgatggcc   1020
actcagcaaa agagcctatg ccagagaact ggacgaacta accccgtca gagggttgac     1080 aaggcaagcc caagcctcta acatgggcac ccatcaggtg acggccacct ggggaaagtg   1140
taccttcgac ggtccttgga ctgaacaagg agaaacccg aaagctgagg gaataacgca    1200
cactccgaaa gagcgtaggt cctggccttg taccataga ggtccgactg gtagcctgtc    1260
ccagcgcaat caattgacag accccgtggt tcaagcgcga cggggagtat gatgggttag   1320
tgtcgaaggc ttagcgcaga gggcgaagct tggtagatac ggcgaaggta ggggcgagtg   1380
gatacgaaga cccccgagga taaccgagga cagaccataa cgacgacact aacgcggaaa   1440
ggggccggct acgccaatgc caaggtttgc cgataaaccc ctttgtcgta tcgggatgtg   1500
tgtcccggct gatgattcct aaaggatgaa acgaccatga ctcaggctct tgacaaaaag   1560
ctgcgtcgca aggccaaccg caaggccaag gctttgggtt acaaccttgg gaatctgggg   1620
aaggcccaac agcgtagtga gcagaagttt gggattattg caagttgtaa caagatcctc   1680
gacgacaaga ccacttcgtt gcaagaaaag gcaggggcgc gtaaacgcaa ggctcttatg   1740
```

```
agtaccgact ggcgtaaccg tgaggttact aaccttcgga actggtataa gccgagcaag    1800
tgcggtaact ctgccgtcat cactgtcgaa gtaaacaact gaggtaatta caatgagcga    1860
ctacaagcgc atcaacggga tcatcaagac cattgccaac cggggtgctg ccctggacaa    1920
gctggttcaa accactggca tggatatcct caagcacatc gacgagcatg gcgaggtgtc    1980
cttggcctgc aagctgttca acgcgatgcc tcaaggctcc cgccggctgg ccctggccca    2040
ctggttcatc gacaacggca agatcgaggc caataccgac aaggaaaagg ccaaggaatt    2100
cccgttcgtc ttcgccaagg acaaggccac tcgtctggag cgtgccgcag agaaaccctg    2160
gttcaagtac aagaaagagc gtgacgtggc cgacgagttc tccctcgatc aagccatcgc    2220
cgccttcaag gccaagatcc agcgtgccat cgacaagggc agctccagg cagcggacga    2280
gcgtatcgcc gtgatccagc gactggaagt caaggacgaa gcgaaggcag cgtaacgccg    2340
ggtgcgccag gggtgtgtac tatgacgcgc ccctggtcta tccctagagt gcatggtagg    2400
tccgtgcatt gtagcgatag accatcagga ggtttccgtg ggttactgta tctttgggca    2460
ggttcattcc atccaaggcc aggattatgt ttctggtttc tgcgatgcaa gggtaggttt    2520
cgacgctggt attgtgtacc gttggacatt caaggacggt aaatttgcct gcggtgtcta    2580
ctccctggat ggtatccgtc tgaacatctg cgggtggatc aaatgaagtc accctacgaa    2640
gcggcccatg aacgtgccca atgattaac cgtctcaaga aactcactag gatgatccgg    2700
gtgcatcccg atccccggtg gattgttgag cgtcaggaac tcataaggaa actaagcaag    2760
tgacaatcgc tatcattgta ccagcattg gtatcgccta cttcttcttt cgtgattgga    2820
aagaggaaat gggtatctaa ccccaactga tgaggccaag gtgattcctg ccgaaaccc    2880
ccaccgacc tatggtcgca ggctggggcg tcttgggaaa tcaactaagg aaaccatccc    2940
gtgaagcgca acgactaccg aaaggtgaat cggaacatgc aagccatcga ggccatcgac    3000
cgcaagattg ccaaggctgt ccgtgagttg actaactccg gaggaaacca cgttggtaaa    3060
accctggagc tgaatcggct gcgggctaag cgtgcatcgc tggccaaggt aagggcacgg    3120
tgagtacatg gaagtctatt gtatgtgccg ccatacgctc acgttccaat gggttgctgc    3180
tggtaacgtg ggtggttctc ttcgtcctgt cctcgatctt ggacagcatc ccttttgcat    3240
cgtgaggtag tcccatggat atcaaggtgt ggccccgcaa cggcgtaacc ctcagttctc    3300
tggttaagtc ccaaaccttt ctcatcaatg gggatgtgta catggtctgc gaactccgaa    3360
gcatcaagat gaagagtgaa tctgacgagg ttcccgttct caatctcaag actggcaacg    3420
tcatttacat gcctccgttg agcctggtat acccagtaac tgccgagctg aattgctacg    3480
aggtgtaaca tgaaactcca atacaacatg attaccagta agatcaaggt tgtgatgtgg    3540
aatgaccttg agccgggttg cctgtacatc ttccagagg atgacgggaa gaagaacccc    3600
aaagtcttcc agtacctgga gcttaatgat gaattcttca tctgcgaaat cttcggcgga    3660
cctgagggcg atgtattctt cagcagcgat gttgactgcg ggttcttccc ggtgactgtc    3720
aagtacgcag agatcgaagt ccatcggttc ggcctaccgg actgagggtg tgtactatga    3780
cgcccgccca atacatctac ctctggttgg tatccaaggt tgtcatccgt cgataccagc    3840
ctaaccccaa actgtacccc aactggtccg ttactcatat ccgtgtgtcg atcttcggca    3900
aacgtgcagg tatcgtctat gaaatccact gaaccccaag tctattggct ggctagcgcc    3960
gatggtgaat tccacctcaa ggtcatcaac ttcggccagt tcatcaccga aacccttac    4020
gaactcggca ttccggtgga ccacaaggtt catcgggtcc actgaggtgc aaccatgtca    4080
```

```
aacaccacct tcactgtagc agcaacccgc ccccggaacg accttcacat cagtaagcgg   4140
gcggatgggg tttatgtgaa ccctaaaaac tctggcgata ttgtcttcct caaggaaggt   4200
aataaggttg tcgtcctcag ccagagcggg ttcagcatcc tcgaagccca gaccatgccc   4260
aacatcgggg aactctgccc ggctaaggag gtccatgtat ccgccagggt atggggccg    4320 tatgaagaat aaacccatga tcggccagat aatgggccag gagcgccgca tgaagcgtcg   4380
tgtagaaaag cggggttca acatgagcct ccaggaaagc ccccaggagc ccgtggtga     4440 gcttggtttc accctggctg ccgtaggtat ggagtccagc cgatcggctt acctgcgtca   4500
cgccagggag gctatgatcc aatccgggga gccttgcccc cattgcatgc cagtcttcgg   4560
tcccaaagag ggtcgttgct gcaactgcgc gagggactgg tgatggatct cggtaatctt   4620
tggtgtctct tgggtgtcca tcggtacaag atacttgatg gtggaccta cgagattcgt    4680 cacaagggtc ggctagtgga actctgccac tattacgacc tgaggtgtga tcgctgcggt   4740
gacgtacatc ggaaggtggt ccgcagcaaa tgatgacata cctcctgata atcccagcga   4800
tcctgatcta tatggcttta tctttgctcg tggctggcat cgccgggttg gcggcaaatt   4860
gcgatgagca tggaaggatg agccagaagg atcaggacat ttcaatcatc ctcggtatcc   4920
tgtggccagt gtcactacct tggatgtgct tctcggttgt tatctggaaa cctttggcta   4980
ccaccatccg tgcggccaaa cgactaatca aggagatta ctaatgcacc gcagagactt    5040
tccctcctgc tgtaccgcaa aaatctacat cggcatggga ccctcgggta ccgctgacca   5100
ttacgccggc ctcgcatcca acgggttcag ccccgtggt ttcgccaagg aactgatcgg    5160
cgccatccgt cgtgaatcca acgagggcca cggtacgatg gtcttcacgg tgaacagcga   5220
gcaggtggta gcagatacca tcctccgccg catgggcagc cactacaacc cctgggcatc   5280
cagcgacaac cactcgacca aggtccgggt ccacgtcatc aacgtgaagt ctgcggcaga   5340
tatcctcatc aaccatgggg ttctccgtcg tcacctcggt ggcttgcagg actaccccgg   5400
taccgtcgag cactcggagt acctcgacaa gctctgtaaa ggtctgtaac atctaggcct   5460
tgacattctg ctggaagtgt ggtataataa ccttaaggtg ccggggttg ctttatatcc     5520 ctaaggtacc taaggttcta ccttctatct tcttcatctt aagaaagagg taagaacaat   5580
ggtcctcaag ctctacactc gggtaatgct cctggctatc cccgcatggg taagcgtaag   5640
gttttctacg agcgtctctg ctccaacggt gaattgaccc tgaacggcaa cctcaaggcc   5700
accaaggtgt cggcaccaac caaaggcaag caacagcgcc gtggcacctt ctaagtaact   5760
tagaggtcgc tagtaatacc cctagtattc ctgtcctggg ggtattgctg gctaactcaa   5820
ccaaggagaa acaaatggc ccgtatcaag tatgccttcg gtatgaaacc caagaagggc    5880
gagggtaaag ccctcaaggt aatgacctct tcctcctgct tcggtacaat ggaaggtccg   5940
gtaacccacg gctataagct cgacggttgg accttcatct gctcccgccg aagcaagaag   6000
ttcatcgatg tgctcaacaa gtgtacccaa ggtgaactca agaccatcac catcggcggc   6060
aaggccttca aaatcccgaa ggtccacttc tggtcttacg aaagcaaggc caaggattcc   6120
cccttcgaga agtattctaa cgggacggaa atgatttccc ccacccatca cggaaaagaa   6180
ggggtctgcg gtatctactt caaccccaag gtacacaccc tggattcctg gtaccccatc   6240
atgaaattcc tcttcaagat gatctccagc ggactcgact accaaggtcg tgaagaggag   6300
gttcacctga agcttgctga gaagtatggc ttctggaagt cctacctcgc aatgtccttc   6360 cacgactga tagccaatgg ctacaccggg tacccactct ccaactacat gttcagtagt    6420
gattgggatg atctcaagaa gggagatatc cacatccaat ccgctgacga gtctatccga   6480
```

```
ttcggtcgtt ggatgcccaa ccgggatgcc ccaggtggac gtgagtgggt aaggaataca    6540
ccctggcggt ctgaattcct gaagattcag ttggacaagg tggaggtagt taccatagca    6600
cctcagccaa ccatcttcgg aaagaaagat ccctacatga ccgtagatag cgagatggga    6660
ggtttcatcc gcctttatcc tcatacctgt gaaaaatacg gagtggtcat gctggggatc    6720
atgggtgagg ttggctgggg gagcggcata aaggatatct tactggccct cgaagacttc    6780
atcgagaaaa acttctgaca accaaggaga aatcaaatgg gaatgtatgc agcccataac    6840
gtgtactatg atgtcgaggg tgctgagatt ggtcactgct gcgtaaaata cgtggctgaa    6900
tataccaact gcttcggtgc attctgcgac gaaacgggac cttccggga tgtagtgtgg     6960 gagaccgggg ttggacacct cctggtgtct acccacgaga acactgctgg taagttggtg    7020
gagttcttga acagtgatct ggtcaacagg atcaccgacg gtggaatcct ctcagcttcc    7080
caggactggc aaccaagtg gtggacagga tctgacgggg ctacccaaaa cctctccaat     7140
cctgaccact tcagcccccc tggccgccga caggctgtgt acgttcgggt ggacctcaag    7200
aagaacgcat cggcaatcat ctgtgccctc cgaatgggag atcgcttgtg gggtgtaggt    7260
gattccatgc gtcgcatcac ccaggaaaat cgtgataaga tcctggtctg caatgcagag    7320
atcctcaccc tcgcggcttg tgcccaggta ggtagcactg ctcattgcga cagctacccg    7380
gccatgttcc cggtgactgc tggtgaatac cgggagggat gcgagagcca cggctgggag    7440
gtggatgaca gctacataag cgaggtcatg gatggtatcg taggtggata caagaatatc    7500
acctacttcg atattaagag catccatgag cggactcgcg aagagttcaa ggacaagctc    7560
aagcatcacg acgctgagtt gtggcagggg tataccaagg atgatgacct gatcgaatgc    7620
gacggtctcg aaggtgtacc taatgaccga atccttcca tcatggcccc aatcaccatt     7680
gacgtcggtg acccaggtcg ggaaaggtcc gaggtcgtac ccaccagcca atacagcatc    7740
cccgaaatcc tcgaaaaact ggagaacatg caatgaacaa cgcaatcccc ctgatcggtg    7800
cagatcccga agttttcgtc ggctacgacc gtaaccccca gagcgtcatc ggcttcatcg    7860
gcggcaccaa ggaagagccc ttggctgtag ccggtggtgc tgtccaggaa gacaacgttc    7920
ttctggagta caacatcgac ccggccagta ccaaggaaga gttcgtggag cgtatcgtct    7980
ccgttcgact cctgggtgcc cagatgctcc accccttcgg catgaacatc atcgagaacc    8040
tgtcctctca cctgtacgac gaggaactcc tccgcagctt cggtccccag gcttacgtct    8100
tcggttgcga ccggactac aactgctgga ctcgtcgtca gaacgtgatg ccgaaggatg      8160
cccctccgac cctgcgtact gccggcggcc acgtccatat cggcttcagc cacatcgagc    8220
gagtcaccaa ggctaccacc agagaagtca tgcagatgtg tgactacctc ctgggcctgg    8280
cctctgtcat cctcgatggt gacacccagc gtaagaagct gtacggcaag gctggcgcaa    8340
tgcgctataa gccctacggc ggcgagtacc gtagcctatc gaacttctgg atcttctctg    8400
tcgatctgac cgagtgggtc tatgaaatgg cagtgcaagc ctacacctcc aagcacctcc    8460
tggaggagta caagtcgatc gtatccggtg atgaagtcca gcggatcatc aacgagaacg    8520
acggcgctgc ggcagttgcg gccctccaag ccctgggggt gaagtatgaa tgacctgaat    8580
aatcgccatc ggttggccgg ggacttcaac atgtactact cctccaccta tgccttcttc    8640
cgggttgacg gtgagcctcg ggtagtgtac gtggacgata ccgagtccat tggtgacgac    8700
cgtcaattcg acgggtttcg tctcctgggt aatgtgtatc gccccgacgg cagtaactac    8760
tacggtgggg ttgtctacag cgaggtagaa agcgtgcggc cctccagtgg gtactatgac    8820
```

```
gtctttggcc gtggggttcg tgatacttat gtatccttcc tcgtgaacaa tcggactcag   8880
cgtaagggta tggaccccag gaacatcctg ctgaaccatg cccaacaggc catcactgga   8940
gaaatgatga tccgaatctt cacccaggcc gaggaaatga tctctgcccc atcccaccgg   9000
gacttcttca tcaaggatgg ggtagttcac tggaagggg tgaaggttgg tcagatggta    9060
gatggccgac tgtccgcaga tgaacaattc aagaaccagg aggacttgct atgtcagtta   9120
ttggcacaca gatagggttc cgtaagaacc agatcattgc cccggaacat cacgaggaac   9180
tgcctgcggt tgcttccttc gggttcgaag tcgaactgga aggcctcaac aactggccgg   9240
aagtggacgg gtgggatctg aagggtgacg gctctctgcg ggatggtatg gagtatgtct   9300
tctccggtcc cgcctctggc cagaaggcaa tcactcgggt tgaatccttt gtgagtgcga   9360
tggaggaaac tcctccggcc cccaccttcc gttgctccac ccacctgcac atggatatgc   9420
gtgacgtaga gtggcctgtt tatgaacgaa cggtcctgac ctacatggca ttcgaggatg   9480
tttttcttcga tcactgccaa ccgtatcgtc gggatagtaa cttctgcatc ccgttcttca   9540
gcaacgactg gctggcccag accttcggtc gccgtatcct ggccccggaa ggtgaccgag   9600
agaaagtctt gggtcttacc tcctggccaa agtattcggc cttgaacctc caggtaaccc   9660
acaacttcgg gtccatcgag ttccgtggtg cccatgctct cactactcgg caggaaatgg   9720
taggcctgat gcagcgtatg ttgtgtctca aggccttcgc catggctcac gcagaaaccc   9780
cgctggaaga gttccttaag gtactctccg aggtgaatct ccgtgatgta ttcttcctgg   9840
gggtatctcc ggactatgaa atgtctccgg gtggtcgtga atgggatc gccagtgcta    9900
ctctcgcggt agcaaccatg ggctttgttc gctccggggt agatcccctg gaagatgaac   9960
agaaccgtca gcgtcgtctc cgggagcagg aacgtgagcg tcagagggct ttggatcgta  10020
ggctgctctt tgctcgcgct attacctcac gactactaga tggtgcagca gagcggtaca  10080
acttggcaat ggtgccaggt acccaggttc gactggatac ggcgattact gcggtaactt  10140
ctctgcgtcg tattggtcac caagtgcgtg tacgagacct tctggaggac caagaggctc  10200
ttcaagatgc cttcgtactg ctcatggata acccgcagca ccttcagcgc cataccggcg  10260
taacaatcga accagatatg tactaaggag aaatacaatg tgtggattgg taggcttctg  10320
ttccacaact aacgcgagtg ataacgaaat cgctcttctc aaatccctcc tggccgtgga  10380
tattatccgt ggtgctcacg ccaccggttt ggccaagatc gacccggtta agaacgaggt  10440
aggaattcac aagcgggcag tagatgccta cgacttcctg gctgatcctg aaaccaagga  10500
gttcctggac aagggtcggg ctcgcatcta catgggtcac aaccgttacg ccacgatggg  10560
cgacaagacg gaccatggga atgcccaccc cttccaggta gaccacatca ccatggtaca  10620
taacggcacc gtagatacct ggggcctgca cctgctggat ggcaatgata agtcaaacgt  10680
ggattcgaac atgctgtgcg ctaccattgc caaccacgga gccaagaaga ccttcgaaga  10740
gaagttctcc ggtgctgctg cggtaatctg tgggactcc aaggaacgta ccctgaactt   10800
catccgcaac gatgagcgtc cgttgttcat ggcggtgacc accactggta ccatcgtgtg  10860
ggcatccgag cctggtatgc tcaaggtttt cctggagcgt cccaacgcta agatccgcct  10920
tcgttctccc atcgctgaac tgaaggctga agtcctggta actatcccgt tcacggaggc  10980
cggagtgcga aagggtgcag aaccccagac cactccggtc acgtttctgg acctcccaat  11040
tcccgaaagc gaaaggcaaa cagcggcatg tggagtcgc tacgtcggtg tctcggacta  11100
tgatgactac agccgaagcc aaggcagcca agcgggaacg aaaggcagcc aagcgggctc  11160
gtcgtatgga acgtctggcg atgcgtacgc aaggaacacc ctccggatca acaacaacct  11220
```

```
cgacgcagca ggtagcacct tcaagcaccg gcaactcgtc accttcgatg ttgtcaagat   11280
cgaggcctac gcaaacggca gcgagtacgg aactgtcact ggaatcgagc gtgaagaaaa   11340
ccttctcatc gaagctcatg gcatcaacgt cgccaaggtc cacggataca ccgtcctccg   11400
agggagtatc tccaatgcct acttcatcgg ccaagaccgt gatctcaagg ttactgtcga   11460
ggatctggcg gtaagctgcc tggacccaaa gcatcggccg actcctgggg agactacccc   11520
agtgttgagg attggaacga tctcatcgga gacgaaatcc cattctaaac ccagggttca   11580
agtcggcggc acctcgggga ataccctcc ggccaacatc agctacccct gaaggttca    11640 gggacacacg ttcaacaacg ttcatgtctt cgggacttc gtatcccagg ggtgtgcatc    11700
ttgcggtaag atccctaccg cgtatgacca gcgtaatcgt catctgacgg tgtacgaggg   11760
tgccaagttc actggtagcc tggatgagtg cgagttcatc tgtggtgagt gtgtaatcga   11820
aaataaatag gaggtcaaaa tgacccaagt aacgatgaag cgtcaagtag tgatccagat   11880
ggagaccgac gcaacccgta agtatccctt ctcccgtgac accctggaca agatccagtc   11940
gattcgtcga gtcaaggagc aggaactcaa tgatgccaac ccggacgagg aattcctggt   12000 accgccccg gtagtcattg cggaagctat cgaccgactc ttcgaagact acttcgagta    12060
aggtagtgcg ttagtaatag tccctggccg acccatgccg gttcctaaga tgcgtacatg   12120
ggatctaact taggattcca ggggctattg ctggcttcac tacccctcaac agaaacagga   12180 gatttgccat gttctatatc tataaaggtg cccgccctc tgctggtgct gtcgctcttc    12240
gtaacgccat gggtgctcga atccttcgct ccgaggggtc tacctatcgg ggtcgttcgg   12300
gtactgcggt aatcaactgg ggaaccgttg gtgcagaggc acgacgccta cagggtatcg   12360
ccccggtctt cctcaacgac ccggctatgg ttgctcgctg caccaacaag ctggatttct   12420
tccgccactt cgaggccaac gcccccccatc tgatcccccg ctggacggat tcctgggcta   12480
atgtccaccc gatcctgaat tcctgcggtc gaatgtacgc tcgtacggac tcaatggtc    12540 atagcggcag gggtatccac ctggtgtgca gcatcaacga cgcagaagtc caggccatcg   12600
atgcccttcg tcgccagggg aactacccgg tacacatctg gggtcatacc cacatcccgg   12660
aggtcgtcga gaacgcccaa ttgttcaccc agggcatcgt cggtaagcgt accgagttcc   12720
gagtccacat gatccgtggg gaggtagccc tgctccaggt caagctccga cgtgttgcca   12780
atgaaatggt gaccaacgaa ggacaaagta tcgttcgtaa cgtagctggc ggctgggtct   12840
atggcgtcaa cgatgcaatg ggacgggatg gcgctgagca ggctatgtcg gcagcagcag   12900
aagctatcca agttgcaggc ctggacttcg gcgctgtgga tattatctac cagcacgcta   12960
ctagccgggc gtttgtcctg gaaatcaaca ccgcgccggg cctggatgca gaaggcagcg   13020
ccctggaggc ctacgtcaag ggcttcaata aaatcttcga ggagactatc taatggctgt   13080
tcgtgttttc gtttatggta ctctcctgtc tggtttgtac aaccactacc ttctggaagg   13140
ggccgagttt gtcggcaatg ctgtatcctg cgagcggggt ctgatgtact ccgctggcgg   13200
cttccctatc ctctccttcg cctcccgtgc tgatctcatc gtaggtgaaa tctggcaact   13260
ccccgaaggc gagaaggggg aggaaatgct ggagaacctg gatgccctgg agggttatcc   13320
gggttggtat gatcgtaccc tcaaggattt ccgaatcaat ggggaacgaa tcaaggccct   13380
ggtgtaccat caggatagcc acatggcgat ggatatcgtc aaggatggcg actggaaggc   13440
acacctggca aaacgacaag gagcagtatg atggatgaaa tgaccgtaga caaagcagta   13500
gaagtctacc gcgatactcc gaacaccttc ggacaccaag agctacatgc ccagaagatg   13560
```

```
ctcctcaagg agatcctggg ccttgtcgcc tcccaacgac acctccaaga ctccatcgag   13620
gtctccaaga ttccggaggc ctcggatagc cccgagacca gctacggcgg gtactgtgac   13680
gagtctgttg gtattcgctt catgtgggag cgactgaaga agatcgagga ccgcctccgt   13740
gaactggaga aggtctacgg tactttcgta acaactcctt acaagaccct gccgggcaac   13800
gtcaacgctg tacctagctt ggtgctcaag agccagatgg aggaataagt gaagcagatt   13860
atcggtgata cggcctgtcc gggttgccga gctaaaggtg gggataaaac aggtaatcac   13920
ctcatcttgt tcgtagacaa agagaaaggt acccgcttcg gtagttgtaa ccgttgcggc   13980
cactatgaag tcctcgaaga agggttcaag gttcctgaac gaagggagaa gtccgaagag   14040
gatatcatcc atgaagtcaa cgaagtcctt gagtatccaa ttaaagccct cgatactcgg   14100
aagatcagca atcaatcgc tgaacgatac ggggtacgtg ttggtctatc acaagaaaac   14160
ggtgaggacg ttatcgagca ttactatcca cgcacccgcg atggggagta ccgagcgttt   14220
aacgtccgaa tcctagaccc taaggctttc tactatcgtg gtagcccaa gggtggtgtt   14280 gacccctttcg gttataacac ccttcggcat aaggatatgg ccacctgcg gttagtcatc   14340 tgcgaggatg aactgtcggc aatgtcagtg gctcagatca tggagtcgaa gctgcccgag   14400
aagtggaagc acctacgtca agcagccatt agctggtcct caggtgttgg ttctgctgga   14460
cgggatatcg cattcctaaa ggaatctggt gtactcgaac ggttcaacga ggtcatctat   14520
tgccacgatg ctgatgacga ggggcgtaag tcagtgaaaa aggtacgtgc cctgtacccc   14580
gagtgtaagt tcgtagagct tccctgaag gatgctaacg acatgcttat gcgtaatcgg   14640
ggggatgagg tctaccagat gatccgattc ggcagcaagg ttaagtcccc ggactgttcc   14700
gtaactgtcg atgaggtata cgctgaggcg ctagaacccc ctaagtgggg taagagctat   14760
ccctgggaag gtctaaccaa ccttacctat ggtcagcgtg atggtgagat catcgggta   14820 ggtggaggta ctggtatcgg taagaccctg ttggcccacg agattgctgc ctggaattgc   14880
attgagcacg gggagaacgt agggacattc ctgttggaag agcaggtagc catgacactg   14940
aagaatatcg cggggaaggt agctaacgta cccttccacc gaccggatat cgagtgggat   15000
gagcaagcct ttaaagacgc tgcgggtaaa ctccgtggca agctcttcat gtggaagaac   15060
aagggtcaga acgattggga tcatatcaag gaatgtattc gcttctgggc agtagccatg   15120
gatgtgaaga ctatcctgct ggataacatg accgccatga ccaaccacct tagtccttcc   15180
gaaatgaaca cggagatcgc ccgtatctgt acagagcttg caggtatggc cgatgagctg   15240
ggtcttcgga tcttcatctt ctcccacctt aacccgccca agggtaatcg tacccacgag   15300
gaaggcgctg aagtaaagga agccagttc accggctccc gagctatgca gcgttggtgt   15360
cagcttatga tcggcttcga gcggaacaag caggctgacg gggaagagaa gcacgagagc   15420
agaatccgtg taatcaagga caggaactac ggtaatactg gactagtgtt taccaagtat   15480
aacccagaga cgggtcgctt ggttgaacgt gagggcagtt acgacgaggt acctgctgac   15540
gatgacaccc caatttgatt acgttatcta tgacctagag ggggacggcc tcttcaatac   15600
ggtcacaagg ctttggtgcg ctgttgttgt agacattccg actgggtag tccggggatt   15660 ccggcccgag gaaatggatg tgttctatag gatcatcgcc catgcaaagt tcgtggtcgg   15720
gcataacatc ctagactacg acaaccgggt ccttgagaaa cttcatggga ttatcatacc   15780
ccccgaccga agctatgata ccttggttgc atcgaggttg acttggccag ataggcccca   15840
gggtcattcc ctgggagcct gggtaagtt cctgaagtgt cacaagggtg acttcaacga   15900
cttctccaag ttctcagagg aaatgtttga gtattgcctt caggatggag tggtcagtca   15960
```

```
cgcactgttc aactacctcc tccgggtact cggcatgact tggcaagagc ttgttgaatg   16020
gaggactgta gattggctaa aaagcgagtg aggaactaca agcgtgagag agaactggct   16080
attcgacgcg gcgaaacggg cgtgggctct aagtcaggag atgctcagcg gcaccgagcc   16140
cgccgaaagg tggaaaagcg tcttggcagg aagctcggaa ccgacgaggt tgtcgatcat   16200
atcaaacgtg ttaaagatgg tggcggtaac ggggattcta atcttcgcgt ccgtggccgt   16260
tcttctaacg ctgctgatgg tggtcgggtg ggcgatcgta aggccaaagg cattcgcaag   16320
aaaaagtaaa tgaagagggg ccttcgggcc cccgaggact cattatgttc aatcgaaagc   16380
taagcatcag taaaatcctc agttcctttg acaacgagat caatctactg aagaccttta   16440
tcaaagagtc ttcggatgaa tctgaacgga tctacaacga gatcagcttc ctgaaggcgg   16500
agcgtaccca ggtcatgcag gacaacctga aggcccagaa ggtactggct aacctggaag   16560
aactgctggg aggtaagagt gaagaagtat cgagttaatg tggggttcca ggacaccaag   16620
gtgttcaacg cagacttcta ccgcatcgag ttggatatca tccggttctt cgcgggagat   16680
tctgatgcca accccatgac cgtccgagcc aatgagatcg gtgctgtccg tggatgggtt   16740
tctgtggagg agattaacga tggcgagtaa gaaggaaagc ctggaggatc aggcacggaa   16800
ggagattgcc ctggagaagg agttctctgg tagctggggt ggccccgaga tcgatgctga   16860
tgacttcccc ttgggtagtg cctgtggcct agatcccgag gtatgcgagt catgcagctg   16920
agccagtgcg taccctggct gtgggctact gatcgatgcg ggtatggggt ccttaccttc   16980
aagaggaaac tcaggaaagc ccaccgggtt gcctactgta tggccaacag tctacaaatt   17040
gaggacatcg acggggttat catcagacat aaatgtgata acccatggtg tgtaaatgta   17100
gatcacctcg aacctggaac tcatcaggat aacgaggatg ataagaccaa agaggtagg    17160 cgacctatgg gagagaaggt tggctcagca aaactgaata gggctcaagt agagtccatc   17220
cggaaggagt atgtaaaaag ctcaaagact ttcggttcgg ttgccctggg taagaaatac   17280
ggggtacatt cctcaacgat cagatacatc atagcaggag atatctggtg agtatcctag   17340
cgcaagtcct tgtcatcttc tggagtgcat tcttccaggt attcctcctg ggattgaact   17400
ctaagctgct ccgggatgac aagatcaagg ctgggttcgt agtgtcttgg tgtatcacgc   17460
tggctcagtt tgcttacatc aaggcggtag cctcctccca cttggatatc ggatggttta   17520
tcttcgtgtc cgggtgggga ggtgcccttg ggattacctc tgctcaatac ttctacaagt   17580
ggtacgacag ggtattccac aagaaggctt gacaaatcca gaaaagtgtg gtataataac   17640
cttaaggtgt ccggggttgc tttaccccta taggagatac aaatgagtga ccatgtaagc   17700
tattccaaac atgtccgtgg caagtacctg tgtaatatgg cctctgccct ccataagagc   17760
atggagatac aaaggactaa catccggaag ttcctcagca gtccccagat tactctccgg   17820
gagaagcgtc gggtattcct gagcctcccc gctggattcc tgggggtgag ctacttctca   17880
ggctcccacc tgaatctgag ttcctactcg cctaaacgca atagccgggt acgggagaag   17940
gatcttagcc tgtacgacga cttctacatc gacaggaata cccagctaga tccgcgagac   18000
ctcttgttta cctcccaaga agagaagaaa tgggagtttc aatacctgaa ggagaagcgg   18060
ggtgatgggt tcgagctatc cgatgaagaa ctgagcgacg ttaaggatat ccagcgcaag   18120
atcgacctgt cctggtacct ggtagacctg gcctgtgaac gtgggtgttc ctacttcatt   18180
ttcgactggt gattacatga gcaagatcaa gagtatcctc atggagcggg tagatgactt   18240
cctgctcaag caagttgctg tggccttcct ggagcagcaa tggaagctgg accgcagtgg   18300
```

```
taccgtggac tacctctcct acctggaggg tgtatcccac gaagctgtgg agacagttgt    18360
agagaatctg gcggagcgtc ttaaggggga ttaagtggat tggagaaagt cactgttcgt    18420
tgagcacaag gtagctgata tcatcagccg ccagagtaaa cgtggagtct acttccagac    18480
tcagcgggcc aagtggctga tccatgtgct tagcgaacga atcctcaaga ttgaccttga    18540
ggctgtcccc cagatgccca tgatgatcgt aagggctggg gccttcagca agccattcct    18600
aaagagtggt aagccgaacc aaaggctcca gtccctgtgg caacgtcttg ggcacttcga    18660
ggtatctgga cccttctctg caatcgagta tgtacccttc gaccttggta agactgccaa    18720
gttcaaggac tggatgctgg atcaggggtg gataccctgac caatggaaca tcaaggatat    18780
tactgtcggc actgatggca agaagctacg tggatctgac cttaatgaat ccttgaataa    18840
gtacattgag gatctccgac agagcaagtc tggacgactc cgaatgaagc tccaggggat    18900
catccctggg aaaactacca ttggggaagt caagagaaag ctcgaaaagc aacgtaaggt    18960
cctaacgact ccgaagatga ctgaagagtc gatggatacc gtccagggag acctgggaaa    19020
gctggtgatg cagcgaatgg tttgggccca ccgtcggtcc ctcttgcagg ggctggtaga    19080
tcaggtgagg cctgatggac gcctagaggg gagtgctaac ccctgtgcaa cacctacggg    19140
ccgtatgagg caccgtgtag tagtcaatat ccccgctgct cgttctcctt tcggacctga    19200
aatccgtggg ttgttccagg ggacacctga ggctggtgaa tggaaatgga ctgtcctccg    19260
ccgtgatctt ggggagaacg aaagggttag gcccttcact aacatcgtgg aggaactcaa    19320
gaagggtaag tggaagactg taggaaagta ccgggtatac gtcccagcga accaattagt    19380
attcgtgggc tacgatggtg ctggtctaga gcttcggatg cttgcatcct acatcaacaa    19440
cccagagtac accaaagagg tggtcgaggg tgatgtacac acggccaacc agatagccgc    19500
agggcttccc acacgggatg atgctaagac gttcatctac gccttcatct acggtgctgg    19560
ggatgccaag atcgggacta tcattggtgg cacaagggcg gacggggcta agctccgggc    19620
ccagttcctt gaagctaacc cagaccttgc tgcactgatt gagagggtta agcaggaagc    19680
cgagaggggt tatctcgaag ggctagacgg acgaaagcta accatgcgac gttctgagtc    19740
tggcgacgtg atgatccaca aggcattgaa caccctcctg caagcagcag gtgctattgt    19800
catgaaatgg gcaatggtac tcctggatga gcgagtccgc aggttaaacc tgagggcttg    19860
gaaagtcttg gatatccacg acgaaggcca gtgggaatgc cacccagagg atctcaaggc    19920
gctacgtgag cagatggaag tctgcgttcg ggatgctggg gaactcctcg gggttaactg    19980
tcctttggct agtgattcta ttgcaggagg atcatggaaa gacactcatt aaagcataaa    20040
gtgggtgcta ttagcgaagc gagagcgaag cttatgtacc taaagagggg ttgggaggtg    20100
tactccccgg atatgcctca aagcagatgc gacttcattg tagatagtgg aaaaggtctt    20160
tttaaagttc aagtaaagac cgcctcttgg tgcaagactg gtaagtttaa tcactgccag    20220
ataaggcttg taaataggaa tggaaacccc tacgagaggg aagactttga tctacttgtt    20280
gtagtagatg ctgactgcat atacgaaata ccccatgatg acatcctcgg gaggacttca    20340
ctctatttca aaagtgataa cccaaacccg aggaagttaa aaagggatta caacccagag    20400
ggttgggtta taacacactg atacatctgg gggttgactt tcagccccct ctgtggtata    20460
ataccttctt ccctacgaga ggtttaagat atgtctaaga aagtttccca acgattcacc    20520
ttcccggtag cgaagctgat cttcccctac atcgtaactc cggacaccga gtacggtgaa    20580
gtctaccaag taaccatctg cattccgacc aaggaagagg cagacaagct ggtccaacag    20640
atggaatcca aagatgcccg tctgaagggt accatcaaat accaagagcg tgatggcgag    20700
```

```
tacctgttca aggtaaagca gaagaagcac gtggattgga tgcaagacgg tgagcgcaag    20760
tctgctgtaa tgaagccggt ggttctgacc tcggacaaca agccgtatga tggcccaac     20820
ccgtggggtg gctctactgg tgaagttggc atcctgatcg agacccaaaa gggcccacga    20880
ggcaagggta ctatgacggc cctgcgactg cgcggtgtac gactccacga gattgtatcc    20940
ggtggtgacg gtgaggacga tccgctgttc ggtggtgcct tcaccgagga agagccagag    21000
gacgtattcg acgaggtatt cgatgacgaa gacgctccta tctaagggt tggaggatca     21060
tgagtcgggg gtatgccggt caggctgccc ctactgctta attgaattcg agagagtgtg    21120
gggtgtaagg gtggtcagtt ctacagctgc atctaataat aaagtagagg tcgatcctaa    21180
tggaatcaag ccgggtgagc cgggcgctaa acttgatagc ggcaaggtgg atgttggaat    21240
catcttcgaa gcgttcccga gggctctata tgcagtggca caagttgcta acttcggagc    21300
cagaaagtat agtcgcgggg gttggaggtc tgtcgagaac ggagtccagc gatatgatgc    21360
tgccttcggt agacacctcc ttgagcgaca caagggtgaa gctttggacc cccaaagtaa    21420
tctaccccac cggtatcacg aagtatggaa cgccctagcg tccctggaac tcgtcattca    21480
gcaagaggag gaatccaatg gaacttctgt tggacccaag ggctaagact gttcctagca    21540
actactctgt gatgggcatt gatgtagacc tggggcttcc cccaggctac agcctaacgg    21600
aggaagctat ggacaaagcc aagcgtcaag agagcgagta ttacgactgg aaggggtatg    21660
aagcactggc caatccagtg gtagagcacc cagagtaccg agccaagggt gaagcctttg    21720
ccctccgtgt cttctgggaa gagaagctca aagaatccca ggtcgtagaa gaggtagcgt    21780
gatgatagct ggtatcgatg gtgacgttct taggtatgag ctaggccacg tggctatgtc    21840
gaaggaacac atcttcgata tccaggtgga gaagccatgg cctgaggaag aggtccataa    21900
gctcgtcgat gataaagtcg aacaaattat caaaagggta aatgcagatg agtgtgaaat    21960
ctaccttact ggccaaggaa atttttaggct ggagcttgcg aaaatcaagc aatataaggg    22020
tactcgaatc ggtcttgaaa agcctcatca ctgggaaacc gtgtcagcca gacttaagga    22080
caagtgggga gcaatcactt tccacggtat cgaggctgat gactggctcg ggattcgagg    22140
cactgaagag ggagctaact ttacagcgtg ttctagagac aaggatatcc gccaagtccc    22200
aggatgctac cattacagtt ggccctgtgg agattcccag ccggagttgg gaccgtttca    22260
agttgatggt cttggaaggg tctccgcttc ttggagaatg tatggcgtta agaagccgca    22320
gaaatcatgg aagcttgagg gcaacggtac ggcattcctc tacgggcaac tccttgttgg    22380
tgactccgtg gataacatac caggcctccc agggacggga ccaaagacag cggcagattt    22440
gcttggggag ctttctagtg agagagatct cttcgcagct tgcgcttacg cctaccaaca    22500
gaagtacgga gataattgga aagagtacct tctggagaat tttcgtctcc tctacctcat    22560
tcgggaccgc tcttggcttg atattcagca gtccggtaac gagtatcact gctcactgaa    22620
gaaacattgg gagattccct atgacgatga agaaatattc tattgatgaa gcacagagga    22680
tctgtgaagg tctctttgag atcctcgaag gtcttggctt cactgactac aaggtcgctg    22740
gtggtttcct tcgggatgca gacaacgggg ttgcacctaa ggatatcgac ctctatgtcc    22800
gtaggccata cgtggaggac cctactgata tcgccgtag ccggttcggc ccacggttga     22860
tcccatgtga tgatgatacc ctagaggtag aggtcactcg gttctacaac aagctgggcc    22920
acaagaaggt ccggtgtagg actggagata agcctgatgg gtatcctgcg gggtttgatg    22980
tgtgggaatc tattggtgtt gacctacccg tcaacctagt cgtgactact cactcccacc    23040
```

```
cagcagagtt cgatgtagga ctatgtgaga tcgcatgttg gcctttaaat cggctgggct      23100
tgaggtctca aatctaccgc acaaagtctt atgagtttga taaggaagag aagtgtatta      23160
ctcttaaccg agtcctagac cctcttctgg atcactctca gcccctaact gacaaccaag      23220
ttgaaaaggt tgtctcccat atccaacgta tcaaactgaa gtatccggag ttccgggtgt      23280
gcctagggga ttggatctgg cttctgattc ggtctaactc tatcctcact gagagtacac      23340
tgtcggttgt ccgtaagctt caagaaggag ggctcattgg caaagcaggg gagattcttc      23400
agaaccaaac tgaagtcatt gattgggacg aagtacgaca gcgaaaccga aagatcgtc       23460 cacgagacga tgccttggat gcagttcaag ccggagccgg tgccatacgt catcaagcac      23520
aagtacaagc cggacttcaa ggtatcgaca ttacaaccct gtggatcgac aagaaccta       23580 ttggtcgagg tcaagggta cttccaggaa gcttcagagg catctaagta catctgggtg       23640
agggaagctc tcccccccaga tactgaactt gtgtttatct tcgagcgccc taatacagct     23700
tgccattggc tttccaagcg taaagatggc acaaagcaat ccatggcgga atgggccgag      23760
cgtaacggct tccgctggtt tactctagag actttcaagg agtccttccc taatgagtaa      23820
gaagtataat gaagacactc tcgtcattgc ggacacccaa gttcgatccg aggtcaacat      23880
cgatcacctc gggaaccttg gggagtggat cgcacgtaac cgcccaagc gaattgttca      23940 tattggggac cattgggaca tgcccagtct gtcaagctac gaccgtggta ccgctaagat      24000
cgaaggccgt cgagtcctcg ctgacataca agctggtaat gatgcgatgc gagttctgct      24060
ggatcctctt cgccgcctac agcaacacca agcgggttgt aagaagcgta tctaccgacc      24120
agaaatgcac ttcttcatcg gaaccacga ggagcgtatc aagcggtatg aaaactctaa       24180
ccctgctctc caaggtttta ttgggtacga tcattttgat ctgtccgatt ggattgtcca      24240
tgatttcctc gacgtgggtg ttatcgaagg tgtcgccttc gcccactact tctacaatcc     24300
caacagtggt cggccatacg gcgggagtgc cgagcatcgc ctcaataaga tcaagcgcag     24360
cttcgtccaa ggccatgagc agggattcaa gtaccacatc gaggcagtag gcaagaagcg     24420
aatccacgga ttggtagtcg gtagcttcta tacccacgat gaatcctaca agggtcctca     24480
gggtaacgac cattggcgag gcgtagcccct cctccggaac cacaaggatg gagagtatga     24540
cctcaagctg atgagtgtgg aggagttcct gtgagtaagt tcttgccaga cctgtactat     24600
attaagtctg agcatgactt cggtcaacgg gggttggcgt taagacgcc gatctccgca      24660 gaactctggc tggatatgaa gtttgggaaa ggggtgctg aggagggct taggcgaggg       24720 atgtattcca tcgaagtcct ggagatcctc tacatcccca gcgttcacct tccggatatc     24780
ttggggtaat ctatgaaaga ccgagtagga cgtaaactag aggtgggga caacgtagtc      24840 ttcctgatcc acaggaacac atcctccac ctagccattg gtaccgtcga tgggtttacc      24900
cccaagatga ttcggatcaa atgcccgacc atgagttgga ctattgacgc tgagtatgtt     24960
ctcaggagca gtgacaaggt ggtgtactat gacaaaggct gaactggaga aagcacttga     25020
agaggcggag agcaatcttg cgaaggtcca agcggaactg gagcttgctt ctgataaagt     25080
ccgagagatt acggaagaat atctcttcct tagctcaatg ttggatatcg tagatcaaag     25140
gtcgaacgtc ttctataaag actggagggg ttatgcgtca agatcaagaa gttaagggtg     25200
gattcccttg gacctacatt gcggtggcag ccttgtttgc cctgctggtt tatgtaggat     25260
atagctgact gatgttactc ctgaccattg gagagatatc cagactcctc gttgaagtgt     25320
tatcttgggc aggttcctta tgaagtatcg agtgaagcaa gtgggaagt tcttcttccc      25380 tcagtataag caatggtttc gttggaggaa tttcgagcag agaaaacagg ggatgggat      25440
```

```
ccactgtgtc agctcgtatc tagagtccct tcctgtagtc ttcgagaacc tacaggatag    25500
ctgttgcttc atccgggacc acatggacag gatatccgaa gatactccta tctaccaccc    25560
cgtcgagtaa ccaaaaaaag gccccaaggg tgttatccca aggggcctta tctttagctc    25620
cggagagcgt tcagtagtgt attgaactta tccacgagtg cctcgtgagt atccgtatag    25680
gaagccacgg ggatctcaga tatcttatcc tggatggaag ccgcaatggc ttcatatagg    25740
ccactcactt cgctagcctt gggtttccag ttacctggtt tagcctcgct agccttagca    25800
cctacctcca gaagcttagg cttcccctca atatcctccc acttcactgg ctcaaaatct    25860
ttcgggccaa tgacttgtcg aagggtccca tcttcattac gtacagcaat agccttcgat    25920
tgaataacga atacactgtt gccgtcgttg tcagcgatat aacctgccat aatctaactc    25980
ctattaaact gccgatttga aggtacccac ggtaccaccg aaaggataca ctcggacagt    26040
gcattcccca aattgaccat cagtttccgt ctgattaccc ttagcatacc aagccttgtc    26100
cggagataca gcgaacttga tcttagctgt agacccttgg ataaagtgga agtgacaacc    26160
tggggttaca tctggaccaa gagtcacggt gatatccgtg gtcccttgag acatgaagaa    26220
ccaaccagac tgctgcttag tcagggtaat gttctgagta agctgctggg tgttgacgac    26280
attaccacca aggtgagtag tcacgaggcg gggatccagg tagttctgtt ggagagaacc    26340
aatgttcttc acaggaccac gcatgtcatc aaactgctcg ataatgtaat ccccgatggt    26400
accaccgttt tggtcatccg ggccaatcac gtgcttaata gccacgtaaa cacccaggtg    26460
ttcccgacga gggtctactc ggaattcact accgaatgca gtaccgcaag gtgcctcaat    26520
catggtctca gagaatagac caatcacgtg gccagggtca cggttaccac ccgaggtttc    26580
cccaggagcg cccacgaggg tgttgaccag gacagatggg ataacggcct ctgatggatt    26640
ctccgggaag gaggctgtaa cgttctctac taccagggct gcgttctcct taactgcata    26700
atagtcaggg aggaactctg tagcggtaac gatgttagta tttacccgac cggcatccga    26760
ggtaatctca atgagatcac catcggaatt acgtcggaag acttttggca catcaaccac    26820
gtaggcacgg ccaccaggac cagcggcatc agtttctaca taagttgcca tattacttct    26880
ccttaaagat ccagagcatc ttccatcgct tccataccgg caacgaaagg acgtgctgga    26940
gtttgcttat acaagaactt ccagatttca cctgcggatg ggtcatcccc aaacgaagcg    27000
atagttttac caacagccat agcaccctca gttgcagcac cagctactgg acccaatagt    27060
acctctgcgg gggtagtccc tcgacggtaa cccgtcagca tgtcgtagat catagaagcc    27120
tggagtggca tctgttgcat cactacgtcc atcatccgtt gttctggact acgggtatcc    27180
tctcggctag acccaccgaa cttagccagt tgacgaagct catcctggag atacccagga    27240
ctcatcatca gaccaagagt gaaggctaca cctgcggcac ccataccagc gttggtccag    27300
gaaccagcga agtgtgggct cattcgtcta cggaacatcg gtaggatgat gttaccatag    27360
gctgctgggt aacccttcaa gagggagaac atctgaacgt ttccgttgct catccacata    27420
ggcttatcag cgaaggtggg atcgaggact acctgatcta caaaccgacg catggccaaa    27480
gtcttgacgt tgttagccat caggacttca gatggggtag ccggggagat caacttgagg    27540
gcatcctgct ggctaccgat gttaaccccc atttcccgaa gctgagcaac cttcagagca    27600
ccattggcag aactgaaggg gagacctgcg gctagatcca tcaggttgtt ctgatagacc    27660
ctcttggcag tctctgttgc aaagattcgg ttaacatggg ttaggatgga caagccgtta    27720
atgaggaact gaccacggat cgtcttttgg atagtagagt taaacacctc agcaccaacc    27780
```

```
cgatcagcca tcagagaggt agcagaggcc agggtgtggt tcatatcact cataaaccga  27840
ccggtctcag actttggaac cccactgtag atcctacggg ctgcttgtct tactacttca  27900
cccatggttg ggagtacagc cccaagggta ggcataaccc ccgccttagc gaagggtagg  27960
ctgaactcag ttagggtaga gaaccctgcg aggggtagtc gggagagcac gagggcacct  28020
gacgtaacag ccgccagctt cttaaggttg gggtctttga tacgaccgtg cataccattg  28080
taggcatcca ctaggtcata catccgatcc acttcttcct tggtaacccg cttaccagcc  28140
cgttgagcct cagctacagc agaagcaatc ttagcgttag ccttctctcc gttgatacca  28200
aaccgttcgg taaaggcaat ccggtgggaa gcccccctcga agtaatctcg gatttcctgg  28260
agacgcttct taggagtatc attaagagaa tacttattga ggatctcttg gggaacggag  28320
ccaaaggccc gactctcttc cagctgacca tacttaggta ccgcatcact ttgggcaaac  28380
cgtccacgta gagtatctgg atcaccctgg atacggtaac gtgggtctac ttcccaagcc  28440
ccggtctgct ggttctgagt aaccaatcga ttaacctcag gggcagtgtt accacgagta  28500
tcatccgaga cttcagccag ccagttagct acagcatctt cagcagcttg tcggttctgg  28560
aagtaaggag tgatatcgtt caggaactct ggggattgaa ccttctcagg gacagccca  28620 aagggcatat agttggggat agtcccaaca gacatgccac cacggttaac agcctcattc  28680
cttacgtcat ccatcaaaga acgtagacgg gtagcctcag gggtgttgac accagcggat  28740
gtatcagcga taatcctatc gatctctttg gaagacttac cctcaaagat gctatctagt  28800
tcagagttcc acttacctgc ctgtagttcc tggtcctcaa agatagtctt accagaggcc  28860
cgcttaccac tcatatcagc acggaaggtc tcagagaact cacgagcgat aggggaggcc  28920
ttagcgagtg gctctaggag cgacgtagct tcgtttccta gggcatccca agccttcttg  28980
accgtacccc taggttcaaa ctcagaagcc ttaggaggtg cctcaggggc gttaggatca  29040
accacggcag atccagcgga gtcctgatga cgacccaggg tgtccatccc cgaggataca  29100
gcaccaccgg cagtacccat agcggtacca gtgaatgcag cagtcaggag gttatccatg  29160
aactgctcag gggtttgtac ctgccctact gcatcatacg cgatagtgtc ctggaggacc  29220
tgctgggcac cagaggtaac accttcagcc acaccagaga ctacagcgtg tttaccagct  29280
tgggttacag cctcaatggc ggtctgctta ggtagtcccg attggaccaa catctggtaa  29340
gcgccatctt taccgatgtg cttgaggagt ggggcagcga taacaacagc acccgcagtg  29400
tctagtaccg agaggccagc accaccgagg actgcggtcc atgggttgct ttgatcgggg  29460
tctagttcct tcatctggtt actcaggca cctacgttga tacccatgga actcaggaag  29520
gaaccaatga gcgctccacc catacgacct ggggccccaa agacagagcc agccttagca  29580
cctgcggcac caccagcaag tacagggcc atcgaaggga gagcctctac aatgttattc  29640
tttaggaacg aaccgatgga tgggatatct tggatatcag cgaaagaccg aacatcgggg  29700
gttccgtact gtgacgcttc ctgagcattc tcctcggcca tctgtgtgcc gtagtctttc  29760
aggtagtcac tgccagtcag ttcaccaagg gtagcaatag taccaccgat gttagactgc  29820
atggtatcaa ccccacgacc aatcgcagag ctaatagaat tagggtcagc cggagttact  29880
agggcactca ggtctggggc aggctcaggg gtagtaggga ctacttcctg gggtgcctct  29940
tcgataacct ctggctcatt caaggaagcc aattcagcgg ctacgtcgag gcccttgacc  30000
tcagccagtt ccgcatcaat agcggccttc agttctggag aaagagccat aagtcacctt  30060
ctagttgctg gaaagagaat aggctcttaa gatgtatctt aggatactaa ccttcttagt  30120
aagtaagtca aaaggaagaa ggaatcttaa gagcctatag gtctattata ctacatttca  30180
```

```
aaccaattac ccgtaggttg aagcttagca gcctcccgct ggataatacc cactgggtta    30240
gccccaggat tagcccgaag ttcatttcgg acagtctggg caatagcatg ttgggcagtc    30300
ttactcagct tcttaccacc cagagcctga gaaccgttga cttcactcag gataccaagg    30360
gcgtccttag tagtaacagc ttcacctcgg gctgccttag ctgccgcttg acgtgcctga    30420
gcgctgatct tagcagtttt gaggcgtaca gcagaactaa gctgggcatt ctcttgagac    30480
atatcctggc cacgtcgagt agtttcagcc tgtagctggg cccgttggtt agccaggtct    30540
tggccacgtc gggtcaactc cagattagcc ctatctacag cagcctggtt gacccactta    30600
tcaaggacgc cctcagtctt acgcttggtt tgctcaagga tcccttcctt aactttcagg    30660
ttgccctccc caaggagtac atcagcagca tccttagcca ccttacgctc cagatccttt    30720
tccttgatct gacgatcagc agctgcggca gccatcttct gctggttgat cccagcctgt    30780
aggttacgat ccagttgacg ctcataggaa gcagcgaaca tatccccggc tttaccagtc    30840
ttgtctaggg ccgaagccag aagaccagta ccaatgagag cgtaagatac ataacgagac    30900
aggtcatcat tatccatagt cctcatctgg gtcaactctt cgttcacccg gttcttaagc    30960
tcttggggtt taagctctac accttctcgc tgggcatcag cctcaactac agcttgggcc    31020
atttcaggac gacttacagc accagtacga agaccctcgg ctgcaccctg ttggatgacc    31080
tggcgattag cctcctcctc atctgctaca gcagcaccag cctcggaagc cacctctggg    31140
gtgatctcag gctcgataga gggttggtta ggggttaccc cataggacaa cagaccggcc    31200
cccgtagggc ctcctgtggc gttctgggct gcacgttggc ctacaccctg gcccattgg     31260 tttgcctctt gagcaacctc gggacccatg ttctcaaccg cttgactagc ctgagccatt    31320
tcttcagcac gagtacgctc tgcatccccg agttctcctg ggttacagc ggcttgtaca     31380 cctacagaga taggaccacc gaggatacct gcgatacgac ccaaggcacc gcgaccagta    31440
gcttcagccg caggtgcaac ctcttgggct gcacgggacc aacgctctgg gttctccagg    31500
gctgcctgag cagcacgacg gacacgatca ggaatacctg agccctctac agccagcggc    31560
agtttgttcc ttgcgattcg cgccatatcc agttcattct gagcagcccg gaggatgcta    31620
gggcgaattg gggacccttc ataagccatg ctggccatag gattaacctc caaatagttt    31680
acttaggatt ccagcttttg gctgctgtcc gaaaccgagt tcttctgcgc taggaaggat    31740
tcccactccc gctcccatgc ctgctgcaac ttccgctgcg cctcgttcgc ttgctcctct    31800
agccccctcg acagaaaagc ttggtactgt ttctgaagaa ggctcacttc cttgcccgag    31860
gagagccgcg agtgctgctc cgcccattgc gccaaagggg tttgattgtc cactagactc    31920
tcccgattgc attgtcccaa ggtgggtggg gcggtaggaa ccttgacggc tcaactgtac    31980
ccgctcctgc ccaccaccta tattctgtcc tatagcgaac agcttctgag gaagggaggc    32040
cattagaaca gaaggccccc taccctacca cctgcgttca taccaacaga agcacccgct    32100
gggccaccga agagagcacc caaggaagca ccaccgagag cacccagggc agacccgagg    32160
ccaccaccac cgccaccacc cgaagaagta gtgacattgg ttccccccat atcgccggag    32220
ataagctcct tataggcgag gaggtcgttg aggctgacgt tattctcata ggcccacttc    32280
tgtagagccc cgttgatttc ctgctgctcc tggttctgaa gcatgctacc agcatctacc    32340
tgcatggcat taccagagcc gaggcccctta gcaatagccg acaggttacc cagggtattc    32400
aacctattct ggttgtaagc ctgctggtct tggaaagcca actgggaagc gttattctgt    32460
tgattctgaa gcagcctagc ggtagcaata ccctcggcta cacccgctcg ggaactgcca    32520
```

| | |
|---|---|
| tactggccag cattagtcgc tcctgcacgc aggtctgggc gtaccgtagt gtcgaagtcc | 32580 |
| cattgcatct gctcgttggc tgcaccaatg gcgttcgcca agccagtttt attgggatcg | 32640 |
| taaggaccaa ggtaatcagc cagagagcta acacctgagc tacccaggag agactgaagg | 32700 |
| gcaccccga gacccccag cccttcgatg ccactaagct ggagagcatt ttggtcagcc | 32760 |
| accgggtcaa agttcggatc gcccccgtaa ttggggtcaa agccccgtt atgtagccaa | 32820 |
| tcactggcac ccgagagtag ttcattatag ttaccttgct gatagggtgt agagacagag | 32880 |
| gtggtctttt gcttcttact accacccttg taagcccgag aatctagggc atcctctaca | 32940 |
| tcgaacccca tcagacgctt tacgttaaat tggaggaagt tcatctggag ttacctcacg | 33000 |
| atagaaggaa acggagtctt cggtgtaccc gagtttctca agggtaggct tccagccccg | 33060 |
| acgaccttca cattggataa accgacagtt aactcgttgg gcgaactgtc cgaggaagtc | 33120 |
| gtctacctcc gagtaatcta ccggggtttc attcccaggc atcttaccac tccagaagaa | 33180 |
| gtgaaggatg ttgcccaagg gggcctggga tacttggatg actcccgcgt acccactctc | 33240 |
| ttcctggtag aagacatagg cctcataatt aaccaggaa tgcaccaagt gctcaaagtc | 33300 |
| ccagaactta cccaagtcag tcctgttaaa agcacgggct agggctggaa ctacggtcgg | 33360 |
| gagggagtct atattctcac gagtaatcaa atgaatcatg gagtcaccac caggggaat | 33420 |
| gtgaatgtac ccccgaagac tgctccttgg ggaattcctt ggattagaac acggccatta | 33480 |
| gctgtgatct taaacattgc ttggttaacc acaccagtct gaatagtagc cctgttgaga | 33540 |
| acatcaaaga cttgatccaa cggaggtgcg ttagggtcag acggaggtgg ataagtaata | 33600 |
| gtgctctgcg ctgggatgat gctggaatag gccgggataa acaactcagc aggaggccaa | 33660 |
| tacgcctggg gaagatccag gacagtagct ccattagtgt agttaccacc agacatgagc | 33720 |
| atggttatcc atacttcatc cttagcagtg ttcatcctat aggcacaggt acccatcggc | 33780 |
| tgatggttgt tctgtggggt aaataggata aaacccccg gcaggtcctt gggtttagta | 33840 |
| cctgcgagtc tccattggtt atccaagtcg taatgataga tgccggatac tggacctacc | 33900 |
| actccggggg caaaatactt tacagtccct ggcttgagct tcttaggggg ctccatagag | 33960 |
| acccccagt agccgtcagc taggtcattc agagtctgtc caaccctaac gaattcttca | 34020 |
| ttaaggaagg gcagcagttc ctcctcttcc tgtggtggaa tcgaagggct gtacttttga | 34080 |
| ctcatcgcat acctgccttc ggggccattt caatagtgta tccgttgaag taccaatctc | 34140 |
| cctccgaaga gaagtcgaac ttcaaggcta tataccggcc cacatgttta gtgtcaatct | 34200 |
| tatagtcctg gccaatccgg tatgggtagg ggcccttcca ccgaatacca gaaccttgta | 34260 |
| cctgagcatt accaacccag atgttgcagg tgccgttacc cgtgatatgc gggatgatag | 34320 |
| cactcacagt cttcatcatt cggtcatccc caagatagat atcggatctc tcaagggtac | 34380 |
| tgacgaagtt ctgcccagag aatgtagagt tattaccgaa gaggaacaac ttcttatcct | 34440 |
| ggaaagacga gaagatcata ctggactttg ctgggttata agagccttca ccccagaccg | 34500 |
| aagtatcggt atcccagggg ttgggtcgt catcccagag gttagacacc ttaggatcga | 34560 |
| tgatcccgta ggctccactg agaacgttgg gaaggtctcg gatactccaa gtgttttcct | 34620 |
| tccagttcca gatgatagcc ctgtcgcagt gcttacctgg ctcagaccta gtggaagagt | 34680 |
| agcataccca catttcagta ttcacgtggt ctgcaagtac gaatgtccgt tgatagttgt | 34740 |
| cagggttaat atccgagaag aagaacttac ggacctgggc atcaataaca gactgcttct | 34800 |
| gaacaccatt gtggacatat acatcaccgt gacctactac aaagtggtta ccatcgaact | 34860 |
| ctactgcaca gttgggccca aggatacctg cgtcgttaaa cagctgctgg aactggaaga | 34920 |

```
tgaacaatcc accgatatac cgcatggagt atacagagtc ttccttgtag atgatgaaag   34980
agtcacgaag cttcacacca tccacgatag caccattggt atcagccaag gtgttctgac   35040
cagcatcttt agtggggtcc gttgggtccc aagatgcagg tacaccacca gcatcagccg   35100
aggtactcca ccagaccatc tgtggcattt ctacagagtc acttgtagcg tttaagccaa   35160
ccaggaagtt cttaaaagac ttaagcctct taaagtagt attcgctggg aagttaggaa    35220
gtaccctaaa ggttgattct gacggtggaa gatgatgagg ggggttaacc ccatcgttag   35280
caaagattac cccgttgaac gaccctacag accacctgtt agttatacta gcagcgtaag   35340
gtcctgggga tacatcgatg attgtagtcc cgtcggctag atacaaccttt gttcagaac    35400 acaggagcca ataggggatg ttattccgga tgaaaggaaa catatccaag attggggcct   35460
gggctgtatc aaagataggc gtatggccca gagccttctg agccttgccg ttcttaaacc   35520
ggacgttgtt cccgaaggac catttctcca gtggcaggtc agcgggggcg atatcggtca   35580
caatccccgt agggttcttg acctcttgtc tctctagggc cattgtatac ctcagttctt   35640
aatgatgaag aacacagaac agaacggtgg gatattaccc aacggcatgt tgatctttac   35700
tgcatggttg tgagtctgac cttgaccagc agggccagtc tcaaggttgg tattggctgc   35760
gttaccagag ccacccgtca gagcacccga gtcacccgca gaaccaacca atgcagcagc   35820
acctctggtt ctccaagtgt gggtgtgtga tgggatctgg gctagggtaa gagcagtacc   35880
ttcagtgaat ccatcccata caatgttagc gctaccacct ctagtcccta cagcctggga   35940
agaaccatcg ataccccaag ggaatgcacc aatcaggtta gggacgggaa tcccgttaga   36000
ggtagtacct accccattgc acaacttcca acctgctggg atctgagcta gtgacccagc   36060
ccacatgata accatcccag gtttaacata ctgggttgta tcagcgactg cgtttagctg   36120
ggctgccgtt acagtgacag cctgagaaat attggggaag gtgttcttaa tagcactctt   36180
aatgagacgc aggtggtcat ccccaaagga tttcagatca gagccggtag ggttcgtagg   36240
caccaactgg ttaatgtaag ttgcgacctc aagacccatt cttggcctcc tttatctctt   36300 cttcatttc ttttcgggtg acataccgct ccccaaagat tgccatagaa atctggagat    36360
cgctcaccgc ttgggtgagc ttctccgtgg cctggatgtt tctttcaagc agagcctgat   36420
taacattctg accgcaaacc gaggaaccta ccgtcactac cgaggatacg accagggcac   36480
tgacgatgct gcccaggtta tcagttagaa gttgcatcct ccgtcttctc cttaaggttg   36540
tcttccagga ctttttacgaa ctcgtcgtca accttagagt tagtcttctc cgccagagcc   36600
ttagcaccag tcacgatgga cttagcgatt accttggttg ggaagagggt agccagaagg   36660
ttgattgcga gggtttttag aaagataggc atctgaatct ccttaacgtt caatgtcttt   36720
gatcgccagt cgagtgctag cgaagtcagc ggcattctcc tcgttctgga gttccataac   36780
agcccgttcg agtttctgac cccagaactg ggaccgagct tcatccatgg tgtacagata   36840
aatctgctca aggacaccat agagataaat ctgcggatac ttcgtcagag cccaagtcgt   36900
tgggttagcg aggcttagct ctgggagtac agtccagtag ttcacaatga acggggcacc   36960
gtcaggaaca acgggaaata ctcgccagaa gttacccaac cgagtgtagt aggttacacc   37020
ctgaggttgg tagttgtagt taacataatg ggtgaaggta tcctgggtga tgtactgaag   37080
agtacgtcca ccgataaggg agtcacccgt gatagatcgt agagcaacaa agtgctcagg   37140
tatctcaatg ccaccaccga aggccattag ggtttcgaag tgttcgttct ccctcacccg   37200
tagcaatcgg ttaagacggt cagtggtatt accaatgaac aacatcagaa gttcttgggt   37260
```

```
aagatcctga cggtcagacc actggatagc ggcaatagcg agatcagtta cgttgttgat   37320
cgtagccatt cattacaccc gtgcctcaga ggtccgcatc cgatagttat ctcggtcatt   37380
aagccaacgg gtaaatcgtg cggcatggtc tgggtcacaa ccgatcaggt taagatcgat   37440
gggaccacct tcagacatgg ggcgattccg tagggcctct acaacaacca gggggatact   37500
tgctaccttg cgcatattat ccttgcggtt gctattgaca cccgagtggc gctcttcggc   37560
gttagcggac aggattgact caacatcttg agtatccttt cggataaaga gcccaaggtc   37620
ttcgtcaatt gcataagtcg attggatact catgatgtac ctcctaaggg gaaacaaagg   37680
gccccgaagg gccccgttgg gttagacctg ggctacaacg tcgcggatca gagcaccgga   37740
cttctcgttg tttacacgca gggtgtactc aaccagcagt tggcgcttct cgctgtcacc   37800
ggtcttagcc agttcatgct ggaagaacga acgcaggtag cagagggcgt gcatcttcgg   37860
atcaaagatg aacatggtgt tttcgtggaa ccagcggttg gcacgaatgg tgtacttacc   37920
gaagtcactc tcgtagacgt ccacggtctg cgcaatgcgg ttgtccgagg catccagggt   37980
gatctcagtt gcacgaccct tcatgttctt gctgatggcc ttcttgatcg agctcgaagt   38040
ctggatcgag ttagcctgac caccgttgcg ccagatggcc tcagaggcat tcaggagcat   38100
gtcttcggtc agaagacgga ggtcaccagc ggtaccagtg tcggaaccat caccagttgg   38160
cagggtaccg ttagcaccta ccgaaccgtt ggtcttgtag taggcaaaga tgtttgccat   38220
ctgacccgga gtagtggtgt tacgctggat cttagcctga ggggcaccga ccatggcgta   38280
ttccatgtcc agcttcagtt ccttcgactt cttagccagc tgatacgcca gttcgttctt   38340
acgaccagcc ttcttgacct tatctgcggt accggtgact tgcagggtct cgtccgagat   38400
ttggcagtag ttgttcaaca tggtggtgaa gctaccagcc ttgatggttg catcctcacc   38460
ttccactcgg gtgttcttac ccggctgcg gagttcatca gtctgccact cgtgggtgat    38520
agcggtagct acgcccttgc cgatagcagt catgaacggg gtgtcatagg gtgcgatgtt   38580
gtagatgata tcgataaggt cttcgcgctt accgttgatc tctacagtgg agacggcatt   38640
agttggagtt gccatataat gtacttcctt ctattagaaa atgtcgagag aggagaagag   38700
agcagcagcg gcttcaaccg actggtcttt cctcagatta gcgcgggcag ctttaacccg   38760
cttagaaccc tctgaggctt ccgccctacg agcagcaggc ttaactgcgg caggtagttc   38820
agtctcctcc ttcttctcta gggcagcctt gcgacggacc tgagattcag cccacttacg   38880
tgctgcatcg agtacagcca gttggcgggc atcagatatc cctcggatct catcctcgga   38940
gtatccaatc gatttgccgt aggacacaat cttgtcaccc caagactcat ccgtggtcat   39000
ttccgggata agtttcttgg ctagctctgt ctgacgctta acgtaggcag agtggacaat   39060
ctcggctcgc ttctcttgca tagccttaat gtcgttacga cgtttgataa gagcctgggc   39120
tcggtctcgg gcttccaggg cttccagtcg aagggtttga tacttctctg gtcctgggc    39180
cttaagctgc tcccagttta cattgtcata ctgattagca ccagcaatag cggtaacagc   39240
atactgctca agctcggcca gtagattaga gcgttcagca tcaagctctt cgaatttagc   39300
tgcatactga tcctctagtt cagcttgtcg agttacaaac tcttcattgc gaaggtagcc   39360
actcttaagc tcttcgaagt taacctcgta gacttcatcc ccaatcggga tctcaaagag   39420
tttatcctca ggatcttcct cggactcaac ctcgggatct tcctcagaac cctcttcttc   39480
ctcctcggac tcaacctctt cggtgtcctc tggagtacct tcgtctacta cctcttcctc   39540
ctcttcttcc cctacgactt taccatccac ggtttcatca ccgggggcca ggaggtcatc   39600
acctagcaaa tctccgaagg cttccgctgc ctcgaattca tccatgcctt gattctcaag   39660
```

-continued

```
gtccattact tatactcctt tagagtgatc gaatccagga tagcctgaat acgaagttgt    39720
acgcggttga gggcatgtag ttcgtggtag atggcctccc tggactctga atccttaggt    39780
gccgtggact tccactctcc ctcgatctct tcttggacaa tacggaaaag ctcaggaaga    39840
acgttctcac gtaccatctg ttgtgccgca tcagtcagca ctagactata gccaaaacgt    39900
tctcccaaga ttaattcctc actgccttag atggcttctt agtctcaggt accttaccgt    39960
ctccgatata agcagcccga gcctgagtag cctcaagatg atactccgct tcgttacgag    40020
cccgttccca agtgaaacga tcacgctcaa gttgtagttc cgcttcctta agggccattt    40080
ctctctgctg aaggacagcc tcttgcttct tcagttcgat ctcagccagt cggatctgag    40140
cctctacctg cttcatctgg gcctccgctt gcttagccat agcgtccgat tgggcacgtt    40200
gggcatcagc ttgggctttg atatcttcag gcttaggttg tgcttccttc tgctctctaa    40260
tggccttagc ccgttgagct tcaggagaat ccgggttagt ccagaagcga tccgggtctt    40320
tgtacccagc gttctctgtg acttccttaa ggatgttgta aagattctgc tcagagacaa    40380
ggacccgag acctccaccc ccgactacag cctgggccat ttcccagata cgcatcaggt    40440
ggagcatctg ctggtctttg ttcatgttgc caataccaac ggtaaccgtc aggtcggatc    40500
tctctcgcca gttggcaggg ttaatagcaa cccacttgcc tcgtagctgg aagacctctt    40560
cctgattctg gtacttgatg gcatggtcat gcagaagttg gaacaaacgc ttaacaccag    40620
tctctgcaaa catccgggca atcaggtcaa tctgttgctc agcagcagtc atcaactggt    40680
ttacactcat agccgcttgg ttagagtgca gggtgttttg gtctagacct cgggtacggt    40740
cagtgatacc tgtccgctta cctctgtctg cctctagtcg atccagcatc ccatagactt    40800
ccccagacaa ctgaggggtc tccagaggca tgatagagtt catggcctta acccgaacga    40860
tacccgctgc ctcgttggtc agcaagtctt cgaggttaac ctggccatcc aggactacag    40920
agcgcccttg gttggtccgg tagatgttat ccatgatgtt ccgcatgagt accgaacgga    40980
tctcttgaat gtctcggatc ttatcgtaga cactcatccc gtggaactta tgggcaattc    41040
gataggcatt caggtcagcg aagggacggc aatcccaagg ctcgttgctg atgatgtagt    41100
cgcccacgta caggatacgg cgcaactcag agataccatc cccatctacg tccagaaggg    41160
tgtagcactc agaggcccat acctcacggt tggcttcagc gtcatcccca gagttatact    41220
ggagttggcc agtcatatcg aagttatcac gtaccaacct ttctggctga ctatcagaga    41280
actcatactc atcgtatgga agctcatcta gtacatcctc gggaacaccc aagagccgaa    41340
ggtcacttac ggtatacttc tcacggtgac agaggaagcg tgcatcatca atgcaggtag    41400
ccaaccgatc aaccaggaag ttctcaggct tgatacaggt gactttaatc tctcgcttct    41460
tcttgtcctt gcgaattta atactgtagg ttccatcctc gtccacactc tgtgctagaa    41520
tctcagtgtc tggatcagcc aggatatccg ctaccatttc ctcagagaga ccagagaatc    41580
gttcgaaggt agggttcagg acctcttcta catagacctt tacaacaccg tcttcatca    41640
tcagagtgtc ttgaaccag tcgaacatta ccttgaaccc ctcgttctta cgcatgaaga    41700
ggtagttcac atactcagtc tcttgctctg cctgttcaac atcttcggca gtctgaggtt    41760
catacttaac tacttgaccg cctgacgtga ataccttcat aagagaaggc ataatccagt    41820
ctacagtctc ttgaacgtcc ctagatacaa tcgcggactt cccagggcgc tcgttaccga    41880
agggctctcc gaagtaatac ttcagggcct cagaacgctg cttggaaagt tccgaagagt    41940
tgaaatcaag ggcgtcgtta acaagttggt ctagatgacg aagtacctgt tcatcatcca    42000
```

```
taggcttaat cttgcgacga cgcttagcca ttagacaata ctcccaaacc aatcagggt    42060
caactttgca gtatcactcc tgtagtatcc actgtttcgt acagcaccag gacgtgcatg  42120
ccgggaagcc atcaacaggg cataccgggt agcggagatc atatcgtcgt ttctgtcgat  42180
aatcttccg tcctttcggt ggtacatttt catttctttt aggaagttcg tacacgtatt   42240
aaacaccttc agatcaccat tctccatacg ggtcaacatc cagttaacgc cgaactctac  42300
agagttaccc ccgtgtttac catcaggacc tggtgggttg ctgaagggct catacactac  42360
attgaggttg tggtcatctt taagaaggtc tacgaatcta cgaccagagg ttgctccatc  42420
gtgcttaaag gcatcgtggg ggacaactac cgggatctgg tgaccaccct tcaagtagat  42480
agcatcagcg tgcatcccaa gggtctcacc actctcactc ctctcatcat agaggtaata  42540
cttgtctttc tcagggtccc aagcaacaca ggcgatagcg ttagggtggt caaacccgag  42600
gtcgataccg atgatcctgt ggaagtggtc agggatctgg aaaggctcac atacaaactt  42660
ctcttccaga atggggaaga ctacaccaga tccgagcata ggaacaccct cggccctcat  42720
cctgcgttct gctggagagt ataccgagag tagctgctct ttaacttctg gactgaggtg  42780
tggagcgtct tcccagcttg catggacaag gaactgacca ggtttaagat cctggaggaa  42840
gtccttgacg atctccgtca gaccatgctc tggggtaaac gtcagatata caataccccc  42900
agtagtagcc gttcgggtta cacactgggt ataaatatcc ttggggcatt cctcatcgag  42960
ccagatgacg tcgatggcag tacccatgaa tttgtcctgg acatttcgt aggacttgaa   43020
gataagggac gagaggcccc cggaggcatg cttaacaact actgcttgca cacatccggg  43080
tttaccttcc ctacgaatcg tctctacgat atcttccttg gggatcatcc ccgttccaaa  43140
agcctcaggg ttcttccagt cacctagtag ttcggactga agaatatccc gagtggtatc  43200
cgtggagatc cccgccgccc agcagttcac tggacgatca tactttctac cagtccacca  43260
ctcagggtag cgaccggtga ggtggcaggc catgataaag gccccggtgt aggttttacc  43320
acagcggtta ccagtcatag ccagcaactg ggcgcagttc gaggaagctg cgataaactt  43380
ctcttgccac ccataaggag tatactggtt catgcggaaa tacttctgcc gctccgccaa  43440
ctccctgact agattccgta gccgctcttg ggtatccatt agaccacctt gtcacctact  43500
gttgatgcac gccacagggc tcgttggaag tcccttacgc gtaccggagt ttgtttggcc  43560
cagaggctat cctctgcctc ccatgcagct tcatcaaacc ttccggattt cagaagattc  43620
cacgtcttgg ggaacttctt cgtccacgct gtacccagct ggaaattgac gctaacgagg  43680
gcatcgaata gctctggagt gcaaaaaggc agctgagata cttgcccttg ggctgcatca  43740
taggctgcct tactatcgtt tctagccaa gtctctgctc gggccagggt aatcggtccg    43800
tcctcaccag ggagttgcaa gtgtccataa ccccggtca ttttcccaag ggagtctttg    43860
taccacttta gaaccaatcc ctcccttcgc ttgattagat caaggtactt aagaggctgg  43920
gaaagaaatg actttagcca actctggctc ttcgtcgaga attcgtcgaa cttcactgat  43980
tagatcctct gcggacatat cttccacatt cttagtagta agctccagtt tctgcttagc  44040
tccgaagcct ccacggtcca ggatatcctg ggctgccttg aggcgaatcc cacctttctc  44100
ttctgggttg ctagcaatct ctacaaccac acgaagcgcc atgggacat gactcccgat    44160
gcgctcagag ataaaggcgt tgatatattc ggcatgcttt cgatggtatg cagcaacgtt  44220
gcgttgagcg tgattaggag agaacccagc ggctatatac gcttgggttt tattcatacc  44280
atctgccaga gcctcacaat agaggtctag ctttctttta gcagaaagag gagcagcccc  44340
aatcgagaca atcttttcgt ctgacataca ctgctccgat ctctctaaat ggtcaccccg  44400
```

```
gtaggactcg aacctacgac ctcctgtgtc caagacaggc actctaacca actgagctac    44460
gaggagttaa tggcgaccca tgtcggattc gaaccgacgg cttctcccta gacaggggag    44520
cactctaacc gctgagttaa tgggccataa tggttgggac ggtagggctc gaacctacga    44580
cctgagagtt atcggctccc tgctctacca actgagctac atcccaatta attctaaagc    44640
acccttaagg ttaatttctc aaccttataa tactattata tcacactttt tctattttgt    44700
caagcccctt ttcatctttt tttatttta gtcgcaagac ccggatttgt taggggtttt    44760
gctggaattg gaaaggggtt cttaagacta tcttaagata accttaaggt aactaacctt    44820
cttagtaagt aagtcaaaag gaagaaggaa tcttaagagc ctataggtct attatactac    44880
attt                                                                 44884
```

<210> SEQ ID NO 5
<211> LENGTH: 45010
<212> TYPE: DNA
<213> ORGANISM: Bacteriophage P1800

<400> SEQUENCE: 5

```
cccctagccc ctccctagga taccatggga ttagtccggg ggtcaacccc ttgagatacc      60
gttcatcggg tggaccctag ggtattcata agaaaaatct tagggtattc aggggggtgga    120 tcgggggaa tatccattga taaccccttg atccccatt gacttccgtt gatacccctat     180 gttaatcaaa gactgtctat atccgggggt ttgctggggg actgatagtc cataggctgt    240
atgaaaaacc agtagacaac cccgtaaaga atatggcgta atggcgccgc cttgagggaa    300
accgataggc aacggggaa accccagggg cttgacaaac cccgcggaac cgggtctaat    360 ggccccacg ttctacctag gccaccatcc cccttgccgc agtgctatcc ggggctgcc     420 aaccagggaa gagcgcccaa gtcgcccaag tgtaaagccg gcaggtatcg ggggttgaca    480
agggatcggt gaagcggtat agttcgcccc acgtcaacgg cataacgtgc atgactccct    540
cgggattagc gtagccttga caagcaagac tgatggccac tcagcaaaag agcctatgcc    600
agagaactgg acgaactaac ccccgtcaga ggggttgacaa gcaagccca agcctctaac   660 atgggcaccc atcaggtgac ggccacctgg ggaaagtgta ccttcgacgg tccttggact    720
gaacaaggga gaaacccgaa agctgaggga ataacgcaca ctccgaaaga gcgtaggtcc    780
tggccttgta ccatagaagg tccgactggt agcctgtccc agcgcaatca attgacagac    840
cccgtggttc aagcgcgacg gggagtatga tgggttagtg tcgaaggctt agcgcagagg    900
gcgaagcttg gtagatacgg cgaaggtagg ggcgagtgga tacgaagacc cccgaggata    960
accgaggaca gaccataacg acgacactaa cgcggaaagg ggccggctac gccaatgcca   1020
aggtttgccg ataaacccct ttgtcgtatc gggatgtgtg tcccggctga tgattcctaa   1080
aggatgaaac gaccatgact caggctcttg acaaaaagct gcgtcgcaag gccaaccgca   1140
aggccaaggc tttgggttac aaccttggga atctggggaa ggcccaacag cgtagtgagc   1200
agaagtttgg gattattgca agttgtaaca agatcctcga cgacaagacc acttcgttgc   1260
aagaaaaggc aggggcgcgt aaacgcaagg ctcttatgag taccgactgg cgtaaccgtg   1320
aggttactaa ccttcggaac tggtataagc cgagcaagtg cggtaactct gccgtcatca   1380
ctgtcgaagt aaacaactga ggtaattaca atgagcgact acaagcgcat caacgggatc   1440
atcaagacca ttgccaaccg gggtgctgcc ctggacaagc tggttcaaac cactggcatg   1500
gatatcctca agcacatcga cgagcatggc gaggtgtcct tggcctgcaa gctgttcaac   1560
```

-continued

```
gcgatgcctc aaggctcccg ccggctggcc ctggcccact ggttcatcga caacggcaag    1620
atcgaggcca ataccgacaa ggaaaaggcc aaggaattcc cgttcgtctt cgccaaggac    1680
aaggccactc gtctggagcg tgccgcagag aaaccctggt tcaagtacaa gaaagagcgt    1740
gacgtggccg acgagttctc cctcgatcaa gccatcgccg ccttcaaggc caagatccag    1800
cgtgccatcg acaagggcca gctccaggca gcggacgagc gtatcgccgt gatccagcga    1860
ctggaagtca aggacgaagc gaaggcagcg taacgccggg tgcgccaggg gtgtgtacta    1920
tgacgcgccc ctggtctatc cctagagtgc atggtaggtc cgtgcattgt agcgatagac    1980
catcaggagg tttccgtggg ttactgtatc tttgggcagg ttcattccat caaggccag    2040 gattatgttt ctggtttctg cgatgcaagg gtaggtttcg acgctggtat tgtgtaccgt    2100
tggacattca aggacggtaa atttgcctgc ggtgtctact ccctggatgg tatccgtctg    2160
aacatctgcg ggtggatcaa atgaagtcac cctacgaagc ggcccatgaa cgtgcccaaa    2220
tgattaaccg tctcaagaaa ctcactagga tgatccgggt gcatcccgat ccccggtgga    2280
ttgttgagcg tcaggaactc ataaggaaac taagcaagtg acaatcgcta tcattgtatc    2340
cagcattggt atcgcctact tcttctttcg tgattggaaa gaggaaatgg gtatctaacc    2400
ccaactgatg aggccaaggt gattcctggc cgaaaccccc accggaccta tggtcgcagg    2460
ctggggcgtc ttgggaaatc aactaaggaa accatcccgt gaagcgcaac gactaccgaa    2520
aggtgaatcg gaacatgcaa gccatcgagg ccatcgaccg caagattgcc aaggctgtcc    2580
gtgagttgac taactccgga ggaaaccacg ttggtaaaac cctggagctg aatcggctgc    2640
gggctaagcg tgcatcgctg gccaaggtaa ggcacggtg agtacatgga agtctattgt    2700
atgtgccgcc atacgctcac gttccaatgg gttgctgctg gtaacgtggg tggttctctt    2760
cgtcctgtcc tcgatcttgg acagcatccc ttttgcatcg tgaggtagtc ccatggatat    2820
caaggtgtgg ccccgcaacg gcgtaaccct cagttctctg gttaagtccc aaacctttct    2880
catcaatggg gatgtgtaca tggtctgcga actccgaagc atcaagatga agagtgaatc    2940
tgacgaggtt cccgttctca atctcaagac tggcaacgtc atttacatgc ctccgttgag    3000
cctggtatac ccagtaactg ccgagctgaa ttgctacgag gtgtaacatg aaactccaat    3060
acaacatgat taccagtaag atcaaggttg tgatgtggaa tgaccttgag ccgggttgcc    3120
tgtacatctt cgcagaggat gacgggaaga agaaccccaa agtcttccag tacctggagc    3180
ttaatgatga attcttcatc tgcgaaatct tcggcggacc tgagggcgat gtattcttca    3240
gcagcgatgt tgactgcggg ttcttcccgg tgactgtcaa gtacgcagag atcgaagtcc    3300
atcggttcgg cctaccggac tgagggtgtg tactatgacg cccgcccaat acatctacct    3360
ctggttggta tccaaggttg tcatccgtcg ataccagcct aaccccaaac tgtaccccaa    3420
ctggtccgtt actcatatcc gtgtgtcgat cttcggcaaa cgtgcaggta tcgtctatga    3480
aatccactga accccaagtc tattggctgg ctagcgccga tggtgaattc cacctcaagg    3540
tcatcaactt cggccagttc atcaccgaaa cccttacga actcggcatt ccggtggacc    3600
acaaggttca tcgggtccac tgaggtgcaa ccatgtcaaa caccaccttc actgtagcag    3660
caacccgccc ccggaacgac cttcacatca gtaagcgggc ggatgggtt tatgtgaacc    3720 ctaaaaactc tggcgatatt gtcttcctca aggaaggtaa taaggttgtc gtcctcagcc    3780
agagcgggtt cagcatcctc gaagcccaga ccatgcccaa catcgggaa ctctgcccgg    3840 ctaaggaggt ccatgtatcc gccagggtat ggggccgta tgaagaataa acccatgatc    3900
ggccagataa tggcccagga gcgccgcatg aagcgtcgtg tagaaaagcg ggggttcaac    3960
```

```
atgagcctcc aggaaagccc ccaggagccc cgtggtgagc ttggtttcac cctggctgcc    4020
gtaggtatgg agtccagccg atcggcttac ctgcgtcacg ccagggaggc tatgatccaa    4080 tccgggagc cttgccccca ttgcatgcca gtcttcggtc ccaaagaggg tcgttgctgc    4140
aactgcgcga gggactggtg atggatctcg gtaatctttg tgtctcttg ggtgtccatc    4200 ggtacaagat acttgatggt ggaccctacg agattcgtca aagggtcgg ctagtggaac    4260 tctgccacta ttacgacctg aggtgtgatc gctgcggtga cgtacatcgg aaggtggtcc    4320
gcagcaaatg atgacatacc tcctgataat cccagcgatc ctgatctata tggctttatc    4380
tttgctcgtg gctggcatcg ccgggttggc ggcaaattgc gatgagcatg aaggatgag    4440 ccagaaggat caggacattt caatcatcct cggtatcctg tggccagtgt cactaccttg    4500
gatgtgcttc tcggttgtta tctggaaacc tttggctacc accatccgtg cggccaaacg    4560
actaatcaaa ggagattact aatgcaccgc agagactttc cctcctgctg taccgcaaaa    4620
atctacatcg gcatgggacc ctcgggtacc gctgaccatt acgccggcct cgcatccaac    4680
gggttcagcc ccgtggtttt cgccaaggaa ctgatcggcg ccatccgtcg tgaatccaac    4740
gagggccacg gtacgatggt cttcacggtg aacagcgagc aggtggtagc agataccatc    4800
ctccgccgca tgggcagcca ctacaacccc tgggcatcca gcgacaacca ctcgaccaag    4860
gtccgggtcc acgtcatcaa cgtgaagtct gcggcagata tcctcatcaa ccatggggtt    4920
ctccgtcgtc acctcggtgg cttgcaggac taccccggta ccgtcgagca ctcggagtac    4980
ctcgacaagc tctgtaaagg tctgtaacat ctaggccttg acattctgct ggaagtgtgg    5040
tataataacc ttaaggtgcc gggggttgct ttatatccct aaggtaccta aggttctacc    5100
ttctatcttc ttcatcttaa gaaagaggta agaacaatgg tcctcaagct ctacactcgg    5160
gtaatgctcc tggctatccc cgcatgggta agcgtaaggt tttctacgag cgtctctgct    5220
ccaacggtga attgaccctg aacggcaacc tcaaggccac caaggtgtcg gcaccaacca    5280
aaggcaagca acagcgccgt ggcaccttct aagtaactta gaggtcgcta gtaataccc    5340 tagtattcct gtcctggggg tattgctggc taactcaacc aaggagaaaa caaatggccc    5400
gtatcaagta tgccttcggt atgaaaccca agaagggcga gggtaaagcc ctcaaggtaa    5460
tgacctcttc ctcctgcttc ggtacaatgg aaggtccggt aacccacggc tataagctcg    5520
acggttggac cttcatctgc tcccgccgaa gcaagaagtt catcgatgtg ctcaacaagt    5580
gtacccaagg tgaactcaag accatcacca tcggcggcaa ggccttcaaa tcccgaagg    5640 tccacttctg gtcttacgaa agcaaggcca aggattcccc cttcgagaag tattctaacg    5700
ggacggaaat gatttccccc acccatcacg gaaagaagg ggtctgcggt atctacttca    5760
accccaaggt acacccctg gattcctggt accccatcat gaaattcctc ttcaagatga    5820
tctccagcgg actcgactac caaggtcgtg aagaggaggt tcacctgaag cttgctgaga    5880
agtatggctt ctggaagtcc tacctcgcaa tgtccttcca cggactgata gccaatggct    5940
acaccgggta cccactctcc aactacatgt tcagtagtga ttgggatgat ctcaagaagg    6000
gagatatcca catccaatcc gctgacgagt ctatccgatt cggtcgttgg atgcccaacc    6060
gggatgcccc aggtggacgt gagtgggtaa ggaatacacc ctggcggtct gaattcctga    6120
agattcagtt ggacaaggtg gaggtagtta ccatagcacc tcagccaacc atcttcggaa    6180
agaaagatcc ctacatgacc gtagatagcg agatgggagg tttcatccgc ctttatcctc    6240 ataccctgtga aaaatacgga gtggtcatgc tggggatcat gggtgaggtt ggctggggga    6300
```

-continued

```
gcggcataaa ggatatctta ctggccctcg aagacttcat cgagaaaaac ttctgacaac    6360
caaggagaaa tcaaatggga atgtatgcag cccataacgt gtactatgat gtcgagggtg    6420
ctgagattgg tcactgctgc gtaaaatacg tggctgaata taccaactgc ttcggtgcat    6480
tctgcgacga aacgggacct ttccgggatg tagtgtggga ccgggggtt ggacacctcc     6540 tggtgtctac ccacgagaac actgctggta agttggtgga gttcttgaac agtgatctgg    6600
tcaacaggat caccgacggt ggaatcctct cagcttccca ggactggcca accaagtggt    6660
ggacaggatc tgacggggct acccaaaacc tctccaatcc tgaccacttc agcccccctg    6720
gccgccgaca ggctgtgtac gttcgggtgg acctcaagaa gaacgcatcg gcaatcatct    6780
gtgccctccg aatgggagat cgcttgtggg gtgtaggtga ttccatgcgt cgcatcaccc    6840
aggaaaatcg tgataagatc ctggtctgca atgcagagat cctcaccctc gcggcttgtg    6900
cccaggtagg tagcactgct cattgcgaca gctacccggc catgttcccg gtgactgctg    6960
gtgaataccg ggagggatgc gagagccacg gctgggaggt ggatgacagc tacataagcg    7020
aggtcatgga tggtatcgta ggtggataca agaatatcac ctacttcgat attaagagca    7080
tccatgagcg gactcgcgaa gagttcaagg acaagctcaa gcatcacgac gctgagttgt    7140
ggcaggggta taccaaggat gatgacctga tcgaatgcga cggtctcgaa ggtgtaccta    7200
atgaccgaat cctttccatc atggcccaa tcaccattga cgtcggtgac ccaggtcggg     7260
aaaggtccga ggtcgtaccc accagccaat acagcatccc cgaaatcctc gaaaaactgg    7320
agaacatgca atgaacaacg caatccccct gatcggtgca gatcccgaag ttttcgtcgg    7380
ctacgaccgt aaccccccaga gcgtcatcgg cttcatcggc ggcaccaagg aagagccctt   7440
ggctgtagcc ggtggtgctg tccaggaaga caacgttctt ctggagtaca catcgaccc     7500 ggccagtacc aaggaagagt tcgtggagcg tatcgtctcc gttcgactcc tgggtgccca    7560
gatgctccac cccttcggca tgaacatcat cgagaacctg tcctctcacc tgtacgacga    7620
ggaactcctc cgcagcttcg gtccccaggc ttacgtcttc ggttgcgagc cggactacaa    7680
ctgctggact cgtcgtcaga acgtgatgcc gaaggatgcc cctccgaccc tgcgtactgc    7740
cggcggccac gtccatatcg gcttcagcca catcgagcga gtcaccaagg ctaccaccag    7800
agaagtcatg cagatgtgtg actacctcct gggcctggcc tctgtcatcc tcgatggtga    7860
cacccagcgt aagaagctgt acggcaaggc tggcgcaatg cgctataagc cctacgcgg     7920 cgagtaccgt agcctatcga acttctggat cttctctgtc gatctgaccg agtgggtcta    7980
tgaaatggca gtgcaagcct acacctccaa gcacctcctg gaggagtaca agtcgatcgt    8040
atccggtgat gaagtccagc ggatcatcaa cgagaacgac ggcgctgcgg cagttgcggc    8100
cctccaagcc ctgggggtga agtatgaatg acctgaataa tcgccatcgg ttggccgggg    8160
acttcaacat gtactactcc tccacctatg ccttcttccg ggttgacggt gagcctcggg    8220
tagtgtacgt ggacgatacc gagtccattg gtgacgaccg tcaattcgac gggtttcgtc    8280
tcctgggtaa tgtgtatcgc cccgacggca gtaactacta cggtggggtt gtctacagcg    8340
aggtagaaag cgtgcggccc tccagtgggt actatgacgt cttttggccgt ggggttcgtg    8400 atacttatgt atccttcctc gtgaacaatc ggactcagcg taagggtatg accccagga    8460 acatcctgct gaaccatgcc caacaggcca tcactggaga aatgatgatc cgaatcttca    8520
cccaggccga ggaaatgatc tctgccccat cccaccggga cttcttcatc aaggatgggg    8580
tagttcactg gaagggggtg aaggtcggcc agatggtgga tgggcggctg tccgcagatg    8640
aacaattcaa gaaccaggag gacttgctat gtcagttatt ggcacacaga tagggttcca    8700
```

```
taagaaccag atcatcgccc cggaacacca cgaggaactt cctgcggttg cttccttcgg    8760
gttcgaagtc gaactggaag gcctcaacaa ctggccagaa gtggatgggt gggatctgaa    8820
gggtgacggc tctctgcggg ggggtatgga gtatgtcttc tccggtcccg cctctggcca    8880
gagggcaatc actcgggttg aatcctttgt gagtgcgatg gaggaaactc ctccggcccc    8940
caccttccgt tgctccaccc acctgcacat ggatatgcgt gacgtagagt ggcctgttta    9000
tgaacgaacg gtcctgacct acatggcatt cgaggatgtt ttcttcgatc actgccaacc    9060
gtatcgtcgg gatagtaact tctgcatccc gttcttcagc aacgactggc tggcccagac    9120
cttcggtcgc cgtatcctgg ccccggaagg tgaccgagag aaagtcttgg gtcttacctc    9180
ctggccaaag tattcggcct tgaacctcca ggtaacccac aacttcgggt ccatcgagtt    9240
ccgtggtgcc catgctctca ctactcggca ggaaatggta ggcctgatgc agcgtatgtt    9300
gtgtctcaag gccttcgcca tggctcacgc agaaaccccg ctggaagagt tccttaaggt    9360
actctccgag gtgaatctcc gtgatgtatt cttcctgggg gtatctccgg actatgaaat    9420
gtctccgggt ggtcgtgaaa tggggatcgc cagtgctact ctcgcggtag caaccatggg    9480 cttttgttcgc tccggggtag atccctggaa agatgaacag aaccgtcagc gtcgtctccg    9540
ggagcaggaa cgtgagcgtc agagggcttt ggatcgtagg ctgctctttg ctcgcgctat    9600
tacctcacga ctactagatg gtgcagcaga gcggtacaac ttggcaatgg tgccaggtac    9660
ccaggttcga ctggatacgg cgattactgc ggtaacttct ctgcgtcgta ttggtcacca    9720
agtgcgtgta cgagaccttc tggaggacca agaggctctt caagatgcct tcgtactgct    9780
catggataac ccgcagcacc ttcagcgcca taccggcgta acaatcgaac cagatatgta    9840
ctaaggagaa atacaatgtg tggattggta ggcttctgtt ccacaactaa cgcgagtgat    9900
aacgaaatcg ctcttctcaa atccctcctg gccgtggata ttatccgtgg tgctcacgcc    9960
accggtttgg ccaagatcga cccggttaag aacgaggtag gaattcacaa gcgggcagta   10020
gatgcctacg acttcctggc tgatcctgaa accaaggagt tcctggacaa gggtcgggct   10080
cgcatctaca tgggtcacaa ccgttacgcc acgatgggcg acaagacgga ccatgggaat   10140
gcccacccct tccaggtaga ccacatcacc atggtacata acggcaccgt agatacctgg   10200
ggcctgcacc tgctggatgg caatgataag tacaacgtgg attcgaacat gctgtgcgct   10260
accattgcca accacggagc caagaagacc ttcgaagaga agttctccgg tgctgctgcg   10320
gtaatctggt gggactccaa ggaacgtacc ctgaacttca tccgcaacga tgagcgtccg   10380
ttgttcatgg cggtgaccac cactggtacc atcgtgtggg catccgagcc tggtatgctc   10440
aaggttttcc tggagcgtcc caacgctaag atccgccttc gttctcccat cgctgaactg   10500
aaggctgaag tcctggtaac tatcccgttc acgaggccg gagtgcgaaa gggtgcagaa   10560
ccccagacca ctccggtcac gtttctggac ctcccaattc ccgaaagcga aaggcaaaca   10620
gcggcatggt ggagtcgcta cgtcggtgtc tcggactatg atgactacag ccgaagccaa   10680
ggcagccaag cgggaacgaa aggcagccaa gcgggctcgt cgtatggaac gtctggcgat   10740
gcgtacgcaa ggaacaccct ccggatcaac aacaacctcg acgcagcagg tagcaccttc   10800
aagcaccggc aactcgtcac cttcgatgtt gtcaagatcg aggcctacgc aaacggcagc   10860
gagtacggaa ctgtcactgg aatcgagcgt gaagaaaacc ttctcatcga agctcatggc   10920
atcaacgtcg ccaaggtcca cggatacacc gtcctccgag ggagtatctc caatgcctac   10980
ttcatcggcc aagaccgtga tctcaaggtt actgtcgagg atctggcggt aagctgcctg   11040
```

```
gacccaaagc atcggccgac tcctggggag actaccccag tgttgaggat tggaacgatc   11100
tcatcggaga cgaaatccca ttctaaaccc agggttcaag tcggcggcac ctcggggaat   11160 accccctccgg ccaacatcag ctaccccttg aaggttcagg gacacacgtt caacaacgtt  11220
catgtctttc gggacttcgt atcccagggg tgtgcatctt gcggtaagat ccctaccgcg   11280
tatgaccagc gtaatcgtca tctgacggtg tacgagggtg ccaagttcac tggtagcctg   11340
gatgagtgcg agttcatctg tggtgagtgt gtaatcgaaa ataaatagga ggtcaaaatg   11400
acccaagtaa cgatgaagcg tcaagtagtg atccagatgg agaccgacgc aacccgtaag   11460
tatcccttct cccgtgacac cctggacaag atccagtcga ttcgtcgagt caaggagcag   11520
gaactcaatg atgccaaccc ggacgaggaa ttcctggtac cggccccggt agtcattgcg   11580
gaagctatcg accgactctt cgaagactac ttcgagtaag gtagtgcgtt agtaatagtc   11640
cctggccgac ccatgccggt tcctaagatg cgtacatggg atctaactta ggattccagg   11700
ggctattgct ggcttcacta ccctcaacag aaacaggaga tttgccatgt tctatatcta   11760
taaaggtgcc cgcccctctg ctggtgctgt cgctcttcgt aacgccatgg gtgctcgaat   11820
ccttcgctcc gaggggtcta cctatcgggg tcgttcgggt actgcggtaa tcaactgggg   11880
aaccgttggt gcagaggcac gacgcctaca gggtatcgcc ccggtcttcc tcaacgaccc   11940
ggctatggtt gctcgctgca ccaacaagct ggatttcttc cgccacttcg aggccaacgc   12000
cccccatctg atccccgct ggacggattc ctgggctaat gtccacccga tcctgaattc   12060
ctgcggtcga atgtacgctc gtacggacct caatggtcat agcggcaggg gtatccacct   12120
ggtgtgcagc atcaacgacg cagaagtcca ggccatcgat gcccttcgtc gccaggggaa   12180
ctacccggta cacatctggg gtcataccca catcccggag gtcgtcgaga acgcccaatt   12240
gttcacccag gcatcgtcg gtaagcgtac cgagttccga gtccacatga tccgtgggga   12300
ggtagccctg ctccaggtca agctccgacg tgttgccaat gaaatggtga ccaacgaagg   12360
acaaagtatc gttcgtaacg tagctggcgg ctgggtctat ggcgtcaacg atgcaatggg   12420
acgggatggc gctgagcagg ctatgtcggc agcagcagaa gctatccaag ttgcaggcct   12480
ggacttcggc gctgtggata ttatctacca gcacgctact agccgggcgt ttgtcctgga   12540
aatcaacacc gcgccgggcc tggatgcaga aggcagcgcc ctggaggcct acgtcaaggg   12600
cttcaataaa atcttcgagg agactatcta atggctgttc gtgttttcgt ttatggtact   12660
ctcctgtctg gtttgtacaa ccactacctt ctggaagggg ccgagtttgt cggcaatgct   12720
gtatcctgcg agcggggtct gatgtactcc gctggcggct tccctatcct ctccttcgcc   12780
tcccgtgctg atctcatcgt aggtgaaatc tggcaactcc ccgaaggcga aaggggggag   12840
gaaatgctgg agaacctgga tgccctggag ggttatccgg gttggtatga tcgtaccctc   12900
aaggatttcc gaatcaatgg ggaacgaatc aaggccctgg tgtaccatca ggatagccac   12960
atggcgatgg atatcgtcaa ggatggcgac tggaaggcac acctggcaaa acgacaagga   13020
gcagtataat gaacgaaatg accgtagaca aagcagtaga agtctaccgc gatactccga   13080
atacattcgg acaccaagag ctacatgccc agaagatgct tctcaaggag atcctgggcc   13140
ttgtagcttc ccagcgacac ctccaagact ctatcgaggt ctccaagatt ccggaggcct   13200
cggatagtcc cgagaccagc tacggtgggt actgtgacga atccattggc attcgcttca   13260
tgtgggagcg actgaagaaa atcgaggatc gtcttcggga actggaggag gtctacggta   13320
ccttcgtaac aactccttat aaaacccta cggcaacgt gaatgctgta ccaagcctgg   13380
ttctcaagag tcaactggag gggtaagtga agaagatcat cggtgatacg gcttgtccgg   13440
```

```
gttgccgagc taaaggtggg gataaaacag gaaatcacct catcttgttc gttgatacag   13500
aaaagggtac tcggttcgga agttgtaacc gttgtggtca ctacgaagtc ctcgaagagg   13560
gtttcaaggt gccagagcgt aaggagaaat ccgaggagga tatcatccat gaagtcaacg   13620
aagtccttga gtatccaatt aaagccctcg atactcgaaa gatcagcaaa tcaatcgctg   13680
aacggtacgg ggtacgtgtt ggtctatcac aagagaatgg tgaggacgtt atcgagcatt   13740
actatccacg cactcgcgaa ggggagtacc gagcgttcaa cgtccgaatc ctagaaccta   13800
aggctttcta ctaccgtgga agccccaagg gcggtgtaga ccccttcggg tataacaccc   13860
ttcggcataa ggatatggga cacctgcggt tagtcatctg cgaagatgaa ctgtcggcta   13920
tgtctgtggc ccagatcatg gagtcgaaac tcccggagaa gtggaagcat cttcgtcagg   13980
catccattag ctggtcctcg ggtgttggtt ctgctggacg ggacattgcg ttccttaagg   14040
agtctggtgt acttgagcgg ttcaacgagg tcatctattg ccacgatgcg gacgacgaag   14100
gccgtaaatc agtagaaaag gtacgtgccc tgtaccccga gtgtaagttt gtcgagctcc   14160
cgctgaagga tgctaacgac atgctcatgc gtaatcgggg ggatgaggtt taccagatga   14220
tacgtttcgg cagcaaggtc aagtctccgg actgttccgt tactgtcgat gaggtatacg   14280
ctgaggctct ggaaccccc aagtggggca agagttaccc gtgggaaggt ttaaccaacc   14340
taacctatgg tcagcgggat ggtgaaatca tcgggtagg cggtggtact ggtatcggta   14400
agaccctgtt ggcccacgag attgctgcct ggaattgcat tgagcacggg gagaacgtag   14460
ggacattcct gttggaagag caggtagcca tgacccttaa gaatatcgcg gggaaggttg   14520
ccaacgtgcc cttccaccga ccggatatcg agtgggatga gcaagccttt aaagatgctg   14580
ctggtaaact ccgtgccaaa ctcttcatgt ggaagaacaa gggtcagaac gattgggatc   14640
atatcaagga gtgtattcgc ttctgggctg tagccatgga tgtgaagact atccttctgg   14700
ataacatgac cgccatgacc aaccaccta gtccttctga atgaacacg gagatagccc   14760 gtatctgtac agaactcgca gggatggccg acagctagg actgcggatc ttcatcttct   14820
cccaccttaa cccacccaag ggtaaccgta cccacgagga gggcgctgaa gtaaaggaaa   14880
gccagttcac tggttcccga gctatgcagc ggtggtgtca gcttatgatc ggcttcgagc   14940
ggaacaagca ggctgacggg gaagagaagc acgagagtcg aatccgtgta atcaaggaca   15000
ggaactacgg taacactggc ctagtgttca ccaagtataa ccctgagacg ggtcgcttgg   15060
ttgagcgcga gggcagttac gacgaggtac ctgctgacga tgacacccca atttgattac   15120
gttatctatg acctagaggg ggacggcctc ttcaatacgg tcacaaggct ttggtgcgct   15180
gttgttgtag acattccgac tggggtagtc cggggattcc ggcccgagga aatggatgtg   15240
ttctatagga tcatcgccca tgcaaagttc gtggtcgggc ataacatcct agactacgac   15300
aaccgggtcc ttgagaaact tcatgggatt atcataccccc ccgaccgaag ctatgatacc   15360
ttggttgcat cgaggttgac ttggccagat aggcccagg gtcattccct gggagcctgg   15420
ggtaagttcc tgaagtgtca caagggtgac ttcaacgact tctccaagtt ctcagaggaa   15480
atgtttgagt attgccttca ggatggagtg gtcagtcacg cactgttcaa ctacctcctc   15540
cgggtactcg gcatgacttg gcaagagctt gttgaatgga ggactgtaga ttggctaaaa   15600
agcgagtgag gaactacaag cgtgagagag aactggctat tcgacgcggc gaaacgggcg   15660
tgggctctaa gtcaggagat gctcagcggc accgagcccg ccgaaaggtg gaaaagcgtc   15720
ttggcaggaa gctcggaacc gacgaggttg tcgatcatat caaacgtgtt aaagatggtg   15780
```

```
gcggtaacgg ggattctaat cttcgcgtcc gtggccgttc ttctaacgct gctgatggtg   15840
gtcgggtggg cgatcgtaag gccaaaggca ttcgcaagaa aaagtaaatg aagaggggcc   15900
ttcgggcccc cgaggactca ttatgttcaa tcgaaagcta agcatcagta aaatcctcag   15960
ttcctttgac aacgagatca atctactgaa gacctttatc aaagagtctt cggatgaatc   16020
tgaacggatc tacaacgaga tcagcttcct gaaggcggag cgtacccagg tcatgcagga   16080
caacctgaag gcccagaagg tactggctaa cctggaagaa ctgctgggag gtaagagtga   16140
agaagtatcg agttaatgtg gggttccagg acaccaaggt gttcaacgca gacttctacc   16200
gcatcgagtt ggatatcatc cggttcttcg cgggagattc tgatgccaac cccatgaccg   16260
tccgagccaa tgagatcggt gctgtccgtg gatgggtttc tgtggaggag attaacgatg   16320
gcgagtaaga aggaaagcct ggaggatcag gcacggaagg agattgccct ggagaaggag   16380
ttctctggta gctggggtgg ccccgagatc gatgctgatg acttcccctt gggtagtgcc   16440
tgtggcctag atcccgaggt atgcgagtca tgcagctgag ccagtgcgta ccctggctgt   16500
gggctactga tcgatgcggg tatggggtcc ttaccttcaa gaggaaactc aggaaagccc   16560
accgggttgc ctactgtatg gccaacagtc tacaaattga ggacatcgac ggggttatca   16620
tcagacataa atgtgataac ccatggtgtg taaatgtaga tcacctcgaa cctggaactc   16680
atcaggataa cgaggatgat aagaccaaaa gaggtaggcg acctatggga gagaaggttg   16740
gctcagcaaa actgaatagg gctcaagtag agtccatccg gaaggagtat gtaaaaagct   16800
caaagacttt cggttcggtt gccctgggta agaaatacgg ggtacattcc tcaacgatca   16860
gatacatcat agcaggagat atctggtgag tatcctagcg caagtccttg tcatcttctg   16920
gagtgcattc ttccaggtat tcctcctggg attgaactct aagctgctcc gggatgacaa   16980
gatcaaggct gggttcgtag tgtcttggtg tatcacgctg gctcagtttg cttacatcaa   17040
ggcggtagcc tcctcccact tggatatcgg atggtttatc ttcgtgtccg ggtggggagg   17100
tgcccttggg attacctctg ctcaatactt ctacaagtgg tacgacaggg ttttccacag   17160
atagtcttga caaatccagc aaagtgtgat ataataacct taaggtgccg ggggttgctt   17220 taccccctata ggagatacaa atgagtgacc atgtaagcta ctccaaacat gtccgtggta   17280
agtacctgtg taatatggct tctgccctac ataagagcat ggaggtacaa aggactaaca   17340
tccggaagtt cctcagcagt ccccacatta ccctacggga aagcgtcgg gtgttcctga   17400 gcctgccaga gggattcctg ggggtgagct acttcacagg ctctcatctt aacctgagtt   17460
cctactcgga tcgtcgaaac gcccggattc gtgacaagga tatgagcctc tacgatgact   17520
tctacgtgga caggggcgcc cagctggacc ctcgggatgt cctgcttacc tcccaagagg   17580
agaagaagtg ggggtttcaa ttccttaaga agaggcgggg tggtgtcttc aacctgtccg   17640
acgaagagtt gagcgatgcc aaggatatcc agcgcaagct tgacctgtcc tggtacctgg   17700
tggaccttgc ctgtgagcgt gggtgttcct acttcatttt cgactggtga taacatgagc   17760
aagatcaaga gtgttctcat ggagcgggta gatgacttcc tgctcaagca agttgctgta   17820
gcgttcttgg aacagcaatg gcgactggac cgaagcggaa ccgtggacta cctctcctac   17880
ctggagggta tctccgacga ggcagtggag gtagtcatag agaatctggc ggagcgtctt   17940
aaggggaatt aagtggattg gagaaagtca ctgttcgttg agcacaaggt agctgatatc   18000
atcagtcgcc agagtaaacg tggagtccac ttcaagactc agcgggccaa gtggctgatc   18060
catgtgctta ccgaacgaat cctcaagatt gaccttgagg ccgtccccca gatgccgatg   18120
atgatcgtaa aggctggggc cttcagcaag ccattcctaa agagtggtaa gccgaaccaa   18180
```

```
aggctccagt ccttatggca acgtcttggg cacttcgagg tatctggacc attcactgca    18240
atcgagtaca tacccttcga ccttggtaag actgccaagt tcaaggattg gatgctggat    18300
cagggatggg ttcctgacca atggaacatc aaggatatta ctgtcggcac tgatggcaag    18360
aagctacgtg gatccgacct taatgaatcc ttgaacaagt acattgaaga cctccgacag    18420
agtaaatctg gacgactccg aatgaagctc cagggtatca tccctggtaa gactacaatc    18480
ggagaggtca agagaaagct agaaaggcaa cgaaaggtac taacgactcc taagatgact    18540
gaagagtcga tggataccgt ccagggagac ctgggaaagc tggtgatgca gcgaatggtt    18600
tgggcccacc gtcggtccct cttgcagggg ctggtagatc aggtgaggcc cgatggacgc    18660
ctagagggga gtgctaaccc ctgtgcaaca cctacgggcc gtatgaggca ccgtgtagta    18720
gttaatatcc ccgctgctcg ttctcccttt ggaccagaaa tccgagggtt gttccagggg    18780
acacctgatg ccggtgaatg gaaatggact gtcctccgcc gagacattgg agagaacgaa    18840
agggttaggc ccttcactaa catcgtggag gaactcaaga aggtaagtg gaagcctgta    18900 ggaaagcaca agatatacgt cccagcgaat caaatgatct tcgtgggcta tgatggtgct    18960
ggactagagc ttcggatgct tgcatcctac atcaataacc cagagtacac caaagaggtg    19020
gtcgagggtg atgtacacac ggccaaccag atagccgcag ggctcccaac ccgtgacgat    19080
gctaagacct tcatctgtga gatatggatg acttgggga aaccctcga ttaaaactgg    19140 gtgaactcag ggaacccttt aatatgggaa tcctgagcca agacacttga catttcccgt    19200
agaatgtgtt atactgatat tttatggag gtgtttatga agtacccaaa tggatggttt    19260
aagattaaga actgtagaaa gtgctcctcg gagttccagc ctactgcccc tagccaccac    19320
tactgctcag acgagtgcaa ggagtggggt aggatcaatg cctactacac cagagtctat    19380
ggactcacgt atgatgaagt aagggctatg gctgatgaac gagaccacaa gtgtgatatc    19440
tgcgggagaa agggattcct gatggactcc tctaagcaca ttgcattctt agtcgttgac    19500
cactgccatg caactggtaa ggttcgtgga ctcttgtgtc acaactgtaa cagagcattg    19560
ggactgatga aagattctcc agagcttctt cggaaggctg ctgagtatct tcaagtgtaa    19620
ggtgcagaga ctattatgta ggacccaagc gggttcgaag cgcccagccc ctggaagaca    19680
gggtgatgat atagtccgat ccccagggga aaccttgggg cagccgagag gcgggccagt    19740
agtagcgaca ctggttgaac ttttgatgcg ttcatctacg gtgctgggga tgccaagatc    19800
gggactatca ttggaggcac cagggcagac ggggctaggc tccgggccca gttccttgag    19860
gctaaccctg atcttgctgc attgattgag agggttaagc aggaagccga gagaggttat    19920
ctcgaagggc tagacggacg gaagctaacc atgcgacgtt ctgagtctgg cgacgtgatg    19980
atccataagg cattgaacac cctcctacaa gcggcaggtg caattgtcat gaagtgggcc    20040
atggtgctcc tagatgaacg ggtccggagg ttgaaccttc gggcttggaa agtcctggat    20100
atccatgacg aaggtcagtg ggaatgccac ccagaggatc tcattgcgct acgtggacag    20160
atggaaatct gtgtccggga tgctggagtt ctccttgggg ttaactgtcc tttggctagt    20220
gattccatcg ctggtcgctc gtggtatgac acacactgat acatctgggg gttgactttc    20280 agccccttt gtggtataat accttcttcc ctacgagagg tttaagatat gtctaagaaa    20340
gtatcccaac gattcacctt cccggtagcg aagctgatct tccctacat cgtaactccg    20400 gacaccgagt acggtgaagt ctaccaagta accatctgca ttccgaccaa ggaagaggcc    20460
gacaatctgg tacagcagat ggagtccaag gatgcccgac tgaagggtac catcaagtac    20520
```

```
caagagcgtg acggagagta cctgttcaag gtcaagcaga agaagcacgt ggattggatg    20580
caagacggtg agcgcaaatc tgccgtgatg aagccggtgg ttctgacctc ggacaacaag    20640
ccgtatgatg gccccaatcc gtggggtggc tctactggtg aagttggcat cctgatcgag    20700
acccaaaagg gccacgagg caagggtact atgacggccc tgcggctgcg cggtgtacga    20760
ctccacgaga tcgtatccgg tggtgacggt gaggacgatc cgctgttcgg tggtgccttc    20820
accgaggaag agcccgagga tgtattcgac gaggtgttcg atgacgaaga cgctcctatc    20880
taaggggttg ggggatcacg aggcgggggt atgcccacgg ggctgcccct actgcttaat    20940
cgaattcgaa agagtgtggg gtgtaagggt ggtcagttct acagctgcat ctaataataa    21000
agtagaggtc gatcctaatg gaatcaagcc gggtgagccg ggcgctaaac ttgatagcgg    21060
caaggtggat gttggaatca tcttcgaagc gttcccgagg gctctatatg cagtggcaca    21120
agttgctaac ttcggagcca gcaagtatag tcgcgggggt tggaggtctg tcgagaacgg    21180
agtccagcga tatgatgctg ccttcggag acacctcctt gagcgacaca agggtgaggc    21240
tttggacccc caaagtaaac tacccccaccg ataccacgaa gtgtgaaacg ctctagcatc    21300
cctggaacta gtcattcagc aagaggagga ctccaatgga acttctgttg gatccaaggg    21360
ctaagactgt tcctagcaac tactctgtaa aaggcgttga tgtagacctg gggcttcccc    21420
caggctacag cctaacggag gaagctatgg acaaggccaa gcgtcaagag agtgaatatt    21480
acgactggaa gggctacgaa gcactggtta atccggtggt agagcaccca gagtatcgag    21540
ccaagggtga agcctttgcc ctccgtgtat tctgggaaga gaagctcaaa gagtctcagg    21600
tcgtagaaga ggtaacgtaa tgattgctgg tatcgatggt gacgttctta ggtatgagct    21660
aggccacgtg gctatgtcga aggaacacat cttcgatatc caggtggaga agccatggcc    21720
tgaggaagaa gtccacaagc tcgtcgatga taaagtcgaa caaattatca aaagggtgaa    21780
tgcagatgag tgtgaaatct accttactgg ccaaggaaat tttaggctgg agcttgcgaa    21840
aatcaagcaa tataagggta ctcgaatcgg tcttgaaaag cctcatcact gggaaaccgt    21900
gtcagccaga cttaaggaca agtggggagc aatcactttc cacggtatcg aggctgatga    21960
ctggctcggg attcgaggga ctgaagaggg agataacttt acagcgtgtt ctagagacaa    22020
ggatatccgc caagtcccag gatgctacca ttacagttgg ccctgtggag attcccagcc    22080
ggagttggga ccgtttcaag ttgatggtct tggaagagtc tccgcttctt ggagaatgta    22140
tggcgttaaa aagccgcaga atcatggaa gcttgagggc aacggtacgg cattcctcta    22200
cgggcaactc cttgttggtg actctgtgga taacatacca ggcctcccag ggacgggacc    22260
aaagacagcg gcagatttgc ttggggagct ttctagtgag agagatctct tcgcagcttg    22320
cgcttacgcc taccaacaga agtacggaga taattggaaa gagtaccttc tggagaattt    22380
tcgtctcctc tacctcattc gggaccgctc ttggcttgat attcagcagt ccggtaacga    22440
gtatcactgc tcactgaaga aacattggga gattccctat gacgatgaag aaatattcta    22500
ttgaggaagc acagaaaatc tgtgaaggcc tctttgagat ccttgagggt cttaacttta    22560
ctgactacaa ggtcgctggt ggtttccttc gggatgcaga caacggggtt gcacccaagg    22620
atatcgacct gtatgtccgt aggccctatg tggaggaccc cactgatact cggcgtagtc    22680
gctttggccc acggttgatc ccctgtgatg acgataccct agaggtagag gtcactcggt    22740
tctacaataa gctgggccac aagaaagtcc ggtgtaggac tggggataag cctgatgggt    22800
atcctgcggg gtttgatgtg tgggaatcca ttggtgttga cctacccgtc aaccttgtcg    22860
tgagtactca ctcccatcca gcagagttcg atgtaggact gtgtgagatt gcatgctggc    22920
```

```
ccataagtat ccgtggactg aaatctcaaa tctaccgttc aagggcttat gagtttgata    22980
aagaagagaa gtgcattact cttaaccgag tcctagaccc tcttctggat cattctcaac    23040
ccctaactga caatcaagtt gaaaaggttg tctctcatat ccaacgtatc aaactgaagt    23100
atccggagtt ccgggtgtgc ctgggggatt ggatctggct tctggttcgg gctaattcta    23160
tcctgactga agggacactc tcggttatct ggaagcttca agaaggaggg ctcattggca    23220
aagcagggga gattcttcag acccaaactg aagtcattga ttgggacgaa gtacgacagc    23280
gaaaccgaga agatcgtcca cgagacgatg ccctggatgc agttcaagcc agaccggtg    23340 agctacgtca tacagcacaa gtacaagccc gacttcaagg tatcgacctc acaaccttgt    23400
ggatcgacga agcacctgct ggtcgaggtc aaggggtact tccaggaagc ctcggaggca    23460
tctaagtaca tctgggtgag ggaggctctc cccccagata ctgaacttgt gtttatcttc    23520
gagcgtccta acacagcttg ccattggctt agtaagcgta aagatggcac aaagcaatcc    23580
atggcggaat gggccgaacg taatggcttc cgctggttta ctctagagac tttcaaggag    23640
tccttcccta atgagtaaga agtataatga agacactctc gtcattgcgg acacccaagt    23700
tcgatccgag gtcaacatcg atcacctcgg gaaccttggg gagtggatcg cacgtaaccg    23760
ccccaagcga attgttcata ttggggacca ttgggacatg cccagtctgt caagctacga    23820
ccgtggtacc gctaagatcg aaggccgccg agtcctcgct gacatacaag ctggtaatga    23880
tgcgatgcga gttctgctcg accctcttcg ccgcctacag caacaccaag cgggttgtaa    23940
gaagcgtatc taccgaccag aaatgcactt cttcatcgga aaccacgagg agcgtatcaa    24000
gcggtatgaa aattctaacc ctgctctcca aggttttatt gggtacgatc attttgatct    24060
gtccgattgg attgtccatg atttcctcga cgtgggtgtt atcgaaggtg tcgccttcgc    24120
ccactacttc tacaatccca acagtggtcg gccatacggc gggagtgccg agcatcgcct    24180
caataagatc aagcgcagct tcgtccaagg ccacgaacag ggattcaagt accacatcga    24240
ggcagtaggc aagaagcgaa tccacgggct tgtagtcggt agcttctaca ctcacgatga    24300
gtcctacaaa gggccccagg gtaacgacca ctggcgaggt gtagccctcc tccggaacca    24360
caaggacgga gagtatgacc tcaagctgat gagtgtggag gagttcctgt gagtaagttc    24420
ttgccagacc tgtactacat taagtctgag catgacttcg gtcaacgggg gttggcgttt    24480
aagacgccga tctccgcaga actctggctg gatatgaagt ttgggaaagg tggtgctgag    24540
gatgggctta gacgagggat gtattccatc gaagtcctgg agatcctcta catccccagc    24600
gttcaccttc cggatatctt ggggtaatct atgaaagatc gagtgggacg taagctagag    24660 gtagggaca gtgtagtctt cctggtccac aggaacacct cctcccatct agccattggc    24720
accgtcgatg ggtttacccc caagatgatt cggatcaaat gcccgaccat gagttggact    24780
attgacgctg agtatgttct aagaagcagt gacaaggtgg tgtactatga caaaggctga    24840
actggagaaa gcacttgaag agacgcaaag cgctcttgcg aaggctgagg cgaaggcctt    24900
ttcctttgaa gaactggctg aagaagctaa aagacagatt gaattcctcg aagggatgct    24960
agacctagta gaccttaggg cttctgtatt ctacggagat tggaggggtt atgcagaaag    25020
atcaaaaggg taagggtgga ttcccttgga cctacattgc ggtagcagcc ttgtttgccc    25080
tgctggttta tgtaggatat agctgactga tgttactcct gaccctggga gaaatatcca    25140
gactcctcat cgatgtatta tcttgggcag gttcactgta ggtatccatc gagtaaccaa    25200
aaaaaaggcc ccaagggtat catcccaagg ggccttatct ttagctccgt agagcgttca    25260
```

```
gcagtgtgtt gaacttatca acgagtgcct cgtgagtatc cgtataggaa gccacgggga  25320
tctcaactac cttacccttg acgtaagccg caatggctgc atctaggcca ctcacttcgc  25380
tagccttggg tttccagtta cctggtttag cctcgctagc cttagcacct acctccagaa  25440
gctcaggctt cccctcaata tcctcccatt tcactggctc aaagtctttc gggccaatga  25500
cttgtcgaag ggtcccatct tcattacgta cagcaatagc cttcgattga ataacgaata  25560
cactgttgcc gtcgttgtca gcgatataac ctgccataat ctaactccta attaaactgc  25620
cgatttgaag gtacccacgg taccaccgaa aggatacact cggacagtgc attccccaaa  25680
ttgaccatca gtctccgtct gattacccct agcataccaa gccttgtccg agatacagc   25740 gaacttgatc ttagctgtag acccttggat aaagtggaag tgacaacctg gggttacatc  25800
cggaccaaga gtaacggtaa tatccgtagt cccctgggac atgaagaacc aaccagactg  25860
ctgcttagta agggtaatgt tctgggtgag ttgctgggtg ttgacaacgt taccaccgag  25920
gtgagtagtc accagtcggg gatccaggta gttctgttga agagaaccaa tgttcttcac  25980
aggaccacgc atgtcgtcaa actgctcgat aatgtaatcc ccgatggtac caccgttttg  26040
gtcatccggg ccaatcacgt gcttaatagc cacgtaaaca cccaggtgtt cccgtcgagg  26100
gtctactcgg aattcactac cgaatgcagt accgcaaggt gcctcaatca tggtctcaga  26160
gaacagacca atcacgtggc cagggtcacg gttaccaccc gaggtttctc caggagcacc  26220
cacgagggta ttgaccagga cagaggggat aacggcctct gagggattct ccgggaagga  26280
ggctgtaacg ttctctacta ccagggctgc gttctcctta actgcataat agtcagggag  26340
gaactctgta gcgtaacga  tgttagtatt tacccgaccg gcatccgagg taatctcaat  26400
gagatcacca tcggcattac gtcggaagac ttttggaaca tcaaccacgt aggcacggcc  26460
accaggacca gcggcatcag tttctacata agttgccata ttacttctcc ttaaagatcc  26520
agagcatctt ccatcgcttc cataccggca acgaaggac  gtgctggagt ttgcttatac  26580
aagaacttcc agatttcacc tgcggatggg tcatccccaa acgaagcgat agttttacca  26640
acagccatag caccctcagt tgcagcacca gctactggac ccaagactac ctctgcgggg  26700
gtagtccctc gacggtaacc cgtcagcatg tcgtagatca tagaagcctg gagtggcatc  26760
tgttgcatca ctacgtccat catccgttgt tctggactac gggtatcctc tcggctagac  26820
ccaccgaact tagccatctg acggagttca tcctggatgt aacccagact catcatcaga  26880
ccaagagtga aggctacacc tgcggcaccc ataccagcgt tggtccaaga accagcgaag  26940
tgtgggctca gtcgtctacg gaacatcggt aggatgatgt taccataggc tgctgggtaa  27000
cccttcaaga gggagaacat ctgaacgttt ccgttgctca tccacatagg cttatcagcg  27060
aaggtggggt ctaggactac ctgatccaca aaccgacgca tagccagagt cttgacgttg  27120
ttagccatca ggacttcaga tggagtggct ggggatacca gcttaagagc atcctgctga  27180
ctaccgatgt taactcccat ttcccgaagc tgagcaacct tcagagcacc attggcagaa  27240
ctgaagggga gccctgcggc tagatccatc aggttattct gatagacccg cttggcagtc  27300
tctgttgcaa ataccggtt  aacatggggtt aggatggaca agccgttgat gaggaactga  27360
ccacggataa cctttttggat ggtagagtta aacacctcag cgccaacacg gtcagccatc  27420
agagaggtag cagaggccag ggtatggttc atatcactca taaaccgacc ggtctcagac  27480
tttggaaccc cactgtagat cctgcgggct gcttgcctta ctacctcacc catggttgga  27540 agtcagccc  caagggtagg cataacccca gccttagcga agggtatgct gaactcggtt   27600
agggtcgaga agccggcgag gggaagtctg gagagcacga gggcacccga cgtaacagcc  27660
```

```
gctagcttct taaggttagg atctttgata cgaccgtgca taccattata ggcatccact    27720
aggtcataca tccgatccac ttcttccttg gtaacccgct taccagcccg ttgagcctca    27780
gctacagcag atgcaatctt agcgttagcc ttctccccgt tgataccaaa cctttcggta    27840
aaggcaatcc ggtgggaagc cccttctaag tagtcccgaa tctcttggag acgcttctta    27900
ggagtatcgt tcagggaata cttgttgagg atctcttggg gtacagaacc aaaggcccga    27960
ctctcttcca attgaccata cttaggtact gcatcactct gggcgaaccg tccccgaagg    28020
gtatcaggat ctccctggat acgataccgt ggatctactt cccaagcacc cgtagtctga    28080
ttctgagtaa ctaggcgggt aacctctggg gcagtattac ctcgggtatc atccgaagtc    28140
tctgccagcc agttagctac agcgtcctca gcagcttgtc ggttctggaa gtacggagta    28200
atgtcgttca ggaactctgg agattgaacc ttctcagggg atagaccaaa tggcatatag    28260
ttggggatag taccaacaga catgccacca cggttaacag cctcattcct tacgtcatcc    28320
agcaaagaac gcagacgggt agcctcaggg gtgttgacac cagcggatgt atcagcgata    28380
atcctatcga tctctttgga agacttaccc tcaaagatgc tatcaagttc ggatttccac    28440
ttacctgcct ggagttcctg gtcctcaaag atagtcttac cagaggctcg cttaccactc    28500
atgtcagccc taaagatctc agagaactca cgggctatcg gggaggcctt agcaagtggc    28560
tccaggaggg ccgtagcttc gtttccaagg gcatcccagg ctttcttaat ggtaccccta    28620
ggctcaagct cagaagcctt aggaggggcc gcagggcgt taggatcaac tacggcagac    28680
ccagctgagt cctgattacg tcccagggtg tccaaaccag aggatacagc accaccggca    28740
gtacccatag cggtaccagt gaatgcagca gtcaggaggt tatccatgaa ctgctcaggg    28800
gattgggtct gcccaacggc atcatacgcg attgtgtcct ggagggcctg ctgggtacca    28860
gaggtaacac cttcagccac accagagact gctgcatgct taccagcctg ggttacagcc    28920
tcaatggcgg tctgcctagg tagtcccgat tggaccaaca tctggtaagc gccatcttta    28980
ccgatgtgct tgaggagtgg ggcagcgata acaacagcac ccgcagtgtc tagtaccgag    29040
aggccagcac caccgaggac tgaggtccat gggttgcttt gatcgggtc tagttccttc    29100
atctggttac tcagggcacc tacgttgata cccatgaac tcaggaagga accaatgagc    29160
gctccaccca tacgacctgg gcccccaaag acagagccag ccttagcacc tgcggcacca    29220
ccagcaagta caggggccat cgaagggaga gcctctacga tgttattctt taggaacgaa    29280
ccgatggatg ggatatcttg gatatcagcg aaagaccgaa catcaggggt tccgtactgt    29340
gacgcttcct gagcattctc ctcggccatc tgtgtgccgt agtctttcag gtagtcactg    29400
ccagtcagtt caccaatggt agcaatagta ccacctatgt tagactgcat ggtatcaacc    29460
ccacgaccaa tcgcagagct aatagaatta gggtcagccg gagttactag ggcactcagg    29520
tctgggcag gctcaggggt agcaggggct acttcctggg gtgcctcttc gataacctct    29580
ggctcattca aggaagccaa ttcagcggct acgtcgaggc ccttgacctc agccagttcc    29640
gcatcaatag cggccttcag ttctggagaa agagccataa gtcaccttct agttgctgga    29700
aagagaatag gctcttaaga tgtatcttag gatactaacc ttcttagtaa gtaagtcaaa    29760
aggaagaagg aatcttaaga gcctataggt ctattatatt acattttgga tactttgtca    29820
agtaccttt atcgggttgg ggcaggatag tccaaatcag caccaaacca gttacccgta    29880
ggttgcagct tagcagcctc ccgctggata ataccccactg ggttagcccc cggattagcc    29940
cgaagttcat ttcggacagt ctgggcaata gcctgttggg cagtcttact caacttctta    30000
```

```
ccacccagag cctgagaacc attgacttca ctcaggatac caagggcgtc cttagtagta    30060
acagcttcac ctcgggctgc cttagctgct gcctgtcgag cctgagcgct gattttagca    30120
gtcttcagac gtacagcaga actgagctgg gcattctctt gagacatatc ctggccacga    30180
cgggctgttt cagcctgtag ctgggcccgt tggttagcca tatcctgacc tcgctgggtt    30240
agggcaaggt tggctcggcc ccgagcagcc tcctcagtcc accgatccag aagaccagtg    30300
ttcttacgag aggtttcctc aagggttccc ttcttgacct ccaggtttcc ttccccgaga    30360
cgtacatcag cagcatcctt agccacctta cgctccagat ccttttcctt gatctgacga    30420
tcagcagctg cggcagccat cttctgctgg ttgatcccag cctgtaggtt acgatccaac    30480
tgacgctcgt aggaagcagc gaacatatcc ccagctttac cagtcttgtc tagggccgaa    30540
gccagaagac cagtaccaat gagagcgtaa gatacataac gagacaggtc atcattatcc    30600
atagtcctca tctgggtcaa ctcttcgttc acccggttct taagctcttg gggtttaagc    30660
tctacaccct ctctctgggc atcagcttca actacagcct gggccatttc aggacgactt    30720
acagcaccag tacgaagacc ctcggctgca ccctgttgga tgacctgacg attagcctcc    30780
tcctcatctg ctacagcagc accagccgca gaggccacct ctggggtgat ctcaggctcg    30840
atagagggtt ggttggggt tacccccatag gacaggagtt cagcccccgt agggccccct    30900
gtggcgttct gggctgcacg ttggcctaca ccctgggccc attggtttgc ctcttgagca    30960
acctcaggcc ccatattctc cacagcctga ctagcctgag ctatttcttc agcacgagta    31020
cgctctgcat ccccaagttc tcctgggggtt acagccgctt ggatgccaac agatactgga    31080
ccaccgagga tacctgcgat acgacccagg gctccacgac cagtagcttc agccgcaggg    31140
accacctctt gggcagcccg agaccaacgg tcagggttct ctagggcagc ctgagcagcc    31200
cgtcggacac gatcagggat tcctgagccc tctacagcca gcggcagttt gttccttgcg    31260
attcgcgcca tgtccagttc attctgagca gcccggagga tgctagggcg aattggggac    31320
ccttcataag acatgctggc cataggatta acctccaaat agtttactta ggattccaga    31380 cttggctgc tgtccgaaac cgagttcttc tgcgctagga aggattccca ctcccgctcc    31440
catacctgct gcaacttccg ctgcgcctcg ttcgcttgct cctctagccc cctcgacaga    31500
aaagcttggt actgtttctg aagaaggctc acttcctttc ccgaggagag ccgcgagtgc    31560
tgctccgccc attgcgccaa aagggtttga ttgtccacta gactctcccg attgcattgt    31620
cccaaggtgg gtgggtcggt aggagccttg acgactcaac tgaacccgct cctgcccacc    31680
acctatattc tgtcctatag cgaacagttt ctgagggagg gaagccatta gaagagaagg    31740 cccccctaccc taccacctgc gttcatacca acagaagcac cagctggacc accgaagaga    31800
gcacccaagg aagcaccacc gagagcaccc agggcagacc cgaggccacc accaccgcca    31860
ccacccgaag aagtagtgac attggttccc cccatatcgc cggagataag ctccttatag    31920
gcgaggaggt cgttgaggct gacgttattc tcataggccc acttctgtag agccccgttg    31980
atttcctgct gctcctggtt ctgaagcatg ctaccagcat ctacctgcat ggcattacca    32040
gagccgaggc ccttagcaat agccgacagg ttacccaggg tgttcaacct attctggttg    32100
taagcctgct ggtcttggaa agccaactgg gaggcgttat tctgttgatt ctggagcaac    32160
ctagcggtag caataccttc tgctacaccc gctcgggaac tcccatactg accagcatta    32220
gtggcccctg ctcgcaggtc tggacgtacc gtagtgtcga agtcccattg catctgctcg    32280
ttggctgcac caatgcgctt cgccaagcca gttttgttgg gatcgtaagg accaaggtaa    32340
tcagccagag agctaacacc tgagctaccc aggagagact gaagggcacc cccgagacca    32400
```

```
cccagcccttt cgatgccacc aagctggaga gcattttggt cagccaccgg gtcaaagttc  32460
ggatcgcccc cgtaattggg gtcaaagccc ccgttatgta gccaatcact ggcacccgag  32520
agtagttcat tatagttacc ttgctgatag ggtgtagaga cagaggtggt cttttgcttc  32580
ttactaccac ccttgtaagc ccgagaatct agggcatcct ctacatcgaa ccccatcaga  32640
cgctttacat taaattggag gaagttcatc tggagttacc tcacgataga aggatacgga  32700
gtcttcggta tacccgagtt tctctagggt aggcttccag ccccgacgac cttcacattg  32760
gataaaccga cagttaactc gttgggcgaa ctgtccgagg aagtcgtcta cctccgagta  32820
atctaccggg gtttcattcc caggcatctt accactccag aagaagtgaa ggatgttacc  32880
caggggtgct tgggacactt gaattacacc agcgtagcca ctctcttctt ggtagaagac  32940
ataggcctcg tagttaacca aggagtgaac caagtgttcg aagtcccaaa acttaccgag  33000
gtccgtcctg ttgaaggctc gggccagagc agggactacg gtaggaagca gatcgatatt  33060
ctcacgagta atcaaatgaa tcatggagtc accaccaggg ggaatgtgaa tgtaccccg   33120 aagactgctc cttggggaat tccttggatt agaacacggc cattagctgt gatcttaaac  33180
attgcttggt taaccacccc agtctgaata gtagccctgt tgagaacatc aaagacttga  33240
tccaacggag gtgcgttagg gtcagacgga ggtggataag taatagtgct ctgcgctggg  33300
atgatgctgg aataggccgg gataaacaac tcagcaggag gccaatacgc ctggggaaga  33360
tccaggacag tagctccatt agtgtagtta ccaccagaca tgagcatggt tatccatact  33420
tcatccttag cagtgttcat cctataggca caggtaccca tcggctgatg gttgttctgt  33480
ggggtaaata ggataaaatc ccccggcagg tccttgggtt tagtacctgc gagtctccat  33540
tggttatcca agtcgtaatg atagatgccg gatactggac ctaccactcc gggggcaaaa  33600
tactttacag tccctggctt gagcttctta gggggctcca tagagacccc ccagtagccg  33660
tcagctaggt cattaagagt ctgtccaacc ctaacgaatt cttcattaag gaagggcagc  33720
agttcctcct cttcctgtgg tggaatcgaa gggctgtact tttgactcat cgcatacctg  33780
ccttcggggc catttcaata gtgtatccgt tgaagtacca atcccctcc gaagagaagt   33840 cgaacttcaa ggctatatac cggcccacat gtttagtgtc aatcttatag tcctgaccaa  33900
tccggtatgg gtaagggcct ttccatcgaa taccagaacc ttgtacctga gcgttaccca  33960
cccagatgtt acaagtaccg ttaccagtaa tgtgtggaat gatggcactc actgtcttca  34020
tcattcgatc atccccgaga tagatatcgg atctctcaag ggtactgacg aagttctgtc  34080
cagagaatgt agagttatta ccaaagagga acaacttctt atcctggaaa gacgagaaga  34140
tcatactgga ctttgctggg ttataagagc cttcaccca gaccgaagta tcggtatccc   34200
aggggttggg gtcgtcatcc cagaggttag acaccttagg atcgatgatc ccgtaggctc  34260
cactgagaac gttgggaagg tctcggatac tccaagtgtt ttccttccag ttccagatga  34320
tagccctgtc gcagtgctta cctggctcag acctagtgga agagtagcat acccacatt   34380 cagtattcac gtggtctgca agtacgaatg tccgttgata gttgtcaggg ttaatatccg  34440
agaagaagaa cttacggacc tgggcatcaa taacagactg cttctgcaca ccgttgtgga  34500
catatacatc accgtgacct actacaaagt ggttaccatc gaactctact gcacagttgg  34560
gcccaaggat acctacgtcg ttaaacagct gctggaattg gaagatgaac aatccaccga  34620
tataccgcat ggagtataca gagtcttcct tgtagatgat gaaggagtca cgaagcttaa  34680
caccatctac gatggcacca ttggtatcag ccaaggtgtt ctgaccagca tccttagtag  34740
```

```
gatctgttgg gtcccaagat gcaggaatac ccccagcatc agccgaggta ctccaccaga   34800
ccatctgtgg catttctaca gagttctggg ttacgttcaa ggcaatcata aagttcttga   34860
acgacttcat tcgtttagcg aacgtgttag ccggccagtt aggcatggga ataaacccac   34920
tattctgggg catcaacacg taagggtagt tgcttgggtt gttagcgaag atgacaccgt   34980
tgaatgaacc ggaggaccat ctactggtta cacttgcaga gtgtccacct ggggatacat   35040
ccacaatggt agtaccatcc gccaagtaca tacgctgttc gccacacagg agccaatagg   35100
gaatattatt ccggatgaaa gggaacatat ccaagattgg ggcctgggct gtatcaaaga   35160
taggcgtatg gcccagagcc ttctgagcct tgccgttctt aaaccggacg ttgttcccga   35220
aggaccattt ctccagtggc aggtcagcgg gggcgatatc ggtcacaatc cccgtagggt   35280
tcttgacctc ttgtctctct agggccattg tatacctcag ttcttaatga tgaagaacac   35340
agaacagaac ggtgggatat tacccaacgg aatgttgatc tttactgcat ggttgtgagt   35400
ctgaccttga ccagcagggc cagtctcaag gttggtattg gctgcgttac cagagcctcc   35460
cgtcagagca cccgagtcac ccgcagaacc ggtgagggta gtagcacccc tagttctcca   35520
agtgtgggtg tgtgatggga tttgggctag ggtaagggca gtaccttcag tgaacccatc   35580
ccatacaatg ttagcgctac cgcctctagt ccctacagcc tgggaagaac catcgatacc   35640
ccaagggaat gcaccaatca ggttagggac gggaatcccg ttagaggtag tacctacccc   35700
attgcacaac ttccaacctg ctgggatctg agctagtgac ccagcccaca tgataaccat   35760
cccaggttta acatactggg ttgtatcagc gactgcgttt agctgggctg ccgttacagt   35820
gacagcctga gaaatattgg ggaaggtgtt cttaatagca ctcttaatga dacgcaggtg   35880
gtcatcccca aaggatttca gatcagagcc ggtagggttc gtaggcacca actggttaat   35940
gtaagttgcg acctcaagac ccattcttgg cctcctttat ctcttctttc atttcttttc   36000
gggtgacata ccgctcccca aagattgcca tagaaatctg gagatcgctc accgcttggg   36060
tgagcttctc cgtggcctgg atgtttcttt caagcagagc ctgattaaca ttctgaccga   36120
caaccgagga acctaccgtc actaccgagg atacgaccag ggcactgacg atgctgccca   36180
ggttatcagt tagaagttgc atcctccgtc ttctccttaa ggttgtcttc caggactttt   36240
acgaactcgt cgtcaaccct tagagttagtc ttctccgcca gagccttagc accagtcacg   36300
atggacttag cgattacctt ggttgggaag agggtagcca gaaggttgat tgcgaggggtt   36360 tttagaaaga taggcatctg aatctcctta acgttcaatg tctttgatcg ccagtcgagt   36420
gctagcgaag tcagcggcat tctcctcgtt ctggagttcc ataacagccc gttcgagttt   36480
ctgaccccag aactgggacc gagcttcatc catggtgtac agataaatct gctcaaggac   36540
accatagaga taaatctgcg gatacttcgt cagagcccaa gtcgttgggt tagcgaggct   36600
tagctctggg agtacagtcc agtagttcac aatgaacggg gcaccgtcag gaacaacggg   36660
gaatactcgc cagaagttac ccaaccgagt gtagtaggtt acaccctgag gttggtagtt   36720
gtagttaaca taatgggtga aggtatcctg ggtgatgtac tgaagagtac gtccaccgat   36780
aagggagtca cccgtgatag atcgtagagc aacaaagtgc tcaggtatct caatgccacc   36840
accgaaggcc attagggttt cgaagtgttc gttctccctc acccgtagca atcggttaag   36900
acggtcagtg gtattaccaa tgaacaacat cagaagttct gggtaagat cctgacggtc   36960 agaccactgg atagcggcaa tagcgagatc agttacgttg ttgatcgtag ccattcatta   37020
cacccgtgcc tcagaggtcc gcatccgata gttatctcgg tcattaagcc aacgggtaaa   37080
tcgtgcggca tggtctgggt cacaaccgat caggttaaga tcgatgggac caccttcaga   37140
```

```
catgggcga ttccgtaggg cctctacaac aaccagggg atacttgcta ccttgcgcat    37200
attatccttg cggttgctat tgacacccga gtggcgctct tcggcgttag cggacaggat    37260
tgactcaaca tcttgagtat cctttcggat aaagagccca aggtcttcgt caattgcata    37320
agtcgattgg atactcatga tgtacctcct aaggggaaac aaagggcccc gaagggcccc    37380
gttgggttag acctgggcta caacgtcgcg gatcagagca ccggacttct cgttgtttac    37440
acgcagggtg tactcaacca gcagttggcg cttctcgctg tcaccggtct tagccagttc    37500
atgctggaag aacggacgca ggtagcagag ggcgtgcatc ttcggatcaa agatgaacat    37560
ggtgttttcg tggaaccagc ggttggcacg aatggtgtac ttaccgaagt cactctcgta    37620
gacgtccacg gtctgcgcaa tgcggttgtc cgaggcatcc agggtgatct cagttgcacg    37680
acccttcatg ttcttgctga tggccttctt gatcgagctc gaagtctgga tcgagttagc    37740
ctgaccaccg ttgcgccaga tggcctcaga ggcattcagg agcatgtctt cggtcagaag    37800
acggaggtca ccagcggtac cagtgtcgga accatcacca gttggcaggg taccgttagc    37860
acctaccgaa ccgttggtct tgtagtaggc aaagatgttt gccatctgac ccggagtagt    37920
ggtgttacgc tggatcttag cctgaggggc accgaccatg gcgtattcca tgtccagctt    37980
cagttccttc gacttcttag ccagctgata cgccagttcg ttcttacgac cagccttctt    38040
gaccttatct gcggtaccgg tgacttgcag ggtctcgtcc gagatttggc agtagttgtt    38100
caacatggtg gtgaagctac cagccttgat ggttgcatcc tcaccttcca ctcgggtgtt    38160 cttaccggc tggcggagtt catcagtctg ccactcgtgg gtgatagcgg tagctacgcc    38220
cttgccgata gcagtcatga acggggtgtc ataggggtgcg atgttgtaga tgatatcgat    38280
aaggtcttcg cgcttaccgt tgatctctac agtggagacg gcattagttg gagttgccat    38340
ataatgtact tccttctatt agaaaatgtc gagagaggag aagagagcag cagcggcttc    38400
aaccgactgg tctttcctca gattagcgcg ggcagcttta acccgcttag aaccctctga    38460
ggcttccgcc ctacgagcag caggcttaac tgcggcaggt agttcagtct cctccttctt    38520
ctctagggca gccttgcgac ggacctgaga ttcagcccac ttacgtgctg catcgagtac    38580
agccagttgg cgggcatcag atatccctcg gatctcatcc tcggagtatc caatcgattt    38640
gccgtaggac acaatcttgt caccccaaga ctcatccgtg gtcatttccg ggataagttt    38700
cttggctagc tctgtctgac gcttaacgta ggcagagtgg acaatctcgg ctcgcttctc    38760
ttgcatagcc ttaatgtcgt tacgacgttt gataagagcc tgggctcggt ctcgggcttc    38820
cagggcttcc agtcgaaggg tttgatactt ctctgggtcc tgggccttaa gctgctccca    38880
gtttacattg tcatactgat tagcaccagc aatagcggta acagcatact gctcaagctc    38940
ggccagtaga ttagagcgtt cagcatcaag ctcttcgaat ttagctgcat actgatcctc    39000
tagttcagct tgtcgagtta caaactcttc attgcgaagg tagccactct taagctcttc    39060
gaagttaacc tcgtagactt catcccaat cgggatctca aagagtttat cctcaggatc    39120
ttcctcggac tcaacctcgg gatcttcctc agaaccctct tcttcctcct cggactcaac    39180
ctcttcggtg tcctctggag taccttcgtc tactacctct tcctcctctt cttcccctac    39240
gactttacca tccacggttt catcaccggg ggccaggagg tcatcaccta gcaaatctcc    39300
gaaggcttcc gctgcctcga attcatccat gccttgattc tcaaggtcca ttacttatac    39360
tcctttagag tgatcgaatc caggatagcc tgaatacgaa gttgtacgcg gttgagggca    39420
tgtagttcgt ggtagatggc ctccctggac tctgaatcct taggtgccgt ggacttccac    39480
```

```
tctccctcga tctcttcttg gacaatacgg aaaagctcag gaagaacgtt ctcacgtacc    39540
atctgttgtg ccgcatcagt cagcactaga ctatagccaa aacgttctcc caagattaat    39600
tcctcactgc cttagatggc ttcttagtct caggtacctt accgtctccg atataagcag    39660
cccgagcctg agtagcctca agatgatact ccgcttcgtt acgagcccgt tcccaagtga    39720
aacgatcacg ctcaagttgt agttccgctt ccttaagggc catttctctc tgctgaagga    39780
cagcctcttg cttcttcagt tcgatctcag ccagtcggat ctgagcctct acctgcttca    39840
tctgggcctc cgcttgctta gccaaggcgt ccgattgggc acgttgggca tcagcttggg    39900
ctttgatatc ttcaggctta ggttgtgctt ccttctgctc tctgatggcc ttagcccgtt    39960
gagcttcagg agaatccggg ttagtccaga agcgatccgg gtctttgtac ccagcgttct    40020
ctgtgacttc cttaaggatg ttgtaaagat tctgctcaga gacaaggacc ccgagacctc    40080
caccccgac tacagcctgg gccatttccc agatacgcat caggtggagc atctgctggt    40140
ctttgttcat gttgccaata ccaacggtaa ccgtcaggtc ggatctctct cgccagttgg    40200
cagggttaat agcaacccac ttgcctcgta gctggaagac ctcttcctga ttctggtact    40260
tgatggcatg gtcatgcaga agttggaaca aacgcttaac accagtctct gcaaacatcc    40320
gggcaatcag gtcaatctgt tgctcagcag cagtcatcaa ctggtttaca ctcatagccg    40380
cttggttaga gtgcagggtg ttttggtcta gacctcgggt acggtcagtg atacctgtcc    40440
gcttacctct gtctgcctct agtcgatcca gcatcccata gacttcccca gacaactgag    40500
gggtctccag aggcatgata gagttcatgg ccttaacccg aacgataccc gctgcctcgt    40560
tggtcagcaa gtcttcgagg ttaacctggc catccaggac tacagatcgc ccttggttgg    40620
tccggtagat attgtccatg atgttgcgca tgagcaccga gcggatctct tgaatgtctc    40680
ggatcttatc gtagacactc atcccgtgga acttatgggc aattcgatag gcattcaggt    40740
cagcgaaggg acggcaatcc caaggctcgt tgctgatgat gtagtcgccc acgtacagga    40800
tacggcgcaa ctcagagata ccatccccat ctacgtccag aagggtgtag cactcggagg    40860
cccatacctc acggttggct tcagcatcat ccccagagtt gtactggagt tggccagtca    40920
tatcgaagtt atcacgtacc aacctttctg gctgactatc agagaattca tactcatcgt    40980
atggaagctc atctagtaca tcctcgggaa cacccaagag ccgcaggtca cttacggtat    41040
acttctcacg gtgacagagg aagcgtgcat cgtcaatgca ggtagccaac cgatcaacca    41100
ggaagttctc tggcttaata caggtgacct taatctctcg cttcttcttg tccttgcgaa    41160
ttttaatact gtaggttcca tcctcgtcca cactctgtgc tagaatctcg gtgtctggat    41220
cagccaggat atccgctacc atttcctcag agagaccaga gaatcgttcg aaggtagggt    41280
tcaggacctc ttctacatag acctttacaa caccggtctt catcatcaga gtgtcttgga    41340
accagtcgaa cattaccttg aaccctcgt tcttacgcat gaagaggtag ttcacatact    41400
cagtctcttg ctctgcctgt tcaacatctt cggcagtctg aggttcatac ttaactactt    41460
gaccgcctga cgtgaatacc ttcataagag aaggcataat ccagtctaca gtctcttgaa    41520
cgtccctaga tacaatcgcg gacttcccag ggcgctcgtt accgaagggc tctccgaagt    41580
aatacttcag ggcctcagaa cgctgcttgg aaagttccga agagttgaaa tcaagggcgt    41640
cgttaacaag ttggtctaga tgacgaagta cctgttcatc atccataggc ttaatcttgc    41700
gacgacgctt agccattaga caatactccc aaaccaatca ggggtcaact ttgcagtatc    41760
actcctgtag tatccactgt ttcgtacagc accaggacgt gcatgccggg aagccatcaa    41820
cagggcatac cgggtagcgg agatcatatc gtcgtttctg tcgataatct ttccgtcctt    41880
```

```
tcggtggtac attttcattt cttttaggaa gttcgtacac gtattaaaca ccttcagatc    41940
accattctcc atacgggtca acatccagtt aacaccgaat tctacagagt tacctccgtg    42000
tttaccatca ggacccggtg ggttgctgaa gggctcatac actacattga ggttgtggtc    42060
atctttaaga aggtctacga atctacgacc agaggttgct ccatcatgct taaaggcatc    42120
atggggaaca actaccggga tctggtgacc acccttcagg tagatagcat cagcgtgcat    42180
cccaagggtc tcaccactct cactcctctc atcatagagg taatacttgt ctttctcggg    42240
atcccaagca acacaggcga tagcgttagg gtggtcaaac ccgaggtcga taccgatgat    42300
cctatggaag tgatcgggga tctggaaagg ctcacataca aacttctctt ccagaatggg    42360
gaagactaca ccagatccga gcataggaac accctcggcc ctcatcctgc gttctgctgg    42420 agtatacc gagagtagct gctctttaac ttctggactg aggtgtgggg cgtcttccca    42480
gcttgcatgg acaaggaact gaccaggttt aagatcctgg aggaagtcct tgacgatctc    42540
cgtcagacca tgctctgggg taaacgtcag atatacaata ccccagtag tagccgttcg    42600 ggttacacac tgggtataaa tatccttggg gcattcctca tcgagccaga tgacgtcgat    42660
ggcagtaccc atgaatttgt cctgggacat ttcgtaggac ttgaagataa gggacgagag    42720
gcccccggag gcatgcttaa caactactgc ttgcacacat ccgggtttac cttccctacg    42780
aatcgtctct acgatatctt ccttggggat catccccgtt ccaaaagcct cagggttctt    42840
ccagtcacct agtagttcgg actgaagaat atcccgagtg gtatccgtgg agatccccgc    42900
cgcccagcag ttcactggac gatcatactt tctaccagtc caccactcag ggtagcgacc    42960
ggtgaggtgg caggccatga taaaggcccc ggtgtaggtt ttaccacagc ggttaccagt    43020
catagccagc aactgggcgc agttcgagga agctgcgata aacttctctt gccacccata    43080
aggagtgtac tggttcatgc ggaaatactt ctgccgctcc gccaactccc tgactagatt    43140
ccgtagccgc tcttgggtat ccattagacc accttgtcac ctactgttga tgcacgccac    43200
agggcccgtt ggaggtccct tacgcgcact ggagtttgtt tagcccagag gctatcttct    43260
gcctcccatg cagcctcgtc aaaccttccg gatttcagaa gattccacgt cttggggaac    43320
ttcttcgtcc acgctgtacc cagctggaaa ttgacgctaa cgagggcatc gaatagctct    43380
ggagtgcaaa aaggcagctg agatacttgc ccttgggctg catcataggc tgccttacta    43440
tctttctcta gccaagtctc tgctcgtgct agggtaatcg gtccgtcttc cccagggagt    43500
tgcaagtggc cataaccacc agttactttc ccgagggagt cttgtacca ctttagtacc    43560 aaccttctc ttcgcttgat taaatcaagg tacttaagcg gttgggaaag aaatgacttt    43620
agccaactct ggctcttcgt cgagaattcg tcgaacttca ctgattagat cctctgcgga    43680
catatcttcc acattcttag tagtaagctc cagtttctgc ttagctccga agcctccacg    43740
atccaggata tcctgggccg ccttgaggcg aatcccacct ttctcttctg ggttgctagc    43800
gatctctaca accacacgaa gcgccatggg gacgtgactc ccgatgcgct cagagataaa    43860
ggcgttgatg tattcggcat gctttcgatg gtatgcagct acgttgcgtt gcgcatgatt    43920
aggagagaac ccagcggcta tatgcttg ggttttgttc ataccatctg ccagagcctc    43980
acaatagagg tctagctttt ctttagcaga aagaggagca gccccaatcg agacaacctt    44040
ttcgtctgac atacactgct ccgatctctc taaatggtca ccccggtagg actcgaacct    44100
acgacctcct gtgtccaaga caggcactct aaccaactga gctacgagga gttaatggcg    44160
acccatgtcg gattcgaacc gacggcttct ccctagacag gggagcactc taaccgctga    44220
```

```
gttaatgggc cataatggtt gggacggtag ggctcgaacc tacgacctga gagttatcgg    44280
ctccctgctc taccaactga gctacatccc aattaattct aaagcaccct taaggttaat    44340
ttctcaacct tataatgcta ttatatcaca cttttctat tttgtcaagc ccctttcat      44400
```
(Note: positions with uncertain digits — verifying below)
```
gttaatgggc cataatggtt gggacggtag ggctcgaacc tacgacctga gagttatcgg    44280
ctccctgctc taccaactga gctacatccc aattaattct aaagcaccct taaggttaat    44340
ttctcaacct tataatgcta ttatatcaca ctttttctat tttgtcaagc ccctttcat     44400
ctttttttta ttttagtcg caagaccgg atttgttagg ggttttgctg gaatgggaaa      44460
ggggttctta agactatctt aagataacct taaggtaact aaccttctta gtaagtaagt    44520
caaaaggaag aaggaatctt aagagcctat aggtctatta tactacattt tcgataccct    44580
gtcaagtact ttttgatatt tctttgataa tcacatgatt tacccgacga acggtatgat    44640
agggttctat agatataccc taagactacc cttcgtaggt tgctggtaag gggtaagtgg    44700
catagggctc ccttgatcca ggttctatag gtataaccta gggctacctc tgttctctat    44760
gccctggtct attgccccct tatccagtaa tataccaaca gttatcgaag ggtgcctttg    44820
atccagggcc tataaccggg ggatacccca aaagtctatt ttatcctccg gtgtatctgg    44880
ggaatatccc cccaggagtc ccccagataa agtgggggtg gcctatcccc aggggtatag    44940
cccctagccc ctccctagga taccatggga ttagtccggg ggtcaacccc ttgagatacc    45000
gttcatcggg                                                          45010

<210> SEQ ID NO 6
<211> LENGTH: 66505
<212> TYPE: DNA
<213> ORGANISM: Bacteriophage P1902

<400> SEQUENCE: 6
tcgccagggc atcgttgaat ttctggatgt tggactcgcc ctggaccctg gactggagtt      60
ccgcagtcgt cagctcagtg acttttccca tggccgggcc gatcttcgcc agggtgctta     120
gatagtctcg cgagacgcca agggcatcgg cgtaggcgga aatttcatcc ggcttcaact     180
tggccatttt cgtggccaga tcggtgatga tgtcgttgag cggccgtatg cccttttgga    240
agctcccgac atcaacgccg gccatacgca gaattcgcgc ttccgggccg actcgtccga    300
tatcgcgata agcgcgccgg aaagtgtccg ccagattttt ggtcatttcc gcgccctgct    360
cgcggctgat ggttccaccg gactggcgaa cgaatttcct ctggtactct tccaagcgtg    420
ccggggcgat gccgatgtcc atcgcctgga tgcgctgttg attgtactgg tccctggtgt    480
tcatgaacgc cttgacgccg gccgcgacca gggccacgcc agtggcgcct attgccagtt    540
gcgcgttcat tccgcgaatt gcgctcgtca cagaatcaat ctgcggaacg actcggccga    600
gttcggtggc cgcgccgtct gcgaagtggc gcaaatcctg aaggccactc gtcgatgcgc    660
tgttcacgcg cctgatctgg ttctggaggc gctccagatt gcgctcggct ctggcagtat    720
cggcctcata ccgaagtatg aattcatcca aatcactaga catgaatcac tccggcttgt    780
tggcgagtcc ttcggcgatc ttcattgctg gaccaatgag cttggacgcc tcggccagaa    840
atgcgatggc catctgcgat ccgacttgtt cccaatagtc cggccggtcg gcgtgcgtgg    900
ccgggtcgat gccattgtgc ttgagaacag agttgaaaac cagttccacg ttcttccagt    960
ggccgaggtg gttgttgatg actgccgcgg tggtcagcgg aatgccggcg tcatcgtcgc   1020
caagcagcac tttcgcatag cccaggattt ccatggtgaa agagcggcgg aagtcggaat   1080
cttggctgac agcgaattcg acgaaacggc gctggaggtc ccagccatcc aatgccgacc   1140
acgcctcgat ttgtacgcga gtttgacggc catcggaag attgatttca agcatgatac   1200
atcctcagaa gtagctggtc acgcgattat atagcgattt tgcggccgaa gatatcgaat   1260
cgccgatggc gcccaaatcc agcaaattag catcagaaag agattgaatc tgtacccat    1320
```

```
aagtcggact atcttgaggg aacgcaggat cgaattcatt caatactgga ggctcaacct   1380
gctcgaattc catattgatc tcagccgcgt tcaacatgtc tggagactga tctacatcga   1440
gcgtcatgat ggccagttta tcggccaata tcgacttaga agtgatagcg aaagtcgagg   1500
tgttatcatt gaaagcgttc atgatacttt caacggtgga caggtccgga cagatagcat   1560
tgatgcggag tcgcaccggt tggatgatct ttccattctt cacatcaatg tccagagctt   1620
cggtgtacac ttgagcttcc gtctggtctt tcgtcgccag aggtttcgac actacggaag   1680
ccggcgagta aatttccact ttcttgactt gaagactctt ccagacagga agtttggtaa   1740
catcatcgcg tatggtgaga gtaggcgtgt tgagaataga cttgaggaaa gagttcaatt   1800
ggcacctcag aacaagtctg cggcgttctg gacgccgttc actgcgtagt cgaacagatc   1860
gccggccgag ccaaccacgt cttcagctag ggccagccct cggtcgatca tagaagagtc   1920
ccctgcattt ctgaacatta taggcttggg attctggacg agaacttggg agaatgtcag   1980
ccgcgcagga gtcgccgata tcagatccgg agtctgattg agcgcttcgc tggtacacat   2040
catccgttcg aataccatgc cgcgagtgat gactttgtac agcgtgtcgc gatccaggag   2100
caattgatty atctgatcga cgacatcaat tgaagggcaa atacttcga tgatgatttc   2160
cataggdtgg atcgttctgg aatccatctt ggtcgtacca tcttccagca tgtggcgttg   2220
ccctacagaa gaaaccgggt tgttgacccg gcttatcctc aaatccgcag caactagctg   2280
gtttgtgttt tggtccacaa tcgaaaaaga tcgcgaactt aggaggctgg tgaaaatccc   2340
taacatcaga ccacctccag taccgattgg ataacgttag aaatggcttg acgcgcagtc   2400
tgggcgccaa gatagctacc gaaaacaaag gtgtacgtgt tgcctttgcg ccgtccggtg   2460
ttctgtatgg tgtcgatggc cggacccttg aggatggttc cattggacag aacggtgcgg   2520
ccgccatcag gaagagtggc cacgagagtc gtcatgtccg ggatgattcc cggaagaaat   2580
ctgaatgatc ccttttgga attgagaagg atgcgaaggt taatatcatc ctcgctccct   2640
gcgatgacgg atacagatac ttccagagga gcagccttgt caaaggcgaa taggccgccg   2700
tcataaagca tctcatatcc gaacggctcc agctctttgg aggatatcgg actctcatca   2760
tcagcgaact tcgacaagga aaacccatc gggaacgatg aggcggaaac tattacaatt   2820
cctgtgccga agccgctgac gttgatcatg tcgagtcctt acttgctggt ggttttgcga   2880
gaggtggcct tggcgggagc cggggcttcc tcttcagcgg ccggcgaggc tgtttcctcg   2940
gcttttcta ctggggcggt ggtcgggct tcctcggcgc ctttctcgtc gccttggccc   3000
gctgcaggag cttcctgggc gccttccggg gccgattcgg ccgcaggagc gtcggtcgat   3060
gccggagccg ggatggttcc gccgttgtcg acattggaat cgacgtttac cggggaacg   3120
ggaagaccgg ccggcgagga gtcgcccttg tcggtgttct tttcgcggtc caggccttcc   3180
agatcttcga cagacgggtt aaacgagggc agcgggtcca ggggcggcgg attttgccg   3240
tccaggaaca gttgggtgcc gttggcgtat tggatgcgga tggtactcat ttcaaactcc   3300
tgtggtaaca ggcccgtgga tggtgatgac tttcgcatcg acgccgaaga cttccccggt   3360
tatgtcgatg tcaagctgct cgatgccggt cacatccggt gaggataaaa ttgcatccgc   3420
gatggatttg cgagcgtcat catagctttt ctgcggcgag aagatgtatt cgaaatacccс   3480
cacaccggag ttcacatcga aaatgttttc gccggtgcgc atgagcatcg ccgcccgaac   3540
gtcctgggcg cacgcttcga catccctgag gataaccatg tttccattgt cgtccaaaag   3600
gatatcgttg ttcgtcccgg ttctgatcgt tgatgtgctc attctttcct cgtggcaagc   3660
```

-continued

```
gcctgatact cggcgaattc ggcgccgtcc agatagaaca ggttaatgcc gtcgccgaac    3720
aatgtccaat cggcgtcgcg gtcgaagacg aaattgccat agtcaggtcg gtactgatgg    3780
ctgtactgga gaagaggaat cccgccgaag cagcggaccc catggcaaac gatcacgccg    3840
tcgcggctga tatcggcatt catcatgtcc atgttctggt acaggcgaat cttccaatag    3900
ctgctaccgg cgttaaatga gatcgcttga ttggggactg ctgtcagcgg aattttcttc    3960
atcagctagt accggctttg atcacttttt caaatcggaa ccgatacggc ttggtcttca    4020
gacggccgac gcttgccacc gcgttgatca gaacgccgtc gattggggtg ccgttggtgc    4080
aggtgatttt gctgccgtcc ggcatcgcca cgaccaggcc gacgacatca cgagcgcccg    4140
acttgtcctt tccggtgcgg ttggcatcca gcaggactgc caggttgcgc tcgccctcgg    4200
tattcggaat gacgttgacg actacttcca ggatgttcgc ccggttccaa actaccatgt    4260
caccgttgag accgacgccg gtatcggcag cggtgaacgg cgggctgtcg atgggatcgg    4320
catcgtcggc gaactcggtg acggtgaatc cgttcgggaa agttctgctt gccgtgaact    4380
ggcagatcga gccgaacgca gaaatgttga tcattgttta ttcctcactc catttatgga    4440
aggtcgcggc ggatcgagtc cgccgcaaac cattagatca tcacatccga cccttcgacg    4500
aagcggatgg catcgccctt cgaatagatc agcgtgtagt tggccttcca ctcggtcaag    4560
ccagtgttgc tgttggtata gctggagaag gtgatgttga tccagtaacc cagggtttgg    4620
acttgacgcc aggcgcggcg atcaccggtg acttgggtga tgtactgctg ctggacggcg    4680
ctgatttcct tgccgtaggt gaacgtgccg ttggcggtcg ccttgtccag aaccggctgc    4740
agcaccgcca gggtcatcgc ctcgccagtg ctgctcgccg gaaccgcatt gacgttcagg    4800
aacaagtcca ggagcgcttg agcgatagcc gacttcagcc agatttcgtt ggcatagacg    4860
ttcatgtcca cagcatcggt cggaccgccg cacagaatgc ctcgctggta gaacgcgagt    4920
tgctggccat tggcctgggt gacgccgatg tagttgcccc ggctcttgtc gacggtgttc    4980
gcaacggtat cgtcggaaac ggtgatgttg cggccaggga attggtagta catgtagttt    5040
tgcgaagcgc ccggctcatc gtagttggtg gcggccagaa tctcgctggg gcactgctcc    5100
acgaagtcgt tggcagcagt cgccgacagc acgttcaggg cggtcccggc gttgccattc    5160
accaaggtga aaagagtgcc gaggttcgcc agggaagtag cgaccgtgta gatgaactgg    5220
ttgttctgag ccgcgttcca ggccgacacg gccttgatct ggtcattgtc gagcggcgca    5280
ccggcgaaca ggaacgaacc gaagttgttg ctgacattgg tgctcttggc aacggccgcg    5340
tcggaagat cggcagcctg gccggcgacg ttgacgacgt tggaggtgga ccagccgagg    5400
gcagtggaca tgtcctgggg gtcggcagat ttcgccacgg ccagaacgcc ggtgccaatg    5460
gtggcgccga ccaaggtgaa ctggttggtg ttctgattcc aggtaacggt agcctgggcc    5520
agctgcgggt cagcgttctt gcggatttcg gtctggatga tcgacgccac gttgtccata    5580
gaagtcgcgg cggacgtatc gatggcggtg atgttctgtt cggccgcgcc gaccatgatg    5640
gtcagaaccc ctgctgagaa gccggcgaaa tcggcgatgc tcttcggcag attgtcacca    5700
actaccatcg gcgcgatggc ggtatttacc cagcgagcga agctgatgct ggacggcgaa    5760
ttcacgcttt tgctgatgaa cttgaagtat gccagcgc gctggtactc ttccgactgc    5820
gcgccgaagt aagacatgac tgcgttggcg ttgtcgaact cgatgacgat tccgggcggg    5880
atgacgttgt tggtcgtcat tacgcgcaga atcagctttc ggcctgcgac cggagcgcct    5940
gcgcctacgc ccgaaatgat ccggatataa cggctctgac tgatcactgg atgatctcct    6000
ggttatgtta ctctgctgct aatcgattga agcatgtgcg ccgtatcgac cagcggtctg    6060
```

```
ttgaatccct ttctcctgac cgtagatgct gagttagcca cccatggccc ggtccttatg   6120
cttctggcta tgtatccttc caacgccagg ccgatctggg caagagcttg atctggagtg   6180
atctgtcctc tggccagcct catggctatc cggttctgga ttgcggcgcg atctgcggaa   6240
aacaagttcc aagcatatcg cataaacggt ctagccggga tggtaattct gtgaggctta   6300
gttacctcgg tttctcccgg aaagtcgttt ctgacgaacc gaacgccaac aaaccggccc   6360
cgaacaatgg cgtccctaat atacctggtc ccgcccggat ggtcgatagt tccgccgtac   6420
tcattgagac gtgcgattct cgcgacttgt attccgaccg acccacctgc cttgtcagga   6480
tatcgagccg tggaatacca tccagctgaa acagacctgc cgcgcatggc tcttaacatc   6540
tggaggtgcg cggcgattag ctctgaatcg cgcctcagac tcatatgcct atcaataccc   6600
catcggccga atatgctgcg ttttcgtaca ggcgaatata ttggttgtaa gtgacaacca   6660
tgtcaaaact gggtggaat tcgaactggt gattgtcgtt ctcgaatgcc tcgttggaaa   6720
tttgagacac gcgaagaatg aggaagtcca gttcctttac gcgctcaatt gtggatcgag   6780
cttggaaata agctctcaca tagttggcga tatcagaagc cgtaaccacg tgagtgattt   6840
caggattctg ccaatgaagg gaactgatct ggaaagtcgt ctctacatgc tgtcgagtta   6900
tttccacata tttgcgggcc gtgttgtcca ggtaccaatc ggtggcaggc cagccgcgag   6960
gaatgtcaaa cagcttctgg aaaaagatgg tcggcctggt tgacgttccc tgttgggtcg   7020
gctgagcttt ctggacgact tcaaaatccg gaactgcaa agcctcttta gcagatgcca   7080
tcgccgcatt cagctcgaca accattttcg ctatcagttc gccgtcaaac atacaccacc   7140
tagaaagtcg gtttccgtc atcggtgaac ttggccgcac cgatatccac ggccaggcaa   7200
actccccagc cgtcctgata aaccaggag ccttgagact ccagctgaaa aactcttccg   7260
gtccagagga actggtcacc ggcaacatcg cgatccaagt caaccatctc aaagttggcg   7320
aagatcataa cataattccg ttggaactct agattaaact ggacatactg atcgcgtcgg   7380
actcgctgga cagatgctgc caggtcgaaa ggctccccga acatggaaac gtactgggct   7440
tgatcattct tcactcgctg ctcaaacttg cgatatctca caatttgagt gccgatgacc   7500
ccgaaggcca tgcgcaggag attcgcccca gggatcacca gaacgtccct ccaaccttcc   7560
ggaatcctcg acgctctgga aggccgccga tgtagaatcc acccacagac ttgacgctga   7620
ggagcgccca cagctcttgg ccgtaaggcg tcccggacag ccaccactgc caaccattct   7680
tggccggggg cgcgagcttg gccacgctaa cttcgccgac agtggcgctg gtgatgaaac   7740
cgccttgggt cccacctgct gttacgccac ctccagccgc gccctgaact tgcatcgtgg   7800
acagcgacag gaggtgggcg gtcagaagat acagacaggc ttccagggct ttaccattga   7860
gaatccggta tggcgaatcg cgatcagaaa tgaattcgca cgcaatgtcg aagtacatct   7920
gcaggcgcac gtccggataa gcggctggat cagcaaactc cggaaacagc gtgcgaaact   7980
tatgttcgtc gaaaatcacc ataccgaaac cctcggttaa atccggaact cttgttcctg   8040
ggaagcgctg gctgtggtca ccttgatttt ctgctgcagg cgagtagcat ccagaggctg   8100
gaatccatcg cgctccatgg tgcgagtctc tttggaaatc cgctggtggt cactggtgat   8160
gtcggtcttc acgactcgca gataaccctt ctccatgtga cgcatgaaaa tcttattggc   8220
ctgaagcagc tcgaaatccg aatcgctcac ggcagtacaa tcgccctgtg gggtccagat   8280
cggacgtccg gcctcgtcgg aaatcatgtc gccgaagccg aagtttcgg atgcgatgcc   8340 tgcgcggccg cgaatcagaa tctttcgctg gaggcgagga ttggacggat cagaggtgtc   8400
```

```
atacgcattg taagacaccg attgagtcat ggaggaaacg atataaacag tcattggcgt    8460
agtcctagta attatgccct aaccggcccc tacaaccgag ttagagtcag agtgaacaaa    8520
ggccggaagc ccggcctttg gtgaataggc atctgttaga tgccgaggta gcgcaccaca    8580
gcccacggac gcttgcacag cgcaccggcg gtgccgttgg agaagtcttc cacgtacgac    8640
ttcgcccgct tttcgacacc cagggtgatg aacttgctct gtaccagctg gctgaacacg    8700
ctgccgccat cggtgctgcc atcgacggcc gcgttcacgt cttcgacgaa gagcaccaga    8760
gcatcttccg gctcttggtt tttcatctgg acgccggaca attccggagc cgacacgatc    8820
cgcattttcg gataggtctg ttcgatccag tccgaaaccg aaatgccgta gggcgtggtg    8880
accgacaggt agtccacctt gctggtagcc agggccaggg tgatcttttc cgccttcgga    8940
tcgatctgat cttggctctg aatacgcagc tggcgaacgg cctcgcggat gtcgccgatg    9000
atgcctgccc agtcggcagt ggaccagccc tggctcggcg gggtctggaa tgccggcagg    9060
ttgggatcgt tcaggaaacc ataggtgcga ttgcccaggc cgctctgcca gccgtagaag    9120
ccgatggcgt tgcggaagat ttccagaccg atggccgcct gttggcgctt ggtttcggcg    9180
ctgttcagac ggatggccga ggcgcgaccc tcttccaggg tgcccaccat catgcccagc    9240
tcgccacgaa cgatggtgcg acgttcgaag ttggggttcc agctggtcag cgggatgttg    9300
gtgtggtcgc cgtattccac cgcagtgccg gccggctcca cgatgccctg gacgatttct    9360
tgatcttccc aggagccaac ggtatcgatg ccgatgattt cgtcgatctt ccgtgcagcg    9420
gtcatgacct tcacgaagcc cggcaaccag gtctgcagga actggatggg agtcgggatg    9480
gacggcgtgg tcaccggggc ggtgaagttg ctgtccatgg ccgagccgga gcggaacgcg    9540
ccggccttcg ccaaggcctt gatctggtcc tggacgacgg cgtgatcgaa taccaggccg    9600
atgcggcgca gagacgccac ggcgtcattg gtgatgtttt tcaggtcgaa aggtttcgca    9660
ttgcggcctg cgaggcgcga atgggtcttg ctgatctggc tcatgacgcc tccttactgc    9720
gtgagctgga cgatggtaac gccagcaacc agattccccg ccgactgggc cggcagactg    9780
atggcgttaa cgatgcgtgc gttgggaatc tggaccaagc cggtcggcat ggagccggcc    9840
ttgaagccaa ccagggcgcc ggccggcagg ccaagcgcgt tgtcggcggt aggcaggttg    9900
tttggtacat aggcgaccag gtcaccatag tccaggtcca gggcggttgc ggcgccgttg    9960
aaaatttcga cgaccaggcc ggtggccatg tcgaagaact cgccttcggc gccatcgggc    10020
agatcatagc tgggagccag ggagtctccg gccgaaccga acagcgcata gtgcttcgga    10080
tgaccgagga caccaaagaa gttggcgccg ccgatcacga cttcagaagc gcgagccgcg    10140
atggtcttcg gctgaccttc gccgagggcg ctgacgtcac cggcgtaacc gaaagcgcga    10200
ctgatgcggt tggggccggt ggcggtggca gccggattta cggcagacag agacatgatt    10260
cgacccggcc gcgcccgctt cgggccgtcc tcgatcagat cgcccggaaa accaggagtg    10320
tactggcggt aaacttgttt ctggaacatg agttactccc ccttcaggta gctgtccagc    10380
tcggcgcact gcggagcaga accggccgaa tcctgggctt tcgattgacg gctggccgcg    10440
ccgcgcgagg cttcgacgcc tttcaggtac atgtcgagcg ccagagcttc ctggcccttc    10500
gcacagctga tgttcagctt tttcacgccg taaacagcga cttcagccga gtccatagct    10560
cggtgatcga acgcaccaac cacggagcta agacgcttgt agaggcgatc tttagcagca    10620
atgtcgcgat agagaccgcg aattgcagca tcttgcgcgt tcttctgtgc catttcagga    10680
agttcctcgc tgttatcctt gctctcacca ccatcgtcgc tggcggtttg cgagccgctg    10740
aggctgctct gctcctccaa gccctcgacg acatcttgac cttcgccatg ctcttcgtct    10800
```

```
gccccttcgg ctaccgtgcc ctccagtcga gccagaatgg ctttgacctg agagatcagt   10860
tcggcgactt cgccttcacc ggacatttcg gatgcggcgc tttcttgatg ctccggctcg   10920
acggcggcca cggccggatc gacaacggga ggctcctctt cctgctcttc gtcatccttc   10980
tgagcacctt ccagagtcgg atgctcggtc aggtgctcgc tgtcggttgg ttcggccgga   11040
gctgcgcctt cctgatgctc cggctcctgc tcttcttcgc ccaggaactt ctggacagac   11100
gcagatagct tcggccacag ggcgcgcaac tcttcgaccg ccgagtcagc agcttgccct   11160
acgcgctgga caggggcctt ccgcttggct ttcttgagac tcatttcatt accctcatcg   11220
gatggtctga aatcaaaact gagatggtca aaacacagac catccaatac tctggccccc   11280
ggcacacgac cctcttttac cagggcgatg tggttgccgc gcatcttgtc ctggacgact   11340
tcataaggcg tcccgttcca gatgccgggt tgctcagtgt agcggcaact atagcctagg   11400
gacaggtctt ctttgcccct ttccagctga ttctgcatgt tgcgggaata gatgcggata   11460
tcgccgcgtg cccatggggc ttcgtagtaa gcgttggatg tgatgatgcc ctccacccct   11520
ttgtcttcgg gggccacgct atcgtcatca tcgtcgaatc ccgacagcat ctcatgctcg   11580
tcgatcaacg ggagattctt cagagattcg atgtactccg gatcgctgac ggcagactcc   11640
gggcgatata cgttgacaat ccgcgtcgga tcgcccggaa gaccgagttg accagcagaa   11700
tattggaaaa cgccataaga gctgatcggg cagccctcta tggtcatata tccattttcg   11760 tcaattttc ttttcgactt tgccatcgtt aattcgaaga gtcgtggact atggctgtat   11820
tatatacgca gtacatctaa gggtaaataa gcggaacaat aattagatgt agccgtgact   11880
gttaacttac attataattt gtattatgat ctaattacca gtttcctcag ccgcgaaaat   11940
tcggtaattt ggtctcggaa acttgacggg atttgtctaa gcctactgcc gcgaggcttt   12000
caactcctaa actaattcaa attaccaatt taccgattaa aaattgaatt tcaatacgtc   12060
tagagcatat agattgacgt tatattataa cgttacttat agatgaattc tattggaacg   12120
ttacttctaa tttcccaggc tatatacttt tgaagcatgc ggctaaatcg gaaattagga   12180
actggctctg ttaaagcctc gcggcagtag gatttccaaa ttactgctat tttccgtaaa   12240
cggtaacttg cggctatccg gactagaatt tttagtcaga atccagattt ttctcagcat   12300
tatcggccaa aagccatcaa gatggcgacg ccgatgattg ccaaatcgat ggcggcaaac   12360
ttcaggctga agaatccgcc gtgaatattg gccctgatta catcgaccac gagtcggcgc   12420
cggcacgtct tgcggttcat ttcacgagcc tcgacagagc gtccaccagg gcgcgaagat   12480
cggcgacgag ctcaggcgaa caatctttcg ccgtcttccc tttctcactg cgctggatgg   12540
aataagcgat ggccgcagcc tgctttgggt ctttaccggc ttcgatttcc cgcttgatgt   12600
tttcagaacg agcctcattg gaagtgccat gaactaacgg catatagcgc tcctatcgat   12660
gtcaaatgac tggtatcttt ctgcatctac agttaatcgc ccatcctggc ggcccctggt   12720
ctgctttcgg accctcccaa agtctggggt cattcagctt gaacctcttc ccatctttct   12780
ccaggtgggt gtggcgagga gtcttgccgg cagaagagtg tagccactcg aactcctcga   12840
ctccattttc cgccattctc tcatcgctca gagaactgta aagcttgctt gtttgatctc   12900
ttgcgatgag ttcgattcga tcttcagaaa acttcccgac tttgcgaagt gcgttagtta   12960
tgccggaagt tccttgctct tccggattcg gggaagtcag agacagcatt actgatgtgt   13020
aaatcttctc gtggacttcc tcttggatct tggtgatgag agtatgattg taagtggttg   13080
cggcctccag ggtgttcctg acgctctcat tatacgcagc tcgtggctga tcgacgccgg   13140
```

```
ccaccgacaa gctgtgaagg gtcgcggcgg tagcggcttc ttcggtccgg ttgacgaact    13200
ccggggcgat cttggccgcg aaaccttcaa aaatgcggct ccatcgctgc tgtaggcttc    13260
gaagggtcat cttgaacagg acgttaacgg attcgtctct ggcgaagaaa cgttcggccg    13320
caggctggga cagcgccttc tcaatctcgt ttcgatagtc ggagatcatg agcttggaca    13380
tatccttcat ctgctttcga taccaggcct cgattcctgc cgatggaatt atgggcttcc    13440
ctcttccgac tggaagaggt gcccggcgct cgcgcttttt ggaggccttg aatgccatca    13500
ctcgcccccg aacggtttgg tggtgtcgcc gttcgccagc cagcgacgga aagcgggcag    13560
gtcaacttca tggatggagc cgagaccatc ccagcccgga cggaagcagg acagatatcc    13620
agacttcgca tcgttgatgt tgttgaagcc gagcatacac ttgtgctcgt caaactgacc    13680
ttccttgttc acttggttga cgacgaagac ccgtttggat cccagattcg gaccgacgaa    13740
gcaatcgact tcatccccat cagcgccttt cgttcccttg atgaacccgt agtgatgttt    13800
catctgaact cgccaactcc catccttgcc ttgtcgaatg cttccgcgcg gattttcgat    13860
caaggtggtt attccattca ccttgattct ctggagttcc gaatgatcac gaggcccgac    13920
gatgcggttg gacgaaaaca ccgaaggctc cataccagac acgccaggtt tggatgtgcg    13980 cttttaagcca ggcgcatcat tgtgctctat gtctacgccg tccggcgcct taatgtcgtc    14040
caggtcttgg agcttcgaca aaagatcgac caacaagttc cgcagctcgg ccttggggtc    14100
cggcctcgac ggcggttcag cggctcgct ggccccttcc tcggccgctt tcgcgagagg    14160
cttagtcccg cgtggagcgg cgggaaccgg gccgcctgcg ccctctacgg cgcccgcctg    14220
ggcttcggct cgctcggctt cgcctttcgc cttggccgac tgtgcaccgg ccttctcgaa    14280
ttcggccagg ttttccggag acatgcccgg ttcggtttcc gcctgatcgt cggtgagtcg    14340
gttgtagccg gaacgcggat cgtcacgcag acgctcgcga acttcatccg gagacacaac    14400
gccagagttg atgtagattt catcggtcgc ggctttctta ttgttcaatt cggcttgttg    14460
ctggctggac gtggagtcca caggattcca gacgatttcc agctgcacat cgatttcttc    14520
cgacttcgcc agaagcaaat agtggcgttc aagaagtggg tcgaatatgt gctcttgaat    14580
ggactccagt tcttcgtgat aagaaatcgt ttcgtgctca ccagtggcat tgaatccttt    14640
tggagaagtg ccgaggagct tcgtggctgg agtcttggcg atggccgcga ccagctgata    14700
ttggttcatg atgatgctgt cgaagtcggc caggttcgtg tcgaactgct ccatgtcttc    14760
gtcaattccc agaactttca cgccgtggtt atcacggttg gcgatccaga acgccaggcg    14820
agcgttgaag gcctcttcgt tcgcgatggc cttctccacg tcaacgtgga tggtgctggt    14880
tcgcttcgac atggcaagca gcggggcttc gttcgccgtc cgttccgctg catacacgcg    14940
ctcatagatt ctctgggtga gcgggatacc gccgaagatg tatgtaggct tcaggatatc    15000
tggcggctgc ggtccacgaa ccaccactag gtggctgcgg tgatatttt taccgctgat    15060 aatccagaaa tccggctcat agaaatgttc ggaagacgga tctgccgtcg agccagcagt    15120
gagctgcggc attgcccagt atggatcgat ctggagatt cccttgtagg agcccgggcgt    15180 gattccatcc ggattgaacg gcttttcgta gtagtccgga tcgtcagact ccacaacgaa    15240
cagcgcgata cgaacgccga aaacgttctt gaatctgttg agttcgacaa ggttgtcttt    15300
gacgcgaaac tccatgtcgc gccgggcgat cagcgcgctt tgttcatcgg atagcttcct    15360
gccgtccgat ttgagttccc atccgttccg tgctgcgtct tccccagaca tggaacaagc    15420
tttgtccacc aaccagtgtt gggaaatgat tgcgcaagct tggtatccga tgaacccttg    15480
ggaattgtac cagtcctgca acatagtcgg gacgacatag ggattctggc cgcccgcagc    15540
```

```
agccttcgcg gccggagttg gtccatcacc atacgcacta tccattgcta cagataggcc   15600
cggctccagg aaatctttca cgctacgaat taccggggct ttctccggct cgacgttcca   15660
gccgcgaatc cttcccagct tgatcattgg gtcgagcgga tcgtgttgag ggattttttgc  15720
gactttctcc ggcgccgatt cagaacaggc agcattatcc tttttgcgcc cgaatatcca   15780
ggaaagttta acattgtag ttccacgtgg ttgttggctg tgtgcgctta ttataggga    15840
aacatcaaac gttcaaaaga gattcaaaca tatacatcag attaacagtt gcaactaatc   15900
agttatgaga aataattct ttacgggaac ttttcggcag attagactct aattatcaac   15960
caatggagat taaacatgaa tactctttg ccaatcgtac atatcgtgtt gaaagacggc    16020
gaagttctgg gcgtattcga ttgcgacaaa tcggcaagat tgttcgcga catgaaaggc   16080
ggcgtgctgg attcctgggt agtggaatcg cagaacagct cgcgttcacg cctcgtcacg   16140
aaagaaagct atgaagtcgg cgatcacgtc atatacctgg acgagcacgg agaagggcac   16200
ggcaaggttc tggcggttga gccgcgaggc gagcgcgctg tcggcggacg ggagctgtac   16260
aacctgtacc aaatcagcag cgacgatccg tccgtggaga tttggatgct cgacgcagac   16320
atcatcggca tttatcccga cgaaaagcgc tttactcctg gcgagcagat ggaatagact   16380
ctgctcatca actaaagagg gtgacgaaat ggcgagtatc accgtatgga ttgctactgc   16440
tttcctttgc actggagacg gctgcgtcca gatgccggac catactagca gacggttcga   16500
cagtaaggct cagtgcgaag acgtcatgct aagagcgatt gataagatgt gggagcggca   16560
ccaattggtc gtccaggccg tttgcacgcc ttatttcctg agcagcactg agactcccgg   16620
attctacagt ccgccgcccc agccgccgac tggtctgaac cgtatgtggg acaattggat   16680
tcgcggcggc ggtctgccat cctatgagcc aggaagaggg tggagcgaat gaagccgcgc   16740
cgtccggaag ttcgggtgag cctggaaacc gccctctgga tgtcgacatc cgctgcactc   16800
ctcgcggcga ttatcgccgg cgcggttttc ccgccttcga cgattcaatg tccggaagaa   16860
agaccgcctg cgaccgagcg ttttcaccat ccggaaaaca gcaagttctt tcctcacata   16920
caaaagggat agtgagtatg aagtatgtag tcctgaagct gacggtccgt ggcatgtcgc   16980
gtgaagttcc tgtgatcttc cccgacctca tcagtcatgt gaacatggcc gcgagtgcaa   17040
ttgtggccct cgatgctgag tgcgaaggct tcaagaaggc cggcgacaaa gttgatatca   17100
ccgcagtatc ggcaggattc ctgtcttcga tggatatcga tgcgaaatgc gacggccagt   17160
cggactcttt gggcggtctg aagtcgagag aatcagagga tgatgagctc atccgaatga   17220
tcgactatac ccatggttac gtcggttaag gcacgctgcc tttcctgcga cagacgcgcc   17280
gtcctggacg aacgaaaact gaagtcgaag cgcccgccaa tttgcagatg gtgtggagga   17340
tcgacctggc gaatagtcag ggaagtcacc tgttatagtt cgtgtagacc ctatccacac   17400
agggctggct cggtcggatg cattctagac cgatcaggct caacaataat cgtcgagctt   17460
cctggagtct cagacgattt tcctttctga ggtgaacatg gctactaagg ccgatttgga   17520
gttggaagtt caacagcttc gacgagtatt aaaatctcgc gagcacgaaa ttgaagagtt   17580
gcacggacga ctggagcgcc atcgcgacat tattcgtcgc gtccggctct acctttggag   17640
tcgcctgctg atccatcgcc ggacggccga aaccctggaa gtcggcgaca gcatcgccaa   17700
gaccatcgcc gcgaaaagac acaaggccgc gaacgacgtt ctaggcatca ttcagcattt   17760
gaacgactac tgcgaaagtt atgttgagta cgactacaac gacggcgctg agcatgggtt   17820
caagatcaat agcgacattt attgattgtc ttcgacccga cgaacggtag tgagaaatcg   17880
```

```
ctaccgtttt tccatttctg gcgtatagtc aactcatcga aacgaactttt ccaaacagga    17940 gaatcgacat gaacgcagca gagaatctgt tcaccggctt cgaagacctg ggtgatgact    18000
tcgctaccgt agagatcaac aacgaagcgc cgaagaccct ggaagacgtg tccatgggtg    18060
cccgcccgaa ctcccggaag gaagtgaagc tgtatcgcga caagtgcacc aaatgcgcag    18120
gcaccggcct gtaccgtggc ccttcgtctt atggtcgcgc ctgctttgcc tgcggcggcg    18180
tcggatacaa agagtacaaa accagcccgg agcagcgcgc caagagccgt gctaaggcgg    18240
cagaaaagcg catcgagaaa atctgtagcg ctgcgcaaga gcgcgacctc aaaattaagg    18300
ccttcgaagc cgcgcacccg gacatcatcg agtggtggac tggaaattcc ttcagcttcg    18360
ctcagagcct tcaggagtcg ttgtataaat acggctcctt gacagaaaat cagatcgctg    18420
ctgcgaagcg cgccatcgaa aacctcgcca gtatcgcga gaaagtggcc gcgcaggaag    18480
ctgctgcgcc gactctggac atttccggca tcgaaaaggc gtttgagaag gcgaaagcat    18540
ctggaatcaa gcgcccgaaa atccgcctgg ctggcgaagg cgaggagccg ctcatcgttg    18600
tggtgaaaga ggctagcgct cacagccgga acgccggtag cttgtacgtc ttgggcgaca    18660
tctacctcgg ccgatcacc aatggcaaat tcatcaagag tcgcgactgc accgacactg    18720
agcacgacga cgttctgaag atgttcgaaa agccgatgga atcggcagtc gcctacggtc    18780
ggaagactgg tcagtgctcc tgctgcggtc gcgagttgac caaccacgca tccatcgaaa    18840
tgggcattgg cccgatctgc gccggaaagt tcttcggatg atttacatga ccatcaaagc    18900
catggcctgg ttcgcccttc tatgggcggc cggcttggcc ctaataaccg taacaattca    18960
cttctgctac tgaggattat tcatgagcac cgtccctgat ccgatgaagg acaagatcac    19020
gctgcacggc ctgggtttca tccaggtcca gcttccggca ggacgcctcc atgtgtggca    19080
tccggaattg ccgcgccggc gttgcttcca acactcgtcc atccacgatc atcgattcga    19140
tttcgagtct ctggtgctgg ttggatcgat ggagaacatc aattatcagg tggatcgctc    19200
ggctcgcctt ggcgcgctga cccatgaagg gtatgagcac tcttctgctc gccaggcttg    19260
cggcggtcgc ggatgggact ctataggttc tgtgtccctg cgtccggtgt ccagccttat    19320
cgtgtccgct gggcagtcct attcgatcca gccttatgtt ccacacaaga cgaatccgct    19380
cggtgacggc cgcgtggcca ctctcatgcg gaaaggcagc gttcacatat ggcctgctac    19440
ttcctatgtg acgctgggcg tcgatcctga aaccgacttc gaccgctacc agtggtcggt    19500
gccgacgctc tgggaagtcg tcaccgatgt actcggtggc gcagagttcc aaatcccctc    19560
catcccgtaa ccgaaggaat ctgaaaatga aaaagttctg tatcgacatc accaatggtc    19620
tggccggctt catcatctgg ggcggcgcaa tcgtcctggc cgcttctgtc tttctcatcg    19680
gcccgctggc cctcctgctg accggcgcct gggttgtgtg tacgtctgtc gtgttcgccc    19740
tctggttcgc cgtcgccggc atctacgaag agtcgcaaaa gcagaccgag tatctgaaat    19800
ccctggtgtc gctccaggcg cgtgaacgcg gcatcggcta cggcccagga gacgccggtt    19860
gcagcgccag cgctccggcc gttcccgtag agcccaagct cagccatccc aaactgaagc    19920
cgggcgcaca gctcgcggcc gctgtcttgt tcttcgccgc tctcattctc ctgctggtag    19980
caggcgattg gatctggaat ttcttccagt ccatgccgaa atagtggaag aaagtgcttt    20040
acttccattc tgaatgaagg cagaataact ccattgaaac gcgaaaccct tcagacaaaa    20100
aggaaccgac catgaccgac cagaacgaat tcacccccgga agccatcgag aaggcgaaag    20160
accgcatccg caaactgacc gccatggctg ccgactcctc cagcccgcac gaagcggcca    20220
tcgcagccga gcgcgtgaag aagctgaagg acaaatatga ccttcacgac ttcgaagcga    20280
```

```
ccggcgagat tcgcgaagag ttcgatgagc aaattgccac tcgttactat tccgcaatcc   20340
cgaactggat gaaattttc  tcggtggccg tggcgacgta caatgattgc atcatggatt   20400
tcgccggtgg catcaacaac catcgggcat cggctaaggc atccagaagc gcccgcgacg   20460
gaagcactac caagcgctgg ggtcatgccg tacgctttaa aggctacaag tcggacgttg   20520
agctggcggt gaacatgttc aactccctgg tcgaggccgt tgatcgtctg tgccgggagt   20580
atcagaaggc tcaagggtac gaacggttca acgtaaaggt tgccgcgcaa ttcaagctgg   20640
ccgcgaccca ggaaatcagc tatcgccttc agtccatcac caggaagcgt atggagctgg   20700
tgtcttcggc cggaacgtct ctggttgtgg tgaaggaagc tgcggttcac gaacatttcg   20760
gcgatcctgg ctacaagaag tccaatgtta ctaagctcat gcgtctggac gatagcgacg   20820
gtcggcgcgc cttcaatgcc gggaccaatg ccgggcgcaa catggaaatc gttcggtcgg   20880
tggaggattg atcatgagct tccctagcga caaagcgatg ctgcgaatcg tccaatccat   20940
cctcgcgatt ctcatcggga tcgcttgggc ctgcgccgac tatggagtcg tggctgctga   21000
acttactcca tcgctgcagg cccatcccgc gaggccaggg cacagcgaag tctcggcccg   21060
cgaccctagg tcgtcgagg  ccgaaaaagc gcgggaagag gccttagaat atgtcctgtc   21120
gctgcgcccg gaagttatcg aggcgaaagc ccgcttcgcg gccgaggcgg cgcagcacgg   21180
aatgtctacc gagaaatacg ctgagatgca gcgcctgtca acgctgatgt ccggcatatt   21240
tgtgccgttt gcgttccttg cgttcatctt catcatgctg ctcatgctgt aataggcctg   21300
agcagcgaac aaccaccaac caaaagagaa tcatcatgaa gaagaaccga attcgactca   21360
gctccatggc ctcggcccgt gccatcgatg cggaattcgc attccggatg gacgagttca   21420
tggcgcgcgt cgctaaagag cacgaagcgc tcgccgcccg actgaatgcc gagcatctgg   21480
tgctctggga cgaaatccgc actgtcgccg gcctgagcgc aaccgacttc ccgaacatcg   21540
ctatggcaca cgacactgcc gatgggaagc tctatgtcat ggatgccgac gagttggagc   21600
gcgtccgcca agcctgtccc tgcccggact gcgaagctgc tcgcgccgaa agcatgccgt   21660
cgcaagccag tggaggtatt cactgatgcc gatcaagcta tcttccgtcc atgtacggat   21720
caccgggcct gatggcaggg ttttgtccga aggccgcgca gaatttttccg gaacggcatt   21780
ctggttggcc gcgcaacgcg aaatgaagtt caaacacctc gtcggaactt ccttcgaagg   21840
cgccctgacc tacctggccg acaacggcta caacgtaaca ttcagcaaag gtgaaaagca   21900
atgatcgaaa gacatgtagt tgatgcggaa accgtcgagc ggattcatgc tcttcgcatt   21960
cggttcaacg tcctggacga aaccctgcaa cgggccgttg acatggccat gcttagccac   22020
cagaaggctc tgcaagacct gcggaccta  t gaggcccagc tctgggacgc gctcaacgcc   22080
cgttacggtc tgtccgtcga aaagacctat gacctgcggt tcgaaggcga agaagccgtg   22140
ctggtcgagg ttccgccagg cgatggccaa ggtgatgact tcatcgtcga gtcggaagcc   22200
gaagcgctcg cggccggtca ggaagctctg ggcgtcggcg aggccgttgc gtcgacactc   22260
agcgccagga accacaccga gtaagacccg aagcccggag cgatccgggc ttttctatgt   22320
ttagaagtcg aagaagcctt tgggcttccg gatcggcaga atggccgaca taataaccga   22380
atcagcgatg ttcggcgact tgatcttgcg tttctcgcgc atatccttct tggactcgac   22440
tttgaaccgg ccgttcatgt ccaggtcttt gcgcggcgac gaaagttcga tacacagctg   22500
attcagtttg tccgggtgaa tcgtttcaga gttaatcgaa atcaattcgt cgaatggata   22560
aaccttttcca tgctcaaccg cttcataagt cttccggaat cgggtcgcga cttcttccca   22620
```

```
cttctgcgcc ttgatgttgc tgaagtggtc tttgttcttg atcgtcgtgt gcggcagctt    22680
catgtaaaca tcatcaggct tatcgacagc gccgcccgcg ttgaatgggt catagatcag    22740
cttgaagtcg gggctggcat cgttcaattc ggcgaacttc gaaccgacgt gagcaccgac    22800
gccgatggag tcataagtga ccgaggcgcc tttcatcttc gccaggttgt aaacgcggct    22860
ggacgacttg agcagttcat cttccaggcc gtcccattcg tccacttcca tgatgacgtt    22920
gccgtgcatg agcgtagtgg cgttcgcatc ctcgccgtcg tccgcaacgt cgaagccgat    22980
gcgcttcgat ccggccggct cccagccgag tttcttgtgg gcgtcgatgg ccgcgagaat    23040
gaacttgagg ttgatgacgg atttgtcgcc tccagtcttc ggaatcccgc cataaatgtg    23100
ctcggcctgc tcccggtcgc gttcataggc ttcgtgaatc actttgagca tcgtctcgct    23160
taggaacgga ttttcgttcc agttgatcat cttgacgcag gagtctttcg gtggtttgac    23220
cacgaagttc tgatacacga aatcggtgac ttcgttaggg ttgaagatga tccagatttc    23280
agagttttct ttccggatgg tcggctcgat aacttcccac tgctcctgtg tcaggtagtg    23340
agcttcctca agccagagaa tgtcgatgcc ttcggtggac ttgatttccg acaggttacg    23400
ggcgatccca taaaacagga actctgagcc ggtaatcttg tgcttgatgg agttcttggt    23460
gaagatgaat tcgccattat actctgagtt ttcgatcttg tctttgatca atgtgtagac    23520
agattcgctg atgcggttct ggaactggcg agcacagagg aatttgagct tgtagttggc    23580
cgcgaggaaa acggctatac cgccagcgtc gtgcgacttc gaagacgccc ggccgccata    23640
gatgactttg taacgggcac gagttcgcca gaccgctcgc agtgcaggat tgagcttgaa    23700
catttaatca gtccattgtt cgcaataggc cgagtatatc gacaccgcag cagacggtcg    23760
agcacaaccg ttcgtcggtg tacagaaatt tcttcgatca gacactttac ttccagtctg    23820
actgtcggca taatctcctc atcgaaacgc gaaacccttc aaacaaaagg aagccgaaat    23880
gaccaaagat caaatcaacg acaaaatccg cgcagccaag atcgcaatca gcgaggctga    23940 aatgaaggc ctgcgcggtc aggcgatgat cgatctgaaa gctgaactgg ccaacctcaa    24000
agcccaattc aaagccgcta agtaaggata cgaaaatgac caaacaagtc cagatcgaag    24060
tcaccaatct cgatgaagct ttcgtccagc acctcctgac tggcggccat ctgttcgatg    24120
tagacgacta tgaagtcgca gaccgcatcc tgatggaagt cgatggcgag caaatggtcc    24180
agttcgagct gaatgctgaa ttgtggaatg aagaaactct gggcgttccg atggatatcg    24240
acagtgacga gttcgccgat gagctgcagg attgggtcga gtcgaaggtg aatttcgcct    24300
tcgaagagtg gctgagcgcg gacgaaggcg aagagtgatt acgatgcgcg gccaggatgg    24360
tcccggccgc gacttcttat gaggattgtg ttatgtccac catttctttc cgaagcatca    24420
agaacgccat ttatgtccct ctggaaatca tctgcgaaga gtcgggcgca tcgcagacgg    24480
tcaaggcgca tgtcgatgcg aaaagctttc gcgcattctg gcctgtggcc gataatctgg    24540
cctgggaccc agacgcctgc aagttcgcgc ctctgtatcg agcccacttc atggccaaga    24600
cagttaagga tacagaccga gcactgctcg ccttcgcggc tgggcaatac tatctgcgca    24660
ataagcaggc cgcagagtcg caagaatcgg acgccgatct gcatgcgctg gagttgtccg    24720
cattgcgagc agaactgcga aggaccaaag tcgccaaaca gcagctggtg cgcgaaaata    24780
ctcgtcttgt cgaccgcctg cagaacttcg tagcccgcga agacaaggtc gccgagcaga    24840
accgccagct tcaactcaga atccaggatt tggaggccga gctagcatcg cagaaggctc    24900
ttcgggaaga gttagacaag agcctggacg gcagcatcaa gaacgccaat tcccagcaca    24960
agacggcgtg cgacgccatg gagcagctta ccaaagccag gaaagaagcc gatttctatc    25020
```

```
gcctcggtat gcagaaagta gcggctatcg caaacgcgaa acctttgag gatcactgac    25080
cgtgcagaaa tacgccatgt cccatatccc tcgcccagga acgctccagt tcgaattcga    25140
atggctcgcc gttacccggt tcggcatcaa ggatggtgct ctggctatgt cgttcgatgg    25200
cgagcgttac tgcaacgaac acatcgactg gctctggcgg cagttcctga cttcaaaagg    25260
tttcagataa tcttaagaaa atgctttact caatgaggtg acttaggtat agtcacctca    25320
ttgaaacgga acaatctcgg agagaaagcg atgccggtat ttaacattga ccagtccgta    25380
actgtagaag ctgaagtaga aaagggctgt atctctcgca ttgcccatct gtgggacgaa    25440
gaggggaatg atcttcctg caaactcggc gcaatccgag ctttgaatgt caaagccgcc    25500
tgtgcttatc ttgttcgcga tcctgccgct aaggaagtga ctactgaatg cggcgtgaca    25560
atccgtcgcg gcaaagccta atccaacgcg cccgattctc cgggtaccac cgaggaacga    25620
aacaatgatc ggcaccgtac acaaagaatc cccgctcacc ttaagcaccc gcatcggctc    25680
cgcatccggc gagaaacata cctacacaat gctggtgggc gagccgctgc ggactccaat    25740
tatcattcgt gatgacggca aaacctttac tttgacatgg ccagagatca tcgacctggc    25800
gcgatcggcg ttcgctatcg atgacgcggc cgattgattt ttgtcttcca gaaattttag    25860
acaatctgtt caaaagtgct ttactcgatg aggtgactga ggtatagtta cctcatcgaa    25920
acgcgaaaca ctccaaaaag aggattgcga catgactagc tccaaatgga acatcggcag    25980
aaacgacaca atcgaagtcg aggccgtaaa cagccgcgaa gatttccgct ggaatggcaa    26040
ggttcgcgtc gtccactaca cgccggtca aatcgtcaac atcatcgagt tctatcacca    26100
cgatctggac tgggcgatca agaatttcgg catcaagctg aaggccattt ccaagggcct    26160
ggaaatcctc cacacctgct acttcgggaa gtgtgtcaag tgatcgtcca actcgattcc    26220
caagaagaga aaatcatcgg cctgagaact ctgtccaagt atcgtcgcgc cggtggcaag    26280
ttcgcaccgg tggacggaac tcagaccggt ccctggggtc cagtcgacaa cgcgctttgg    26340
gcgaagctcg aagccgaagc cagggcagaa tacatccgca acaggagcg caaagcatga    26400
tcaagcaaga cctgtacaag cagatcgcct tcgcggcgat tggctccggc atcaagatgt    26460
tcgtcaagct ttactgcaac gacaccatcc tggaagtcat cggcgtcgag gaatcccaca    26520
ttgatgggac gactcggctg cgttacaccg gccgcgccga tggtgtcgat gtccatttct    26580
tcgtcaatga aatcgacatg gtgatggtat gattggtcat tcgctattcg actttgaagt    26640
cgattgcaat agcaccacca atagcgccac catggaaatc gatcccggtt cattctatgt    26700
aggcttcggg tttggcgcga ctgctctgtc agtcctgatc tatgtagatg gagtttgggt    26760
gactgaacgt acaccatgga tccacgatcc aaaggaaata tcgccatgag caagcgcaaa    26820
aactatcagg gcggctgggc gcaacccggc gatgctcgca aagtccactt cttcacttcg    26880
gacggccgca gcctgtgcaa gcgctggctg tacctaggca agacttacag cgagctgccc    26940
gacctggaaa tcacctgcgc gatatgcgag aagaagcgcc agagtccttt cgagaaatac    27000
tgcgacacca ttctctaacg ttcaagcctt ccaaaaccga ggaacagtta tgaaactcta    27060
ccatgcaaaa gtcagtcctc catccttcta tcgccacaac cagaccgacg aagagcggaa    27120
agccttggag gcggaatatg tcagcaagct ccacgttctc ctggggaacc tggaaggcgt    27180
aacaatcggg aatcctggtg agcggaactg ggagccgtcc acctggagca acgacgttcc    27240
tgtgacgtgt aatgaaatcg gcctgggccg tctgaccgct tcggcctggg atctggacaa    27300
ggactatccg tacaccatca tcaacctggt cctgctctgg gacgatgtcg acccggaagc    27360
```

```
cgctctgcgg cccatgctgg agcgcctgga gctggccgcg agccgtctac agggacgctc    27420
gccaggctac atatctgagc cgcagatggt gctcggcatc gaaggctgga actcggtcac    27480
cggctcggcc atccctggtc cgaatctcca gggcgtcaac cgtctcctac tcaaggaaga    27540
ctgctgcacg gacgaactcc agtatgccct ggacgcagga tggcgccttc tcgccgtttg    27600
tccgcaggaa gcgcgccggc ccgactacat cctggggcgg ttcgatcctg tcccgccgac    27660
cggaccgcgt ggcgcggcca ggagcatcga ttaaatgacc atggtaggcc cggctggcaa    27720
gcgctactgg cttcggtatg aaaccaaata ctgggaatgt cttgacggac acaccctgcg    27780
cctggtcttc gtcatcaacg gtcgccgata cgaaatcaat cggcgggtga atgtcgacat    27840
cctggctagc cggcgccggc tcgaatcctt cggccgagtc ctggcaagga tggaaatcag    27900
cttgtggttc gaagtctgtg agcaagaagg gccatggcgt gggagcgtag caatcagcga    27960
taccgcgctt tggttccatt taactggaga attggtacac aagtgcttta ctcgatggcg    28020
atgatcaggc ataatctctt caccggctga gtagccggac ccgaagtcca aaaggaatc     28080 tcgaaatgta cagaattccc tcgtccaaat tcttgttcat ctgcaacggc ctcgcccaga    28140
acacagaagt gacggttctg ctaagaaagc agaagccgga agatgtatgg gtggtggacg    28200
aagctccagt tgcgaacctg attcgcatcc atgaacgcag caatccgcgc cgtcgccgta    28260
ccatcagcat cctcgacgtg gacgccgtgt ccatccttcg caagcgttaa tccatctgcg    28320
cggctgggat cgtcctggcc gcgccttctc ataggagtgt attatggcca aaatattgat    28380
ggcctgtgag ttgctcgtcg gcgacgaaat actcactcat gttgacgtca atgatcccgt    28440
tcggcgtcgg gctatagtcc tgcgatctgg agctgcgccg caccgcaaag taagcatcga    28500
agtcgcggcg ctcatcggtg ctgactgggt ggacttcaag ctcaagctgg ccagggacta    28560
tcccaccatc tgcttacatg acatcgaccc gatccgtcct cgtggcgcga cccaatagga    28620
gaacaccatg gctaaaatag taagagtcga tgagctgaaa actggcgatg aaattctgat    28680
taagctcaga gcagattcag cagccaggaa caaggcgatt gtcctttctg tcgaatgctg    28740
gcgcgacgaa atcactctgg agcttacctg cccggccggc gactactggg aagactggcg    28800
cggtaaatat cgcgcatatg acaaagtcgt tctgttgaag cgcgactaac aacaaccagc    28860
ctctgcgact cggcagaggc tttctcattg gagggcagct tatgtccgat aaagaacaaa    28920
gtggccatta ctgggtaacg gtcagtccga ccgatctgtc tagcgcgtcg gccgcgcagc    28980
gactctgcga aacgatccat ctgaacatga cgcgaggcgt cgcggcctac atcaagttct    29040
acggctcgaa aggcgaaggc ctggtgacgc gagtcattcc gcaccagtgc gaactattcg    29100
tcaatgacga gtcgggcacg aatcggcgtc gaacggcgat gatgatcgaa tacgtccgct    29160
tcaaagttcc ggccggtatg tctctggtcg aacaccaaaa gcaaccttat tgagggcgcc    29220
atgaggaacg taaagatcga tcataaatgg gagtcgagcg aactaagctc aggcatgaac    29280
gtctggaagc cagatgatcg ctacagcggg agcgcctggg aacgctgctt catcgcaggg    29340
ttggaaggaa cggaccactt tgcgatcatc cgtcacgaca acgtggcact gacgccgttc    29400
tggccacgac tgaagatcgc ctactacctt cgaaagaaca atttcgccaa agaggagtaa    29460
caccatgctg tacatctggg aagatcaaga tatccaccac aacatcgaaa ccctggcttt    29520
cgtcggcgag tccaggtcca actacagaat catcgggttc aagctcggtg atctgttcgc    29580
cgtcgccgaa gagtctactg gccagatcgt ggtaagcccg ctgactcggc aagggatggc    29640
ggaatggctt accatggacg gccatattcc tgccagatc atcagccacg acccggcaa     29700 ccacaagaat ccgtatgtct gggcagattc catagttctg aaaaatctgc ctacccatcc    29760
```

```
gaacatgcgc tgcgttacca ctccattcac gggcttcgat ccggcagagc cgggcggcga   29820
caagacggcc ataggtcaag tcatcaaggg caaccgatcc gccgaaatgt tcggcgacaa   29880
tccggcgcag cagtcgcagc ggtcctttgg cggcatagcg ccgagtcttc ccgatcttcc   29940
cgatcttccg gaacctccca gggcgccgat ggctcctcca ggcctgccgg ttccgcccgc   30000
gcctcctgcg ccaaaagcgc ctccagctcc gcaggtgagc aggcagtcgg aatctctgga   30060
gcttcggtcc ggcgcaatcc cgtccagtcc ggcgcccgca tcggacaacg acaagcccgg   30120
cgatccgccc atcgagccta tcacgatccc gacgttctga ccatcaccct cgcccacaaa   30180
caccgcagcc cgttctgcgg tgttttcaca tccgacaacc gttcgtcggc tttgcgatca   30240
atctgatgaa ataaatgtag acacgcagca tcgacctagg cataatctct ttcaacgggg   30300
cgacaaaccg aagcccgaaa gaaatcttcc aaaacagagg atcgcaaaaa tgaccaactc   30360
catcaaaacc ttcggcgaca tccagaacgc agaaatgaaa gaactggtcg ccttctacaa   30420
cgctcacaac gccgatgcga ctgtcaagcg cttctctgac cgcaagaccg ctgagcgtcg   30480
ctgcctcgcc atcctgaacg ctctgccggc cgaggaagag gccttccagg aagaggaagc   30540
cccggccaaa gtctacaaaa cccgcacttc caagaagaag ggagaagaga aggccgagga   30600
agagaatctg aagcctgaag aagagatcac cgaagaggaa gcgctggaag aaatccggaa   30660
gatgcgcgaa gaggccaaga acgctccgga gaaagccaaa gagtccaaag acctgtcggc   30720
agccatcgcc aactcctgga agacccggaa agtttccaag aaacgcactc agcgccatgg   30780
cgtggctgtg actgtcaaag gcaagcgcgg cgagttccgg tccaccaacg cagcattcat   30840
cgagttcggc ctgccttctt cgaaacacat ccgcttccgc atgcagctga aggcggctgg   30900
caaaatgact ttcgagcacg aaggcgtcaa atacaacttc gaaatcatcg aagctggcga   30960
ataaggcgcc caaaagaaag ccccggattc tgaactagag tccggggctt tgtcgtttct   31020
gagggttagg ctacgacttc ctagaaccgc cctagaatcg tttttcgtcc cttcccgcta   31080
ccgtcgcctt agttcggtcc gattcgggcc tagaacgatg ttattttatg tctaaatggg   31140
gttggcgcgg tcttcctcgg tcagttccgg cgtcggagac gggaaatctc cctcttcgcc   31200
ttccggcaca tagccattgg cttcggccgc agcagcgacg gtggcggtct gagcctcggc   31260
ttctgatgcg tagaagtcgg ccaggccgcg accgatcctg gtcttgcccg actcgtccac   31320
gaacgtgatt tcagccagaa cgttcaattc cttgatggcc gacagacggc tggagtcctt   31380
gacggtgggg tcacgaacca tttggaggag ttcgtggagc gccgtctttg gattccacaa   31440
atcggacgtt ttggtcgcgt tcaacttggc cttgaactgc ttgcgatagt acggggttgga   31500
ctccatcgcg aagatgcggg cttgcgcggg accgtccata tgctcctcgc cccagatggc   31560
ccggaagacc cgccaggagc tgtaaccttg gacgcgcagg tcgatgtaca ggtcgaatcg   31620
cttttggttg atcgccgcga aatgcgggtc tgcgaattcc tgtggcgtga ctagatcgtc   31680
ggggctgtag aatttggtca tttggcgctg cgtccctgag ttcgattctg gagtcgtcgc   31740
ggtggctcgg ttggtggatg gggcctggtg ctctgtcgcg acactgagta tggcgcgatt   31800
gtactatggg gccagggatc gcgtctatgg gctgcttgtg ggtgggctgt aggtctgggt   31860
gggtttgatg atgaatgagt gttaggtggt gttataggggt gttatacggg cgatccgctg   31920
gtgggtgagg atcgagtcgg cggttggtgg gtgacgatgg cggtgagtgt tgagaggag   31980
tgttaaatcg aatgttagaa atatgtccag ctgagctatt ttgtcgtgcg cccaaattcc   32040
cggttccgtt cgtcgagttt tggtccttgc cgcttagtcc gccgtggtgt tgccgcgacc   32100
```

```
catgcattgg aagtccggaa gtttccggcg accctgccgc gagctggctg gaatcggaaa    32160
cttgacggga tatgtacaag cttagtgcag cgaggctttc aaataccaaa gtataccaaa    32220
ttaccaaatt actattaatt taattaattt taaagatagg taacgtccgt gatagatttt    32280
ttctattagg attgtgcaat cgattttcgc tgtagtatac ttttgcggct gcatccgaaa    32340
ccggaaagta tccgaagaaa cccttcaagc ccacgcggca ctaaggctcg accctaattc    32400
ctggtttcgg taattaccgg ctagccagcc gcggccgacc ccaaaaatcc agtcagaatc    32460
gtcgattttc cataattcat ccaatcacca cacagaatct tcgatccacc gtccacgaac    32520
tttccacact gcacggccat cgcccccaac ctaattcccg gatagcttcc gaatctcact    32580
cggccacaac ctaaatcgaa tgtacgtcgc accaaagaaa aagaccgccc gaaggcggcc    32640
tagtccaagt acactccatc actccattag aaatcctcgc ccaatattct tgcgcgctcg    32700
gctttgactt tgcggatttg aatcatggcg gcttcatcag taacctcaga atccaccttc    32760
ctcagcaaat acaccagcgc atcattgaac ggcggcaacg tcgtatgcat acccttcgac    32820
catccaggtg caaccttatc aaccggcaaa caccatccgt tcagtccgtt cttgttctga    32880
acgagtccca gcgctttcag gtgcggagtt aaatggcgag aaatcggctt cttcctggcg    32940
agaatatcga accatttcag aatttcgact gtgttgactc tccatccagg attctttgaa    33000
ttcccgcccg gcttaacctc ttcgaactcg caactgatca gcacgttgat cagatacatg    33060
tcaatcgtat cgtcacgaac tacaccacgc gcattctcca tttccgaaat agagaatttc    33120
tgcacttcgt tattggtcgc ccgaactaga tcaagatatc cctccactcc attcgcctca    33180
atccaggcgc gacattcagc catagcctgc cagaacttgc ggccgaagtc ggtgaagtca    33240
acgcggaaag tctcgttacc atcacccggc ttaacccagt tcggctttcc atcttcgtcg    33300
ggcagttgcg caacgaacat cggatagaat cgacggttcc ccgactcatc cctctggagt    33360
ccgtcgtagc cgttgccgtc catgatggtg atccattgtc ggctgatcgt ctcgcctggt    33420
tcgaacttct gatcgaaagt gtcatcggac cgcaccagga attccttaat gcgttccatg    33480
tcgccctttt tgaagccgga catttcgccg acgttcgcaa taaccgagtt gccggtgata    33540
ttgcgaagga acgcgtctg atcgtgccgg ctcaggtcga gctggactgg cgataacttt    33600
cggtcgcccg acagctcttt acagatcaag attgaaaagt aagtctttcc cgcatcctgc    33660
ccaccaatca acgccaacga gatcggcgcc gagattccag ggtagttgat gcggcagtac    33720
aagctcagcc agaaatactt gctcaccatc cggttaagct cggtgtcgaa cggtttgaac    33780
aagtcgatca gcagcgtgtc aatccgctct ttgccatccc actccggtat cttcttctca    33840
aacgtctcga tcaaagagtt gcggcgatat cgacgcgccc acacgcagca agtctcaatc    33900
gtcttcttaa tcgagggatc gtccaaggcc gcagccgcga gggcgcccat caggtcaatc    33960
ggatcgaggg tcttgttgtt gaacgccacg cctcggtggt ccaccagccg ccgcgaaac    34020
tcgtcgaagt gcggatgcgg gacggttccg tcgcctttac agaacaacgt atcatagacc    34080
gcgaggtagt tgctgtctga agtcgaactg tactttgtga tgaagtcatc gaacggtcct    34140
ttcaccagcc ggctgaccgg aagatcaaag gcctgatcga gcatcaacaa tcgcgctcgc    34200
ttcttcaaat ctggttccgc atacgcctcg gcatactttg ctgcctttg cgcgcggtac    34260
gtctcattcc tcgcaatcgc atcatcggcc gctttacttg cggcggtcat caaagggtcc    34320
attccagcat cttctatctg tgtgagatcg aactcattgg accccgattc gtcatcatca    34380
agaatgttat cgtcgtcgat aatcatgtta ggtttgccgc cttctgcttt acatgatcgg    34440
atataacact gcctctacat attgaggcga aagggacggc tattatctcc tacctaaacc    34500
```

```
ggcagagcta ataagttccg tccccatccg aaaatttccg gaccgttcgt cgactaaaac    34560
acgtcaaacg ccaagacgaa ccagcaggtt aaagcagaaa ggccgaaaaa gaagcacagg    34620
agcgacgcca gaaagttcgc tactggtatt ttccatccct tcaggccttc gaagaagatg    34680
aggaggccga gaagcaacaa gccgatggcg gtaatcagaa ttccaggatc attttgcata    34740
gttactactc ctcgccgatg tgacggcggt tgatgcgttc caattgttcg acgatatagg    34800
gcaggacgac ttcatcagtg aaggccgccc acgtccgtcg atgctctttg cggcaagtat    34860
cgtgtccgca gccgaacaca tattcgtgct cggcgccagg tatcggtccg cgaaagtatg    34920
cgccgaaagg atcgccgttg gtgtgctcgt cgccccaggg acagcggatg cggtattttc    34980
cagacatgtt ctgctggacc tggccgcctg ccgcttcgcc catcttgtat ttcgtgcaga    35040
tgtgctcggc atacttcagc catacttggt catacaccca atcgtcgcgg tttatctcca    35100
ccttcttcat ctgtggcatg atgatgcgga cgccgaaggc ctgggcaatc tcttccggcg    35160
agtagcgctt ggaatagtcg gcgctgtaca gtcgcacgag ttcgggcttg ccattttcgt    35220
cggcatactt gaacttgccg tctttccccgc gcttgttgtt gaagccgaat ggcatccgac    35280
cgtaacggct gacgtccttg actgtgttgt cgccgccttt ctttaacacc tggtccacga    35340
acgaatagag cagcgccttg aactggagca tgtgggacat cggctctttg aagaaatacc    35400
agaactgata gttgttcggc gaagtctcca caatcgcggt cggctccagt cgctcgcgga    35460
actcgtcgcg gtcgaagtcg cccttggacc ctttgccgga gccgatgtca tcgaccatca    35520
acgccaggcc gtggccgaaa gaggcttcgc cgcgccagta tcgcatctgg ccggtcttcg    35580
ggttgggcgt cttgatggac gacgagatac acgcgtaggc gttggatctg gagttgatgt    35640
atttcccttc tttccagggc acaggccacc agccggcgtt gagcttgcgg ccgttctcgt    35700
cggtttggac tgtggcctct tcagcgtagc cgaccatcac ccgttcgtcg tccggaatcc    35760
ctcggccgag ttcgcgcagg aactcttcgg cctgtgccag tcttatttcg tgaggcttca    35820
tgcaagtcgc tccgggcgcc ccttgcgtcg cggcacttcc acgaactgtc gcgcagcgct    35880
cgcctttctg gcggagttta ggccatcttc atggattcga ctccaggctt caatgatctt    35940
gtgctgtctc gccttttcga gcgccggggg aatcttcgca tcgtcgatgc cgcgcaccca    36000
catgaacatg aggaacgtcg ccaggtccag gaggttgttc tcatttccct tcagcgcatg    36060
ttcggcgaat ccgttgatca gaatatcttc gtcgcagtcg atccagccgc tcggcctttt    36120
atcgcgggag cgctgcagtt tctggcggat cgctgctgcg aacatggaca cggcgcactc    36180
gtcctgcgct tctggcttcg cctttcgaag aatgcgaatg tcgagatcgg tcatggcgat    36240
ggctccatct acttccgaag gtttctgctg ttccattaca taaactcctt acttggcact    36300
taccgctcgc acccgcagcg ggcaggatag gcctgtggtt gctggcacgg ctgaggatgc    36360
gcggccggat cgatgggtga gggcgctact gcgagcattt gccggtaaat ctcgccgatg    36420
ctgtttaccg agtcataacg cagggactgg ccgacgaatg tcatttgcgg cgtcggttcc    36480
atcggaacgg gtttccaccc atcaggcacg ctgggttgag cctggactac aggcgcggtg    36540
tagagggaac ctttcctgag cgtcaatgag tcgctgcttc ggtgcatgtc gaggatatac    36600
gcctctatct gagcctcagt ttcgcattgc gtatacagct tgccgtcgcg cttcccgccg    36660
aaatggaagg cccccatgcc accggctctt gtttctccag ctcggccagc ttcatcttca    36720
gctcatgaat ctccatttcc atgccgccag cagcgtggcg ggcagcatca ccctttgctg    36780
ctgcgtcgcg tgccatcgcc agttctttct ccagctccgc caccctggcc agggcgactt    36840
```

```
ctagctgttt tgcgttctcg tctcgctcgt acatcatctt catgcatctg tcgaagctgc    36900
cagaaggatc gcattttgat tctcgcaggc gctcgacttc ggccagggcg gcgtcgcgtt    36960
ccactttata acgacaataa ggatgaccgt gttcatcgcc gatcacgcca tcgcaatagc    37020
tcgcggccag ttcgctcccg cgcttttcgg attcggacaa ttccttttcc agctcagcga    37080
tcctggccag ggctgcgtag cgctcggatg ttactttgcg gatttcaact tgcgccaaag    37140
ctaggcggtt accagcgcaa ttccataggt tgttgtagcg attgcgcgcc tcagtcatcg    37200
aggttaatgc agtcagcagc tccccgacta tgcggtcgtg ctgggagaca agcatcatcg    37260
gctcaggatt ctgcagtcca tagtcctttt catagaccat gcgagaagcc gcgctgcgat    37320
agccgactac ctctggccgt tccacttctg ccagatcgcg tgtgcgcttt tcggattcgt    37380
cccacttctt ctccagctcc gcaatcgtct ccagagcctc ataaagtttt ttggcgtcga    37440
tcttctcgaa ctccggaata ctgggctttc ccaaatcttc catatcattc acctcaatta    37500
cagatggcga tgttgagaac tttatcgcgc ccggccgcga acttctccag gaagtccacc    37560
aggtcattca ggatggtccc cgctcgacct agcttgtggc cgatcaggag ctgcgcgact    37620
cggtgtccga cgaatttccc cgaaggaatt ttcggccatg tttcaccgat gcttttgagc    37680
actgcatcag tgtagatttt gtccgcgccg actttgtggt gatcgaggat tgtgcgatca    37740
cgaacatacc gattgatgat ccgccgcagg aactcgtctt cagtcccggc cagggcgccg    37800
cactcgcgga gttggcgcag gagacgccac cccaagttcc gctcccactt ttcagcgaac    37860
tcttccgctt cggcgaatga cgctcgcatg atgtgatcga ctggaatgat gacggcgccg    37920
ccttctttcg ttccggattc catgaccgcc cattcgccgt gctcgcgatg ctcgatgaag    37980
ccgatcagca tgcctatgaa agctccatct tccggaactc cggtcacgcg aacgactgaa    38040
tggcgcggga aggctttcga tccatagagg ctggactgtg aattgaccca tccggccatg    38100
gccaagtcgg acgcttcggc gtggatcagc tcgcgacgaa tgcgaacgga cagcgccggg    38160
tccagctcgc ggctccggcg caggaaaccg gttttaggt tcgggtcgcg ggtcttgtcg    38220
acattgggat tcggattacc gaccgggagt tggtcgcggg aaatcttgca ttcttgcatt    38280
taatgtatcc tctgtttgg agggcagtac aggcggcggc gctagtatcg gccactttcc    38340
tgccgaagta aagttggatt aaattcgctc gctttggcga gtcagctgat agtatactct    38400
tcctgcgcag aggtaaagca taactgtacg ttataaagga acattcgatg gcggaacata    38460
tttttactca cgaaggcaca gtggtgttcg agggcgatc ccgaacggtc aagctccggc    38520
gcggcaacca ccactgggta gacttcgata gacatcgcta tagcccacag gacggccgcg    38580
ccgcttccca ggctattaag ggtgcggtcc tggtcctttc gaccgtccgc tggctccctg    38640
gggccaaaga ggccgcagag caggcgaagg ctttcccgta taaggaagg gtccacgcgc    38700 ttggagctgc ttggcattat gttctgctgc ggcgcacgaa gaacttctat gtcgatccgc    38760
aaggccgcaa gtatcgtcgt gatactggct ggtctgtgga cggcgtgctt aaactgagcc    38820
tcgattcaat taaacctagc gttggagaac gcaaatatgt cagcatctaa cttcaccgtc    38880
gatcagatcg aagagcgatt cggctttcga ccaaacagtc agcagatcga cgcgatcaat    38940
tccgttgtgg actggtatcg cggttggtgt gatcgagcgc accgccgcca ggtctatcga    39000
ctcgctggtt tcgccggaac tggtaagact tccatcgcga agatcatcgc cgaactttgc    39060
tgctcgatgg actggacggt cttcgtcgcg ccaaccggga aagcagcagc gcggcttcgc    39120
gagaagggtt gcaccaatgc ccggaccctc cacagcttca tctatcggcc gattggcgaa    39180
gatgaagacg gcgaaatcat gtttgccaac aaagactcgc tcgacgagaa gccgaagttg    39240
```

```
gtcgtgctcg acgaggcgtc aatgaccggt gagtgggatg aagagcgctt gttggcgcat   39300
cgaattccgg ttctggagat cggcgacttt ggccaagttc ccctgtgcg cggcgttcag    39360
gttttccacg aacatagctg cgacacagtc atgactgaaa tcgagcgtaa cgccgggaat   39420
atcgttcgag cgtcgatgtt cgtccgccag ggcaagcgcc taccctgccg cgagtatgac   39480
gacattctgg tacgggccgg attcgacatg tcggacgacg aaatgcggac gttcttggac   39540
gatgacggcg tgatcctttg cgcctacaac aatactcgtc gccgtttgaa cgccagggcg   39600
cgccgcatcc tcggctacaa gggtgtacaa ccggaaatcg gcgagaagct ggtgtgcacc   39660
gggaaccagc acgaatatgg catcatgaac ggcgagcaag caattctgct ggacttcaag   39720
ccggtccccg aaggccaaga agatgatgac gagccggatg aaatgttgtt cgccaaagtt   39780
cgcattatcg gcacgaacta tgagcgctgg gtgaagttca atcccttgag cttttcggtc   39840
gaggaagatg tgcggctgga ggcgcagaag gccattggcg gattcgactt cggctgggcg   39900
atgacgttcc acaagtcgca gggatcggaa tggaaacggg ttgccatgct ggaagaaaac   39960
ttgccgtcaa ttccttatag tcagttgatg tatactggca taactcgtgc aattgaatac   40020
ttgttgtttt tgcgtaagag ttgaaaactt cgcgaacata aataagttcc tggagtctgg   40080
actttcccga aggaaaata tttagagaag ttcaggcgaa aggtattccc ttcttcaatt   40140
agtttagaga taatcccctc acaggccaat aagccatccc tttaaacatt cccgagtaa    40200
gaacatggaa cagaaagacc agaacgagca gacccaaggc gaagagctga ccaaggaaca   40260
agcagccgcc ctgcgcaagg ccgagaaggc cgctgagcgt caacgtaaag agcgcgagcg   40320
cgccgagaag gccgaggcca aggccaagga agccaacag aagaaagccg agcgcgaaga    40380
gaagcgcaag gccgagcgtg agaagaagga agccgagcgc gccgagaagg cgaagggaaa   40440
ggccgccgcc aaggaagccg agcgtgctga aaaggccaag gcgaaggaag ccgagcaggc   40500
cgagaaggcg aaggccaagg aagccgagcg cgagcagaag aaggccgaga aggaagccga   40560
gcgcgccaag aaggccgaag agaagaaggc cgcgcaggaa gcccagaaag ccgcacgcga   40620
agaagagcgc aagcgcctgg ccgagcagaa gaaggcagag cgcgaagccg agaagcagcg   40680
ccgcaaggaa gagcaggaag agcgccgcgc gaaggccgaa gcccgccgcg aagacctgaa   40740
gtccaacggc tcgcgtcgcc cccgcgccac tcacttcatc ccgaccggcg acggccatgg   40800
aaccccgcag gccttctcga ctcgcggcaa ggtgtttgct tacatcaacg agcactgcac   40860
cgttggtgag ccggtcgaaa tcgaatcctt cggcgagaag gtggcccacc tgctgtacgg   40920
cacctcggtt cgcagctacc tgagcaagct ggaaatcatg gctgggtcg atctggttgc    40980
catcgcttcg aaggaagacg aagctggcca gggcgatgac gagaaggccg atgaaggcca   41040
ggagcacgac ggtgaaggtc agggcgccga cggttccgat ggtgaagaag agtaagccgc   41100
cgctcttctg agaccgaatc gtctagctct tcaagggact catgaaaatg ggtcccttt    41160
ttatcctctc aagttttgta cactcataag ggacacatca tgattcctga tcagaaagta   41220
atcatcgtag gtgccggact cgccggactg atcgccgcgc atcgctttcc tcaagcccaa   41280
atcatcgacg cggcgacgcc ggagaataag gagcgccaca acgcacttct gcgattccgc   41340
tcgccagtga ttggccaact caccggcatc ccgttccgcg aagtcactgt gcacaaagct   41400
atctacatcg acggcgagtt catttcccag ccgcgcatcg accactgcaa catgtactcc   41460
aggaaagtaa ctgcggcct gtcggaccgg tccatctgga atctggcgac tgaaaagcgt    41520
tggatcgcac cggccgacta ctatgagcag ctggtggcta agcttgcgaa tcgtatcact   41580
```

```
tggagccgtc ctttcgacgc ctctttcttc cagtatcttc gccggcaaga tgaccacgtg    41640
aatatcatca gcaccgcgcc gttccgcgcc aatctggctg cggcagggct ggacctggga    41700
atcgacccgt cattcggtga aggaacctcc atcatcgtga gtcgatacaa gctttccatc    41760
ccctgtgatg tcttccagac cgtgtatttc cctggtccta aagtgggaac gtttcgagcg    41820
tccatcaccg gtgatactct gatcgtcgaa tccatcacta aggggatagt ggagacttta    41880
gatggtaaaa tcgaaaccat cgaatgggac agcgactggg acatggatta cgtttgcgcg    41940
gccttcggca tcaggaaaag gcatctcatc gaggacggcg agccgaccat ccagaccaaa    42000
ggcaaaatcg ttccgctcgg ccgcgacgag cgcgaatcca tgatctggaa tctcacccat    42060
gaagccggca tcttctcgct cggccggttc gctacctggc gcaacgtcct tctggacgat    42120
ctggtttctg acatggacgt catcgagcgc ctgatgactt cttcgtctta tcagaaggcc    42180
aagaaaatgt tcgtgaagta atttacaaaa gtgctttact tctggatcag gtgggcgtaa    42240
cattccctca tcgaaacgcg aaaccccttca accaaaagga atcgacaaat ggcccgcgaa    42300
gtaaccttct ccaccgacaa gaaccacacc aagacctacg ccaccaaggc caatctcgaa    42360
cgcgccatcg ccaaggccga ttggctcggt gaaggcgccc gctacttcgt ccatatgacc    42420
gaggatggcc gcctgactcc tgtgttcctt ctgaatagtc ttcctgcagg gaccggtgcc    42480
gtgtggtgcg ctcagcacgg ctggaacgtg gtaggttaat ggccgtcgat cctcgcgaag    42540
cagcgctcaa gcgggcgctg ctagcttcct tcagggacac cgatgccctt ggcggcggga    42600
gtctcacaat aacggcccga atcgtcgggc cagagggcga caggaagttt cgcgccagtt    42660
atttcctgaa tggcgagaag ttaagcctgt ccgatataat cgctaaagtg gaggctgaag    42720
atgggccgga tcgttaatat caaagcagtc atttcgcgca ccaccgagcg cgattccatg    42780
gggtcgccgt acatccatga gtcttaccgc actttctctt tctccgcttc caccgcactg    42840
gtcgcggcca tcgactgggt gaaaggccag tgcccggaaa tcgttgacat gctcatctat    42900
gagccggaaa ccgtagctgc tcagcaggag cgctattaat gtacgcacca gatcatcctg    42960
aagaggttcc catgtctttc ctcgaaatgc aaatcgaccc gccgcaaacg cgacagacag    43020
cgccgtcttt cgtgctggta ggcgtcctgt acctgattgg cgatgggcgc ctggacgata    43080
agcctttcac ttcgttcaac ctgtcgttcg gcagtcgaga agaggccgag cgcgcccgcg    43140
ataagattcg tgagcactac ctcgaccgtc gagatatccg cgccgaaatc atccgctgct    43200
actgaggtca tcatgtcgat tgaacttgtg taccgaacct ctgatggagc cgtcttctca    43260
tccgtccatg aggctgaaga gtatgaggcg cgtctgcgag cctgcgaact gctcaaggaa    43320
gagatagagc agtatggcct taacagggag caagcccaag gcctggccct ggctctcacc    43380
gaaaaattcc acttcacgcc aattccggaa gatttctgat gaagatttct ctgattagtt    43440
acacccagaa cgcctgggaa ttgctcttgg gaacgaagtc caccccgcatg cgcggccaag    43500 acccggcgac catgaccgag gccgaaaagc tcgaccactg gaagtacatg ctggacacca    43560
tccgctcgcc gttcgagttc gtggacttca ttttccagat cgagggtgtc agcaagaact    43620
tcacccatca actcgttcgg actcgtaccg gggcttacca gcaggaaacc agtcgcgctc    43680
tggaaatcag cgccgtcgtt cagccggaag ccttccgctg gaattcgac gaaccggcta    43740 cggtaaatgg cgagcctgac ccgacctacc atgtccgcga agagctgaac cgcctgtggc    43800
acgacgccat tgccgacgcg caaaccagct accagaagct tctggaggcc ggcgcgtcgc    43860
tccaggacgt ctgtgccatc atcccttcca acatggaaac gaagatcgcg gccaagttca    43920
atctgcggac tctcagcgac atggcgaagg ttcgcctgtg cgttcggacc cagggtgaat    43980
```

```
atcaggaagt attccgcgaa atgcgccggc tggttctgga agtctatcct atgttcgaca    44040
gcctgctcca gccgcactgc gtcgccaccg gctcctgcgc cttcccgcgc tatgggtcga    44100
aggtgatgaa tgaagaggaa atccagcaga aatcctatga ccggttcatg gccgctctgg    44160
agacaaagcc aggtcagatt cctgtgattg atgttccgtt ggaacctatc taccagtgca    44220
agttctatcg cccctggatg gatcgctcgg ccgagcagga agaactgcgc cgcgatttct    44280
ggggatcgga aaaacaagag gccaaccctg tggccgtcaa tgggaagtcc atgtaacatg    44340
aagatcattg tcgagaaagt tggcgacatc gcacaagtcg aagtgaccaa cggcagcgaa    44400
tccattcgca tcacgatgaa cgtgcaatcg ttcgatttca tccagaatgg cgaagttttc    44460
cgcctcactt ctgatgggac attcatcgat aaaaccgtca cccagaaagc aaccagtaag    44520
gaaatctgaa tatggaacgc aaaccaaaga atggcatcat catcttcgac ctggacggct    44580
gcgtattcga cgatagccac cgcaagagct tcgccttgga acggcaatgg gacgagtatc    44640
attctcgtct cgacaaggac actctcaacc cgcacgctgt aggtcgcatc aggaatgcca    44700
tcgacgccga cctcatgatt ttcttcgtca ccggccgaac cgacaaccac ttttccaga    44760 ccagggccaa gctccaccgc gaactcggca tcgccgaaca tcgcgagtat gaactcatca    44820
tgcggccgta tggtaacacc gagccggcgc ctcagttcaa gcgggcagtc gcgctcgaca    44880
tcctgaagaa aatcgaaggc gtcaccaaga tcgtcgcggc gttcgatgat cgccaggaca    44940
tcatcgatgc ctacaatagc ctggggatcg actcctacat cctgaacctg gaaggttgcg    45000
atgcgccgtt cttcgccgtc gcggccgata gcgaccccga tagcgcgccc aacgacatgg    45060
caggcgagcc gttcccggcc gccccgaact ccgcccctac cctcgacgag gcgtttgcga    45120 aagcccgtc tccgctcgct gaaacggctc agtccgaaga cccgaccgaa gacgtcgcgc    45180
cgttcgccat ggaatccgtc tggcctggcg aagatgacgc tcatcccgat gatttcgcgg    45240
aagatgttct caacaatctg tacgccgcag cagaagtctt ccgcgcccgc cagagcacct    45300
atggtcgcaa tgatctgatg tacggaaaga tcatggaaat cctcttcccg aacggcctgg    45360
tggcgaagac cgccgatgat catcgactcg ccctgttcgt gatgcatatg gtgggtaaac    45420
tcactcgcct ggcgaatagc gggttcaagg atgccgattc ggccttggac tcgatcaact    45480
attcggcgtt tgttcacgcc accatgcgct ccggccgcat cacgccgaaa gacggacaga    45540
aggcgtaaat cttcagccgt cgcggtatac tcctcaggcc ggtcgcgaaa gcagccggcc    45600
tttcgacata agagggaaca aacatgatat tcgctgtatg ggatactgag accacaggac    45660
tcccgttcca ccagagggtg agtctgagaa agcagccgag aatcatcgaa ttcgcaggcg    45720
tgataactga tggcgaaaag atttttggatg aagtagagtt catctgcaat cctggaatcg    45780
tcatcgagga aatcatcacc aagatcaccg ggttgaagaa cgaagacctg atcaagcacc    45840
catctttcct cgatcagcgc cagaaagttc gcgacttctt ttccagagcc gacgcgaata    45900
ttgcccacaa cctaccattc gataagttca tgctgacctg cgatctggct cgcggcaagt    45960
tcggcctgga cgaagtcaat ttcccatcac tcgatatctg tactgtggaa gagtcggcgc    46020
cgttgttcgg ccaccgcatg cggttgcaac atctttatga gcactactgc ggcccatatg    46080
tacagaaaca ccgggcactg gacgacgtgc ggctgctcca cgaagtctgt aagcgcatgg    46140
gagtatatcg ggcatatcaa gcaatggagg ccgcataatg tctttccctc agcttcgcgt    46200
tcgctctggc tactcctacg gcgccgcata tggccgattc ccggagatca tcgagcgcgc    46260
caaagagatc gaatccccat tcgtcgccat cgtcgatgat ggaacatggg gtcacgtccg    46320
```

```
ttgggagcag gccgctatca aagcagaact gcctcgcgga ttcggcatgg aaataccgat    46380
caaatgcgcc gacgatggcg agaaagagct gaagctcaaa gcctgggtgc tcgccaagga    46440
caccaagaag ttctaccgct tgacttccaa gtcggtccag aatcaaggat tgactccgca    46500
agaattccag gaagctgacg gcgtcatcaa attcgctggc gaggcctatg cccatctgga    46560
tctggccgga atcgactaca ttgacatcaa tcccgcgtcg atggtcgccg cgcacggcgc    46620
tatggagacg gccagggcat tcggaaagcc ggtggtaatt acctcttaca acgacatgcc    46680
gtccatcgac catgctgatt tcgcgtcggc ctggaaggtg cgggaatcgg tcggccttcg    46740
ccacatcgcc accgaagagg agctgtggag ccgtttacgc cacatcatga ctcgcgaaga    46800
gttcgacgcc gccgccgcca atactcgtgc ggtagtcgaa caattggcgg atgtgaaact    46860
ggcgaaggcg cctatgatcc acctggatgg ggatatcgtc gcgctggctc gcgaggggca    46920
agcctaccgt ctcagtcgcg gccacatcaa ggaatggacc caggagtatg aggatcgatt    46980
ccaagaagag atcaagcaga ttcagctgaa agatttcgac agctacttcc tggtcgtggc    47040
agatctggtc gcgttcgcca agaagcatat gctggtcggc ccagctcgcg gctcttcggc    47100
cggctctttg gtctgctatc tccttggcat taccgaggtt gacccgctcc ctcatcgcct    47160
tctcttccag cgctttatcg acatttcccg gtccgatctt cccgatatag atatcgactt    47220
cgccgatacc catcgctatc tagtgttcga atatctccag cagaagtatg gcacttggaa    47280
cgtggtgaag ttgggtaaca ttaacacgct caaggccgca tcggttatcg ctcacgtcgg    47340
aaagcgcttc ggcatcccct tccacgatac cgacaacatc aaaaactcga tcatcgaata    47400
tacatcggcg gacgaacgat atggaaaagg attggaggat actttcgaaa aaactcagcc    47460
cggccgcgac ttccgcgaaa agtatgagat cgcgtccgcc tgcatgggcg acctcgaaat    47520
tcacccatcc cactctggcg tccacgcggc aggcatcctg gtctgcaacg atgaagtcat    47580
caacttctgt acggtaactt ctgaaggtgt cgcgcagctc gacaagcccg attcggaata    47640
tctgaatctt ctcaaaattg atgcgctcgg ccttcgaact ctgggagtca tccaggacgc    47700
gaactgcgtg accgcgcaag agttgtacga cttgcctttg aacgacaagg cggttctgga    47760
cgtcctcaat gaagacaaaa tgtccggcat cttccagttc gaagggcagg ccgttcgctc    47820
ggtagcgaac gcgatcaaca tcaccgcgtt cgagaacatc gaccacatca cggcgctcgc    47880
ccgtccgggt ccgttgtctt ctggtatggc aaccaagtat atcgagcgcg tggccggccg    47940
cgagcctgtg acctatacca ttccgcaggt cgagcaatat ctgtcaggga cgtacggagt    48000
cttcctgtat caggaacaga tcatgtccat cgtcaaggac atcggccagt cgactgggaa    48060
acaaacgtcg gcaatccgga aggccatgtc tgcgcgaaag ggcgaagagt tcttcaacaa    48120
gcgccgggaa ttgttcatcg agggcgccaa gaccataggc gtcgcccccgg acgatgctca    48180 tcgtgtatgg caggaaatgg tgacattcgg cgcctgggga ttcaaccgct cccactcggt    48240
cagctacgct gtggtgacgt actgaccctg ctacatgaag cggtatcatc gcctggaata    48300
cgcggccgcg tgtcttcggg cggcgaaaga cgaccagcaa actgtgtcaa tccttcgcga    48360
attggccaag gaaggcgtag aatatacggc cctggacccg gagcattccg aacttaactg    48420
ggtagtggcg gacggacgcc tgatcggcgg catcatgaac gccaaaggct tcggcccggc    48480
gaaggcagag aagttcctgc gccttcgtga tgacgtcaag gccgcgagga tcgccctggc    48540
caattgcccg atatcggcac aggatgttga ggacaaggct gctgatgtag cagcgctgga    48600
agcccagatt ctttcggcga aaatcagcca agacaaagaa ctggaaaaac tgttgaaggc    48660
cgatctgaag gagttaaagg ccgatcttag ggagctgaaa gctcaatata aagagctggc    48720
```

```
cggaacccac ctgaagacgc ttcaggattg ggagaaagtc gccgcgagtc tgtcgaattc   48780
tgaagttcaa ttcgcagatt tgaacgaagc tcacacgctc tggggtcatg cttatgacaa   48840
tccggagctg gttggagtaa cttccggaaa ccccatccag aacattcggg atatccgcga   48900
tggagacgat ggcctggtca ttgtcaagat ggtgaaaaaa gttctgtctg atgagaacga   48960
accgattcgc cagaagaaga gggcagatca agggaaaaac ccggtgtaca agggccagtc   49020
gcagtttctc gacatcatgt gtgttgacga ctcggttgat cagccgatac gtttcagaat   49080
taggcctgaa aaatatctgc aatacggaaa gcagattgct gaaggaacgc cgacaggctc   49140
ttggttcctc atcaaaggct ggaagctcag cggaatcgat atgttcatcg tgaaggccgt   49200
caagaggatt ttgaccgaac gcgaaaaagc aaagctggca gcgcaagcag agaaagtttc   49260
caaagagggc gaaggcgatg aatgatcgcg aaacgaaagc ggcgaatgcg tttaagcaac   49320
gctcactcgg ccgaatcctg atcgactttc tggagacgcg gcggtctggt atgtccgatt   49380
cgatttgcct gaatcgtcga ggcgtccagt tctgggtcga gttcaaggcg ttggaggagt   49440
ggccgaaacg cgcctccacc tgcccaatgg ccagatgttt cgagcctggg caaatccctt   49500
tccttcggga acggatcggc tggggcggcc gtggcttcgt cctggccaag atcgggaccg   49560
attggctgct gctgaatccc atgctcgatt tgttcgagct taacagccgc gacttggtgg   49620
aagttgcgag ctatgcagaa ggactggata acattgttca gttcctcgcc gatttggaga   49680
acaaatgaaa gccaaaacat atcccgtcaa gggcatgaag accgaggcca tgcagcacca   49740
gttcaatgcc ctggccgcgt ccctgaacaa acggaatttc gcatacctga tggagcaggg   49800
caccgggaag acttggacga cttttggccga tgccgttcgc ctcttcctac aggggcgcgt   49860
ggacgcgctg ctcatcgtcg cccccaaagg cgtccacacc aactggattc tgcgcgagat   49920
tcccacccac gtcgcgatca agactttgag cgtggattgg cgcggccgac cgacttccaa   49980
aaaggccaga gcgcgcttgg atcgtctgta tgccgagacg ttcgcagatg aaaaagttct   50040
tcgcgtcttc gccataaacg ttgacgcaat caaccaccag gctggctatg atgaggtcga   50100
gcgattcctt gatacattca aagtttgcgc aattgtggac gagtcaacga ggatcaaaaa   50160
cccacaagcc aagcgtgcga aaaagatcgt aaagctggga gaaaaggccg tggcccgtcg   50220
catcctttcg ggaactcctc tgacgcgggc gccgaccgat ttgttcatgc agttccaatt   50280
tttgcgcaat ggcattcttg gaacgaaatc ctatcgggcg tttgtggccg aatttttccgt   50340 tttggttccc agtgacgatc ctcgaatgat cgctatcatg cgcaagctgg aaggtaagca   50400
gacgatgccg ccgcaactgg tcgaaaaaga cgagtgtggg cgcccggtat tccggaacct   50460
ggacaagctt cggtccctga tcgagccgca cagtttccgg gttacgaaga aggaagcact   50520
cccattcctg ccggacaaag tgtacaagcg catatacttc gaaatgtcgc cggagcagcg   50580
aaaggtttac cagcgcgtgg aagaagacta ccacttcgtt ctcaagaacg aagacttcat   50640
gctggacgta tctttcgatg ctgcggcagc gcgttcgaag ctcaagcaag ttgcatccgg   50700
ctatatcaac gtctatggcg agccggtgat cctgccgccc gaagacaacc cgcgattcgc   50760
cgtgttcact gatcttctgg agggtctact ggaggaagac ccggagcgtt ccatcatcat   50820
ctgggcaatg cgcattcagg aaatcgacca gatcaaggca tatctggagg cgcatggat   50880 ttcgtttggc acctactacg gcgagaccaa agaggccgag cgggaaaaat tgatcgacga   50940
tttccaggcc aagcgcgtcc aggtattcct gggcaacccg gccgcagcag ggatcgggat   51000
cacgctcaca gccgcagacg tggccatcta ctacacgacc gacgaagaca acgagctgcg   51060
```

-continued

```
gatgcagtcc gaagaccgaa atcaccgaat cggcaccgtc aactctgttc tgtacttcga   51120
cctgatatgt ttggattcca tcgacgagaa aatccaggtc agcttggagt ggaaacgcaa   51180
cctggcaagt tatgtcgttg atggcgtgtt tgaggctgac gttagcactc gcgacgaaat   51240
ttaatatgta aatcagtagc cgtatcaagg aagatgcggc ataatatcta ctcaatactt   51300
ggttcaagta agggaacatc actaagttgg aggcggacat gaaagagcaa gagcttgaaa   51360
tcccggaata cttgaaagag aacgcgccgg gcgaaatcga ctattttggc gtcatggatg   51420
aaatggcggt tgaagccacc gacatcggcc atcgactgct gaacttggtg gacaaggctt   51480
cgcagctgga cggcgaaatc ctcgatcttc aaaaggcgct ggccgaaaag gaagaggagc   51540
tgaagaccct caagcgtaac accattccgg agctgttgga ggagcttggt cagaagacca   51600
ctactctggc ggacggtcgc acggtaaaag tagagccgaa ggccatcatt tccgtcaagg   51660
aagagaacaa atcgaagttc tggaagtggc tggaagacac cgacaacgac ggcatcatca   51720
agaccaaggt tctggccgaa ttcggtcgcg gcgaaatgga agatgcgaag aaggcggccg   51780
aggctatcat tgaagccggc tatgacgcta ctatcaaccg cgatgtccac taccagaccc   51840
ttcaggcgtt cgggcgcgag tgtctggaga agggcgaaga gctgccagat ttcatcggcg   51900
tgcacgaata caaagaggcc aaaatcacga aaccgaaggt gaaaagagc aaatcctaat   51960 atgtaatttg ctttacttag ctgcaacttc cgttattata gacccacagt tagcgataac   52020
tgaaattcga caaacaagga gcctaacatg gctggtaaga aaaccgaaac ttccgaagca   52080
accgaagaaa ccaaggccgt agcagttgcc accggtggcg gcgccgtcgc gactaccgaa   52140
gttcccgact tcatggattt gggatcgtat gacggcgcag gcttcgaagg cgccgatgcc   52200
gagtcctatg ccatcccctt catccaggtt ttgcagaaga tgtctcccca ggtcgatgaa   52260
gatgacccga agtacatcga aggcgcgaag gccggcatgt tcctgaacac cgtcaccagc   52320
aagatttacg acggcaagac cggcctgctg atcattccgg ccgcgtaccg ccgcgagttc   52380
atccgctggg ccggtcgcga ggccgagggc ggtttcaagg gcgccatcag cgtcgaagac   52440
ttcaaggaaa tgatgaaaga cccgaccaag gtgaaggaag tcgaagggcg cctgtacgcg   52500
ccgaacgaag atggttcggt cagcgacaag aagtctgact acttcgccga cacccgtggt   52560
cattacgtca tcgtcatcga tccggacacc ggcgatttcg gccaggctct gatctccctg   52620
tcgtcttcgc agatcaaggc ctcgaagaag ctcatgaccg cgctgtccca gaaaaaggtt   52680
cagactccgc agggcctgcg caccccgccg actttcgcca acctggtacg catgaccacc   52740
gtcggcatgt cgaacgacaa ggggagctgg tccggcgtcc agttcgaact ggaaggcctg   52800
gtgaagaacc cggatcactt caaggctgcg gccgaccttt acaagtcatt cgtcggcggc   52860
gaggtgaaag tggactacag caagcaggaa cagcctcgca gtgacgccgg tggcgtcggc   52920
gatgcgaccg aagccgaaga gttctaaaaa tcaccggccg gagaaaggcg ctgtaatggc   52980
gcctttcttc taaggagtcg aaaatggact ggaaggacat aggtagtaag atcggcgcgg   53040
ctgccccggc tctggggtcg ctcctgggtg ggcctgcagg cgccgccgtg ggctctatcg   53100
tcgcgacggc gctggggtcg aaggccgacc cagcctcggt cgcgagcgct ctagacgcga   53160
atccggaagc tctagcgcgc ctcgccgaac tccagcgcgc cgagcgcgtt cgtctccagg   53220
agcttgcgat tcaagccgaa caaaaccgtc ttcagtctga gcagaaccag ctccaggccg   53280
agcttagcca gttcgcagca gaggctgccg cagggattc ggcgaggaga cttgccgcgc   53340
agcagaacga tttcgttcgc ccggcgatta ccttcgctct tctgacaggc tccattctca   53400
ttatcatcgc aatcttcacc ttcggccgcg aggctctgat ggacccgaca tcctcggtcg   53460
```

```
ccatcggcac catcatcggc tattggttcg ccgagctgaa gtcggtcatg gccttctact    53520
tcggcaccac caaggatgga tcgcgccaga gcacggcgtc catcatcaac gcagtcaaat    53580
cccaaatcca aaaggaatcg aaagaatgaa tgtcgaacag atcatcatcg aacaaatcat    53640
gagtcgcgaa cttcacgacc tggttgttaa atggggttcc gaccggaacc tgatcaaagg    53700
atcttcggcc aaggatcaat tcctgaagtt ggtcgaagag ttcgcagaag tttgcgaagc    53760
ctgggtttat aacaaaccag tcgaggtgaa agacggcatc ggcgacgtaa tggtggttgc    53820
cacgatcatg gccgcgcaac tcggtgaaaa tctgttcgat catctatcgg tcttcagcga    53880
gactgtcgaa gttcatccca cctacggcga ctatttgcag cacctcggac atctggccga    53940
cgcgctggca cgcggaaatc atggattagc catcaagagc ctggtcttgg ccgtcatgac    54000
tctgttcgat gtgacggaag agtacgcaca taccatgctc gcctgctacg ctgcggccta    54060
cgacaccatc aaggatcgca aaggcgtcat gtacgacggc gtgttcatca aggagtcgga    54120
cgagcgctat gcgtcgatca tggccgaact gaaccacgcc aacgaaacca tctgagccgg    54180
cttaccgcca tttagcccgg ttcgccgggc ttcttgtctg gagaactgta tgaaacccat    54240
gctcgcatcg aattttgacc agaagctgct ggaaggccaa ctgccgatgt atttctcacc    54300
gaagatcgat ggatttcgct gcttcatatt cgaaggcgag gcgctgactc gtcaactcaa    54360
gcgtcagacc aatcagtcga tctacgaata cctcagcgat aaactgttca acggcctgga    54420
cggcgagctg gtctgcggcg acatcagcga cccgaaagtt ttccagaagt cgtctggcga    54480
tcttcgccgc cacagcggtg agccggactg gtctttccat gtgttcgatg atttcaccga    54540
tcctcgcgca ccgaccaaag agcgcctagc cattgcggct gagcgcgtga acttcctgcg    54600
caactgcatc ggctgtgaga ggattcacct ggtcgagcag gagctggtga cttccatcga    54660
acagttcagc gaagtcgagc gccgccacac gatgctggga ttcgaaggtt ccatgggcaa    54720
gcgcgccgat ggactgtaca gttcggtcg ctcgacggcc aaggaagggc attgcgtgaa    54780
agtcaagcgc tacgactacg atgaagctga gatcatcgac gtggaagagt tgatgcacaa    54840
caacaatgaa gctttcatca atgaacttgg taacacggcc cgctccagtc atgcggaaaa    54900
cctgtcgccg tccggaatgg tcggcgcgtt cgtctgccgc aacgaacgtc tgtggcctgg    54960
cgtcaccttc aacgtgtcgg cctccagcct gacccacgac gagaaacagc gccgctggaa    55020
tgacagggca tacctcaagg gccaggtcat ccgattcaag cacttctccc atggcgccaa    55080
ggacaagccg agacacgccg tcttcgattg ctggctggac ggatgggcg gaagccactg    55140 attctagcgc acactagatc gagataaacc cggacgcctt gtcctacagg cgatccgggt    55200
tttctcgttt taatgtcgac aaattaggcc ttagaccgga ccaggccgcc agagttcctt    55260
ggccagaaag aaggcgattt aatatcgcgg tgcgtatcgt taaacagtta agcgcgagca    55320
ttttcgacga gttataatag cgcccgaacc ttccgattaa cacagcgcat ccccaagcca    55380
ttatcggggt gaggagaaga ccgcagacag aggactaaac atgaaacgca aagagcatcg    55440
caagcgcttt cggccaagaa tcagccccag actccgggaa gagttaatat ccgttctgac    55500
caagatcata ggcgagacag tcaaggacaa ggtggtaaga gcgctgttaa tcggcgttct    55560
gagttcacta gggaactatg tggattcggt cactcaggaa gagtccgccg cgccggttga    55620
agtcaagatg gttgaagagg caaagccaga aagcaaaaag gccgctgaat aagcggcctt    55680
ttctttgggt ggaatatcag gagccttgat tgatcgcggc gatggtcttc atatagcggt    55740
tgatccggag ctggccgtgg ttcgcatcgt tcggcgcggc gccattgatg gttttaacga    55800
```

```
ccatggagaa gttgttggac tccgccatgg ggatgcagcg attgcgccag aagaaccagg    55860
cagaagacat cgacgcgccg gccggagttt ccagaagctc cggcttctcc agaacgtcca    55920
tgccggagtc ttcggcgaac agtgaatagt tcgacttccc ggtcagctgg atcaggccgc    55980
gcccgcgata cttccaaccg tcaccatcct gctcacagcc attacccata cgatccgcgt    56040
acacgttgtt ggcgatggca accgggttac gggccaggcg gttcgccaga gcattcggga    56100
catacgggcg gactcgcggg tctactgcgt accggcgcgg ccaggtgttg gccaacccctt   56160 gggcgctgta gttgagattc tccaccagac ttaccagtcc gccggactcg acgccgatgt    56220
tggcgaggta ggccgcgatg gctcgcggtg actcgatgtg gaacttgtcc atggccgcct    56280
gtacatcatc cagccacttg atcgcccgat ccgtggtgca cccggttccg gtgatcagaa    56340
catccttcgt gattttcatc aatactcctg attttgaac attgttttca gagccatggg     56400
aagtcgcggc cgatccccgc tattccaatc gcgaatctgc tgcctccagt gaacaagggc    56460
tgctatcagc ccaggcccgt ccgtggtttc gatacccagc cgcctctgct cgtcgtgacg    56520
atctatgggc catcgggtat cgcgaaggat agcccgcttt ccctgtctc gtatagcgtc     56580 ctgcaaggcc tgctcccgcg tcgagtctac tggggcgata gggccgtgcg ccccggacag    56640
gatcgcagcg tgaatggccc ttccgtgggc ctccacgtcg tgcggattgg cggtgaaagg    56700
aacttctcca atccctcga aagtaaccat ggcgtggatg tttaccgcgt ccagccaacg      56760
tgggtttctg atccgcgtcc atttcatgtt acgttacccg ctggaatagg gatgccgagt    56820
cgccgttggt ggagtctcgg ttatacacat accccatgca gcgccaggtg cccgtcggac    56880
gggcgctgct gcgataggtc gaatcgcagg acgaatagaa cagcttggaa ctgtccatga    56940
tcgttccggg ggcaatggac gctgccggcg cggatgtgtc caatacggca aggatcgcgt    57000
aggaaccgac gccgccaaga cctacctgaa ccagcgcctg gttgatgtag ttgttgtagt    57060
tgccggagtg gatgatggga tatgctacgc cgcccattgt gccgccaccg atctttacca    57120
cgttgtccga atccaggccg aagttgacct gatatttctg cggcgaatgg aacgtgatgg    57180
cggctgcggt attggtgacg ctgttgtttt ccacaaccaa cgcaccgacc tgtccggttg    57240
atgcgattcc ggacgcccca taactgaata ttgtagggga tgacgtcgta ttgcgagctg    57300
ccaaagtcgc cttggtgtct gggttgaagt ttcccgacct ccagatggtc tgcccgttcc    57360
agttcggcgc ggcagcgtgg gatgaccaca ggctcatgag gttgttggag tcggcaatct    57420
cgaacgcgac ggcacctaga aatagccgc cccatttcag cttgttgtcc gtgtccaggc     57480
cgaacagaac gcctcgtgcc ccgttacgaa caaacgaaat tacagcagca cgattcccgg    57540
tcggcgtcga agcctcatag ttgaagaacg acatggccgc gtcgccataa cttgtcatgg    57600
cggctatccc tacgtccttc gcggcgctgt ttaccatcct ggtgtattgg ctatcgttga    57660
atgcgtccaa cgtaagctta gtgttcggat tgaagttcca cggaccccag aactcgacat    57720 tccccaaat cgggcgcgca gccattgtgt tgatatgggt tcggatgttg gattcgtcgg     57780
tgatcacata ggagttattg ccgagcgacc agccggcccg cttgagctgt ccatccttgt    57840
ccatgcccag ataccatccg gtctgggagt tgtcgaaata gatcgcggca ggctcaccgc    57900
ccccttttcc gaagatttga atggcagcat tgccatagga tgccgtcgtg gagcgggaac    57960
cccaggtgtt catgttgccg gtgttgccgt tggtattccg aatcccggtt gggccggcga    58020
tttggttcgt ggcattcacc gtcaacttgg tggaaggatc gaagttccca gaatcccaag    58080
gggtgtattg accggcgaag agcggacggt tgttgaatat gacgtcgtg gacgcccagt     58140 cccatcgcat gacctgtgaa cgataggaac cgtccggatt ggtggtattg actgcgatca    58200
```

```
ccgcgttgtt gttcgcgtcc acgccttgtg caaaggtgaa tttccaaccg ggctgatcgg    58260
cggtggtgtt ctgccaaagg gggccagagt tcgcgatgta cgcgaggttt ttcgccacat    58320
cgagtcgcgg ctggaagaaa gtcacggaat ttcggttgaa caggatgtcc tgggtaggcc    58380
cagcagaccc ctgccgcgaa tagaaagcca gcgatccgtc tgcttcagat atcagccgat    58440
agtcaaaatc tttggcgcga ttgctgttga agtggaaatc gatgaaaggc cgagcatcgg    58500
acagctccag attggcgaac cacgcgttg tatcttggat agcgacgttc ggcttgttga     58560
cgacatccgt ccaatccact tcggtgagct tttgggacgc gacatagtct ttaacttgct    58620
tccaactcgg cgcctggtag tcctgatcgg cgttgccgac ttgtatgcgc ggcgcgcctg    58680
ccagaatcct ccagcggtcg cctgctgcgt cgaagacaag ctcagcgatg agtccttggc    58740
caagttcgcc gccagtgaga gggaagttgg ccgcgccgac gatggctttg cgccgagtc     58800
cggagacgtt gatggtagta gcgccggtgt tcatggtgtt gaacttgacc cgaagaatca    58860
tgccatccac caggccgcct tggagctgcg gaactagcgt caacgtgtaa gcgttcgccg    58920
atccggccgc gactccatag gtgacccgac cttgttgaag ggccatgacg tttaccgcat    58980
acatccagtt ggtccacgct ccggcattaa gcccgcgcac agcgacgttc ccgacgcgat    59040
cagtgtagcg ttgacgcag aacgtattgg ctccggacac ccaagatttc gcctccaaca     59100
tgccagcagc ggcaccagcg gaagccggat atacgggggc attctgagaa gcgataacca    59160
ctgaatcaga gaagaactcc cacgtcccat ttaacaggtc gttgaagttg cggccggtcg    59220
tgatgacttc tccgccagaa gataggcctg ggcctccggc cggcatcggg atgttggagc    59280
gcatcgccga ccatgcgggt tgttcttccc aagtcgtgct gctgagaggg tcgctcgcat    59340
tggcattcac catggaacga taacgccgca ttatgccgtc atttccgacg cgcacgactt    59400
ctgcattctg ttcgtagccg ccaggcatgc cctgaaacca cggcggcgcc atttgtcgct    59460
gccacgcctg tgcgttctgg gtcgcgatga agaagagttg gttttgaatt ttccgctcga    59520
ccgctttggc ctgcgggttg ttcgacgcca ggctgatttc gtagtccggc gtatagccgt    59580
cgcgaaggtt tgcgaagcca gtggaggagg tttgtggaat cgggtcttta tcgccctgag    59640
cggcaaacgg actgggatc agttcgggtg tgatcacgtc attactcctg aatgactttg      59700
acatcgcaac cggcgcaagt cggcataata ccaactgccc ggtcattcat gaggttgatc    59760
aattgcggcg acagattaag cgccggacca accctgtatt ctagcttgaa cgccccactg    59820
gtgggtaggc cgatgtatgc ggggtctgac agagtaaacg tatcctgagt cccattcccg    59880
actgcgaatc tggccggttc tgctgcagtc ccgccttcc agtctccagt ccaatacgct      59940
tctactccgg tcggaagggg ctgtgtgaac ttgactgttc cggtctgggc gttctgcaaa    60000
acataatcg tcatggttac gggcgccccg gtagtttcca agtatccagt tggagtatca     60060
cccagttcga tctgagcgcc ccagataagc acgtcaatcg ccgcgctgga attcgaatca    60120
atccagctga agttggtttc tgccggagcg acgtaagcag cgcggaacga agagctgacg    60180
gtcttggtcg tgagaacgca acgccaccag ccatttttcca gacgaatcat tcgggcgctt   60240
accacgctgc tgtccagcat ctgatcgctg atcacgttcc cggaatccag gtcgaaaacg    60300
gcatcggctc gactggggaa atcggcagcc gactgaattg caatgaaacg ggtggagccg    60360
gctttcgcga agaacgagaa cgttacagtg ctaccggacc ccagcggccc atctatcggc    60420
gcggagacgt aagcggtact cccggccggc ttagtaagct tgcacaccgt ggcggagccg    60480
tccggggccg tagcggacgc cgtttcgacc gttaccggaa gaccgctcgc ggccggatcg    60540
```

```
actcccggcc aatcggcgtc gctggcaggg gtcgatgtca gcacatggtt cgttctgggc    60600
gaactggaca acagcaccat accttcccaa tctttccgat atatggccaa gttctccaca    60660
gggccattct cgccggttga gtccatgaga tagaagtaca gaccggtcgc ctcgtcccat    60720
ggctcatcat cattgaatat gtaacgaagc atgcgattga tgtatgcaat cgagccgttc    60780
gaaatcagcg ctacatatct tagctgaagc actttcctga tttcgtccaa gttgagaatt    60840
tcggcattgc cgccaccgta gaagttgccg ccaggcgatg cgtctgccgg tggcgggact    60900
tgtgtaccgc tatagatgaa gttctggcgt agccgaccga atgcccaaga actgttcttt    60960
ggataaaggc cgaaccctttt cgaaggcgtg ccgaggatga tgcaccaaac cataaggccg    61020
aacgggttgg cggtcttcaa gttgaaaacg tcgcgctccc agttggccca gaattggcgg    61080
ctgaatctgt cataccattg cgcctttctc tggatcaggc cggtgattcc aggcgcctgg    61140
ttatggagcc atttcagagc ttgttggatg tccgaattgt acgcaggcag agtcatacga    61200
aagtcacccg aacgttacca acggaaatgg tagcctggcc gaatgcgctc atgacgtatt    61260
ccgaagtgaa atcccggga gccggagccg gcgagccagc cgcgacgcac gcgacctggc    61320
agagtttgat gtagatgccg ggaatttcgc gagcgatggc accggcgact tcgaatgccg    61380
acagactcgc gcccaccacc agcccctctt ctccttcaac tttcccctgg gcgtaattga    61440
ccactgcgtt ctgaatggct tccggagcta cagaggagga gccttgctgg acggttacgt    61500
taacatatcc atcgtgcatg attggagtgg tccacttcac gacatacttt cgaccggacg    61560
ccggatcgcg cacaggaacg ccagtcggac cgtccaccgg gacgccgttg ttcgtcgcac    61620
catagtccca tggagttccg ccgttatggg cggcccacaa cgcatcggcg actgcttgtt    61680
tatccgggtt tccggcgacg cagacccaaa cagcatacgg aagggtaaac gagactccat    61740
tcaccacttg aacggcgccg gtgttgttct cgattacgtt caccgacgtg acgtttggaa    61800
cggcgctcac atacgccttg atggccatag tcgagttgcg gccttggatg gccaatcgat    61860
taacgcgggc attcttcaac tctgcatcgc tcatttggcg gctgcccgga tcgacgcgag    61920
tggaggcgat gactttcgct ccggaccagc caattgttcc gtcgatgatg atgagattcc    61980
cgaccggcag aggaatgttg ccatactcct gcgatttgat atcgatggtc gcgacaccac    62040
cagcaggaat cgtgacatca ctcatcactg tgaagatcgc gccggccgga gtctggaccc    62100
tagacccggt ggaaatgcgg gtttggctgc ggccggtgac ttgaactcca tagccgaagg    62160
ttgacaggtc agaaccgcgc tcgatcccca tcaaggcaca gatcgcgtcc aggaacgttc    62220
cgaatgaaac gttcgggttt atggtattgg caattcgcgc ttcattccgc atgacactgg    62280
aacgggcgat ggcctcggcc gcgacaagcg atccctgcgg agtgctcgcg gccaagttga    62340
tattggcacc gagggcggca cggaactcgg cctcaacgtc gctcagaacg tcggcggtat    62400
ctgcgactat cacaccagta tcgacgatgt agttgtagtt agccattaca accccccccc    62460
gctgttaaat cagaaaaatc aaaacttgcc atgaaaatct ccttaagcaa tcatgccgcc    62520
tttcgtccgg gcatcaggcg ggttgttttc gaggtggccg tggttgttca cgttgatgcc    62580
gtttacgacc agggtgttag cgatagtcac attgccggtg aagttcgcct gcggagtatc    62640
cacagtaacg ttcgacggcg cagttatctt gatgttatcg ccgcgaatcg aaattctggt    62700
cgctccggaa gtcgattgta tgaccatagc ggccgaatct tcggaattga tggtgtatcg    62760
acggaatacg tccgggatga acaggccatg ctcgaactta tggatgcggc cggtgttcgg    62820
cttcgacatt gacaacgact ccaggaactg agacgtgtcg cggtcggccg cataaatcca    62880
gcctatgtcg ccttgctgaa tcgggaaact tatgtggaag ccgccagccc ccatggaaat    62940
```

-continued

| | | | | | |
|---|---|---|---|---|---|
| tacaggaata | tcaaccagct | gatgcctttg | dacggcgttg | tgttcagtgt | caacccaggt | 63000 |
| gatgagaggt | tgaatcgtcg | cgatattctc | ggcccggtca | tattgaacaa | cctgagccgg | 63060 |
| tatcattact | tcgaaatcta | gagcatcccg | ccgcgaccga | gcgtcaagag | cggcgatcag | 63120 |
| tcgcgtcctg | tcgggagctt | ttgcggatgt | tagagaaata | ttggacatgg | gaaagcctct | 63180 |
| gattttgcag | gtctagtata | gccttcccag | gcccggttag | gaattatccc | ttttttgattc | 63240 |
| tgttgtgcga | tgcttcggac | gccaaggcct | cgttcacgct | cttcgccgtc | atgatatcta | 63300 |
| tcatcttaaa | ggcatcttga | gtcgaataat | actcttccaa | ctcgcgcata | gaggccgaac | 63360 |
| cgttcgctac | caaactcgca | actacagaag | gtgaatgtgc | cgtcttcaca | cttttgatat | 63420 |
| cttcgacaaa | tctggatgga | atcttgactc | cggtccagtc | tttgagaaaa | ccaaagttcc | 63480 |
| agtcgattac | cacttctgac | agcagtgcaa | gaacttgtac | gggagctatt | actttcgctc | 63540 |
| ggtcaacgac | ataaagattg | atgttcgcag | cggtcaatgg | aagccagatg | ccttccggat | 63600 |
| ggtcttccgg | atgcgccaat | acatcggtgc | ccttgagcaa | ttcttctggc | ggcacgctct | 63660 |
| gaatttccga | catcatgctg | agcccatcga | cagcagagaa | ttgccgcgaa | gtatagtgaa | 63720 |
| ctccgaacat | gttgaacgat | ttgatttccc | tggccattat | gctgctggac | tcccatgac | 63780 |
| tttgatatag | aacggccgat | cccgacttgc | caaatcgtat | tccagagcgg | ttattacata | 63840 |
| gttaccattg | acgcttggat | tcatgagaga | ttcgaccgct | acgcctccag | ccacacgaat | 63900 |
| cgatggctca | aacagacact | ggaattccac | gccccattca | gaccaagatg | gaattccaac | 63960 |
| aaacgagttg | acgttggtca | cctcatccgg | acgaatgact | ttatcgcggt | ccttcacgat | 64020 |
| caatatgtca | tcatcgacga | acgcggccac | gtccggcatg | tacatgtcct | gaatcgacgc | 64080 |
| caggattgcc | gacgcgacag | tgatagaccg | gcccggattc | ttcagaactt | gatcgttgta | 64140 |
| actggtatcg | cagatgaagt | tcaatcccat | ttcgttcgcg | ccccactcga | cgaacttgac | 64200 |
| aaacgtcgtg | ttggcgggcg | gcatattccg | aatggtcttc | gtcctgtcga | tttgcctggt | 64260 |
| atagcactgg | atgcggattc | caatgtccgg | tggcggagaa | atgatatcga | caatggcaac | 64320 |
| ttcgccgaca | aagactctgg | aaacttgctc | gcgcccctgg | tcagagtagc | cggcttccac | 64380 |
| cgacaccttg | atcatcaatt | catcttccct | gcccacttga | cgttgccgat | gcttccacgc | 64440 |
| ggtgaactgc | gacagaagag | actcgcgcag | ctgagtggtg | aggccgaaaa | tttccatcgt | 64500 |
| cgcccggttc | tgaatccgca | acgcagcctt | cataatccgg | acccgaacat | ccagatcttc | 64560 |
| gcggatgact | tcgggtccat | aaggcatgtt | gaatgttact | cgcagaattc | tcttttcat | 64620 |
| cagtagagta | tcttagttgc | ggaatcgttt | tgagcgtcct | ggattgccgt | agtcagctgg | 64680 |
| tctgcagtct | gcttgctgaa | tatctcgcga | gcctcttccg | gagaattcgc | gccggtgacg | 64740 |
| ttgaccaaca | tgtcgattcg | accgatggtc | agctcctggc | cgcgctctgg | agcgctcttc | 64800 |
| agaagttgct | cgccgtacgt | cctgagaata | tccatctctc | gcgatgcggc | gttcaccttg | 64860 |
| gccgtggctt | cggcaagctt | ggctggagac | aggaatacgt | tgttggcttc | ggtcgcggcg | 64920 |
| gccttgatct | cctgttgctt | gcccaggatg | gcttggttgt | atccgaacag | caagtcagaa | 64980 |
| cggctgattt | cgcggcgcat | gatctggttt | gggttaacgc | cgatcacttg | cgcgatggct | 65040 |
| ccggcagtga | gttgagcctg | gatgttctgc | ttggtctcgc | cgcgaacttg | attcgggaac | 65100 |
| ttccggaatc | cagaatctgc | ccggtcggcc | tcttgacgtc | tagacatctt | gaggatttcg | 65160 |
| ccgtcgctgc | ggtctggcat | gcggtcgatg | atgcgaattt | ccggtcgcac | aaccctgtcg | 65220 |
| tcatatcgac | gggcttcgcg | gcgctcatct | tccttcttgc | cctggtctgg | ggtttccagt | 65280 |

| | | | | | |
|---|---|---|---|---|---|
|cgcccgccat|cataggacg|aatgtccatg|tcgccgcctt|ccggggcgaa|cgtctcgttg 65340|
|gcgacggtca|tggccgcagc|cttctgcttg|cgctgagcct|cttccatcag|ctcgattgga 65400|
|gcgctcatta|ccaaacccgg|atatgcgcga|gtccttggac|cccagttctt|cggatcgagt 65460|
|ccgccatgat|agtaggtcaa|ggccaaccgc|atgtcgccgt|ttgctcgatc|taggttttcc 65520|
|cgcagtaggc|gcgttccgcc|gaggatgttc|tggcgagggt|catatacgtc|agtgatacca 65580|
|tacgccttgg|cgatttccgg|catcagctgc|atgaggcctt|tcgctccggc|ttcgctggtg 65640|
|gccctggcgt|tgaatcggct|ttcggtgtat|atgagtttct|tgatgtccag|ctcaggaatg 65700|
|ttgtacatct|tcgaagcatc|tttgatgata|tcgttgatgt|acgatggaac|ggtgaccggc 65760|
|tctgccttgc|gctgcggcga|gaacatgcga|ttgcgaagag|actgggcgcc|gattggctcg 65820|
|ccgaagacct|gtccggccgc|gccactcttc|gactgatcat|agatcgcgtg|cggatagacg 65880|
|ccggtggccc|gcgaagtcgg|cgcggtgctt|cccataccga|ccgcccgacc|aatttccccc 65940|
|gcccaggctg|cccaagcttg|gcgctcgtca|acggcattcg|cgaacgacga|taccgcgcca 66000|
|ctgaacatgt|tgatagccac|cgcaaaatca|ttggtagact|tcgtggtctg|gtcagccagc 66060|
|ttctctagct|cttttcatgga|cttagtagcc|ttgtcctggt|cttcttgttt|cttggctagg 66120|
|tcttcgctgg|tttgagcgcc|gggaaccttg|tccttgtcga|tgagccctga|ttcttccatg 66180|
|ccgcgacgag|tccccacgc|tgccaggcga|ccgagcaggg|cgccggggct|gagtagggat 66240|
|aggatatcac|tgccaacggt|cgccttcccg|agcactccat|cttcccaacg|ggatttggtg 66300|
|tccttcgcga|agctttccac|ttcattggga|atagcctgga|ctatcttgtc|gatgatttcg 66360|
|atcagcttgg|tgaacgcagg|cgcgagcttt|tcgccgactc|ggttttccag|ggtagtgaac 66420|
|gtctggttga|gattcgccag|ggcatcgttg|aatttctgga|tgttggactc|gccctggacc 66480|
|ctggactgga|gttccgcagt|cgtca| | |66505|

<210> SEQ ID NO 7
<211> LENGTH: 43145
<212> TYPE: DNA
<213> ORGANISM: Bacteriophage P1940

<400> SEQUENCE: 7

| | | | | | |
|---|---|---|---|---|---|
|atggttccac|gcgatcccga|acggcggtag|ccgtggcgac|gacgaacagt|cgcgcaagat 60|
|acgcggcggc|cagatgaagg|ccgaaggcgc|acggcagggc|atcgccgata|cgttcttgcc 120|
|ttggccggtc|tacgaacaaa|gcccgaccga|ttcgcaacaa|atggtcgtaa|aatggtgcgg 180|
|cctttatatc|gaaatgaaga|agccatcgct|tcgcccgaag|tctgccgaag|ccaaaggcgg 240|
|cgcatcggac|gaacaaatag|ccttcggcca|gtacgcgcag|cgcgtcggct|atgggtgggc 300|
|cgtctgctat|gattgggaac|aggccgttag|ttaccttcgt|agctatatcg|aatgggggca 360|
|gaaatgaaca|agacgaagc|cgccgcactg|ttcgaacaag|tcaaggcgaa|ccgtgctaag 420|
|attgacggat|gccgaaaaca|ccgcttcgac|attggcgacc|cgccgtatcg|cttcggacag 480|
|aagttcgtat|gcgccaactg|cggggggcgaa|atggacgccg|tacaggcgtt|ccgctactgc 540|
|caaggctacg|aagcggcggg|cggcgacccg|aacgaagtta|taccgggctt|ccgctaatgg 600|
|attgcctgaa|atgcgaacta|acacgcgcga|agcttaaaac|ggctggcctg|ctaattgtgg 660|
|gctggccgtt|gtcgcgtatt|gctgaacacc|tttcggactg|ctacggcgaa|cggtactacg 720|
|tcgaaggcga|caacctgtat|cgcgcgtcga|agcttccgcc|gtatgaaccg|cacttgataa 780|
|ggagtaatgg|caatgacgct|tgacgaagcc|aagaagaagg|cgcgcgaaag|ccgttgtttc 840|
|atcgtaacga|agcctgattg|tttcttgctg|taccgcgaat|gcgaaccgaa|gaacgtatgc 900|

```
gtcggaaagc gcaaggacga aaaaggcatc atcgcgctag tgaaaaaagc ttgcgcgacc      960
gcttgacgta gtttcgaaac cgtcgtagac tatgcccata gtcaacgaac aagggggcacg   1020
aaatgggcgc atacaccgta acaactgaat tcgaaatgaa cgacggtcgc attctgtcgt   1080
gcgaatacgg cgtatcgttc accccggtt atatcagcgg cccgcccgaa cactgctacc    1140
cggacgaaag cgaagtaggc gaaccgacgt actatatcga cggcgaagaa gtcgattaca   1200
aggatttgcc gaaaggtctt gacaagatcg ccgataagtt gtacgaagcc gggccgggcg   1260
aatacggcta caaagaaagc gaaccggact acgacggccc ggacttcgaa cccgacgact   1320
attactaagg agttaccgca atgcctaccc ttgccgaact gttttggcac ttcgtaacgc   1380
tgtccagcgg cgtaactatc ggcctaatgt tggctgcatg gttgcgtatg caatcgaaag   1440
tgaccgaaga aacctacgac accgattgcg aattcgtaac cgaatatatc gccaacatgg   1500
aaagcggccc gaagatcatt cgtcgcccgc tgtcgcaatg gccgatatgg gcggacagca   1560
ttaacccggc caagacgaac ccgcccgaac ctgaaccgcc gattcgcatt gaacgaaatt   1620
ttatcggcaa aaaggattga caaccattcg gaaccgtcgt agtcttgttc gtaccaactg   1680
gcaacctaaa ggaatcgccg ccatgtacgc acttattctt atcgcttgca ctgtcgttgc   1740
tgtcgctatt cacttcgggc ttatccgtcc cgtaatgcac gccatcgaac gccagcgcga   1800
agaatcgcgg cgtcgtgcgg cgcttgaagc tggcttggcc gctgcggcgc gcttacaggc   1860
gttcaacgcc cgtaagccgt cgaatcatcg cggcgcaaag ctgaacgccg aacgcgaatg   1920
gcggtcgcag gaatgaagcg cggacacgtc atttacacgc acccgacga actgtcgaaa    1980
tgggatcgcc ggtttatcga actggcggaa caagtcgcgt catggtcgaa ggggccgcgc   2040
aagcgcatag gcgcggccat cgttcggcct gataggtcta tcgcgtcgct tggctacaac   2100
ggcccgccgc gcggcttcga cgatgaagcc ttcttgcgca tgacgcgcga agaacaacac   2160
gccgtcgtaa ttcacgccga agcgaacgcc attgcgcagg cgcacgacgg cgaagccttg   2220
gccggttaca cgctgtacgt gtcgccgctg tttccctgcg ccgtctgcgc acgcttgatc   2280
gtgtccgcag gcatccggcg tgtcgtcgcc tattgtgggc acatttcccc ggactggcgc   2340
gcgtctgccg atgaagccga agaagttttt atcgctgcgg gcgtcgaatg tctgttcagt   2400
atggattaac gaagatgacc ctagaccatt cgcaaatcga aggactgttg ttcttcgaag   2460
accccgtaac gcataacgta atcggcgcag ccaaggccgc accgctggac atggccggac   2520
acttcgtcgc attcgggccg cgcatcaccg ttgacccgca gttgaagaac ctgtttcttg   2580
ccgcgccgac gctgtatcaa acgctgtcgc aacagtacca agcgattcaa ggtcttatcg   2640
aaatcgccga aggcttgccg cagacgccgg aacttgataa gctgcaacgg tcgttcgtcg   2700
aaatgcaaaa cggcatgtta atggcgcagc ttgtcgcgca aaaggtatc gaagaagtag   2760
cgaattcgct tgacaagctt tagaagcggt cgtagaattc ccaacatcga aacgaaacaa   2820
ggtgcccaca atgacccgca acgctaagaa ttggttaatc gccgccgctg ttgtcgcagc   2880
attgggcatc gtcggttcga tggattacgc cgacgaagtg cgcgaacagg tttcatattg   2940
cgaaaacgtg aaggcgggcg tatgcccga ctacaacggc acgtatgaaa ctgaatgcac    3000
cgccgaacgt ctgaaagaat atcaagaaat tttgcgttga ccgcttgaca cgtcgaacgg   3060
tcggcgtaga ataaccctg tcgcaatcac gcgacgctaa cttaccttcg aaggagttac    3120
acaaatggct agcaagaagt ccaccaagaa caccgccgcc gctgttgccg ctatcggcct   3180
tgccgaaatc gttgcagccg gggcaaacgg tctgtatact cgccccgaag ttcacggccc   3240
```

```
gcttgtcgaa cagggcttcg tcgaactgaa ccccgccggg ccgaacgaat ccggcgaaac    3300
tctcacccgc gccacgcaga aaggtatcga aagcatgaac accgcaaaca acaccgccgc    3360
ccccgccgct tcggccccgg tcgccccgtc gtccttcgcc atcgaagacg gcatcgccat    3420
gccgaccgct tccggtcgcg gtcgtggcgg caacgtgtac cccttcgacg ccctgaacgt    3480
cggccaatcg ttcttcgtcc cgaacaccga agacaagccg aacgccgcca agtcgctggc    3540
ttcgaccgtt tccagcgcga ccgcgcgtta cgccgaagtc gtcgaaggcc agttcaagac    3600
gaacaagaag ggcgaacagg tgcccgtgac ccgcgaaacc cgcaagttcg ttgttcgcag    3660
cgtcgaaggc ggcgcgcgcg tctggcgtac cgcctaagcg ccccggcgtg cggcctacgg    3720
gccgcgctac ggccagaacg aagccccggc actgtccggg gcttcttttt gcctttctgc    3780
tggcctacgg ccattttttc gggtactatc gggacaattc ggggcgcagt tcgccccttg    3840
cgcgtattaa ggggctacgt agtgccattg aacaacgaag cggggcagga tatgaacgaa    3900
cgtccgcaga agatcataga cgcaaaattg ccgttacctt ggcttatcgg ttcggcttgc    3960
gccgtagtct tttcaatggg cggcgtattc gtcaaactgg acgccgtagg cgcatcgctt    4020
acgaagctgg aagcgaagac cgacacgcgc gacgaacgaa tttcaacgct gcgcaatcg    4080 ttgatacagc aggccggaaa gaacgatacg caggacgcgc aaaattaccc gcaacgccgca    4140 gacattaccg acttgaaacg cgacgttgaa gacatacgca agtcgcaacg ttggatgccg    4200
aagtaatgaa aaagaaagtc gaactaatcg aagattggcg caccgcccat aagctttggt    4260
cggttcgact gtcggccatc ggtgccgccg taatgggcgt gtttaccgta tggcccgaat    4320
ccgcgttgta tctttggtcg gccatgccgt ccgaagtgcg cgcgttgatc cccgaacggt    4380
tcgtatccgg catcgcgctt ttcgtattca ccatgtccgc actgtcgcgg atcgtcaagc    4440
aaaggccgaa gaatgaacga atcgaacgaa agcccgcaga agaaacagcc gaataaaaag    4500
acgcttgcgg gcgtccttgg cgcaggtgcc gccgcaatcc tgctaggcgt agccgggcaa    4560
accggcttta ccgaacgctt cgaaggcatg gttcttcgcg gctaccttga ccctatcggc    4620
gttccgacga agtgcgcagg cgatacatac ggcgtcgaag tcggcaagcg atacaccatc    4680
gaagaatgcc gcgaatcgct ggaacagggt ttgattaaac acgccgaacc cgtgttgaag    4740
tgcgcgccga acctgcgaac gcaaggctac cccttcgcac tggccgccgc agtcgatcat    4800
aactaccatt tcggcacgtt ctgcggaact tcaatcgacg cagcgtttaa gcgcggcgac    4860
tatcgtacag gttgcgcacg cttcaacgaa aacgccgcag gccgtccgca atgggtgtac    4920
gtcaaggacg gcaagggcgg ttacaagacc cttcccggcc ttatcacgcg ggccgcagcg    4980
cgccgcgaac tttgcatgaa aggggccgga taatgtgggc tatcatcgta gcgggcgcaa    5040
agcgtttcgg cggctggatt ctggccgcat tgtcgtttct ggcaatgctg gcgacagttt    5100
ggcttacgtc ccgaaaagtc ggtaagtccg aaggacaagc cgaagcggcg aacaacgcg    5160 cagccgaccg cgaaactatc gcagtacgcg aagttaacga agcgcgcgaa gcttccgaac    5220
gtcaaacaaa ggcggtgcaa aatgcgaacg aagttgcttc cgataatgct gttcttgacg    5280
acgacggcgt ttctaagcgg ctgcgcgacg aatggtcgcg cgactaagcc gccgcaatcc    5340
atcgccgaaa ccgtacaaac gaagcccgta gtaatcgaca cggcttgcga ttgggtgcgg    5400
gcgatttggg tttcgaagtc ggacgacata acgcccggca cggcgcgcca aatcctgaac    5460
cataatcaag ccgtcgtaaa gaactgcggg ccgcagaaac cgcccaaggt cgattcgcct    5520
taacagaacg tcggccttgc ggtatagtga aggcaaatgc gaatgacagg ccgacgccat    5580
gaccgaccaa cgtaacgaat ccgaagaaaa ggccgcatat gcggccttgc ttttgaagga    5640
```

```
acgcgacccc ttcaaggctg cgcttcaact gttccccgac aacacgaatc gcgccctatg   5700
ggtggcgaat cattggccga ttgacgccga agtaaaggcc gaacaagaac ggctaatggg   5760
cgaagacgac ggttcgtcgt tccttccgtc gaaggccgaa cttgcccgcg acatttggca   5820
acgtatgcag ggcacgaccc ttgcaaacgg cgtgaccatt ccgccgaccc ccgaagaata   5880
cgcgaagctt gcgaagcttt atgccgacgt tcgcgggttc atcgaaaagc cgcaaacgaa   5940
tgtgaacgta acgacgaacg tacagcgtgt cgtcgaagtt cccgttttcc aaagtgaaag   6000
cgaatgggaa aacgccgccg cacgtcaaca gcgggaattg ttagaaaatg cccgcactcg   6060
ccattaaagc gccagaagcg ccgccgctga ttctacagaa agcgccgcca atcgaagtcg   6120
tatttaagcc gcttcccggt tcgcagacta tcgcgctttg ttcgcacgct gcgcataccc   6180
tgtacgaagg cgcacgcggc cccggcaaaa ctttaacgca gttaatgcgc tattaccgta   6240
acgtcggcaa aggttacggt aagttctggc gcggcgttat cttcgatctt gaattcgacc   6300
atttggccgg acttgtcgcc gaatctaaaa aatggttcgg cgataatggc aagctgaaag   6360
acggggcgaa gttcttagaa tcaccgtcgc aatacaaatg ggtttggccg actggcgaag   6420
aactgttgtt tcgccacgta aaaaaggtcg ccgattacga aggcttccac ggccacgaat   6480
acccgtatat cggatggaac gaattaacga agcatcctag cggcgacctg tacgacaagt   6540
ttatgtcggt caaccgcgtt acgttcgatc cgatcaaaga cacgccgaaa gacccgaaga   6600
ccgggcgtta tttgacgcct aacggcctgc cgttgcctga atcaagtgc gaagtattca   6660 gcacgacgaa cccaagcggc cccggtcata attgggtgaa gaagcggttt attacaattg   6720
cgccgcgcgg cactgtcgtt cgtcgcagta tccagattta taacccgaag accgaacaag   6780
aagaaacgca cgtaattacg caaattgcga tcttcggttc atacaaggaa aacccgtatc   6840
ttccggcgtc gtatattgcc gaactggaaa gcattaaaga accgaacctt cgcaaagctt   6900
ggttgtatgg cgattgggac gttaccgcag gcggcgcaat cgacgacctt tggcaatcgc   6960
atatacacgt cgtaccgcgc tttgtcgtgc cgccaagctg gcgcatcgac cgcacatacg   7020
acgacggcag ttcgcacccg tttagtgtgg gctggtgggc ggaagcggac ggcaccgaag   7080
cgactatcgt tctttccgat ggaaccgaat tcgtgttctg tccgcaaccg ggttcgttga   7140
ttcagatatt cgaatggtac ggatgcaaga aggacgaaaa gggcgaattc ttgccgaacg   7200
tcggtcttaa aatatcggcg tcggacgtag cgcaaggcat tatcgaccgc gaagtttcga   7260
tgatggcaaa cggctggatt tcgtcgcagc cttggcccgg ccctgcggat aatcgcattc   7320
gacaagttat cgacgttgaa ctagatacga ccgaaaagct tatgtcgaag aagggcgttc   7380
gctggatgga atcggacaaa tcgtcgggtt cgcgtgttat cggcctacag cttttccgcg   7440
accgactaga agcgtctgtt aaacgcgaag gccgggggt atacttcatg tcgaattgcg   7500
ttgcaagcat tgatattttg cccacattgc cccgcgacga aagaaaatc gacgacgtag   7560 acacaagcgc agaagatcac gtttacgaca tggtgcgtta tcgtgtattg aaaggcgcga   7620
acaaagcggc tacgaaagtc aaagtatcaa tgccaactta aaggaatcga atcatgccg   7680 aacgtatctt ttgtgcgtcc tgaactgtcg aagttgcttc ccatgtacta ccttattcgg   7740
gacgcaatcg caggcgaacc aacggttaaa gaagcgcgga cgaagtatct tccgatgccg   7800
aacgcttccg accaatcgaa ggaaaacaag gcgcgttatg atgcgtatat cgcgcgggcc   7860
gtgttctaca acgtagcccg tcgaaccctg ttcggtctta tcggacaggt gtttatgcgc   7920
gatccggtcg taaaggttcc ggcgctgctg aacccgcttg tcgcaaacgc gaccggatcg   7980
```

```
ggcattaacc ttacgcagct ttcgaagaag gccgtatcgt tgaacttggc gtattcgcgc   8040
gccggaattt tggtcgatta cccgacgacc gaaggacagg gcggcgcgtc ggttgccgaa   8100
ctggaagcgg gcaagattcg cccgacgctg tacgtctatg cgccgaccga aattatcaat   8160
tggcggacga ttgatcgcgg cgcggaagaa gttttgtcgt tggtcgttat ctttgaaacg   8220
tggtgcgttc aagatgacgg cttcgaaatg aagaacagcg gtcaattccg cgttttgcgt   8280
ttggacgacg aaggttatta cgtccatgaa atttggcgcg aaccgaaccc gaccaaagcg   8340
gacggtacga agattccgcg cggcaattac caacttcacg aagtattcaa gccgaccgat   8400
gcaaacggga atcgccttga cgaaatcccg tttatgttca tgggttccga aaacaacgac   8460
gttaacccgg ataatccgaa cttctacgac cttgcgtcgc tgaacttggc gcactatcgc   8520
aacagcgcgg attatgaaga atcgtgctac gtcgtaggcc agccgacgcc cgtacttacc   8580
ggcctaacgg aagaatgggt taacaacgtt ctgaaaggaa cggtcaactt cggatcacgc   8640
ggcggcattc cgcttccgac cggggccgac gcaaagctgt tgcaggccga acctaacacc   8700
atgcttaaag aagcaatgga cacaaaagaa cgccaaatgg tcgcacttgg cgcaaagctt   8760
gtcgaacaga aagaagtaca gcgcaccgca accgaagccg aattggaagc ggcgtcggaa   8820
ggttctacgc tgtccagcgc aacgaagaac gttagcgccg cgttcgaatg ggcgttgaaa   8880
tgggcggcgc gctggatcgg cgcgggcgac gctggcgtta agttcgaact gaatacagat   8940
ttcgacattg cccgcatgac gccggacgaa cgccgccaga ttatcgaaga atggcagaag   9000
ggcgcgatta cctttaccga aatgcgtaca gggcttcgga aggctggcat tgccaccgaa   9060
gacgacgcga aggcgaaggc cgacattgcc aaggacaccg ccgaagcgat ggcccttgcc   9120
atgccggaca acgtgccggg cgacggcaac acgcccccgg ctggtaatgt gggcaacggg   9180
ggtgcgtaat catggcgcta tcggataaca agcgcctata cgacatttca acgcggcttg   9240
ccgtatatgt cgaaggcgtc aaagttcagc agtcccgcca attcaacttc gtattgcgcg   9300
atattagcga agttctgaaa aagcttcttg gtcgtgttcg ttacaagacc cttgacggtc   9360
tttcgaaggc gcaactaaat aagcttgtcg cagaactgcg cgaatcgcaa tcgaagattt   9420
acagcgcgta cacgtcgcag cttatcgaac agcttaaagc gttcatggct gcggacttgg   9480
aagtaaaccg ccgcgcatgg gttacgggct atatcgaact tgacggcgat tcgccggacg   9540
aaattatttc ggacgaagac gcaatacagt tcttaatcga agccaacgac agcggcgcaa   9600
atccgttgtt cggcatcgcg gccattactg gcggcgacga acgtatttgg tcgcaagtta   9660
cgaattcgcc gcttccggcg aacgggcttt atcttctgcc gtttatcaag acgtttacaa   9720
cgtcggcgca agcgtcaatc gaaagcatta ttcgcaaggc atgggcgaac cgctggactg   9780
ttgacgaaac cttgcgcgaa atcatcggcg aagaaggcgc acgccaaggc acgccgtcgc   9840
agcttgcgcg gatcaataat caagccgcgt cggttatcca taccgccttc gcgcatactg   9900
cggcaatcgt agcggctggc gtagcgtctg cggttttcag ttggtacatt tggttttcgg   9960
ttatggatgg caacacgacc gaaatttgcc gaagccgcaa tcgcaagcgt tatcggtttg  10020
gggccgggcc gttgccgcct gcgcacattc gttgccggtc gcatactgcc ccggcgaata  10080
cggctagtga cctaatcgac gaaacgtttt atacttggct tgcgcgtcaa ccgctggaag  10140
tgcaagacga catattaggc accgaaggcg gcgaagcttt acgcgatggc aaattgaaag  10200
cttccgatat tccgaagtat gaagccgacg aaccgctaac gcttgacgaa ttccgacgca  10260
agattaaaca gattctttcc cgctgatacg gtgtatcggc ataacctgta ggagtcctac  10320
gaaatggcac tgaaaaagcg tattaccaaa gaagaacatt cgaagcttgc cgacgcgctg  10380
```

```
aaattcgaat acgtcgaaga cggcgacggt ttccgtctgg acgttgacgg cgacgaagac   10440
accggcccgc ttcgtcgcgc gaaagatcgt gaagcgcagt tgcgccgcga tgctgaaaag   10500
cgcgccaaag aagccgaaga ccgtttggcc gaactggaag cgacgacgc ccgtaaaaag    10560
ggcgacattg ctacgctcga aaagtcgtgg caaaagaagc ttgacgacgc gaacgccgca   10620
tcgcaagcca aaatcgacaa gcttacgtcg catacgacga aaaccttgt cgataacgtc    10680
gcgctgtcgg tcgcaaccaa aatcagcaac gcgccgtcga tcatccttcc ccacattcgc   10740
gcgcgcctgc aagcgaactt cgacggcgac gaaccgacga ccgttgttct tggcaaggat   10800
ggcaagcctt ccgcaatgac catcgacgaa ctgtcggcgg aatttgttgc aaacaaggat   10860
ttttctgcta tcatcacggg cagtaaggcg tccggcggtg ccggtaagcc ttcgcaaaac   10920
ggcggcggtg ccccgaagat ttccggtcaa tccgacaaac ccgccgacct ttcgaagatg   10980
aatccgcaag aacttgcggc gcatctgaaa gaagcgaagg ctactactga ataaggacgc   11040
tttatcatgg cactttccga cctcgcggtt tactccgaat acgcctattc ttcgttttcc   11100
gaagtcctgc ggcagcaaat cgacctgttc aacgctgcaa cgggcggcgc gatcatcctt   11160
caaggtgcgg cgcaccaagg cgactttagc gacgtggcgt ttttcgccaa ggttgcgggc   11220
ggccttgtcc gtcgtcgtaa cgcctacggt tccggcgctg tcgccgaaaa ggtgatgaaa   11280
caccttgtcg atacttcggt gaaggttgcg gcaggtacgc cgccgattcg ccttgacccc   11340
ggccaattcc gttggattca gcagaacccg gaagtcgcgg gcgctgcgat gggccaacag   11400
cttgccgtcg atacgatggc cgacatgctg aataccggcc ttggcgcgac ctacgccgcg   11460
cttacgcagg ttgcggcggt caagtacgac gctaccggca acaccgcgcc ggacgacggc   11520
ccgacgtgga acaacctgaa caacggccaa gcgaagttcg gcgaccaatc gtcgcagatt   11580
gcggcatgga tcatgcacag cacgcccatg cacaagctgt acgcaacaa cctgaacaac    11640
tccgaacgcc tgttcaccta cggcaccgtc aacgtgattc gtgatccgtt cggcaagctg   11700
ctggtgatga ccgacagtcc gaacctgttt gcggcgggta cgccgaacgt ctatcacatt   11760
cttggccttg tgccgggtgc ggtgatgatc ggccagaaca acgacttcga cgcgatggaa   11820
gaaggcaaga ccggcgacga aaacctgatt cgggtttacc aagccgaatg gtcgtacaac   11880
gtcggtgttc gcggcttcgc atgggacaag ggcaacggcg gcaagtcgcc gaccgacgcg   11940
gccctgttca cttcgacgaa ttgggatcgt tacgccacgt ccgaaaagga tttggctggc   12000
gtcatcgtcg aagttcacta accaacgaac gaacgggcgg ggcttcggcc ccgttcgttt   12060
aacgttccca aacgaaggag ttacgaagca tgaaacctgc aaagattctg tttttcgtcg   12120
atggcccggc accgaccccc gaagatttcg ccgcagccgc cgaactgaac gcaagcgttt   12180
cgttccgcaa cgcacgcgcc gtaccgtccg aagcgcattc gctggaaatc tgcgacggcg   12240
tggcgggcgc agttccgccg atctacgccg aaaagttccc cgacgccgcc gaagctatca   12300
agaagaaggc cgccgaactg aaagaactta cttcgaaggt cggcgacagt ccggcaccga   12360
aggccaaggg cggcaagacc ggccagcaag cgccgcagca gccgcagacc ccggccccg    12420
caactggcgg ccagcagccc gcagcgggcc agcaaggcgg cgacgcgccg tcgtggaacc   12480
cgaacccggc gcagtaaggc cgggcgcagc gtagggcgcg gcctgttcgc ctagtgtggg   12540
caggccgttt ttataggcgc aacgaaagga cagacgaaca tgcaacgcat tgtctatttt   12600
accgcaggca ttaccccgac ttcgggcgaa ctggccgata ttgccaaaact taacgcagcc   12660
gccgaagccg cctacgaagt caccgtagtt aacggcgcag cgaatgcgaa gtatggcgaa   12720
```

```
acgaaccgtc ttattccgtg cgatttggtc gcgggcaccg ttccgaccat ttacaacgcg    12780
aaagaagtta tcgaccccga cgcaatcccg gcgcgcggtt tgtcggatac gcaagccgtt    12840
gtcgaaaatg gcgaagcgtt gacagttccc gttactggaa cttacaccga taccgcaacc    12900
gttaccgtcg tcgatggcgc tgtaactgcc attgcacttt cgtaaggatt cggcgtcatg    12960
gcaattacta tcgtagtcga agacggaagc ggcgtagcca acgcgaacag ttacgtaagc    13020
gtcgcggatg cgcgcgtata cgcgaccaat cggggcaccg aacttccgtc caatgacgac    13080
gaagtagccg cgatgctgat tcgtgcgacg gactacctag aagcgcagga atgccggtat    13140
caaggcaaac gcacgtcgcc gacgcaggcg cttgcgtggc cgcgtaccgg cgtattcctg    13200
aactgcgatg aagtcccgtc gaacgttatt ccgaaatcgc ttatcgccgc acaagttcaa    13260
ttggcgatgg cgattaacgc aggcttcgac ctgcaaccga acatttcgcc gcaggactac    13320
gtaacgcgcg aaaaggtcgg cccaatcgaa acggaatacg ccgacccggt agccgttggc    13380
atcatgccca cgtttaccgc agcgaacgcg cttcttgcgc cgctgttcgg cgaatgcgct    13440
tcgaacaagt ttgcacttcg gacaattcgg gtttgacgta tggcacgctt cgaccgcgcg    13500
attcaaacgg cgttgcgatt gatcgcaaag aacggcgaaa aggtgaaatg gcgcgtcatt    13560
gacgacgcag ccgcgcccga tccgtcgcag ccgtggaacc ccggcccggc aacgcccgaa    13620
gacaaggacg taactatttg cttcttgccg gttgatcggc aaacgatgga acatttacg    13680 tttatcaaag gcaccgaagt tccgaagggt tcggtaatgg ggcttatggg aaacgtgccg    13740
tttaatccta acttgaaaga cgtagttatt cgggatggcg tagaacttcg aatcgcaaat    13800
atcgacgttc tttcgccgaa tgggcaaaag gtactttaca cggtagtttt tcaagcatga    13860
tcgaatttga ccaagcccgc gacgaaatca atacgctgtt tcttacggcg tggaacgcta    13920
acgcgggcgc ggtcgtcggc tatgttcccg aaattcgttg gcagggcgta caataccgag    13980
atttgccgga cggttcgaag ttttgggttc gcgtgtcgaa acaaaccgtt ttcgaagaac    14040
aaacaacgct ttcaacttgc gaaggaaaac cgggacaaaa acgttatacg gcgtcggggc    14100 ttgtttcgt gcaagtgttt tgcccgaaat cgaatacgca agctttcgca cttggtcaaa     14160
cgctggcgaa gattgcccgc aatgcttttc gcggaaagac tacgccgggg aagatttggt    14220
ttcgaaatgt tcgcataaac gaacttgacc ccgaagaact gtacgaacgg tttaacgtcg    14280
ttaccgaatt tgaatacgac gaattaggtt gaaggagtta cgaaaatggc cgattgcgct    14340
atcaacaaaa tcgactcgaa cattaccgga ctggcgtatg ccgaagaaga atgcttgaag    14400
caacttccgg cgtccgtcac ttggtacgga ctggaaccga acagctattc ggacttcggc    14460
ggcgaactgt ccaccgtagc ccgtgcgcct atcgacccgt cgcgccagaa caagaaaggc    14520
acgattaccg atcttgacgc atcgggcggc ttcaattcgg actttacgaa gtcgaacctt    14580
actcgcattc tgcaagggtt cttcttcgca gacgcgcgcg aactgccgtc tactgcgccg    14640
ctgaacgccg cagctatcgc aatttcggct gtcgatgctg cgacgaaaac ctataccgtt    14700
gcaagcggtg gcgcggcgtt cgctgcgaac atgcttgtca acgcaaccgg cttcgcaaac    14760
gctgcgaaca acggccttaa aaccgtcgct tcgtccaccg caacgactgt cgttgttaac    14820
gaaacgctta tcgacgaagc cgcgccgcct gctggcgtga actgaagt cgtcgggcgt    14880 caactggccg cagccgatgc gaacatcgcc gttacttccg gcgtcgcttc gttggtcgtc    14940
accgctggcg actttacgac catgcccgaa ctgttcccg tcgttgggt gttcatcggc     15000 ggcgacgcg cgtcgaaccg ctttgcaaat aatgtgggct acgctcgcat taagtcggtt    15060
tcggcgaagg cgcttgtttt cgacgatacg accttcgcgg ctgcaaccga aaccggaacc    15120
```

```
ggcaagtcga ttcgtctgtt cgtcggcgtc gttatcaaga acgaaaaaga cccggccctt   15180
atcaagcgtc gttcgtacaa catcgaacgc acgttgggca acggcgaaaa cggcgttcaa   15240
tgcgaatact tggaaggtgc ggtagccaac gaatttacgt tgaacattcc gcaggccgac   15300
aagctgaacg ccgatcttac gttcatcgcg tgcgataaca cgcaccgcag cggcgacccc   15360
ggcgacgaac agaaggccgg tacgcgcatt tcggcaccgg gcgaagatgc gtacaacact   15420
tcgtcggaca tttaccgtat caagatggca gttcacgacg acacttcgtc gaatcctgcc   15480
gccctgttcg gttacgtgtc cgaagcgaac gtttcgatta acaacaacgt tcgccgaac    15540 aaggccgtcg gtatcttggg cgcgttcgac acgacggcgg gtaacttcga agtcggcggt   15600
tcgattaccg cttactttac gaccgtcgca gcggtgaagg cggttcgtgc gaatgccgac   15660
gttggtttgt cggttatcag cgcggcgaag aacgccggtt tcatcttcga tattccgttg   15720
cttggtttgg gcggcggtcg gttgaacgtc gaaaaggacg cgccgattac cgttccgctt   15780
gaacccgcag gcgcggaaaa cgaaaacggt tatacgatgc tgtacgaagt gttttcgtac   15840
ctgccaacgg tagccatgcc cgattaagtc gggtacactt gaagggccgg acttttccgg   15900
cccttctttc atccatcgga gtaaatcaaa tgtctggact gtttaagcaa ttcaaaacga   15960
attcggcgaa ggaaaccgaa ggcgtcgaaa tcgaatttcc cgaagcgcag aacgacgacg   16020
gcaccgttcc cacgttcatc atttcgcgca tgggcaagtc gaacaaagcg tattccaagt   16080
cgctggaagc cgcgacccgc ccgtatcgcc gacaggtcga attgggcacc atgaaaaacg   16140
aagtcgccga acagcttttc atgggcgttt tcgtcgatac catcctgcgc ggctggaaga   16200
acgttcagga cgaaaagggc gaagccatcg cctattcgaa ggacgcggca atttcgcttc   16260
tgtccgaact gcccgacgtt tacgaacgtc tgcaagaaga agccaagttg tcggccaact   16320
tccgcgattc ggtgttggaa accgaatcgg gaaactgata gaagttctag cgtatctgtt   16380
cgaactaggc ccgcacgaac agaccatagc aaaacaggcg atgcggtcgg gccagccgtt   16440
acccgaccgc atcgccaacg cgccagaact tgaaccgggc ttgcagttgt atttgcaagc   16500
cttcttcgat ttggatagcg aacgaacgca cgcaatggga ttgacgccga ttccttggac   16560
aagtattgcg gcgtatgcgt cggcattcga attcgacgaa gaacagcggg aagacttgtt   16620
ttattttgtt cgtaaactgg attcggaaca tttgaagaaa ctagaagcaa agcataaggc   16680
gaataaaggc aatggcaaac gaccttctaa gtctggccgt tagtctggaa cgcaaggcta   16740
aggcaatcga cgaagcggct tctaaagcag ccgtcgatac tgcaatggct attgtgggcg   16800
acttggcgta taagacgccc gtagatactt cgcaagcttt gtcgaactgg cgcgttacgc   16860
ttgattcgcc agcaaccggg acgattgcac cgcattaccc cggcattcaa ggttcgtcgc   16920
aacgggcaag cgcagccgaa acgatcaacg cggcaaaaag cgtacttgca acaagaagc    16980 ccggtcaagc gattttttatt acgaacaacc ttccgtatat caaacggctt aacgacggat   17040
attcagcgca agcgcctgcg ggattcgtcg aacgtgcggt attgattggc cgcaagatgc   17100
ttgcgaagtt caagattaag gattaagacg aaatggccga aacatcgaa attaaagtac    17160 aggataaagt cgattcgtcc atttcgacca agcttaaagg catcgcttcg gatgcccgca   17220
ccgccgacag cgccgtaaag gcgttgcaat cgtcgttgaa gtcgatttcg gcttcgtccg   17280
gtctttcgcg ccttcaaagc gaacttgcac gtaccgccat tctacagcag aagcttgcca   17340
ccgaaacgca gaaaacgcaa gtcgcaatgg cgaacgttga agcggcgttg caacgtgcta   17400
tcgcagccga agccaaggcg aacgccgcga ttaaccaact ttccgccgcg caatcgaagg   17460
```

```
ccgccaccga agcgcaacgt ttggcgacgg cccaacagca aaccgccgcc gcagcggcgc    17520
aggcgcaggc cgcacaagcg aacttggccg cagcgcaaac caacagcgcg accgcatcgc    17580
agcggcttgc cacggcgcag caacagacga ccgcagcaac ggccaacgcc gccgcagcgc    17640 agacgcgcg ggctacggcg caggtacagg gccagaccgc cgcgcagaac cttgcagcgg    17700
ccaccacgcg cgccagcacg gcccaaacgc aggggggcgaa cgctgcgcag cggcttgcca   17760
ccgaacagca gcgtacagcc gtccagacgg ccaacgcggc agcggccaac gaccgggcgg    17820
cccttgcagc cctgcggctg gcccaagcgc agcagcgggc cgggcaggcg tcgcagaccg    17880
caggccagca aatcgccgga tatgtcaaag ccgccgcagg catcgcaggc gtaacgctgt    17940
cggctggcgc tattctcgca tcggcggacg catatacgac gctgcaaaac aagttgcaga    18000
acgtcaccga atcgcaatcg caagtcgtaa cgcttacgaa agaattgttc gacttggcga    18060
accgcacgcg cgcgggcgtc gaagaaaccg cgacggcgtt tacgcgcttt gatcgtgcgt    18120
tgaagttcat gggcaaatcg caagaagatt cgttgcgttt gaccgaaacc attaacaaag    18180
cccttatcgt ttccggcgca actgcgcaag aagcgtcgtc ggctttgttg cagctttcgc    18240
agggcttcaa cgccggtaag ctgcaaggcg acgaattccg cgccgtatcc gaaaatatgc    18300
cgatggttct tgacgcagta gcgaaggcgc ttaacgtgcc tatcaaccgc gttaagcaac    18360
tttcgaccga aggcaaaatc acgtccgaag ttctgtttaa cgcattccag cttatacaga    18420
agtcggtcga tgacacgttc gcaaaaacga cgcccacaat cggccaaagc cttaccgtct    18480
tgaagaatag cgcaatcgaa ttcttcggcg aattgaacaa ggcgaccggc gttacggctg    18540
cgctgtcgaa ggcgattctt tggcttgccg acaacatgaa gaccgttgcc gtcgtagtta    18600
cggcgcttgg aacggcgatg cttcttgcat tcgggccgca gattgtcgcg gctatcgttt    18660
ccgcaacgac tgccgtaaag gcattcaccg tcgcgcttgc gtcgaacccg attggcctta    18720
tcgccatcgc actggcaacc gtcattgcgt accttacgct gttccgcgac gaaattaact    18780
tgggaatcga cgacgttacc acgttgggcg atttcttccg cgcgaccttc gaaggcatcg    18840
ggcaggttat tagcgacgtg accttgattg tcggccaatt gtgggcagac atgaccgaag    18900
gcgcatccgg ggcgcttggc gaaatttcgt cgttcgttgg cgatgctgtt ccggctgga    18960 cggaagacta tacgtcgttc ttccagaccg aacgcaccgg atgggccgcc gcgctggaaa    19020
acaccgcgaa agttcttgac gcaatcgccg gattcattac cggccttgca acgtttgccg    19080
gtcgtgctat ggccgaagtc gtgattaccg ttcaaaacgg aatcgcaaac ggctataact    19140
atatcgtcgg atggattgaa cgggttacga atctggcgat tgaatcggcg aacaagcttc    19200
gcgcgatggt cggcaagtcg gcatacgaac ttgtcaactt cgaacgcatg ggccaagccg    19260
gacaaaccga attcgaatct tggggcaagc tttgggccga atcgcttgaa gacggctta    19320 agtcccaagg cggcgcaatg caaaaggtcg tcgaaggtct tatgacgcgc gcgcaacaaa    19380
tcggcgcgaa tcgtcgcgca agcgaaaacg cttcgcttcg cggcgcaggt gcgaaccaac    19440
ttagcgcagc taccgacgac aaggcggcga aggccgcaga acgtcgcggc ttggcgttgg    19500
aaaagatcaa tacgcagctt gataacgaat tgaaccgcat gtttacgctt caaccgcaac    19560
gcgaagcgca agcgaaaatg gatcaaatcg aagaatcgtt gattcaacgt aaaatcaagc    19620
ttaccgaaga cgaacgcgct tcgatcatgg cgaagattca ggccgtccag caagcgcaaa    19680
tcgtgcaaca gaagttcgac gcgatttata cgaagctgt cggcccgcaa cgcgattaca    19740
ccgccacgct tgaagcttcg aaaaagcttc ttgaccttgg cgcgatttcg caagaacagt    19800
attcgcgcgc agtaacgaag gcaaccgaag aattcaagaa cgcgcaagac ccgatgcgcg    19860
```

```
cgtataaccg cgaccttgac caacagttgc agcttttgca gttgttgccg aagcaacgcg   19920
aaatcgaaca gcaggttatg caagtgcaaa acgacctgtt gacgaagggt attacgctta   19980
atgccgaaga acttacgcaa ctgcgcgaac ggcttacgct gttgcagcag gcgaacgcgc   20040
tttcgcagca agaagccgcg ttaatggacg caagcgttac gaagcgccaa cagtatatcg   20100
accaattgaa ggcgattaac gcgcttaaaa acaatccgca aagcggtttc acgcaaggcg   20160
acgcggctaa cgccgtaatg aacgcgaata gcgatcttga tttcacgaat accgatacgt   20220
atttcgaagg tcaagcgcag aaatacgaag atatgtattc gcgtatcgac caactgcgcc   20280
aacaggactt gattagcgaa caaaccgccg caacgctgcg ccaacgtatt tggctggatc   20340
aacagaacca aacgttaaac gccgcgtcgg gtttcttcgg acaaatggcg caattgcaga   20400
agtccgaaaa tagcaagatg gccgccgttg gcaaggccgc agccatcgcg caagcgatga   20460
ttaacacgta tcaggctgcg accggcgcgt attcgtcgct tgcgtcgatt ccttatgtcg   20520
gcccggcgtt gggcgcggct gcggctgcgg ctgcgattgc cgcaggcttg gcgaacgttc   20580
aacaaatccg gtcgcaaaat accgggttta tgtcgggcgg ttacactggc gacattccga   20640
cgaatgccgt agcgggtgcc gtgcatggtc aagaattcgt aatgaacgca gcttcgacga   20700
accgcattgg cgttgataac ctgcaagccc tgcaaagcgg cgcggccagc gtccagcgca   20760
acggggataa tgtgggcacc ggccaagcgg ccccggctgc tgcgcccgaa gtaaatgtaa   20820
ctacgccggt aactgccgtc gtggtacaat cgaaagaagc cgccttggct gcgatgaagt   20880
ccagcgaagg caaagcattt gttatcgaaa ctatcgaaga aaacggcggc accgtcgccc   20940
gaatcgtagg ggttaaataa tgggatacgc aataggcacc gtgactaaag gtagcggcgg   21000
cgacgcttat tatcagcttt tagctattat caaaactttg gccgaagcta acggatggac   21060
tacccttcgt tatgtcaaca ccggaacaaa tcgggaatgg atcggaaaag cgtcggtct   21120 ttccggtctt gaagaaattt ttatcggttt caaaacttac aacaacgtta gcggtgatta   21180
ttacaatttt caagccgcaa ctatgattgg ctatgtagct ggaaatagtt tcgaaacgca   21240
gccgggaatt caaatttcgg gcgtacctgc ccacaataac gcaattacct atttcattac   21300
tgcgaatccg caacgcataa ccggatgcct taaagtaggg acgccggttt acgaacattt   21360
ctatttaggg aaaatgtttc cgtatgcgcg tccgggtgaa ttcccgtcgc ctttggtttg   21420
cgctggaatg tttaacggcg cagaagcgaa acgttttcg gatacgaacc aagttttccc   21480
gtatccgggc gaatattatt cgtcgcaatg ctatatgtgg ctgcgctatc aaactggcgt   21540
atggactaaa gtttggtcgt atccttttac gaatgcaaac acaaacaacg gtttgccact   21600
ggcagggccg caaggaacga atacgcttgt tcctgccgac gtttattacc aacttgaacc   21660
gataattatt tcgcaacttc aaactaacgc gggaagcggc aacgtttggg gggaattgga   21720
cggcgtttat ttttgttccg gcttcaacaa tgggccggaa aatgtcgttc aaatgggcgg   21780
aagttctgtc gtagatcaaa caggaatgac ggtacttcaa gctgtagacg caattatagc   21840
agttggcggg cgcgctttcg taatgtgcca gaacgttaac cgtacaactt ggcgcgattt   21900
tgtcgctttg gaaatgaaat aatgccctac tataacggaa gtgccgcgac tttcgcggat   21960
ttgaaaaccg ctatcgaaaa cgcttgcgtc gctaacggct ggacgctttc taacggcatt   22020
ctttcgaaga acggttgttt tttccaactt gtcgccacta cgccgcaact tacgttgcaa   22080 ggcgaaccg gccaaactgg ttcaaccttg aacggcggcc cgtctagctt cgtaaaagtc   22140
atgtcgccaa ctggaacgcc tatcgttttt ccagttaact acgaaatcca tgtaatgact   22200
```

| | | | | | |
|---|---|---|---|---|---|
| tcgccagaag | acgaagttta | ttgcgtaatt | aactacaatg | ccgatttta | ccagcaactg 22260 |
| tcgttcggaa | agtcgttgat | ttccggcatt | ggtggaactg | gcgcatggtt | taccggaagt 22320 |
| tatgacagtc | gtgtagggca | aagcggaaac | ggaaaccaat | tcgacatgaa | ttccggcagt 22380 |
| aacatggatt | ctggcggaac | ccgtggtttt | tggggactgg | ctggcggact | tttcttcgaa 22440 |
| tcgttaagcg | ggggtagtta | cagcggcaat | tattttcatt | gcggacttga | cgccgtaaat 22500 |
| tggtacaaca | cgcgcggttc | taatcttggc | tatccgcatt | gcgccgcaat | cattaacgca 22560 |
| ttaccaaatc | aatcaaattc | ggcaaccgta | cttgttccgg | taaaaggaat | aaaaacacgc 22620 |
| ggaagcggcg | gccttactat | cgtagtcaat | ccgccaagcg | ttcgttattg | ccgaatcgac 22680 |
| aacttggaac | ccggaagttt | ggtcacatac | ggcccggatc | aatggaaggt | ttatccgttt 22740 |
| tatcggaaag | accttacgca | acggcaagga | tcgtcaagtt | ctattcacag | tggaacttac 22800 |
| ggatacgcta | tcaaatacac | cggaagctaa | acaatggccg | gacgaattgg | cgtatttacg 22860 |
| caacctttta | tttatggtga | agataacccc | gactattcta | ccgaacttga | caaatattcg 22920 |
| gaagttgaat | atttgcctgt | cggcatcgac | gtaatcgggc | gtcgtatttt | cggcccttat 22980 |
| gcggtttggc | gcgttcatgc | ggcgaaccgc | tggcctattg | tgggcgaaga | attcgaaaac 23040 |
| tttttcaaag | attactattt | ccgaattcac | gtatcgccgc | aagaaattga | tttgcaaacg 23100 |
| attgcaagta | cgcaaacgcg | cgaagttgac | gtatggaacg | catatccgtt | tacttccgcg 23160 |
| atcatgcaag | atattttggt | taataatccg | ataggcgttg | aaataatcgg | gccgaatccg 23220 |
| tttaccttcc | cgccattgtt | tgaacagact | tacgaaattg | aagtaggaac | ttccggcccg 23280 |
| gcgaacattg | atcttcaaat | tttgttcgac | tttgccaacg | taacgaatcc | gcttccggta 23340 |
| cttgtaaccg | gcacgcgcgc | cgttaagttc | gacattatcc | ccgaaacgcc | ggtaacggaa 23400 |
| gaatggcaat | ggcttaccga | taatatcgta | gctgttgacg | gcaccgaaca | gcgcatcgcg 23460 |
| ctgcgcggcg | aaatgccgcg | cgtcgaagaa | aatttgaaag | ttatttttcga | cgattcgacg 23520 |
| aagattcgga | agtttttatag | cgatcttatg | gccgcagtcg | gtcggctttg | gattcctgaa 23580 |
| tttcagtacg | caacgcgcac | gctttcggcc | agcgtaacgg | gcggctttaa | cctttacttc 23640 |
| gacacgtcga | agaccgacat | tcgcgcaggt | gaatacgttt | tgattcaaac | gccgttgact 23700 |
| aatgcacttg | tcgaaataga | cgtattgact | gtaaccggcg | ctactgtaac | ttcgcaattg 23760 |
| ctatttgata | ttcccgcagg | atcgttaatc | atgccgggtt | cccccgcact | gttgaatgac 23820 |
| ggttcgggac | tgtcgcgtta | tgccgttaac | gaagttgccg | aaacgacgtt | ggtttgcaag 23880 |
| atgcttcgcc | agcgtgcgca | gcttgtgcgc | cccggatcaa | ccgtaacact | tccgacgtat 23940 |
| cttggcgttc | cggtcttcga | aaagcgaccg | cttgccgatg | aaatggtaga | cgacaacgta 24000 |
| tctaccggcc | aacaatcaat | cgacaatcaa | accggattgc | cggacattat | ttcgcgttgg 24060 |
| gactatagcc | gtataggcgg | cgcacgttcg | tacaaagtga | accgcattca | acgtcccgaa 24120 |
| gaaatggact | attggaaaac | gctatttgcg | tatatgcgcg | gtgcggcgcg | taaagtttgg 24180 |
| gtgcccacat | accgaaccga | tatgcgattg | gttgttcaac | cttcggacgg | cgcttcaact 24240 |
| ttcacaattg | aaggtgtcga | atatgccgaa | aaagtctttc | ctattgtaac | gcatcgttat 24300 |
| attgaagttg | aaacgcttc | cggtattcat | cgaacacaag | taaccggcgc | agccgtcgca 24360 |
| ggaaccggcc | tttctacaat | catcgttttc | gatcctgcgt | tgcctgttgg | cgcaggctgg 24420 |
| acggacatta | aacgaatttc | gtttctgttg | cctatgcgaa | tggccgaaga | caaggtaaca 24480 |
| tggaagcatt | acgattagaa | aagtttactt | caacttttcgt | tgattacggc | ggaaccttaa 24540 |
| atgtccgatt | acgacgacaa | agaaataagc | cagcaagacg | gcgcgccata | cgaacttttac 24600 |

```
gaatgggtcg gaacttaccg tagttattac atgactacgg atagcatacc gcacgttttc    24660
aacagtacga cgtataatcc ggtttcgggt ttgaagcgta gcacgttaaa agccggaacg    24720
cacgaagaag acaatatcga ccttacgatt attgttccga ttaccgaaca gcttgtaaaa    24780
gactacggat ttcaaacgac gccgcccgcg cttgatttga cgatttatcg tttccagcgc    24840
gacgcagcgg catacgttcc gtattggaaa gggccggttg cttcgatcat cattagcggc    24900
gaagaagcaa cgttgcggac gccaagcaag ttcggcaata tcctgcaagg caacataccg    24960
aacgtttacg ttcaaccgcc ttgcaataac gttctgttcg atgaacgttg caaggtaagt    25020
cgcgtatcta attcgctgga tactgtcgta tctgcgataa gttcggacgg cttgcaaatc    25080
agcatcccgt cgattggcgg tttccctaac ggatggtttg tcggcggtga atcgcaatt    25140 ccggcacgca acgaacgtcg aatgatcgtt gcacaaactg gcgcaattct aacggtcaac    25200
tatggatttt cgcgtatttc tgtcggcacg tcgattcaag ttacggcggg ctgcgatcat    25260
agcttcacaa gcgcgaacgg ttgtccgaag ttcaacaacc aaataaactt cggcggttgc    25320
ccgtttgttc cggcgaatc gaataaccca tttacgaacg gaattagcta atatgtgggt    25380
cgcaatcgtt atcgcggtaa ttgcgttgct tatggtcgcg tttatgccga aaccgaacgt    25440
cgaaaacgcg cgggcggcga agcttggcga cttccaagtt ccccggtcga aatacggcga    25500
tcctatgccc ttagtgtggg gaactgttcg ccaaaagtcg ccgattacgt tttggttcgg    25560
cgacttccgc ccggttccga ttaagaagaa agtttcttcg ggcttgttca gttcgaagaa    25620
ggttattacg ggttataaaa actacgtcgg tatcgactgc tgtttgtgcc ttgggccggg    25680
cgtcgtactt cgtaagtttt gggccggtac gtatcttgtt tggactggca ccgcttcagg    25740
tattacgaat atcgtaatca atcaacctaa cttgtttggc ggcgaagatc aacgcggcgg    25800
ccttcaaggt acgtttacat tctacgacgg tcgttacgat ccgccgcgcg attcgtatt    25860 ggcttcggtt cttgatccga acgttccggc gtacaacggt tttgcgcgtg ccttattcaa    25920
gtcgttttat atcggcacga cgactaatct tgaaatgttc agcttcgaaa tttcgcgtat    25980
gacttccggt cttcacgcga catattcgat tatgccgaac ggtcttgatt taaacccgat    26040
ggaaattgcg tatgatgcca ttacgcaaaa gttcgggcgc ttcggcaact tgccttcggt    26100
tctggacttg ccttcgttcg ttgcgtgcgc gcaaacgttg tataacgaac aaatgggcat    26160
gtctatggcc gcgcaatcgg ccattacggg caaagacctg ttagaagaaa ttatgcggca    26220
atgcgacggc ttgctgtatc aagacccggc aacttcaaag attgttgcga gttgattcg    26280 tcaagactac gacattaaca ctttgccggt tcttgacgaa tccattatta aggatttgaa    26340
gaacttttcg aaaacgactt gggatagtac gttcaatcaa tgccgcgtta cgttcaagga    26400
tcgcgcgggg gattacgacg acagcgtagc cattgcccaa gacttcgcaa atatcaacta    26460
tcaacagcgc gtcaagtcta ccgaaatttc ttcgccgggc tgtacgactg ccgaagttgc    26520
aaacaagctt gcggcgcgtc aactttcgtt gattagcgtt ccgttgtata agtgcgatat    26580
tacttgcaat cgcaaggctt cgacgcttcg tccgggcgac gtgttcgttc tgaattgggg    26640
gccgttcaac ctgcaaaaaa tggtcatgcg agtttcgaaa atcgaccttg gcgaacttac    26700
gtcgggggaa gtgaagattt cttgcgttca agaccgattc gctacggcga cacctacgtt    26760
tgcgccgcct gattcttcga attggacgcc gattaacaca agtgcaaatg ccgtgacggt    26820
gcgtaacttc tttacgccgc cgcacttctt ggcgcgcgtt tctccgaacg aagccctttc    26880
gacgttcgac agtcaaggcc ggttgtatat cttggctaag gggccgtcgt ccgcttctat    26940
```

```
ttcgttcgat gctatgttca gcggcgataa cttcgctacc gatcccacac tagccattga  27000
agcggccccg tacaatggcg gcggcacgct gtcggctgca tatgcgaata cagttgcggc  27060
agatacgcga cacgacacga caggcgtatt caaagtgcaa ggcgtatcgt cggcagacat  27120
tgcgaacttg caacaatata cgacgcttga ccaagcgcgc gacggttccg cgttgcttat  27180
ggtcaataac gaactgttcg tttatgtcgg cttcgttgac aacggcgacg gttccgttac  27240
tttcccgaac ctgtatcgcg gcgttctgga taccgcaccg gcaagccatg cggcgggcga  27300
ccgtgtttgg ttcgttggcg gtatcgacgg cttgattccg cagcttgtga acaacagtgc  27360
gaccgggtac gttaagctgt tggatacgac gacttcggac aagttgccgc tgtcgtccgc  27420
cccgaccgta tccgccgcgc agaatggccg cgcacgcctg ccgtatcagc cgcagaacct  27480
tacgcttgac ggtagccgca cccctgcccc ggccacgggc gcaacgtcga tcacggcggc  27540
atgggcacgc cgcagccgcg aagcgcaagc cctgtccgtc ttcaacgatc cagacgccgg  27600
gctagaaacc gggacgcaaa cgcgcgtgcg gtggcgcgtc ggcggtggcg gatatactac  27660
ggtcatgctt tccggcactt cgacggcgct taacgtaacc ggccttgtcg gtacgttgga  27720
agttatcgta gatacgcaaa tcacggcaag cgggctgttc agtacgaaca gcgaacgctt  27780
gaccatgacg ctatcttaaa agaacgcaag ttcgccgttc ttggctttct tcaaacgtcc  27840
gcagtcgtac agcatttcga ccgcttcgtt aatgtaccag tcgtaattta tatcgtcggg  27900
aaattcggtc ggcaagtcca ttacaggacg cgcgccgtcc gttttcccga ctttgtttcc  27960
gctggcaacg taagcgatat gcccggcttc gttcttcggg taataccagc gaacgacctt  28020
gcccaagaaa cgcccgttct tttcgccgcc gccgtgaaca ttcttcacgc atacgaagcg  28080
ccggaagtcg cggcattcct taatcgtctt ttctaccggc gttccttcga caaggaaccg  28140
aataacagcg tcggaacata ccaaagcttc ggggttcttc gacagaatcg aattaagcgc  28200
ggaaccgcgt tcacaataag cgcccttcgt cttagcgcct aattttcat ccaagaagcg  28260
cgcttcggcg tcgccgccgt cgtccttgat tgcgacataa ctattcacgt cgcgcgaata  28320
tacggctttg tatcgcgttt cttcggtctt gtatcccgta tgcgcttccc atgctgcaat  28380
caagttgcgg acttcttcat gccgcgactt gtgatatttc gaaatgaagc cgtccgtatt  28440
gccggaaata acttcgacgc cgattccttc gattgcttcg ataagcataa gcaatacaag  28500
ctgtccggta atcgtcactt gcaacataag ttgcggcgcg tacagcgttg aatatttgtt  28560
gccaagtttg ccgaagcttc cgttaatcgt aatcttcaag ctgtcggcaa ttactttcca  28620
tttcttcgcg cccttgcggt cgccttcttt cttgcacttc gccgccatcg ccttagcgtg  28680
aattcgcgtt tcgacgatct tgttataaac cgtcaagaac gcttcgccca agtgcggcgg  28740
gaacagcttt tgattaagga ttgtgcgcgg atagaacgat tctacgtcgt tatccgctag  28800
aataatgtct tcggttgcga catgcgcggt cttcttttct gtcgaatgaa ggccgcccat  28860
tccaagtttg tacgtcgatt tgccgatagt tactttcagc ttttcaattt cggtcggcat  28920
gatgggcgaa cccaagccgt ccagatagaa tgccgcgccg cgcacgactt ctagcatttg  28980
ctgtaactgc ggcgtctgga aacaaacgaa gtccggtacg ttgtaataca cgggccgtc   29040
gtctgttagt gtgggcttct tcggatagta acccaacacc ttttcaagtt ctttattgat  29100
taccgcttcg gctacctgcg catcggattt cgaccgaagt tctacgccgt attcttccga  29160
catttcggcc cgcaacttca attcgggcgc aagttcgtta aacagaagtt ccgtattcgc  29220
aaggtcgttg cagcagtacg ggcgaacgat tgcggcatct tcgcgcgtca atacgtcgt   29280
ttcaggaaat ggcaagtcct gcatacgttc gcaatgcagc cgaccggcgt acagcttcaa  29340
```

```
cgatgccggg cgcgcagtaa cgccgccgtt caccgggcaa acgttgaaca agtcgatatg   29400
gttgtagcgg ccaatttgta cgccgtactt cttttcgaag tcgaacggtg taaccttctt   29460
tgtaccgtag gccgggccgc ttttaatgat gaagtccgaa gcttctttaa gcttggcgca   29520
cgatgcaccg cgcgccgcaa gttctatcat gggcaagtca tacgatgcac tgttgaagcc   29580
cacaatacag aatcgccaaa gcatccaaag aagcttcgtc gggttaaagt catggtcggg   29640
tgaacgttca aacgcgacga actttccggt atcaagcgac ttaaacgcga cataccaaaa   29700
gttgatatac gtttcaacgt caaagacgaa gacgcttcca gcgggaagcg ccattagttc   29760
ttcgtccgac atgaattcga caggccgcaa agcatggcga atgcttgcgg ccaacttatc   29820
gacgacgcgg cttttcttgg caacgatgaa gccttgttcg ttcaacatat gacagcccct   29880
tagaacggta tatcgtccga atacggatca tccgaagttc ggttaatgta cgtatcttcc   29940
gactgttcag tatacgacgc ttcggttcca agatcaagcc ccataactgc gccgcgcacg   30000
ttgtcgccgt agaaaattac tttgttcgtt tcggcgtcga aatgcgcttt cttgaatgcg   30060
tgttcgacgg aaagcaaaag ctttgcactg aaccccattc gttccggcaa gccttcgata   30120
cgatacgtcg aagcttcttc tttgtgcata cgcgacaata ccgcgccatc ttcgaagaag   30180
acatggccgt tcgggctgaa cgattcgata gcacgaacgc cccggtaaaa gtcttcgggg   30240
atcggccaaa ggttcagatt cggaacgtcc agaaccgaag cataattcgg gtaacgttcg   30300
ccgtaaagct gcgacttgat aaacgaaccg tcttcgaaat agaacgtcgc cgatgactgc   30360
gaatagccga accggtaagc gccttcgat gccttcgcaa tggccgacgc tgcggccttc   30420
ggaagcataa ggccgggcgg aaggtcgatg ccgtgccacg cttccagcag ggccgccccg   30480
ttcgtcgcta cggcgcttcc agcttgcagc aggacggcgg cataggtcgc attcggcgcg   30540
ccgtccgttg ccagccctgc gaccgcagcc aaggccgctt taacccggtc gtcgatcacg   30600
gcgcattgtg gatcgggcgg catgatgggc acttcgtcga acgctacgca cggcacaagc   30660
gcccggaata cgccagacga tacggcaagc gtgttcgctg taagttgcgt aatcgacaat   30720
tcgtcgccag ccttcgacag tgcgtcgata aactgcaacg tatgcgggca cgcggtcaag   30780
tcttcttcaa tcggcgcggc cacggtcaag acgccatcga aggccgccgc ccaattgtgg   30840
gcaatgtggc cgaactggat atttaccggc ccggccttct tttgcgcaac cgaaataaac   30900
ttcaatgctg cgataagcga agcggcgggg ttcgccgtct tcttcgctgt cgtaccttcg   30960
gcttgcttgc gggcgcggct tttgcgcttc ggcttttccg gcgttgcagg aatcggaacg   31020
tcgttttcaa tttgcgttgt catagtttca ccattcagcg gaaagaactt cgggatactt   31080
cttgttcacc caaacgcgaa gccttgcggg cgttcgaagt tcggatacac gttgcaaagc   31140
ttgatacgtc gtcggcggcg gttcttcgcg gtgccgctgt cgccaccaat cccgcgaacg   31200
tttcgccgca agtccggggt gttcaagcat cacaaattcg ttaaacattt ggaagccgca   31260
aaagtacgat actttaatca ttggcggctt tgtcaagttg ccttgtgcgt cgcgttttc   31320 gtgaaggttg tatatcacct tttgtacgtc gaaatattcg actatcgggg catcgctgcg   31380
caacggttcg gcgacgcccg gcgttgcaaa caacttcgtt tcgaagctga attcggcacc   31440
gcagttaatg cactggcgcg cggcggcatg attgtatacg ccgcaaactt cgcaaatacg   31500
aaccggcgcg tcgccgccac ctttgccggg gcgattcgga atacgcgggt cgttgatcgg   31560
gccaagccga cgaatgttcg ccgcgaagtc gccgacaaga caattcatct tgccggtttc   31620
gggacttggg cgcgttccgc gtccgtactt ctgtacgtgt ttgcccggcg ataacgtcgg   31680
```

```
gttcaaatcg ccgatgaagt cgattgccgg atggtcgaag cccgttgtaa gtttctggcc    31740
ggatacgata ccgcgaagtt cgcccgcttt gaatgcgcgc aaacgttcgg tattaacctt    31800
gtctttcaac ttcgaatgca cgggcaacac ttccagcccg taggactgaa ttacgtttgc    31860
gacgtgttcc gtattgtcaa tgccagttgc gaagacaagc caagtcgaac ggttatacgc    31920
catttccatc atttcgcgga cggcgttaaa tactacgtcg tcatcgtctg cggcttttc    31980 aagttgcttc gaattgaatt cgccgccgat tacgccaacg cctgaaatgt caatttcggt    32040
tttcgtcggg cgcgcgataa gcggcgacaa gtaaccttcg gcgattaacc gattaaacga    32100
ttcaacgccg gtaatgtcgt aacaaatatc ggtgaagatt ccgttatcgg taatcatgcc    32160
cattttcata cgatagggcg ttgcggtgaa tccgataact ttaagatgcg ggttaatcgc    32220
gcgcaattcg gcgataatgt actgatagaa cgaatcttct ttgtccgaaa gcaaatggca    32280
ttcgtcaatc aacagcaaat cacgccatcc gaaatggcga agatgcggcg ggcgtccgtc    32340
gttctgttca agcgcctttt taatcgccgg ggctacggat tgaacgccgc cgaatacgat    32400
aggcataatc atttcgcggc tgttcaagcc tgcggaatag ataccaaggg gcgcagtcgg    32460
ccaaaccgac attagctttt cggcgttctg ttcgatcaat tctttaacgt gcgtcaacat    32520
cattattcgc tgattcggcc aaagtccgaa aatgcgacga atgaagttcg caattacaac    32580
agatttgccg gttccggtcg gcatagcgac gaccgggttt ccgacgtttc cgcgctggaa    32640
atagtcgaag attgaatatt cggcttcgtc ctgataccag cgcggtacgt agatactaga    32700
cattttgcgt tgtcgccgtg ataggtacgt aagacgggca agcttgcggt acgaagtcgc    32760
ggggaattac gccgttatgt acgtcgcaaa accattcgcc gttttcgacc ggacgggccg    32820
ccttgcagct acgacagttc tttttcaggaa tcgcgccttt gtggcaaatg tccttcgccg    32880
cgcaatacgt gcaatccttg aacgtcggat tatcggaaag acgcggcggc ggttcctgcg    32940
acagaatgat ttgttcggcc ttttcccgca tttgctggcc taaccgatga tccaacttca    33000
caagttcgac gtgtaacgaa tcgtcgttct tgttaatgtt gaagtacagt acgtaacgga    33060
atccgtatgc cgcgtcgctt ccatacgttg aagtttggca aaaatgctgc ggcttcgcaa    33120
caggcatacc ggcttcgcca agcttgttaa agcctgcgcc ggttccgttc gtcttgaatt    33180
ccagcaatac aggttcgtcg attccatagc gcgccggaag ctttgcgatg ccgtcaagcg    33240
atccaccgaa atgcccattc accgccgaca cgcggtattg tgggaattcc aagccgtccg    33300
ccttcgcgcg tgcgacgtgt tgcgtatagt acggatgttc cttcgtaatc ggtgacgaaa    33360
ggccgtcgcc ttcttcgccg ggcttcgcaa tccaatacga atcgctttcg gcgtgataca    33420
taaggccgtc gcggttttcg taccaaactt cggcccccgat gccttccagc cattcgataa    33480
agcgggcttc ttcacgatgc ccacgattaa acagccgttg cttgcgtccg tccgtctgtt    33540
cgcggaacgt ccatcggaac agataccaaa gcttgcgctt gcagccgtcg ccgatcaacg    33600
acgcgccaag gtgccagcgg tggccgccgt cataggtgcg aacgcaatat tcgtctatgt    33660
cttcaaggat gcgcttagaa agcgccttcg ctacgccggg cgcgtcaagt gcgacgtttt    33720
gttttccggc gtcgggcttc gtcgctggcg cgtcgttcag cgttaattgc gcgttcggtt    33780
cgcttttctt gcttggcatc gttcttcacc tttcgccgga caagtgcggc gtaattgttc    33840
gttagatagt cggcggaaag cgtcgcaacg tctttaagtt gatccttcga taaccaactg    33900
atatggcatt cggaagcgtc tatgccaagt tgcgccgcaa gccaattgta cgccttcgac    33960
cgtgacatta agccagtttg ccaaagacgg tcgaattcgt catgcgcttt tgttcgaagc    34020
tgtcgcgtag cacggtcggc catacgacca agcggaataa acgtgccggg gtgacagccg    34080
```

```
acagcggcgc gacagtcgtt gcaaaaataa atatgcggcc aatcgccgta acggcgaccg   34140
taaatccggt cgtttgttgt tagttcgatg ttgaatgaac aacaggtatc gcattgttca   34200
ggtacgggca atgcgtcttt gattttcgac atacttacgc ttttcccat aaaagaacgc    34260 cggggccggt aaaagccccg gcgatgttac gccgctacgc tagttcgtct tagcgtgcgc   34320
cccaaggtgc ggcaccgcca gccggtgcgc cgccctgcgg ttgctgctgc cagccgcccg   34380
gctgtccgcc ctgcggggcc gcgttctgct gcggctgctg gccgcccaa gctgcgccgt    34440 tgccctgcgg ctgctgcggc tgctgttggg gctgctggcc ccatgccgcg ccgccttggg   34500
ccggttgctg ctgcgcgggc tgctgctggc cctgcgctg gccgcccat cgccgccct     34560 gcgcgggctg ttgctgcggc tgttgaccga agccgccttg gccctgcggc tgctgtccga   34620
agcctgcggc ggcctgctgc ggctgcgccg gggctgcgcc ctgtccggcc ttgcccggtt   34680
cgttgccgtt catgtcgaac acctttttaa cttcggtgta ctgcgggtcg ttcttctgcg   34740
gcccgacttc gataaggaac gggattccgt gaagctgcga cgaatcgttg atttggaaca   34800
cgccgataac gtggcagact gcggacaact ggcggtgcgc gatttcgacc gtctgttggt   34860
tcgtatggta caggttcagg cgatacgcgc cggtcgtgcc agcctgcggg ccgtcgatga   34920
tccgcaagtt aagttgcaga taaccgccgt cgttcgcctt gtttgccttc acttcggaac   34980
tttcgacgat aaccggatgc ttgccgatag gcaggcttcc gacgccttgg gtcgggtcgt   35040
attgctgcgc gttgaaaggt tgaatcagtt gcatggtatt taccttttcg aaaagtcttc   35100
gccgttggtt acggtggcaa agttaccgtt tttggctgcg ccggtaggat tcgaacctac   35160
gaataccgga atcaaaatcc ggtgccttac cgcttggcga cggcgcaaaa gcttattgca   35220
tcgctttcgt gaaaagcgcc gacaaatcgg gcggttcaag ttcgcccaag ttgcccaaac   35280
gatcacgcgc gaacacttcg ggaatttcct tcgtccgcaa cgcccgaacc ggcttcggct   35340
ggcccggtac gatagcttcg cccaagtgca acacgttgtc gaacaggtgc ggaacccttta  35400 cgttaaggtc tttgccgggg aagaacggtc gcttttgcat gatcggttcg tatacgactt   35460
cgccgccctg caagatggtt tgccgtccgt tttccatgac gccttgtttc gcaatcatta   35520
cgatatgctt ttgcggcatg taatacaagt cgttgcaaat cttcatcgtg cgttcggaca   35580
tattgccgta tgccttcatg ccgtgtttga ccttcgacag ttcttcggcc aagatgattt   35640
cggcaatgtt cgaaatactg tcaatgccca aggtatcgaa gttcgcggct tcgcgcgact   35700
tcataaacca ttcgaagaat tcggtaatca gcggcgggga atacgcttcc catgcgggca   35760
cattcgaacc gcgcatagac aacatgccgg gttcagtgac aacagcacg gggcgcggcg    35820 cggtgttgat aagcggcgtc ttgcccgaac cgggcgaacc gaatacgacg gactttacgc   35880
catagcgtcg ggccagttgc gacgccggtt taagctgcga catttgcatt tgtttactc    35940 cgattaaagc ggcattattg acgacgccga cgctttcgct ttcccgactg tccgttatgg   36000
cactatgcga cgcgatgcgc ggcccggact ttcgatgccg tcaagaatgc cgccttgatt   36060
gtgggcaagg cggcaagtgc attacttctt cgccttcggt tccttgattt caagggtcgg   36120
cgtaccttcc gacgtaacga taacgtcgtc gatgatcttg cggaagttgt cgggcagttg   36180
cttgtattcg gtaagcgaaa gttcaggcgt ccacttaacc aaacgttcgg cgatcaattc   36240
gccagcctgt ccggtctttt cgatcttcga caacgccttt tcaatgcgcg ccttgtcggt   36300
cttgccttcg gcgttctgga tgaagccgta gcgaaccgga accttcatcg tcgctttgta   36360
gccgccgccg agttcgacgt tttcggtcgt gccggacttc gccgggtcgt gcatgaacat   36420
```

```
cacggccagc ttgcgggctt ccaattcggc ttctttggcg acttcaagcg cggccttctt    36480
cgcctgccaa tcgaccaaca gacggtcgcg ttcggcgata tattcggctt cgctgtagtt    36540
cttgacttcg cccgtttccg ggttcgttac ctgaatgata ttcggggtca tctttgcacc    36600
tttcttcgtt gggccgccgc acgttgcgcc ggtatgtgcg taatgtacga cggcccgttt    36660
cggttgtcaa gccttttgtt caagaatttt tcgttcttcg aacaagtccc gattgttcgc    36720
gtcgtgttcg gtgaacttct gcgggaaccg cttacgaagc ttggcgatgt tcacggcctg    36780
cgcttcaccg aagttcgaac caatggcgcg aagcaacagc gcatcgtacc aaaagccgtc    36840
gccgacttct tcaagcgcgt tcacgtcgtc gaatacggca ccttcggcgg tcgccgacag    36900
ggcttccagc agttcgcccg cttcggtcgc tttaccgatg atcgcatgaa cgatattgac    36960
ggcgcgcgcg ttggcttcgt cggtgccatc ggtggcgatc caatcgggca gcttggcaag    37020
cgtgccggtg ttgtcgccgg gggcgggaac gccgcagtcg cggccataga aaagcgtctt    37080
cttgatcgcg tccagcttca ccagtgcggc gacagcttcg gcgatggttt cgcggaagta    37140
gccaagcgac acgcggtcgc cgtgatagct acccgacgcg gttacgtgcg cttcttcgat    37200
atagtcgaag gtcttttcgg gttcgttcat tgcttgcacc tttcaaagtc gccgggcacc    37260
gcgccgcagc gttccgacac tgtagcgccg ggcatgttgc ctgtcaacaa aattttgtct    37320
tgcctgctag aattttgtcg ggtatagtgt cgttcatctt gcccacattg aaccgccgac    37380
atggtgaaaa catggccgaa gttaccaaac tgcgggatga aacccgcgaa ctgttgttga    37440
accgcccggc gtcgatagac gttggcacca ttgcggaagc catcggcgtt cgaagtctt    37500 gggttaattc ctttgcgcgc ggcgacatac cgaaccccgg cgtcgtcacg attgaaaccc    37560
ttaacgcttt tttgaagaag tgcgcgaaga aggcgaatta agaatgtatc aaaacatacc    37620
tatcgaaatg cggacatatc cgcaatgggt tatgtggcgg tacgaagaca cggattcgaa    37680
gaaacctact aaggttccgt attctgcccg taccggcgca ctagccagcg ttaccgattc    37740
gaacacttgg ggaacgtttg acgaatgttt gcacgcgctt aattccggct ggtataacgg    37800
aatcgggttc gtgttgaccg acgccgaccc gtattcgttt atcgaccttg acgacacgaa    37860
aggcgatcaa acgcgcttg atcgtcaaat caaaatctac aacgaattcg acagctacgc    37920
cgaacgttcg ccgtccggtt cggggctgca tatcattgta aagggcgcgg ttcccgctgg    37980
ccggcgtcgg tcgtttattg aagtgtattc gtcgcttcgt tatatgacca tgacgggcga    38040
cgtttaccgc aatgcgccaa tcaaagaaca aaacgaactg ttgaacattc tttggggcca    38100
aatggggcaa ggttctgtcg ccgttgcgca ttacgaagc gtcgccgaag ccaaggaaac    38160
cgacgaacag gtttataacc gtgccgtcgc cgcagccaac ggggataagt tcgccgaact    38220
gttcgcgggt aaatgggaag gcatgtacgc ttcgcagtcc gaagccgact tcgcattggt    38280
cgatattatc gcgttctata cgcagaaccg ggcgcagatt gcccgcatgt tccgactgtc    38340
cggcttgggc caacgtgaca aggcgaagcg tgacgattac gtgtcgtaca tgctgaacaa    38400
atgctttgat cgcatgttgc cgcccgtcga tattgacgga ttgaaaaaca gcttgacga    38460 agcaatagcc gcaaaagaag cccgcgaccg tgccgaagcc gcatcgttga ataccaacgt    38520
tccgcaagcg ccaatcgtcg cgccatccat ccccgaaacg tcgaaggtgt attcagtgcc    38580
gcccggactt gtcggcgaaa tcgcccaata tatctacgca caagcgcccc gcccggttcc    38640
cgaaatcgcg ttggctggcg cgcttggtct tgtcgctggc atcgtaggcc gtgcgtacaa    38700
tatcagcgga accggcctta atcagtacgt attgctgttg gccccgaccg gaacaggtaa    38760
agaagccatc gcatccggca ttgataagct aatggcgcaa gtaatccgca ccgtaccggc    38820
```

```
tgcaagcgac ttcatcggcc ccggcgaaat cgcatcggcg caagcgatca ttaagtatat   38880
gtcgaagggg ccaacgtcgt tcgtatcgtt ggtcggcgaa ttcggcatct atcttcaaca   38940
aatggcaagc ttgaacgcgc cgccgcatct tttgggctg cgccgtttca tgctggacgc    39000
ttacaacaaa tccggcgaag gtaaggttct tcgtccgtct atctattcgg acaaggacaa   39060
gaacactacc gcagttcttg cgccgtcgtt ttcgttgctt ggcgaatcaa cgcccgaaaa   39120
gttttacgaa ggtttgcacg aaggtttgat taccgaaggt cttttgccgc gctttacgat   39180
gattgaatat catggtcaag tgccgccgtt gaacaaagcc ggggcgcgcg tgcaaccgtc   39240
gttcgaactt atcgaccgcc tttcgacgct tgcgcgcat tcgcttatgt tgaacagcca    39300
acataaagca atccatgttc aattcgccga aggcgtcgaa caagcttccg acaagttcga   39360
agaacattgc cgcaataacg taaacagtag cgaccgcgac gttaagcgcc aactttggtc   39420
gcgcgcccat atgaaggcgt taaagctggc cggtatcgta gcagtcggca ataacccata   39480 cgacccccgtt attacgtcgg acgttctgtc atgggcaacc ggcgtaatcg ttgcagacgt   39540
gcgcaacttg cttgcacgct tcgacgctgg cgaaattggc gtagacaacg acgaaacgaa   39600
acagcttgcg aaggtaattg cgacggttaa agatttcgtc gtatcgcctt ggccggaagt   39660
tgcgaagtat gcaggcgaag gcgcaagcaa cttgcattcg aaccgcattg ttccgtacag   39720
ctacgtacag cgtcggcttg ccgccgtgtc ggtcttccgt aaagatcgca tcggcgcgtc   39780
tggcgcaatc aagcgcgcat tgaagacgct atgcgaacgg ggcgacctgc aagaagtgtc   39840
gcgggctacg ctgtcgaagg actacggaac gtccgccgtc gcgtacatga tcgcgcatcc   39900
gggcgtcttc ggcctgtagc ggggccggga tagtgtgggc agaactggcc gccttcgggc   39960 ggcttttttcg tgcctgaacg aaacataaat aaagcgacga acggtcgtcg taggtcttga   40020
cgaagcttcg aaactatcgt acaatcgtcg catacaagaa aggagtttca acaatgcagc   40080
atcccgacga cgtagaatat ttcgaacgtt tgcgcgccat aggattcgaa atcgcaaagg   40140
ctaacaacat tcgttgcctt gtcatagaac ctaagcgtcg cgcaggcggt gcatacggac   40200
ttgcgtattt gtctgaatgt cgaatcagca ttgaagttcg cggcaaagaa cttatgcgcg   40260
atggcggcga atgggcgaag aatcgttatc gccatgcttg caacttgcat acgttggcgc   40320
acgaattggc gcatttgcaa gaacaccaaa cgcacggcaa gaccggacac ggcccgcgct   40380
tccgtactta cgaaaccgcg ttacttgctg cggttatgca gcttgacgcg acttccccac   40440
attaaccgaa ggtgccagct atggaaatcc gcatagacaa cgtgaacgaa gttctagccg   40500
caatcggctt gaccggacag cacgaacgca agggccaagg ctggcaccgc gtttacattc   40560
acgccccgca agaaggaacc gacgtaacgt tgtaccttgg ccgcgtcatg tttcaacatg   40620
gcgtattcca atgggtgaaa tggtgcgtac cgccgaacga aggcgaattg caggattacg   40680
acgtatattg gttccgttgg gccgtataca ccgcaaccgg caagcatcta gggccgaagt   40740
cttgggcgcg gttgaaggcc aaggcgcagg aacgcgcgca ggccaagcgc gacgccgcca   40800
aggccgcacg ggacgccctg aacgccgaca gggtagccgc aggcaagaag ccccggacgc   40860
gcgcccttgc gcctgtcaat ccgcgccggg cggcgtgcat gatcgtcggc gaatggctgt   40920
ccgccgaact tggccgcgaa gttcatttgt tcgcattcta acgaaggagt attgaatatg   40980
accgcattta ttgtcgcgct ttgcgcatct ttggcgctgg cgttctggcg tctggccgct   41040
actgcattcg aagccgctta ctactgcgca aagaacggtg aacgttcgaa ggcatggcgc   41100
ttcatccttc gcggtatctt ttgcgcgttt tggctttcgc taatgattgc gcccgtcgtt   41160
```

```
cgtttcttcg atagcttcga cgtgattagc atagacgaag cgccgcctac tgttgcgccg   41220
aagcgttcga cagaccttcg cgtataatag acgacgatcc gtttaacggt gccgtataac   41280
acgcaaagcc ttgatacgcc tagctttcag ggcatttata acaagtataa agtttaacgg   41340
caaagtcacc cgatccccca gcttgtaacc taataaccgt tatcactaaa taacactact   41400
tttcagtatt atacttatta tactttttat atttctttta ttttcaatgg tttaggactt   41460
ttacagcccc ttcaatccgt ataatggccc cggaacgatg cgttacgctt gactaacccg   41520
ttatcacctg atagagttac aaacgtcata actgttaagg agtgttcgaa atgtcgtacc   41580
caatcgttca agcgtcgccg acggcgatgg aaaagaagga acaggccgaa cgcagcgcgt   41640
acccgttcgc agaactggcc gtaggtcaat cgttccttgt gccaattgcc gacgtgaccg   41700
aagtaaactt gcgcatggcc gtaagtcgcc agaacaaaaa gaaggacggc aagcgtttta   41760
ccgtcgtcaa gcatggcgac ccgcataacg tgttcgaagt cgcacgcacg gcatgaacgc   41820
gcgggccaat gtgggcaagc tgcaacgggt gtttgcgccg cattacttga cgcttcgcgc   41880
gcaatggccg caggcgttcg caatcaaacc aacacgcggc ggctatgaag ccgtcgtatt   41940
catcgaaggg gcgaccaatg tacgaaatcc agaacgggca caagatgccg aaggcgcgtc   42000
gcaaggctgg aagcgaaccg ccagcggtga agaccgcatt taacgaatac gcggacgcat   42060
acaaagctgt ttacggcgtg cgtccgctgt cgtatactta cgacgcagca acgaagttta   42120
ttcgcatcga aaacagcggc ggcgtaagct tgtcgcgttt gcgcgaaatg acgaagcaac   42180
ttcgttaccg caaaggttga cagcttcgaa gtttcatcgt agtgtgacca tgcgaaccgg   42240
gcgcttcccg gcatttcaaa ggagttaacg caatgtgcat cgtttgcgaa atcaaagccg   42300
atttgtcgaa gaccaaagcg accgccgaac aggccgccgc catcatggcg aacgttgaaa   42360
agctggcccg tgcaatgggc ggcgttatcg acgtggtaga agctgcgcac gtgcgcaagc   42420
ccgacgtgtt caagccggaa gaactggcga ccatcgccga agccgaagaa ctgttcgcgc   42480
agtccgaagc cctgccccg ttggccgccg ccctgttggg cgcgctgttg ggcggtagcg   42540
tgaaagtcga agtcgcgcat atccagatga aggacggcga gaatcccgaa caggctatcg   42600
aacgttacat ggctgaacgt aacgccgaag gttcgacgaa acattgacca aacagccccg   42660
gctagtgtat agtcggggct tcttcgtagg ggaacgaaac agacatggcc gacgaaatag   42720
acgcaacagc cgaccgcatg gacaacgaac tatcgttgat tctggcgaac actagccgcc   42780
ttgccgcgcg ataccgaaag gttatcccgg cgaatgcttt ttctgcggcg aagaattcgc   42840
cagcgtcgtc gaagtgaccg acccgcgcag cggcgaacgt gtcgattcct gcgggcgctg   42900
tcgtgacgca aggggcataa aatgacaccg aacaaacttg cgaaggaatc cgaacattcg   42960
caacaggtcg cattgttcgc atacgtagct gtcgcgtact tgcacggctt cgacgtagcg   43020
gacgaatggt gcaagaccgg caagctaccg aagcgcgatc cgaacgcacc gccagccgtc   43080
ccggcgcttg aatggttcca cgcgatcccg aacggcggta gccgtggcga cgacgaacag   43140
tcgcg                                                              43145
```